US012365718B2

(12) United States Patent
Orentas et al.

(10) Patent No.: US 12,365,718 B2
(45) **Date of Patent: *Jul. 22, 2025**

(54) COMPOSITIONS AND METHODS FOR TREATING CANCER WITH DuoCARs

(71) Applicant: Lentigen Technology, Inc., Gaithersburg, MD (US)

(72) Inventors: Rimas J. Orentas, Seattle, WA (US); Dina Schneider, Potomac, MD (US); Waleed M. Haso, Santa Monica, CA (US); Stefan Miltenyi, Bergisch Gladbach (DE); Boro Dropulic, Ellicott City, MD (US)

(73) Assignee: LENTIGEN TECHNOLOGY, INC., Gaithersburg, MD (US)

( * ) Notice: Subject to any disclaimer, the term of this patent is extended or adjusted under 35 U.S.C. 154(b) by 835 days.

This patent is subject to a terminal disclaimer.

(21) Appl. No.: 17/540,377

(22) Filed: Dec. 2, 2021

(65) Prior Publication Data

US 2022/0169698 A1 Jun. 2, 2022

Related U.S. Application Data

(63) Continuation of application No. 16/692,957, filed on Nov. 22, 2019, now Pat. No. 11,208,455, which is a continuation-in-part of application No. PCT/US2019/051734, filed on Sep. 18, 2019, which is a continuation of application No. 16/134,735, filed on Sep. 18, 2018, now Pat. No. 10,689,431, which is a continuation-in-part of application No. 16/078,269, filed as application No. PCT/US2017/049923 on Sep. 1, 2017, now Pat. No. 11,453,712.

(60) Provisional application No. 62/382,791, filed on Sep. 2, 2016.

(51) Int. Cl.

| | |
|---|---|
| ***C12N 15/85*** | (2006.01) |
| ***A61K 35/17*** | (2025.01) |
| ***A61K 39/00*** | (2006.01) |
| ***A61K 40/11*** | (2025.01) |
| ***A61K 40/31*** | (2025.01) |
| ***A61K 40/42*** | (2025.01) |
| ***A61P 35/02*** | (2006.01) |
| ***C07K 14/705*** | (2006.01) |
| ***C07K 14/725*** | (2006.01) |
| ***C07K 16/28*** | (2006.01) |

(52) U.S. Cl.

CPC .......... *C07K 14/7051* (2013.01); *A61K 40/11* (2025.01); *A61K 40/31* (2025.01); *A61K 40/4211* (2025.01); *A61K 40/4212* (2025.01); *A61K 40/4221* (2025.01); *A61P 35/02* (2018.01); *C07K 14/70517* (2013.01); *C07K 14/70521* (2013.01); *C07K 14/70578* (2013.01); *C07K 16/2803* (2013.01); *C07K 16/2887* (2013.01); *C12N 15/85* (2013.01); *A61K 2239/48* (2023.05); *C07K 2317/31* (2013.01); *C07K 2317/622* (2013.01); *C07K 2319/00* (2013.01); *C07K 2319/02* (2013.01); *C07K 2319/03* (2013.01); *C07K 2319/75* (2013.01)

(58) Field of Classification Search

None

See application file for complete search history.

(56) References Cited

U.S. PATENT DOCUMENTS

| | | | | |
|---|---|---|---|---|
| 10,689,431 | B2 | 6/2020 | Orentas | |
| 11,208,455 | B2 * | 12/2021 | Orentas | C07K 16/2827 |
| 2005/0136428 | A1 | 6/2005 | Crea | |
| 2015/0299317 | A1 | 10/2015 | Orentas | |
| 2016/0145337 | A1 | 5/2016 | Galletto | |
| 2016/0311910 | A1 | 10/2016 | Qin | |
| 2017/0107286 | A1 | 4/2017 | Kochenderfer | |
| 2017/0183418 | A1 | 6/2017 | Galletto | |
| 2018/0092968 | A1 | 4/2018 | Albelda | |
| 2018/0148508 | A1 | 5/2018 | Wang | |
| 2018/0280438 | A1 | 10/2018 | Orentas | |
| 2019/0083596 | A1 | 3/2019 | Orentas et al. | |
| 2019/0119635 | A1 | 4/2019 | Robbins | |
| 2019/0134091 | A1 | 5/2019 | Dropulic et al. | |
| 2019/0241641 | A1 | 8/2019 | Orentas et al. | |
| 2020/0231648 | A1 | 7/2020 | Orentas et al. | |
| 2020/0392200 | A1 | 12/2020 | Orentas et al. | |

FOREIGN PATENT DOCUMENTS

| | | |
|---|---|---|
| CN | 103483453 | 1/2014 |
| CN | 104822705 | 8/2015 |
| CN | 105331586 | 2/2016 |

(Continued)

OTHER PUBLICATIONS

Bielamowicz et al., "Multispecific CAR T cells for the treatment of high grade glioma," Neuro Oncol., 2015, 17(Suppl. 3):iii16.

(Continued)

*Primary Examiner* — Maria Marvich

(74) *Attorney, Agent, or Firm* — Serge Sira, Esq.; Gregory J. Hwa, Esq.; Fish & Richardson P.C.

(57) ABSTRACT

Novel therapeutic immunotherapy compositions comprising at least two vectors, each vector encoding a functional CAR, whereby the combination of vectors results in the expression of two or more non-identical binding domains, wherein each vector encoded binding domain(s) are covalently linked to a transmembrane domain and one or more non-identical intracellular signaling motifs are provided herein as well as are methods of use of same in a patient-specific immunotherapy that can be used to treat cancers and other diseases and conditions.

8 Claims, 28 Drawing Sheets

Specification includes a Sequence Listing.

(56) References Cited

FOREIGN PATENT DOCUMENTS

| | | | |
|---|---|---|---|
| JP | 2018-514199 A | 6/2018 |
| JP | 2018-518974 A | 7/2018 |
| JP | 2019-512234 | 5/2019 |
| WO | WO 2014055657 | 4/2014 |
| WO | WO 2014065961 | 5/2014 |
| WO | 2015-513394 | 5/2015 |
| WO | WO 2015075468 | 5/2015 |
| WO | WO 2016/057705 | 4/2016 |
| WO | WO 2016/100232 | 6/2016 |
| WO | WO 2016102965 | 6/2016 |
| WO | WO 2017/062820 | 4/2017 |
| WO | WO 2017062952 | 4/2017 |
| WO | WO 2018045325 | 3/2018 |

OTHER PUBLICATIONS

Bielamowicz et al., "Trivalent CAR T cells overcome interpatient antigenic variability in glioblastoma," Neuro-Oncology, 2017, 20(4):506-518.

Brenner and Okur, "Overview of gene therapy clinical progress including cancer treatment with gene-modified T cells," Hematology Am. Soc. Hematol. Educ. Program, 2009, pp. 675-681.

Brentjens et al., "Safety and persistence of adoptively transferred autologous CD19-targeted T cells in patients with relapsed or chemotherapy refractory B-cell leukemias," Blood, 2011, 118(18):4817-4828.

Chen et al, "A compound chimeric antigen receptor strategy for targeting multiple myeloma," Leukemia, 2018. 32(2):402-412.

D'Aloia et al., "CAR-T cells: the long and winding road to solid tumors," Cell Death and Disease, 2018, 9(282), 12 pages.

Eisenberg et al., "T-cells "à la CAR-T (e)"-Genetically engineering T-cell response against cancer," Advanced Drug Delivery Reviews, Feb. 15, 2019, 141:23-40.

Fousek et al., "Targeting CD19-negative relapsed B-acute lymphoblastic leukemia using trivalent CAR T cells," J. Clin. Oncol., 2018, 36(5 Suppl 1):121.

Fousek et al., "Trivalent CAR T cells mitigate CD19-negative relapse and improve tumor control in primary pre-B cell acute lymphoblastic leukemia (B-ALL) (Abstract A50)," Proceedings of the AACR Special Conference on Tumor Immunology and Immunotherapy, 2018, 6(9):Suppl 1.

Fumoto et al., "Targeted Gene Delivery: Importance of Administration Routes," Intech, 2013, 30 pages.

Hegde et al., "Combinational targeting offsets antigen escape and enhances effector functions of adoptively transferred T cells in gioblastoma," Mol. Ther., 2013, 21(11):2087-2101.

Jensen et al., "Antitransgene rejection responses contribute to attenuated persistence of adoptively transferred CD20/CD19-specific chimeric antigen receptor redirected T cells in humans," Biol. Blood Marrow Transplant, 2010, 16:1245-1256.

Kueberuwa et al., "CD19 CAR T Cells Expressing IL-12 Eradicate Lymphoma in Fully Lymphoreplete Mice through Induction of Host Immunity," Mol. Ther., Oncolytics, 2018, 19(8):41-51.

Mirzaei et al., "Chimeric Antigen Receptors T Cell Therapy in Solid Tumor: Challenges and Clinical Applications," Frontiers in Immunology, 2017, 8:1850, 13 pages.

NEBiolabs, Recleavable Filled-in 5' Overhangs, downloaded Jan. 20, 2019, 2 pages.

Newick et al., "Chimeric antigen receptor T-cell therapy for solid tumors," Molecular Therapy—Oncolytics, 2016, 3:16006, 7 pages.

Sridhar and Petrocca, "Regional Delivery of Chimeric Antigen Receptor (CAR) T-Cells for Cancer Therapy," Cancers (Basel), 2017, 9:92, 10 pages.

Xiong et al., "Mitigating tumor escape: tandem anti-CD20- and CD19 SCFV-based chimeric antigen receptors (CARs) in leukemia/lymphoma," Mol. Ther., 2016, 24(Suppl. 1):S257.

Zah et al., "T cells expressing CD19/CD20 bispecific chimeric or antigen receptors prevent antigen escape by malignant B cells," Cancer Immunol. Res., 2016, 4(6):498-508.

Bielamowicz et al., "IM-05, Multispecific Car T Cells for the Treatment of High Grade Glioma," abstract, Neuro-Oncology, Jun. 2015, 17(Suppl 3):iii16, 1 page.

* cited by examiner

|   | | | | | | | DuoCAR sets |
|---|---|---|---|---|---|---|---|
| Product 1 | a-CD19 | | 8/z | + | a-CD22 | 8/BB/z | Example 1 |
| Product 2 | a-CD19 | | 8/CD28/z | + | a-CD22 | 8/BB/z | Example 2 |
| Product 3 | | a-CD22 | 8/BB/z | + | a-CD19 | 8/CD28/z | Example 3 |
| Product 4 | | a-CD22 | 8/BB/z | + | a-CD19 | 8/z | Example 4 |

SEQUENCE LISTING

<160> NUMBER OF SEQ ID NOS: 126

<210> SEQ ID NO 1
<211> LENGTH: 729
<212> TYPE: DNA
<213> ORGANISM: Artificial
<220> FEATURE:
<223> OTHER INFORMATION: CD20-reactive scFv binding domain (LTG1495)

<400> SEQUENCE: 1

```
gaggtgcagt tgcaacagtc aggagctgaa ctggtcaagc caggagccag cgtgaagatg     60

agctgcaagg cctccggtta caccttcacc tcctacaaca tgcactgggt gaaacagacc    120

ccgggacaag ggctcgaatg gattggcgcc atctaccccg ggaatggcga tacttcgtac    180

aaccagaagt tcaagggaaa ggccaccctg accgccgaca agagctcctc caccgcgtat    240

atgcagttga gctccctgac ctccgaggac tccgccgact actactgcgc acggtccaac    300

tactatggaa gctcgtactg gttcttcgat gtctgggggg ccggcaccac tgtgaccgtc    360

agctccgggg gcggaggatc cggtggaggc ggaagcgggg gtggaggatc cgacattgtg    420

ctgactcagt ccccggcaat cctgtcggcc tcaccgggcg aaaaggtcac gatgacttgt    480

agagcgtcgt ccagcgtgaa ctacatggat tggtaccaaa agaagcctgg atcgtcaccc    540

aagccttgga tctacgctac atctaacctg gcctccggcg tgccagcgcg gttcagcggg    600

tccggctcgg gcacctcata ctcgctgacc atctcccgcg tggaggctga ggacgccgcg    660

acctactact gccagcagtg gtccttcaac ccgccgactt ttggaggcgg tactaagctg    720

gagatcaaa                                                            729
```

<210> SEQ ID NO 2
<211> LENGTH: 243
<212> TYPE: PRT
<213> ORGANISM: Artificial
<220> FEATURE:
<223> OTHER INFORMATION: CD20-reactive scFv binding domain (LTG1495)

<400> SEQUENCE: 2

```
Glu Val Gln Leu Gln Gln Ser Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Asp Tyr Tyr Cys
                85                  90                  95

Ala Arg Ser Asn Tyr Tyr Gly Ser Ser Tyr Trp Phe Phe Asp Val Trp
            100                 105                 110

Gly Ala Gly Thr Thr Val Thr Val Ser Ser Gly Gly Gly Gly Ser Gly
        115                 120                 125
```

-continued

```
Gly Gly Gly Ser Gly Gly Gly Gly Ser Asp Ile Val Leu Thr Gln Ser
    130                 135                 140

Pro Ala Ile Leu Ser Ala Ser Pro Gly Glu Lys Val Thr Met Thr Cys
145                 150                 155                 160

Arg Ala Ser Ser Ser Val Asn Tyr Met Asp Trp Tyr Gln Lys Lys Pro
                165                 170                 175

Gly Ser Ser Pro Lys Pro Trp Ile Tyr Ala Thr Ser Asn Leu Ala Ser
            180                 185                 190

Gly Val Pro Ala Arg Phe Ser Gly Ser Gly Ser Gly Thr Ser Tyr Ser
        195                 200                 205

Leu Thr Ile Ser Arg Val Glu Ala Glu Asp Ala Ala Thr Tyr Tyr Cys
    210                 215                 220

Gln Gln Trp Ser Phe Asn Pro Pro Thr Phe Gly Gly Gly Thr Lys Leu
225                 230                 235                 240

Glu Ile Lys


<210> SEQ ID NO 3
<211> LENGTH: 1473
<212> TYPE: DNA
<213> ORGANISM: Artificial
<220> FEATURE:
<223> OTHER INFORMATION: CAR LTG1495 (LP-1495-CD8 TM-41BB-CD3zeta)

<400> SEQUENCE: 3

atgctccttc tcgtgacctc cctgcttctc tgcgaactgc cccatcctgc cttcctgctg      60

attcccgagg tgcagttgca acagtcagga gctgaactgg tcaagccagg agccagcgtg     120

aagatgagct gcaaggcctc cggttacacc ttcacctcct acaacatgca ctgggtgaaa     180

cagaccccgg gacaagggct cgaatggatt ggcgccatct accccgggaa tggcgatact     240

tcgtacaacc agaagttcaa gggaaaggcc accctgaccg ccgacaagag ctcctccacc     300

gcgtatatgc agttgagctc cctgacctcc gaggactccg ccgactacta ctgcgcacgg     360

tccaactact atggaagctc gtactggttc ttcgatgtct gggggggccgg caccactgtg     420

accgtcagct ccgggggcgg aggatccggt ggaggcggaa gcgggggtgg aggatccgac     480

attgtgctga ctcagtcccc ggcaatcctg tcggcctcac cgggcgaaaa ggtcacgatg     540

acttgtagag cgtcgtccag cgtgaactac atggattggt accaaaagaa gcctggatcg     600

tcacccaagc cttggatcta cgctacatct aacctggcct ccggcgtgcc agcgcggttc     660

agcgggtccg gctcgggcac ctcatactcg ctgaccatct cccgcgtgga ggctgaggac     720

gccgcgacct actactgcca gcagtggtcc ttcaacccgc cgacttttgg aggcggtact     780

aagctggaga tcaaagcggc cgcaactacc acccctgccc ctcggccgcc gactccggcc     840

ccaaccatcg caagccaacc cctctccttg cgccccgaag cttgccgccc ggccgcgggt     900

ggagccgtgc atacccgggg gctggacttt gcctgcgata tctacatttg ggccccgctg     960

gccggcactt gcggcgtgct cctgctgtcg ctggtcatca ccctttactg caagaggggc    1020

cggaagaagc tgctttacat cttcaagcag ccgttcatgc ggcccgtgca gacgactcag    1080

gaagaggacg gatgctcgtg cagattccct gaggaggaag agggggggatg cgaactgcgc    1140

gtcaagttct cacggtccgc cgacgccccc gcatatcaac agggccagaa tcagctctac    1200

aacgagctga acctgggaag gagagaggag tacgacgtgc tggacaagcg acgcggacgc    1260

gacccggaga tgggggggaa accacggcgg aaaaaccctc aggaaggact gtacaacgaa    1320

ctccagaaag acaagatggc ggaagcctac tcagaaatcg ggatgaaggg agagcggagg    1380
```

aggggaaagg gtcacgacgg gctgtaccag ggactgagca ccgccactaa ggatacctac 1440
gatgccttgc atatgcaagc actcccaccc cgg 1473

<210> SEQ ID NO 4
<211> LENGTH: 491
<212> TYPE: PRT
<213> ORGANISM: Artificial
<220> FEATURE:
<223> OTHER INFORMATION: CAR LTG1495 (LP-1495-CD8 TM-41BB-CD3zeta)

<400> SEQUENCE: 4

```
Met Leu Leu Leu Val Thr Ser Leu Leu Leu Cys Glu Leu Pro His Pro
1               5                   10                  15

Ala Phe Leu Leu Ile Pro Glu Val Gln Leu Gln Gln Ser Gly Ala Glu
            20                  25                  30

Leu Val Lys Pro Gly Ala Ser Val Lys Met Ser Cys Lys Ala Ser Gly
        35                  40                  45

Tyr Thr Phe Thr Ser Tyr Asn Met His Trp Val Lys Gln Thr Pro Gly
    50                  55                  60

Gln Gly Leu Glu Trp Ile Gly Ala Ile Tyr Pro Gly Asn Gly Asp Thr
65                  70                  75                  80

Ser Tyr Asn Gln Lys Phe Lys Gly Lys Ala Thr Leu Thr Ala Asp Lys
                85                  90                  95

Ser Ser Ser Thr Ala Tyr Met Gln Leu Ser Ser Leu Thr Ser Glu Asp
            100                 105                 110

Ser Ala Asp Tyr Tyr Cys Ala Arg Ser Asn Tyr Tyr Gly Ser Ser Tyr
        115                 120                 125

Trp Phe Phe Asp Val Trp Gly Ala Gly Thr Thr Val Thr Val Ser Ser
    130                 135                 140

Gly Gly Gly Gly Ser Gly Gly Gly Gly Ser Gly Gly Gly Gly Ser Asp
145                 150                 155                 160

Ile Val Leu Thr Gln Ser Pro Ala Ile Leu Ser Ala Ser Pro Gly Glu
                165                 170                 175

Lys Val Thr Met Thr Cys Arg Ala Ser Ser Ser Val Asn Tyr Met Asp
            180                 185                 190

Trp Tyr Gln Lys Lys Pro Gly Ser Ser Pro Lys Pro Trp Ile Tyr Ala
        195                 200                 205

Thr Ser Asn Leu Ala Ser Gly Val Pro Ala Arg Phe Ser Gly Ser Gly
    210                 215                 220

Ser Gly Thr Ser Tyr Ser Leu Thr Ile Ser Arg Val Glu Ala Glu Asp
225                 230                 235                 240

Ala Ala Thr Tyr Tyr Cys Gln Gln Trp Ser Phe Asn Pro Pro Thr Phe
                245                 250                 255

Gly Gly Gly Thr Lys Leu Glu Ile Lys Ala Ala Ala Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350
```

Met Arg Pro Val Gln Thr Thr Gln Glu Glu Asp Gly Cys Ser Cys Arg
355 360 365

Phe Pro Glu Glu Glu Glu Gly Gly Cys Glu Leu Arg Val Lys Phe Ser
370 375 380

Arg Ser Ala Asp Ala Pro Ala Tyr Gln Gln Gly Gln Asn Gln Leu Tyr
385 390 395 400

Asn Glu Leu Asn Leu Gly Arg Arg Glu Glu Tyr Asp Val Leu Asp Lys
405 410 415

Arg Arg Gly Arg Asp Pro Glu Met Gly Gly Lys Pro Arg Arg Lys Asn
420 425 430

Pro Gln Glu Gly Leu Tyr Asn Glu Leu Gln Lys Asp Lys Met Ala Glu
435 440 445

Ala Tyr Ser Glu Ile Gly Met Lys Gly Glu Arg Arg Arg Gly Lys Gly
450 455 460

His Asp Gly Leu Tyr Gln Gly Leu Ser Thr Ala Thr Lys Asp Thr Tyr
465 470 475 480

Asp Ala Leu His Met Gln Ala Leu Pro Pro Arg
485 490

<210> SEQ ID NO 5
<211> LENGTH: 66
<212> TYPE: DNA
<213> ORGANISM: Artificial
<220> FEATURE:
<223> OTHER INFORMATION: synthetic oligonucleotide

<400> SEQUENCE: 5
atgctgctgc tggtgaccag cctgctgctg tgcgaactgc cgcatccggc gtttctgctg 60
attccg 66

<210> SEQ ID NO 6
<211> LENGTH: 22
<212> TYPE: PRT
<213> ORGANISM: Artificial
<220> FEATURE:
<223> OTHER INFORMATION: synthetic polypeptide

<400> SEQUENCE: 6

Met Leu Leu Leu Val Thr Ser Leu Leu Leu Cys Glu Leu Pro His Pro
1 5 10 15

Ala Phe Leu Leu Ile Pro
20

<210> SEQ ID NO 7
<211> LENGTH: 747
<212> TYPE: DNA
<213> ORGANISM: Artificial
<220> FEATURE:
<223> OTHER INFORMATION: CD22-reactive scFv binding domain LTG2200)

<400> SEQUENCE: 7
caggtacagc tccagcagag tggcccaggg ctcgtgaagc caagccagac gctgtccctg 60
acttgtgcaa tttcagggga ttcagtttca tcaaatagcg cggcgtggaa ttggattcga 120
caatctcctt cccgagggtt ggaatggctt ggacgaacat attacagatc caaatggtat 180
aacgactatg cggtatcagt aaagtcaaga ataaccatta accccgacac aagcaagaac 240
caattctctt tgcagcttaa ctctgtcacg ccagaagaca cggcagtcta ttattgcgct 300
cgcgaggtaa cgggtgacct ggaagacgct tttgacattt gggggcaggg tacgatggtg 360

-continued acagtcagtt caggggggcgg tgggagtggg ggagggggta gcgggggggg agggtcagac 420
attcagatga cccagtcccc ttcatccttg tctgcctccg tcggtgacag ggtgacaata 480
acatgcagag caagccaaac aatctggagc tatctcaact ggtaccagca gcgaccagga 540
aaagcgccaa acctgctgat ttacgctgct tcctccctcc aatcaggcgt gcctagtaga 600
tttagcggta ggggctccgg caccgatttt acgctcacta taagctctct tcaagcagaa 660
gattttgcga cttattactg ccagcagtcc tatagtatac ctcagacttt cggacagggt 720
accaagttgg agattaaggc ggccgca 747

<210> SEQ ID NO 8
<211> LENGTH: 249
<212> TYPE: PRT
<213> ORGANISM: Artificial
<220> FEATURE:
<223> OTHER INFORMATION: CD22-reactive scFv binding domain (LTG2200)

<400> SEQUENCE: 8

Gln Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser Ser Asn
20 25 30

Ser Ala Ala Trp Asn Trp Ile Arg Gln Ser Pro Ser Arg Gly Leu Glu
35 40 45

Trp Leu Gly Arg Thr Tyr Tyr Arg Ser Lys Trp Tyr Asn Asp Tyr Ala
50 55 60

Val Ser Val Lys Ser Arg Ile Thr Ile Asn Pro Asp Thr Ser Lys Asn
65 70 75 80

Gln Phe Ser Leu Gln Leu Asn Ser Val Thr Pro Glu Asp Thr Ala Val
85 90 95

Tyr Tyr Cys Ala Arg Glu Val Thr Gly Asp Leu Glu Asp Ala Phe Asp
100 105 110

Ile Trp Gly Gln Gly Thr Met Val Thr Val Ser Ser Gly Gly Gly Gly
115 120 125

Ser Gly Gly Gly Gly Ser Gly Gly Gly Gly Ser Asp Ile Gln Met Thr
130 135 140

Gln Ser Pro Ser Ser Leu Ser Ala Ser Val Gly Asp Arg Val Thr Ile
145 150 155 160

Thr Cys Arg Ala Ser Gln Thr Ile Trp Ser Tyr Leu Asn Trp Tyr Gln
165 170 175

Gln Arg Pro Gly Lys Ala Pro Asn Leu Leu Ile Tyr Ala Ala Ser Ser
180 185 190

Leu Gln Ser Gly Val Pro Ser Arg Phe Ser Gly Arg Gly Ser Gly Thr
195 200 205

Asp Phe Thr Leu Thr Ile Ser Ser Leu Gln Ala Glu Asp Phe Ala Thr
210 215 220

Tyr Tyr Cys Gln Gln Ser Tyr Ser Ile Pro Gln Thr Phe Gly Gln Gly
225 230 235 240

Thr Lys Leu Glu Ile Lys Ala Ala Ala
245

<210> SEQ ID NO 9
<211> LENGTH: 1482
<212> TYPE: DNA
<213> ORGANISM: Artificial
<220> FEATURE:

<223> OTHER INFORMATION: CAR LTG2200 (LP-2200-CD8 TM-41BB-CD3zeta)

<400> SEQUENCE: 9

```
atgcttcttt tggtgacttc ccttttgctg tgcgagttgc cacaccccgc cttcctgctt     60
attccccagg tacagctcca gcagagtggc ccagggctcg tgaagccaag ccagacgctg    120
tccctgactt gtgcaatttc aggggattca gtttcatcaa atagcgcggc gtggaattgg    180
attcgacaat ctccttcccg agggttggaa tggcttggac gaacatatta cagatccaaa    240
tggtataacg actatgcggt atcagtaaag tcaagaataa ccattaaccc cgacacaagc    300
aagaaccaat tctctttgca gcttaactct gtcacgccag aagacacggc agtctattat    360
tgcgctcgcg aggtaacggg tgacctggaa gacgcttttg acatttgggg gcagggtacg    420
atggtgacag tcagttcagg gggcggtggg agtgggggag gggggtagcgg ggggggaggg    480
tcagacattc agatgaccca gtccccttca tccttgtctg cctccgtcgg tgacagggtg    540
acaataacat gcagagcaag ccaaacaatc tggagctatc tcaactggta ccagcagcga    600
ccaggaaaag cgccaaacct gctgatttac gctgcttcct ccctccaatc aggcgtgcct    660
agtagattta gcggtagggg ctccggcacc gattttacgc tcactataag ctctcttcaa    720
gcagaagatt ttgcgactta ttactgccag cagtcctata gtatacctca gactttcgga    780
cagggtacca agttggagat taaggcggcc gcaactacca cccctgcccc tcggccgccg    840
actccggccc caaccatcgc aagccaaccc ctctccttgc gccccgaagc ttgccgcccg    900
gccgcgggtg gagccgtgca tacccggggg ctggactttg cctgcgatat ctacatttgg    960
gccccgctgg ccggcacttg cggcgtgctc ctgctgtcgc tggtcatcac cctttactgc   1020
aagaggggcc ggaagaagct gctttacatc ttcaagcagc cgttcatgcg gcccgtgcag   1080
acgactcagg aagaggacgg atgctcgtgc agattccctg aggaggaaga gggggggatgc   1140
gaactgcgcg tcaagttctc acggtccgcc gacgcccccg catatcaaca gggccagaat   1200
cagctctaca acgagctgaa cctgggaagg agagaggagt acgacgtgct ggacaagcga   1260
cgcggacgcg acccggagat ggggggggaaa ccacggcgga aaaaccctca ggaaggactg   1320
tacaacgaac tccagaaaga caagatggcg gaagcctact cagaaatcgg gatgaaggga   1380
gagcggagga ggggaaaggg tcacgacggg ctgtaccagg gactgagcac cgccactaag   1440
gatacctacg atgccttgca tatgcaagca ctcccacccc gg                     1482
```

<210> SEQ ID NO 10
<211> LENGTH: 494
<212> TYPE: PRT
<213> ORGANISM: Artificial
<220> FEATURE:
<223> OTHER INFORMATION: CAR LTG2200(LP-2200-CD8 TM-41BB-CD3zeta)

<400> SEQUENCE: 10

```
Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys Pro Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80
```

-continued

```
Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Arg Glu Val Thr Gly Asp
        115                 120                 125

Leu Glu Asp Ala Phe Asp Ile Trp Gly Gln Gly Thr Met Val Thr Val
    130                 135                 140

Ser Ser Gly Gly Gly Gly Ser Gly Gly Gly Gly Ser Gly Gly Gly Gly
145                 150                 155                 160

Ser Asp Ile Gln Met Thr Gln Ser Pro Ser Ser Leu Ser Ala Ser Val
                165                 170                 175

Gly Asp Arg Val Thr Ile Thr Cys Arg Ala Ser Gln Thr Ile Trp Ser
            180                 185                 190

Tyr Leu Asn Trp Tyr Gln Gln Arg Pro Gly Lys Ala Pro Asn Leu Leu
        195                 200                 205

Ile Tyr Ala Ala Ser Ser Leu Gln Ser Gly Val Pro Ser Arg Phe Ser
    210                 215                 220

Gly Arg Gly Ser Gly Thr Asp Phe Thr Leu Thr Ile Ser Ser Leu Gln
225                 230                 235                 240

Ala Glu Asp Phe Ala Thr Tyr Tyr Cys Gln Gln Ser Tyr Ser Ile Pro
                245                 250                 255

Gln Thr Phe Gly Gln Gly Thr Lys Leu Glu Ile Lys Ala Ala Ala Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Lys Arg Gly Arg Lys Lys Leu Leu Tyr Ile Phe Lys
            340                 345                 350

Gln Pro Phe Met Arg Pro Val Gln Thr Thr Gln Glu Glu Asp Gly Cys
        355                 360                 365

Ser Cys Arg Phe Pro Glu Glu Glu Glu Gly Gly Cys Glu Leu Arg Val
    370                 375                 380

Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490
```

<210> SEQ ID NO 11
<211> LENGTH: 72
<212> TYPE: DNA
<213> ORGANISM: Artificial
<220> FEATURE:
<223> OTHER INFORMATION: CD8 transmembrane domain

<400> SEQUENCE: 11
atctacatct gggcgccctt ggccgggact tgtggggtcc ttctcctgtc actggttatc 60
accctttact gc 72

<210> SEQ ID NO 12
<211> LENGTH: 22
<212> TYPE: PRT
<213> ORGANISM: Artificial
<220> FEATURE:
<223> OTHER INFORMATION: CD8 transmembrane domain

<400> SEQUENCE: 12

Ile Trp Ala Pro Leu Ala Gly Thr Cys Gly Val Leu Leu Leu Ser Leu
1 5 10 15

Val Ile Thr Leu Tyr Cys
20

<210> SEQ ID NO 13
<211> LENGTH: 141
<212> TYPE: DNA
<213> ORGANISM: Artificial
<220> FEATURE:
<223> OTHER INFORMATION: CD8 hinge domain

<400> SEQUENCE: 13
accacgacgc cagcgccgcg accaccaaca ccggcgccca ccatcgcgtc gcagcccctg 60
tccctgcgcc cagaggcgtg ccggccagcg gcggggggcg cagtgcacac gagggggctg 120
gactttgcct gcgatatcta c 141

<210> SEQ ID NO 14
<211> LENGTH: 47
<212> TYPE: PRT
<213> ORGANISM: Artificial
<220> FEATURE:
<223> OTHER INFORMATION: CD8 hinge domain

<400> SEQUENCE: 14

Thr Thr Thr Pro Ala Pro Arg Pro Pro Thr Pro Ala Pro Thr Ile Ala
1 5 10 15

Ser Gln Pro Leu Ser Leu Arg Pro Glu Ala Cys Arg Pro Ala Ala Gly
20 25 30

Gly Ala Val His Thr Arg Gly Leu Asp Phe Ala Cys Asp Ile Tyr
35 40 45

<210> SEQ ID NO 15
<211> LENGTH: 69
<212> TYPE: PRT
<213> ORGANISM: Artificial
<220> FEATURE:
<223> OTHER INFORMATION: hinge and transmembrane region of CD8.alpha

<400> SEQUENCE: 15

Thr Thr Thr Pro Ala Pro Arg Pro Pro Thr Pro Ala Pro Thr Ile Ala
1 5 10 15

Ser Gln Pro Leu Ser Leu Arg Pro Glu Ala Cys Arg Pro Ala Ala Gly
20 25 30

Gly Ala Val His Thr Arg Gly Leu Asp Phe Ala Cys Asp Ile Tyr Ile
35 40 45

Trp Ala Pro Leu Ala Gly Thr Cys Gly Val Leu Leu Leu Ser Leu Val
50 55 60

Ile Thr Leu Tyr Cys
65

<210> SEQ ID NO 16
<211> LENGTH: 106
<212> TYPE: PRT
<213> ORGANISM: Artificial
<220> FEATURE:
<223> OTHER INFORMATION: Human IgG CL

<400> SEQUENCE: 16

Gly Gln Pro Lys Ala Ala Pro Ser Val Thr Leu Phe Pro Pro Ser Ser
1 5 10 15

Glu Glu Leu Gln Ala Asn Lys Ala Thr Leu Val Cys Leu Ile Ser Asp
20 25 30

Phe Tyr Pro Gly Ala Val Thr Val Ala Trp Lys Ala Asp Ser Ser Pro
35 40 45

Val Lys Ala Gly Val Glu Thr Thr Thr Pro Ser Lys Gln Ser Asn Asn
50 55 60

Lys Tyr Ala Ala Ser Ser Tyr Leu Ser Leu Thr Pro Glu Gln Trp Lys
65 70 75 80

Ser His Arg Ser Tyr Ser Cys Gln Val Thr His Glu Gly Ser Thr Val
85 90 95

Glu Lys Thr Val Ala Pro Thr Glu Cys Ser
100 105

<210> SEQ ID NO 17
<211> LENGTH: 126
<212> TYPE: DNA
<213> ORGANISM: Artificial
<220> FEATURE:
<223> OTHER INFORMATION: synthetic oligonucleotide

<400> SEQUENCE: 17
aaacggggca gaaagaaact cctgtatata ttcaaacaac catttatgag accagtacaa 60
actactcaag aggaagatgg ctgtagctgc cgatttccag aagaagaaga aggaggatgt 120
gaactg 126

<210> SEQ ID NO 18
<211> LENGTH: 42
<212> TYPE: PRT
<213> ORGANISM: Artificial
<220> FEATURE:
<223> OTHER INFORMATION: synthetic polypeptide

<400> SEQUENCE: 18

Lys Arg Gly Arg Lys Lys Leu Leu Tyr Ile Phe Lys Gln Pro Phe Met
1 5 10 15

Arg Pro Val Gln Thr Thr Gln Glu Glu Asp Gly Cys Ser Cys Arg Phe
20 25 30

Pro Glu Glu Glu Glu Gly Gly Cys Glu Leu
35 40

<210> SEQ ID NO 19
<211> LENGTH: 336

```
<212> TYPE: DNA
<213> ORGANISM: Artificial
<220> FEATURE:
<223> OTHER INFORMATION: signaling domain of CD3-zeta

<400> SEQUENCE: 19

agagtgaagt tcagcaggag cgcagacgcc cccgcgtaca agcagggcca gaaccagctc     60

tataacgagc tcaatctagg acgaagagag gagtacgatg ttttggacaa gagacgtggc    120

cgggaccctg agatgggggg aaagccgaga aggaagaacc ctcaggaagg cctgtacaat    180

gaactgcaga aagataagat ggcggaggcc tacagtgaga ttgggatgaa aggcgagcgc    240

cggaggggca aggggcacga tggcctttac cagggtctca gtacagccac caaggacacc    300

tacgacgccc ttcacatgca ggccctgccc cctcgc                              336


<210> SEQ ID NO 20
<211> LENGTH: 112
<212> TYPE: PRT
<213> ORGANISM: Artificial
<220> FEATURE:
<223> OTHER INFORMATION: synthetic polypeptide

<400> SEQUENCE: 20

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 21
<211> LENGTH: 1467
<212> TYPE: DNA
<213> ORGANISM: Artificial
<220> FEATURE:
<223> OTHER INFORMATION: CAR LTG1562 (LP-CD19binder-CD8linker-CD4tm-4-
      1BB-CD3-zeta)

<400> SEQUENCE: 21

atgctgctgc tggtgaccag cctgctgctg tgcgaactgc cgcatccggc gtttctgctg     60

attccggata ttcagatgac ccagaccacc agcagcctga gcgcgagcct gggcgatcgc    120

gtgaccatta gctgccgcgc gagccaggat attagcaaat atctgaactg gtatcagcag    180

aaaccggatg gcaccgtgaa actgctgatt tatcatacca gccgcctgca tagcggcgtg    240

ccgagccgct ttagcggcag cggcagcggc accgattata gcctgaccat tagcaacctg    300

gaacaggaag atattgcgac ctatttttgc cagcagggca acaccctgcc gtataccttt    360

ggcggcggca ccaaactgga aattaccggc ggcggcggca gcggcggcgg cggcagcggc    420

ggcggcggca gcgaagtgaa actgcaggaa agcggcccgg gcctggtggc gccgagccag    480

agcctgagcg tgacctgcac cgtgagcggc gtgagcctgc cggattatgg cgtgagctgg    540
```

-continued

```
attcgccagc cgccgcgcaa aggcctggaa tggctgggcg tgatttgggg cagcgaaacc    600

acctattata acagcgcgct gaaaagccgc ctgaccatta ttaaagataa cagcaaaagc    660

caggtgtttc tgaaaatgaa cagcctgcag accgatgata ccgcgattta ttattgcgcg    720

aaacattatt attatggcgg cagctatgcg atggattatt ggggccaggg caccagcgtg    780

accgtgagca gcgcggcggc gccggcgccg cgcccgccga ccccggcgcc gaccattgcg    840

agccagccgc tgagcctgcg cccggaagcg tgccgcccgg cggcgggcgg cgcggtgcat    900

acccgcggcc tggattttgt gcagccgatg gcgctgattg tgctgggcgg cgtggcgggc    960

ctgctgctgt ttattggcct gggcattttt ttttgcgtgc gctgccgccc gcgccgcaaa   1020

aaactgctgt atatttttaa acagccgttt atgcgcccgg tgcagaccac ccaggaagaa   1080

gatggctgca gctgccgctt tccggaagaa gaagaaggcg gctgcgaact gcgcgtgaaa   1140

tttagccgca gcgcggatgc gccggcgtat cagcagggcc agaaccagct gtataacgaa   1200

ctgaacctgg gccgccgcga agaatatgat gtgctggata aacgccgcgg ccgcgatccg   1260

gaaatgggcg gcaaaccgcg ccgcaaaaac ccgcaggaag gcctgtataa cgaactgcag   1320

aaagataaaa tggcggaagc gtatagcgaa attggcatga aaggcgaacg ccgccgcggc   1380

aaaggccatg atggcctgta tcagggcctg agcaccgcga ccaaagatac ctatgatgcg   1440

ctgcatatgc aggcgctgcc gccgcgc                                        1467
```

```
<210> SEQ ID NO 22
<211> LENGTH: 489
<212> TYPE: PRT
<213> ORGANISM: Artificial
<220> FEATURE:
<223> OTHER INFORMATION: CAR LTG1562 (LP-CD19binder-CD8link-CD4tm-41BB-
      CD3zeta)

<400> SEQUENCE: 22

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Gly Gly Gly Ser Gly Gly Gly Gly Ser Gly Gly Gly Gly Ser
    130                 135                 140

Glu Val Lys Leu Gln Glu Ser Gly Pro Gly Leu Val Ala Pro Ser Gln
145                 150                 155                 160

Ser Leu Ser Val Thr Cys Thr Val Ser Gly Val Ser Leu Pro Asp Tyr
                165                 170                 175

Gly Val Ser Trp Ile Arg Gln Pro Pro Arg Lys Gly Leu Glu Trp Leu
            180                 185                 190
```

-continued

```
Gly Val Ile Trp Gly Ser Glu Thr Thr Tyr Tyr Asn Ser Ala Leu Lys
        195                 200                 205

Ser Arg Leu Thr Ile Ile Lys Asp Asn Ser Lys Ser Gln Val Phe Leu
    210                 215                 220

Lys Met Asn Ser Leu Gln Thr Asp Asp Thr Ala Ile Tyr Tyr Cys Ala
225                 230                 235                 240

Lys His Tyr Tyr Tyr Gly Gly Ser Tyr Ala Met Asp Tyr Trp Gly Gln
                245                 250                 255

Gly Thr Ser Val Thr Val Ser Ser Ala Ala Ala Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
    290                 295                 300

Asp Phe Val Gln Pro Met Ala Leu Ile Val Leu Gly Gly Val Ala Gly
305                 310                 315                 320

Leu Leu Leu Phe Ile Gly Leu Gly Ile Phe Phe Cys Val Arg Cys Arg
                325                 330                 335

Pro Arg Arg Lys Lys Leu Leu Tyr Ile Phe Lys Gln Pro Phe Met Arg
            340                 345                 350

Pro Val Gln Thr Thr Gln Glu Glu Asp Gly Cys Ser Cys Arg Phe Pro
        355                 360                 365

Glu Glu Glu Glu Gly Gly Cys Glu Leu Arg Val Lys Phe Ser Arg Ser
    370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485
```

<210> SEQ ID NO 23
<211> LENGTH: 1548
<212> TYPE: DNA
<213> ORGANISM: Artificial
<220> FEATURE:
<223> OTHER INFORMATION: CD20_19-reactive scFv binding domain (LTG1497 dual specific binder)

<400> SEQUENCE: 23

```
gaggtgcagt tgcaacagtc aggagctgaa ctggtcaagc caggagccag cgtgaagatg      60

agctgcaagg cctccggtta caccttcacc tcctacaaca tgcactgggt gaaacagacc     120

ccgggacaag ggctcgaatg gattggcgcc atctaccccg ggaatggcga tacttcgtac     180

aaccagaagt tcaagggaaa ggccaccctg accgccgaca agagctcctc caccgcgtat     240

atgcagttga gctccctgac ctccgaggac tccgccgact actactgcgc acggtccaac     300

tactatggaa gctcgtactg gttcttcgat gtctgggggg ccggcaccac tgtgaccgtc     360
```

```
agctccgggg gcggaggatc cggtggaggc ggaagcgggg gtggaggatc cgacattgtg    420

ctgactcagt ccccggcaat cctgtcggcc tcaccgggcg aaaaggtcac gatgacttgt    480

agagcgtcgt ccagcgtgaa ctacatggat tggtaccaaa agaagcctgg atcgtcaccc    540

aagccttgga tctacgctac atctaacctg gcctccggcg tgccagcgcg gttcagcggg    600

tccggctcgg gcacctcata ctcgctgacc atctcccgcg tggaggctga ggacgccgcg    660

acctactact gccagcagtg gtccttcaac ccgccgactt ttggaggcgg tactaagctg    720

gagatcaaag gaggcggcgg cagcggcggg ggagggtccg gagggggtgg ttctggtgga    780

ggaggatcgg gaggcggtgg cagcgacatt cagatgactc agaccacctc ctccctgtcc    840

gcctccctgg gcgaccgcgt gaccatctca tgccgcgcca gccaggacat ctcgaagtac    900

ctcaactggt accagcagaa gcccgacgga accgtgaagc tcctgatcta ccacacctcc    960

cggctgcaca gcggagtgcc gtctagattc tcgggttcgg ggtcgggaac tgactactcc   1020

cttactattt ccaacctgga gcaggaggat attgccacct acttctgcca acaaggaaac   1080

accctgccgt acacttttgg cggggggaacc aagctggaaa tcactggcag cacatccggt   1140

tccgggaagc ccggctccgg agagggcagc accaaggggg aagtcaagct gcaggaatca   1200

ggacctggcc tggtggcccc gagccagtca ctgtccgtga cttgtactgt gtccggagtg   1260

tcgctcccgg attacggagt gtcctggatc aggcagccac ctcggaaagg attggaatgg   1320

ctcggagtca tctggggttc cgaaaccacc tattacaact cggcactgaa atccaggctc   1380

accattatca aggataactc caagtcacaa gtgttcctga agatgaatag cctgcagact   1440

gacgacacgg cgatctacta ttgcgccaag cactactact acggcggatc ctacgctatg   1500

gactactggg gccaggggac cagcgtgacc gtgtcatccg cggccgca                1548
```

<210> SEQ ID NO 24
<211> LENGTH: 516
<212> TYPE: PRT
<213> ORGANISM: Artificial
<220> FEATURE:
<223> OTHER INFORMATION: CD20_19-reactive scFv binding domain (LTG1497 dual specific binder)

<400> SEQUENCE: 24

```
Glu Val Gln Leu Gln Gln Ser Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Asp Tyr Tyr Cys
                85                  90                  95

Ala Arg Ser Asn Tyr Tyr Gly Ser Ser Tyr Trp Phe Phe Asp Val Trp
            100                 105                 110

Gly Ala Gly Thr Thr Val Thr Val Ser Ser Gly Gly Gly Gly Ser Gly
        115                 120                 125

Gly Gly Gly Ser Gly Gly Gly Gly Ser Asp Ile Val Leu Thr Gln Ser
    130                 135                 140
```

```
Pro Ala Ile Leu Ser Ala Ser Pro Gly Glu Lys Val Thr Met Thr Cys
145                 150                 155                 160

Arg Ala Ser Ser Ser Val Asn Tyr Met Asp Trp Tyr Gln Lys Lys Pro
                165                 170                 175

Gly Ser Ser Pro Lys Pro Trp Ile Tyr Ala Thr Ser Asn Leu Ala Ser
            180                 185                 190

Gly Val Pro Ala Arg Phe Ser Gly Ser Gly Ser Gly Thr Ser Tyr Ser
        195                 200                 205

Leu Thr Ile Ser Arg Val Glu Ala Glu Asp Ala Ala Thr Tyr Tyr Cys
    210                 215                 220

Gln Gln Trp Ser Phe Asn Pro Pro Thr Phe Gly Gly Gly Thr Lys Leu
225                 230                 235                 240

Glu Ile Lys Gly Gly Gly Gly Ser Gly Gly Gly Gly Ser Gly Gly Gly
                245                 250                 255

Gly Ser Gly Gly Gly Gly Ser Gly Gly Gly Gly Ser Asp Ile Gln Met
            260                 265                 270

Thr Gln Thr Thr Ser Ser Leu Ser Ala Ser Leu Gly Asp Arg Val Thr
        275                 280                 285

Ile Ser Cys Arg Ala Ser Gln Asp Ile Ser Lys Tyr Leu Asn Trp Tyr
    290                 295                 300

Gln Gln Lys Pro Asp Gly Thr Val Lys Leu Leu Ile Tyr His Thr Ser
305                 310                 315                 320

Arg Leu His Ser Gly Val Pro Ser Arg Phe Ser Gly Ser Gly Ser Gly
                325                 330                 335

Thr Asp Tyr Ser Leu Thr Ile Ser Asn Leu Glu Gln Glu Asp Ile Ala
            340                 345                 350

Thr Tyr Phe Cys Gln Gln Gly Asn Thr Leu Pro Tyr Thr Phe Gly Gly
        355                 360                 365

Gly Thr Lys Leu Glu Ile Thr Gly Ser Thr Ser Gly Ser Gly Lys Pro
    370                 375                 380

Gly Ser Gly Glu Gly Ser Thr Lys Gly Glu Val Lys Leu Gln Glu Ser
385                 390                 395                 400

Gly Pro Gly Leu Val Ala Pro Ser Gln Ser Leu Ser Val Thr Cys Thr
                405                 410                 415

Val Ser Gly Val Ser Leu Pro Asp Tyr Gly Val Ser Trp Ile Arg Gln
            420                 425                 430

Pro Pro Arg Lys Gly Leu Glu Trp Leu Gly Val Ile Trp Gly Ser Glu
        435                 440                 445

Thr Thr Tyr Tyr Asn Ser Ala Leu Lys Ser Arg Leu Thr Ile Ile Lys
    450                 455                 460

Asp Asn Ser Lys Ser Gln Val Phe Leu Lys Met Asn Ser Leu Gln Thr
465                 470                 475                 480

Asp Asp Thr Ala Ile Tyr Tyr Cys Ala Lys His Tyr Tyr Tyr Gly Gly
                485                 490                 495

Ser Tyr Ala Met Asp Tyr Trp Gly Gln Gly Thr Ser Val Thr Val Ser
            500                 505                 510

Ser Ala Ala Ala
        515
```

<210> SEQ ID NO 25
<211> LENGTH: 2283
<212> TYPE: DNA
<213> ORGANISM: Artificial
<220> FEATURE:
<223> OTHER INFORMATION: CAR LTG1497 (LP-LTG1497-CD8 TM-41BB-CD3zeta) or -continued (LP-CD20 VH-(GGGGS)3-CD20 VL-(GGGGS)5-CD19VL-Whitlow linker-CD19 VH-CD8 hinge41BB-CD3zeta)

<400> SEQUENCE: 25

```
atgctccttc tcgtgacctc cctgcttctc tgcgaactgc cccatcctgc cttcctgctg     60
attcccgagg tgcagttgca acagtcagga gctgaactgg tcaagccagg agccagcgtg    120
aagatgagct gcaaggcctc cggttacacc ttcacctcct acaacatgca ctgggtgaaa    180
cagaccccgg gacaagggct cgaatggatt ggcgccatct accccgggaa tggcgatact    240
tcgtacaacc agaagttcaa gggaaaggcc accctgaccg ccgacaagag ctcctccacc    300
gcgtatatgc agttgagctc cctgacctcc gaggactccg ccgactacta ctgcgcacgg    360
tccaactact atggaagctc gtactggttc ttcgatgtct ggggggccgg caccactgtg    420
accgtcagct ccgggggcgg aggatccggt ggaggcggaa gcgggggtgg aggatccgac    480
attgtgctga ctcagtcccc ggcaatcctg tcggcctcac cgggcgaaaa ggtcacgatg    540
acttgtagag cgtcgtccag cgtgaactac atggattggt accaaaagaa gcctggatcg    600
tcacccaagc cttggatcta cgctacatct aacctggcct ccggcgtgcc agcgcggttc    660
agcgggtccg gctcgggcac ctcatactcg ctgaccatct cccgcgtgga ggctgaggac    720
gccgcgacct actactgcca gcagtggtcc ttcaacccgc cgacttttgg aggcggtact    780
aagctggaga tcaaaggagg cggcggcagc ggcgggggag ggtccggagg gggtggttct    840
ggtggaggag gatcgggagg cggtggcagc gacattcaga tgactcagac cacctcctcc    900
ctgtccgcct ccctgggcga ccgcgtgacc atctcatgcc gcgccagcca ggacatctcg    960
aagtacctca actggtacca gcagaagccc gacggaaccg tgaagctcct gatctaccac   1020
acctcccggc tgcacagcgg agtgccgtct agattctcgg gttcggggtc gggaactgac   1080
tactccctta ctatttccaa cctggagcag gaggatattg ccacctactt ctgccaacaa   1140
ggaaacaccc tgccgtacac ttttggcggg ggaaccaagc tggaaatcac tggcagcaca   1200
tccggttccg ggaagcccgg ctccggagag ggcagcacca agggggaagt caagctgcag   1260
gaatcaggac ctggcctggt ggccccgagc cagtcactgt ccgtgacttg tactgtgtcc   1320
ggagtgtcgc tcccggatta cggagtgtcc tggatcaggc agccacctcg gaaaggattg   1380
gaatggctcg gagtcatctg gggttccgaa accacctatt acaactcggc actgaaatcc   1440
aggctcacca ttatcaagga taactccaag tcacaagtgt tcctgaagat gaatagcctg   1500
cagactgacg acacggcgat ctactattgc gccaagcact actactacgg cggatcctac   1560
gctatggact actggggcca ggggaccagc gtgaccgtgt catccgcggc cgcaactacc   1620
acccctgccc ctcggccgcc gactccggcc ccaaccatcg caagccaacc cctctccttg   1680
cgccccgaag cttgccgccc ggccgcgggt ggagccgtgc atacccgggg gctggacttt   1740
gcctgcgata tctacatttg ggccccgctg gccggcactt gcggcgtgct cctgctgtcg   1800
ctggtcatca ccctttactg caagagaggg cggaagaagc tgctttacat cttcaagcag   1860
ccgttcatgc ggcccgtgca gacgactcag gaagaggacg gatgctcgtg cagattccct   1920
gaggaggaag aggggggatg cgaactgcgc gtcaagttct cacggtccgc cgacgccccc   1980
gcatatcaac agggccagaa tcagctctac aacgagctga acctgggaag gagagaggag   2040
tacgacgtgc tggacaagcg acgcggacgc gacccggaga tggggggaa accacggcgg   2100
aaaaaccctc aggaaggact gtacaacgaa ctccagaaag acaagatggc ggaagcctac   2160
tcagaaatcg ggatgaaggg agagcggagg aggggaaagg gtcacgacgg gctgtaccag   2220
```

ggactgagca ccgccactaa ggatacctac gatgccttgc atatgcaagc actcccaccc 2280
cgg 2283

<210> SEQ ID NO 26
<211> LENGTH: 761
<212> TYPE: PRT
<213> ORGANISM: Artificial
<220> FEATURE:
<223> OTHER INFORMATION: CAR LTG1497 (LP-LTG1497-CD8 TM-41BB-CD3zeta) or (LP-CD20 VH (GGGGS)3-CD20 VL-(GGGGS)5-CD19 VL-Whitlow linker-CD19 VH-CD8 hinge41BB-CD3zeta)

<400> SEQUENCE: 26

Met Leu Leu Leu Val Thr Ser Leu Leu Leu Cys Glu Leu Pro His Pro
1 5 10 15

Ala Phe Leu Leu Ile Pro Glu Val Gln Leu Gln Gln Ser Gly Ala Glu
20 25 30

Leu Val Lys Pro Gly Ala Ser Val Lys Met Ser Cys Lys Ala Ser Gly
35 40 45

Tyr Thr Phe Thr Ser Tyr Asn Met His Trp Val Lys Gln Thr Pro Gly
50 55 60

Gln Gly Leu Glu Trp Ile Gly Ala Ile Tyr Pro Gly Asn Gly Asp Thr
65 70 75 80

Ser Tyr Asn Gln Lys Phe Lys Gly Lys Ala Thr Leu Thr Ala Asp Lys
85 90 95

Ser Ser Ser Thr Ala Tyr Met Gln Leu Ser Ser Leu Thr Ser Glu Asp
100 105 110

Ser Ala Asp Tyr Tyr Cys Ala Arg Ser Asn Tyr Tyr Gly Ser Ser Tyr
115 120 125

Trp Phe Phe Asp Val Trp Gly Ala Gly Thr Thr Val Thr Val Ser Ser
130 135 140

Gly Gly Gly Gly Ser Gly Gly Gly Gly Ser Gly Gly Gly Gly Ser Asp
145 150 155 160

Ile Val Leu Thr Gln Ser Pro Ala Ile Leu Ser Ala Ser Pro Gly Glu
165 170 175

Lys Val Thr Met Thr Cys Arg Ala Ser Ser Ser Val Asn Tyr Met Asp
180 185 190

Trp Tyr Gln Lys Lys Pro Gly Ser Ser Pro Lys Pro Trp Ile Tyr Ala
195 200 205

Thr Ser Asn Leu Ala Ser Gly Val Pro Ala Arg Phe Ser Gly Ser Gly
210 215 220

Ser Gly Thr Ser Tyr Ser Leu Thr Ile Ser Arg Val Glu Ala Glu Asp
225 230 235 240

Ala Ala Thr Tyr Tyr Cys Gln Gln Trp Ser Phe Asn Pro Pro Thr Phe
245 250 255

Gly Gly Gly Thr Lys Leu Glu Ile Lys Gly Gly Gly Gly Ser Gly Gly
260 265 270

Gly Gly Ser Gly Gly Gly Gly Ser Gly Gly Gly Gly Ser Gly Gly Gly
275 280 285

Gly Ser Asp Ile Gln Met Thr Gln Thr Thr Ser Ser Leu Ser Ala Ser
290 295 300

Leu Gly Asp Arg Val Thr Ile Ser Cys Arg Ala Ser Gln Asp Ile Ser
305 310 315 320

Lys Tyr Leu Asn Trp Tyr Gln Gln Lys Pro Asp Gly Thr Val Lys Leu
325 330 335

-continued

```
Leu Ile Tyr His Thr Ser Arg Leu His Ser Gly Val Pro Ser Arg Phe
            340                 345                 350

Ser Gly Ser Gly Ser Gly Thr Asp Tyr Ser Leu Thr Ile Ser Asn Leu
        355                 360                 365

Glu Gln Glu Asp Ile Ala Thr Tyr Phe Cys Gln Gln Gly Asn Thr Leu
    370                 375                 380

Pro Tyr Thr Phe Gly Gly Gly Thr Lys Leu Glu Ile Thr Gly Ser Thr
385                 390                 395                 400

Ser Gly Ser Gly Lys Pro Gly Ser Gly Glu Gly Ser Thr Lys Gly Glu
                405                 410                 415

Val Lys Leu Gln Glu Ser Gly Pro Gly Leu Val Ala Pro Ser Gln Ser
            420                 425                 430

Leu Ser Val Thr Cys Thr Val Ser Gly Val Ser Leu Pro Asp Tyr Gly
        435                 440                 445

Val Ser Trp Ile Arg Gln Pro Pro Arg Lys Gly Leu Glu Trp Leu Gly
    450                 455                 460

Val Ile Trp Gly Ser Glu Thr Thr Tyr Tyr Asn Ser Ala Leu Lys Ser
465                 470                 475                 480

Arg Leu Thr Ile Ile Lys Asp Asn Ser Lys Ser Gln Val Phe Leu Lys
                485                 490                 495

Met Asn Ser Leu Gln Thr Asp Asp Thr Ala Ile Tyr Tyr Cys Ala Lys
            500                 505                 510

His Tyr Tyr Tyr Gly Gly Ser Tyr Ala Met Asp Tyr Trp Gly Gln Gly
        515                 520                 525

Thr Ser Val Thr Val Ser Ser Ala Ala Ala Thr Thr Thr Pro Ala Pro
    530                 535                 540

Arg Pro Pro Thr Pro Ala Pro Thr Ile Ala Ser Gln Pro Leu Ser Leu
545                 550                 555                 560

Arg Pro Glu Ala Cys Arg Pro Ala Ala Gly Gly Ala Val His Thr Arg
                565                 570                 575

Gly Leu Asp Phe Ala Cys Asp Ile Tyr Ile Trp Ala Pro Leu Ala Gly
            580                 585                 590

Thr Cys Gly Val Leu Leu Leu Ser Leu Val Ile Thr Leu Tyr Cys Lys
        595                 600                 605

Arg Gly Arg Lys Lys Leu Leu Tyr Ile Phe Lys Gln Pro Phe Met Arg
    610                 615                 620

Pro Val Gln Thr Thr Gln Glu Glu Asp Gly Cys Ser Cys Arg Phe Pro
625                 630                 635                 640

Glu Glu Glu Glu Gly Gly Cys Glu Leu Arg Val Lys Phe Ser Arg Ser
                645                 650                 655

Ala Asp Ala Pro Ala Tyr Gln Gln Gly Gln Asn Gln Leu Tyr Asn Glu
            660                 665                 670

Leu Asn Leu Gly Arg Arg Glu Glu Tyr Asp Val Leu Asp Lys Arg Arg
        675                 680                 685

Gly Arg Asp Pro Glu Met Gly Gly Lys Pro Arg Arg Lys Asn Pro Gln
    690                 695                 700

Glu Gly Leu Tyr Asn Glu Leu Gln Lys Asp Lys Met Ala Glu Ala Tyr
705                 710                 715                 720

Ser Glu Ile Gly Met Lys Gly Glu Arg Arg Arg Gly Lys Gly His Asp
                725                 730                 735

Gly Leu Tyr Gln Gly Leu Ser Thr Ala Thr Lys Asp Thr Tyr Asp Ala
            740                 745                 750

Leu His Met Gln Ala Leu Pro Pro Arg
```

755 760

<210> SEQ ID NO 27
<211> LENGTH: 726
<212> TYPE: DNA
<213> ORGANISM: Artificial
<220> FEATURE:
<223> OTHER INFORMATION: synthetic oligonucleotide

<400> SEQUENCE: 27
gacatccaga tgacacagac tacatcctcc ctgtctgcct ctctgggaga cagagtcacc 60
atcagttgca gggcaagtca ggacattagt aaatatttaa attggtatca gcagaaacca 120
gatggaactg ttaaactcct gatctaccat acatcaagat tacactcagg agtcccatca 180
aggttcagtg gcagtgggtc tggaacagat tattctctca ccattagcaa cctggagcaa 240
gaagatattg ccacttactt ttgccaacag ggtaatacgc ttccgtacac gttcggaggg 300
gggaccaagc tggagatcac aggtggcggt ggctcgggcg gtggtgggtc gggtggcggc 360
ggatctgagg tgaaactgca ggagtcagga cctggcctgg tggcgccctc acagagcctg 420
tccgtcacat gcactgtctc aggggtctca ttacccgact atggtgtaag ctggattcgc 480
cagcctccac gaaagggtct ggagtggctg ggagtaatat ggggtagtga aaccacatac 540
tataattcag ctctcaaatc cagactgacc atcatcaagg acaactccaa gagccaagtt 600
ttcttaaaaa tgaacagtct gcaaactgat gacacagcca tttactactg tgccaaacat 660
tattactacg gtggtagcta tgctatggac tactggggcc aaggaacctc agtcaccgtc 720
tcctca 726

<210> SEQ ID NO 28
<211> LENGTH: 242
<212> TYPE: PRT
<213> ORGANISM: Artificial
<220> FEATURE:
<223> OTHER INFORMATION: synthetic polypeptide

<400> SEQUENCE: 28

Asp Ile Gln Met Thr Gln Thr Thr Ser Ser Leu Ser Ala Ser Leu Gly
1 5 10 15

Asp Arg Val Thr Ile Ser Cys Arg Ala Ser Gln Asp Ile Ser Lys Tyr
20 25 30

Leu Asn Trp Tyr Gln Gln Lys Pro Asp Gly Thr Val Lys Leu Leu Ile
35 40 45

Tyr His Thr Ser Arg Leu His Ser Gly Val Pro Ser Arg Phe Ser Gly
50 55 60

Ser Gly Ser Gly Thr Asp Tyr Ser Leu Thr Ile Ser Asn Leu Glu Gln
65 70 75 80

Glu Asp Ile Ala Thr Tyr Phe Cys Gln Gln Gly Asn Thr Leu Pro Tyr
85 90 95

Thr Phe Gly Gly Gly Thr Lys Leu Glu Ile Thr Gly Gly Gly Gly Ser
100 105 110

Gly Gly Gly Gly Ser Gly Gly Gly Gly Ser Glu Val Lys Leu Gln Glu
115 120 125

Ser Gly Pro Gly Leu Val Ala Pro Ser Gln Ser Leu Ser Val Thr Cys
130 135 140

Thr Val Ser Gly Val Ser Leu Pro Asp Tyr Gly Val Ser Trp Ile Arg
145 150 155 160

Gln Pro Pro Arg Lys Gly Leu Glu Trp Leu Gly Val Ile Trp Gly Ser

-continued

```
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser


<210> SEQ ID NO 29
<211> LENGTH: 1485
<212> TYPE: DNA
<213> ORGANISM: Artificial
<220> FEATURE:
<223> OTHER INFORMATION: CAR LTG 1494 (LP-CD19binder-CD8link-CD8tm-41BB-
      CD3zeta)

<400> SEQUENCE: 29

atgcttctcc tggtcacctc cctgctcctc tgcgaactgc ctcaccctgc cttccttctg     60

attcctgaca ctgacattca gatgactcag accacctctt ccttgtccgc gtcactggga    120

gacagagtga ccatctcgtg tcgcgcaagc caggatatct ccaagtacct gaactggtac    180

caacagaagc ccgacgggac tgtgaagctg ctgatctacc acacctcacg cctgcacagc    240

ggagtgccaa gcagattctc cggctccggc tcgggaaccg attactcgct taccattagc    300

aacctcgagc aggaggacat cgctacctac ttctgccagc aaggaaatac cctgccctac    360

accttcggcg gaggaaccaa attggaaatc accggctcca cgagcggctc cgggaagcct    420

ggttccgggg aaggctccac taagggtgaa gtgaagctcc aggagtccgg ccccggcctg    480

gtggcgccgt cgcaatcact ctctgtgacc tgtaccgtgt cgggagtgtc cctgcctgat    540

tacggcgtga gctggattcg gcagccgccg cggaagggcc tggaatggct gggtgtcatc    600

tggggatccg agactaccta ctacaactcg gccctgaagt cccgcctgac tatcatcaaa    660

gacaactcga agtcccaggt ctttctgaag atgaactccc tgcaaactga cgacaccgcc    720

atctattact gtgctaagca ctactactac ggtggaagct atgctatgga ctactggggc    780

caggggacat ccgtgacagt cagctccgcg gccgcaacta ccacccctgc ccctcggccg    840

ccgactccgg ccccaaccat cgcaagccaa cccctctcct tgcgccccga agcttgccgc    900

ccggccgcgg gtggagccgt gcatacccgg gggctggact ttgcctgcga tatctacatt    960

tgggccccgc tggccggcac ttgcggcgtg ctcctgctgt cgctggtcat caccctttac   1020

tgcaagaggg gccggaagaa gctgctttac atcttcaagc agccgttcat gcggcccgtg   1080

cagacgactc aggaagagga cggatgctcg tgcagattcc ctgaggagga agaggggga    1140

tgcgaactgc gcgtcaagtt ctcacggtcc gccgacgccc ccgcatatca acagggccag   1200

aatcagctct acaacgagct gaacctggga aggagagagg agtacgacgt gctggacaag   1260

cgacgcggac gcgacccgga gatgggggg aaaccacggc ggaaaaaccc tcaggaagga    1320

ctgtacaacg aactccagaa agacaagatg gcggaagcct actcagaaat cgggatgaag   1380

ggagagcgga ggaggggaaa gggtcacgac gggctgtacc agggactgag caccgccact   1440

aaggatacct acgatgcctt gcatatgcaa gcactcccac cccgg                   1485


<210> SEQ ID NO 30
```

<211> LENGTH: 495
<212> TYPE: PRT
<213> ORGANISM: Artificial
<220> FEATURE:
<223> OTHER INFORMATION: CAR LTG1494 (LP-CD19binder-CD8link-CD8tm-41BB-CD3zeta)

<400> SEQUENCE: 30

Met Leu Leu Leu Val Thr Ser Leu Leu Leu Cys Glu Leu Pro His Pro
1               5                   10                  15

Ala Phe Leu Leu Ile Pro Asp Thr Asp Ile Gln Met Thr Gln Thr Thr
            20                  25                  30

Ser Ser Leu Ser Ala Ser Leu Gly Asp Arg Val Thr Ile Ser Cys Arg
        35                  40                  45

Ala Ser Gln Asp Ile Ser Lys Tyr Leu Asn Trp Tyr Gln Gln Lys Pro
    50                  55                  60

Asp Gly Thr Val Lys Leu Leu Ile Tyr His Thr Ser Arg Leu His Ser
65                  70                  75                  80

Gly Val Pro Ser Arg Phe Ser Gly Ser Gly Ser Gly Thr Asp Tyr Ser
                85                  90                  95

Leu Thr Ile Ser Asn Leu Glu Gln Glu Asp Ile Ala Thr Tyr Phe Cys
            100                 105                 110

Gln Gln Gly Asn Thr Leu Pro Tyr Thr Phe Gly Gly Gly Thr Lys Leu
        115                 120                 125

Glu Ile Thr Gly Ser Thr Ser Gly Ser Gly Lys Pro Gly Ser Gly Glu
    130                 135                 140

Gly Ser Thr Lys Gly Glu Val Lys Leu Gln Glu Ser Gly Pro Gly Leu
145                 150                 155                 160

Val Ala Pro Ser Gln Ser Leu Ser Val Thr Cys Thr Val Ser Gly Val
                165                 170                 175

Ser Leu Pro Asp Tyr Gly Val Ser Trp Ile Arg Gln Pro Pro Arg Lys
            180                 185                 190

Gly Leu Glu Trp Leu Gly Val Ile Trp Gly Ser Glu Thr Thr Tyr Tyr
        195                 200                 205

Asn Ser Ala Leu Lys Ser Arg Leu Thr Ile Ile Lys Asp Asn Ser Lys
    210                 215                 220

Ser Gln Val Phe Leu Lys Met Asn Ser Leu Gln Thr Asp Asp Thr Ala
225                 230                 235                 240

Ile Tyr Tyr Cys Ala Lys His Tyr Tyr Tyr Gly Gly Ser Tyr Ala Met
                245                 250                 255

Asp Tyr Trp Gly Gln Gly Thr Ser Val Thr Val Ser Ser Ala Ala Ala
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Lys Arg Gly Arg Lys Lys Leu Leu Tyr Ile Phe
            340                 345                 350

Lys Gln Pro Phe Met Arg Pro Val Gln Thr Thr Gln Glu Glu Asp Gly
        355                 360                 365

Cys Ser Cys Arg Phe Pro Glu Glu Glu Glu Gly Gly Cys Glu Leu Arg

-continued

```
    370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
    450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495


<210> SEQ ID NO 31
<211> LENGTH: 1470
<212> TYPE: DNA
<213> ORGANISM: Artificial
<220> FEATURE:
<223> OTHER INFORMATION: CAR LTG1538 (LP-CD19binder-CD8link-CD8tm-
      signals (LTI re-engineered CD19 CAR)

<400> SEQUENCE: 31

atgcttctcc tggtcacctc cctgctcctc tgcgaactgc ctcaccctgc cttccttctg      60

attcctgaca ttcagatgac tcagaccacc tcttccttgt ccgcgtcact gggagacaga     120

gtgaccatct cgtgtcgcgc aagccaggat atctccaagt acctgaactg gtaccaacag     180

aagcccgacg ggactgtgaa gctgctgatc taccacacct cacgcctgca cagcggagtg     240

ccaagcagat tctccggctc cggctcggga accgattact cgcttaccat tagcaacctc     300

gagcaggagg acatcgctac ctacttctgc cagcaaggaa ataccctgcc ctacaccttc     360

ggcggaggaa ccaaattgga aatcaccggc ggaggaggct ccgggggagg aggttccggg     420

ggcgggggtt ccgaagtgaa gctccaggag tccggccccg gcctggtggc gccgtcgcaa     480

tcactctctg tgacctgtac cgtgtcggga gtgtccctgc ctgattacgg cgtgagctgg     540

attcggcagc cgccgcggaa gggcctggaa tggctgggtg tcatctgggg atccgagact     600

acctactaca actcggccct gaagtcccgc ctgactatca tcaaagacaa ctcgaagtcc     660

caggtctttc tgaagatgaa ctccctgcaa actgacgaca ccgccatcta ttactgtgct     720

aagcactact actacggtgg aagctatgct atggactact gggggcaagg cacttcggtg     780

actgtgtcaa gcgcggccgc aactaccacc cctgcccctc ggccgccgac tccggcccca     840

accatcgcaa gccaacccct ctccttgcgc cccgaagctt gccgcccggc cgcgggtgga     900

gccgtgcata cccgggggct ggactttgcc tgcgatatct acatttgggc cccgctggcc     960

ggcacttgcg gcgtgctcct gctgtcgctg gtcatcaccc tttactgcaa gaggggccgg    1020

aagaagctgc tttacatctt caagcagccg ttcatgcggc ccgtgcagac gactcaggaa    1080

gaggacggat gctcgtgcag attccctgag gaggaagagg ggggatgcga actgcgcgtc    1140

aagttctcac ggtccgccga cgcccccgca tatcaacagg gccagaatca gctctacaac    1200

gagctgaacc tgggaaggag agaggagtac gacgtgctgg acaagcgacg cggacgcgac    1260

ccggagatgg gggggaaacc acggcggaaa aaccctcagg aaggactgta caacgaactc    1320

cagaaagaca agatggcgga agcctactca gaaatcggga tgaagggaga gcggaggagg    1380
```

```
ggaaagggtc acgacgggct gtaccaggga ctgagcaccg ccactaagga tacctacgat   1440

gccttgcata tgcaagcact cccaccccgg                                    1470


<210> SEQ ID NO 32
<211> LENGTH: 490
<212> TYPE: PRT
<213> ORGANISM: Artificial
<220> FEATURE:
<223> OTHER INFORMATION: CAR LTG1538 (LP-CD19binder-CD8link-CD8tm-
      signals (LTI re-engineered CD19 CAR)

<400> SEQUENCE: 32

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Gly Gly Gly Ser Gly Gly Gly Gly Ser Gly Gly Gly Gly Ser
    130                 135                 140

Glu Val Lys Leu Gln Glu Ser Gly Pro Gly Leu Val Ala Pro Ser Gln
145                 150                 155                 160

Ser Leu Ser Val Thr Cys Thr Val Ser Gly Val Ser Leu Pro Asp Tyr
                165                 170                 175

Gly Val Ser Trp Ile Arg Gln Pro Pro Arg Lys Gly Leu Glu Trp Leu
            180                 185                 190

Gly Val Ile Trp Gly Ser Glu Thr Thr Tyr Tyr Asn Ser Ala Leu Lys
        195                 200                 205

Ser Arg Leu Thr Ile Ile Lys Asp Asn Ser Lys Ser Gln Val Phe Leu
    210                 215                 220

Lys Met Asn Ser Leu Gln Thr Asp Asp Thr Ala Ile Tyr Tyr Cys Ala
225                 230                 235                 240

Lys His Tyr Tyr Tyr Gly Gly Ser Tyr Ala Met Asp Tyr Trp Gly Gln
                245                 250                 255

Gly Thr Ser Val Thr Val Ser Ser Ala Ala Ala Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335
```

-continued

```
Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490


<210> SEQ ID NO 33
<211> LENGTH: 1548
<212> TYPE: DNA
<213> ORGANISM: Artificial
<220> FEATURE:
<223> OTHER INFORMATION: CD19_20-reactive scFv binding domain (LTG1496)

<400> SEQUENCE: 33

gacattcaga tgactcagac cacctcctcc ctgtccgcct ccctgggcga ccgcgtgacc     60

atctcatgcc gcgccagcca ggacatctcg aagtacctca actggtacca gcagaagccc    120

gacggaaccg tgaagctcct gatctaccac acctcccggc tgcacagcgg agtgccgtct    180

agattctcgg gttcggggtc gggaactgac tactccctta ctatttccaa cctggagcag    240

gaggatattg ccacctactt ctgccaacaa ggaaacaccc tgccgtacac ttttggcggg    300

ggaaccaagc tggaaatcac tggcagcaca tccggttccg ggaagcccgg ctccggagag    360

ggcagcacca agggggaagt caagctgcag gaatcaggac ctggcctggt ggccccgagc    420

cagtcactgt ccgtgacttg tactgtgtcc ggagtgtcgc tcccggatta cggagtgtcc    480

tggatcaggc agccacctcg gaaaggattg gaatggctcg gagtcatctg ggttccgaa     540

accacctatt acaactcggc actgaaatcc aggctcacca ttatcaagga taactccaag    600

tcacaagtgt tcctgaagat gaatagcctg cagactgacg acacggcgat ctactattgc    660

gccaagcact actactacgg cggatcctac gctatggact actggggcca ggggaccagc    720

gtgaccgtgt catccggagg cggcggcagc ggcgggggag ggtccggagg gggtggttct    780

ggtggaggag gatcgggagg cggtggcagc gaggtgcagt tgcaacagtc aggagctgaa    840

ctggtcaagc caggagccag cgtgaagatg agctgcaagg cctccggtta caccttcacc    900

tcctacaaca tgcactgggt gaaacagacc ccgggacaag ggctcgaatg gattggcgcc    960

atctaccccg ggaatggcga tacttcgtac aaccagaagt tcaagggaaa ggccaccctg   1020

accgccgaca agagctcctc caccgcgtat atgcagttga gctccctgac ctccgaggac   1080

tccgccgact actactgcgc acggtccaac tactatggaa gctcgtactg gttcttcgat   1140

gtctgggggg ccggcaccac tgtgaccgtc agctccgggg gcggaggatc cggtggaggc   1200
```

-continued

```
ggaagcgggg gtggaggatc cgacattgtg ctgactcagt ccccggcaat cctgtcggcc   1260

tcaccgggcg aaaaggtcac gatgacttgt agagcgtcgt ccagcgtgaa ctacatggat   1320

tggtaccaaa agaagcctgg atcgtcaccc aagccttgga tctacgctac atctaacctg   1380

gcctccggcg tgccagcgcg gttcagcggg tccggctcgg gcacctcata ctcgctgacc   1440

atctcccgcg tggaggctga ggacgccgcg acctactact gccagcagtg gtccttcaac   1500

ccgccgactt ttggaggcgg tactaagctg gagatcaaag cggccgca                1548
```

```
<210> SEQ ID NO 34
<211> LENGTH: 516
<212> TYPE: PRT
<213> ORGANISM: Artificial
<220> FEATURE:
<223> OTHER INFORMATION: CD19_20-reactive scFv binding domain (LTG1496)

<400> SEQUENCE: 34

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser Gly Gly Gly Gly Ser Gly Gly Gly Gly Ser Gly
                245                 250                 255

Gly Gly Gly Ser Gly Gly Gly Gly Ser Gly Gly Gly Gly Ser Glu Val
            260                 265                 270

Gln Leu Gln Gln Ser Gly Ala Glu Leu Val Lys Pro Gly Ala Ser Val
        275                 280                 285

Lys Met Ser Cys Lys Ala Ser Gly Tyr Thr Phe Thr Ser Tyr Asn Met
    290                 295                 300
```

His Trp Val Lys Gln Thr Pro Gly Gln Gly Leu Glu Trp Ile Gly Ala
305 310 315 320

Ile Tyr Pro Gly Asn Gly Asp Thr Ser Tyr Asn Gln Lys Phe Lys Gly
325 330 335

Lys Ala Thr Leu Thr Ala Asp Lys Ser Ser Ser Thr Ala Tyr Met Gln
340 345 350

Leu Ser Ser Leu Thr Ser Glu Asp Ser Ala Asp Tyr Tyr Cys Ala Arg
355 360 365

Ser Asn Tyr Tyr Gly Ser Ser Tyr Trp Phe Phe Asp Val Trp Gly Ala
370 375 380

Gly Thr Thr Val Thr Val Ser Ser Gly Gly Gly Gly Ser Gly Gly Gly
385 390 395 400

Gly Ser Gly Gly Gly Gly Ser Asp Ile Val Leu Thr Gln Ser Pro Ala
405 410 415

Ile Leu Ser Ala Ser Pro Gly Glu Lys Val Thr Met Thr Cys Arg Ala
420 425 430

Ser Ser Ser Val Asn Tyr Met Asp Trp Tyr Gln Lys Lys Pro Gly Ser
435 440 445

Ser Pro Lys Pro Trp Ile Tyr Ala Thr Ser Asn Leu Ala Ser Gly Val
450 455 460

Pro Ala Arg Phe Ser Gly Ser Gly Ser Gly Thr Ser Tyr Ser Leu Thr
465 470 475 480

Ile Ser Arg Val Glu Ala Glu Asp Ala Ala Thr Tyr Tyr Cys Gln Gln
485 490 495

Trp Ser Phe Asn Pro Pro Thr Phe Gly Gly Gly Thr Lys Leu Glu Ile
500 505 510

Lys Ala Ala Ala
515

<210> SEQ ID NO 35
<211> LENGTH: 2283
<212> TYPE: DNA
<213> ORGANISM: Artificial
<220> FEATURE:
<223> OTHER INFORMATION: CAR LTG1496 (LP-LTG1496-CD8 TM-41BB-CD3zeta) or (LP-CD19 VL-Whitlow linker-CD19 VH (GGGGS)5 CD20 VH (GGGGS)3-CD20 VL CD8 hinge41BB-CD3zeta)

<400> SEQUENCE: 35
atgctccttc tcgtgacctc cctgcttctc tgcgaactgc cccatcctgc cttcctgctg 60
attcccgaca ttcagatgac tcagaccacc tcctccctgt ccgcctccct gggcgaccgc 120
gtgaccatct catgccgcgc cagccaggac atctcgaagt acctcaactg gtaccagcag 180
aagcccgacg gaaccgtgaa gctcctgatc taccacacct cccggctgca cagcggagtg 240
ccgtctagat tctcgggttc ggggtcggga actgactact cccttactat ttccaacctg 300
gagcaggagg atattgccac ctacttctgc caacaaggaa acaccctgcc gtacactttt 360
ggcgggggaa ccaagctgga aatcactggc agcacatccg gttccgggaa gcccggctcc 420
ggagagggca gcaccaaggg ggaagtcaag ctgcaggaat caggacctgg cctggtggcc 480
ccgagccagt cactgtccgt gacttgtact gtgtccggag tgtcgctccc ggattacgga 540
gtgtcctgga tcaggcagcc acctcggaaa ggattggaat ggctcggagt catctggggt 600
tccgaaacca cctattacaa ctcggcactg aaatccaggc tcaccattat caaggataac 660
tccaagtcac aagtgttcct gaagatgaat agcctgcaga ctgacgacac ggcgatctac 720

```
tattgcgcca agcactacta ctacggcgga tcctacgcta tggactactg gggccagggg    780
accagcgtga ccgtgtcatc cggaggcggc ggcagcggcg ggggagggtc cggagggggt    840
ggttctggtg gaggaggatc gggaggcggt ggcagcgagg tgcagttgca acagtcagga    900
gctgaactgg tcaagccagg agccagcgtg aagatgagct gcaaggcctc cggttacacc    960
ttcacctcct acaacatgca ctgggtgaaa cagaccccgg gacaagggct cgaatggatt   1020
ggcgccatct accccgggaa tggcgatact tcgtacaacc agaagttcaa gggaaaggcc   1080
accctgaccg ccgacaagag ctcctccacc gcgtatatgc agttgagctc cctgacctcc   1140
gaggactccg ccgactacta ctgcgcacgg tccaactact atggaagctc gtactggttc   1200
ttcgatgtct gggggccgg caccactgtg accgtcagct ccgggggcgg aggatccggt   1260
ggaggcggaa gcgggggtgg aggatccgac attgtgctga ctcagtcccc ggcaatcctg   1320
tcggcctcac cgggcgaaaa ggtcacgatg acttgtagag cgtcgtccag cgtgaactac   1380
atggattggt accaaaagaa gcctggatcg tcacccaagc cttggatcta cgctacatct   1440
aacctggcct ccggcgtgcc agcgcggttc agcgggtccg gctcgggcac ctcatactcg   1500
ctgaccatct cccgcgtgga ggctgaggac gccgcgacct actactgcca gcagtggtcc   1560
ttcaacccgc cgacttttgg aggcggtact aagctggaga tcaaagcggc cgcaactacc   1620
acccctgccc ctcggccgcc gactccggcc ccaaccatcg caagccaacc cctctccttg   1680
cgccccgaag cttgccgccc ggccgcgggt ggagccgtgc atacccgggg gctggacttt   1740
gcctgcgata tctacatttg ggccccgctg gccggcactt gcggcgtgct cctgctgtcg   1800
ctggtcatca ccctttactg caagaggggc cggaagaagc tgctttacat cttcaagcag   1860
ccgttcatgc ggcccgtgca gacgactcag gaagaggacg gatgctcgtg cagattccct   1920
gaggaggaag aggggggatg cgaactgcgc gtcaagttct cacggtccgc cgacgccccc   1980
gcatatcaac agggccagaa tcagctctac aacgagctga acctgggaag gagagaggag   2040
tacgacgtgc tggacaagcg acgcggacgc gacccggaga tgggggggaa accacggcgg   2100
aaaaaccctc aggaaggact gtacaacgaa ctccagaaag acaagatggc ggaagcctac   2160
tcagaaatcg ggatgaaggg agagcggagg aggggaaagg gtcacgacgg gctgtaccag   2220
ggactgagca ccgccactaa ggatacctac gatgccttgc atatgcaagc actcccaccc   2280
cgg                                                                 2283
```

<210> SEQ ID NO 36
<211> LENGTH: 761
<212> TYPE: PRT
<213> ORGANISM: Artificial
<220> FEATURE:
<223> OTHER INFORMATION: CAR LTG1496 (LP-LTG1496-CD8 TM-41BB-CD3zeta) or (LP-CD19 VL-Whitlow linker-CD19 VH-(GGGGS)5-CD20 VH (GGGGS)3-CD20 VL-CD8 hinge41BB-CD3zeta)

<400> SEQUENCE: 36

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
```

```
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser Gly Gly Gly Gly Ser
            260                 265                 270

Gly Gly Gly Gly Ser Gly Gly Gly Gly Ser Gly Gly Gly Gly Ser Gly
        275                 280                 285

Gly Gly Gly Ser Glu Val Gln Leu Gln Gln Ser Gly Ala Glu Leu Val
    290                 295                 300

Lys Pro Gly Ala Ser Val Lys Met Ser Cys Lys Ala Ser Gly Tyr Thr
305                 310                 315                 320

Phe Thr Ser Tyr Asn Met His Trp Val Lys Gln Thr Pro Gly Gln Gly
                325                 330                 335

Leu Glu Trp Ile Gly Ala Ile Tyr Pro Gly Asn Gly Asp Thr Ser Tyr
            340                 345                 350

Asn Gln Lys Phe Lys Gly Lys Ala Thr Leu Thr Ala Asp Lys Ser Ser
        355                 360                 365

Ser Thr Ala Tyr Met Gln Leu Ser Ser Leu Thr Ser Glu Asp Ser Ala
    370                 375                 380

Asp Tyr Tyr Cys Ala Arg Ser Asn Tyr Tyr Gly Ser Ser Tyr Trp Phe
385                 390                 395                 400

Phe Asp Val Trp Gly Ala Gly Thr Thr Val Thr Val Ser Ser Gly Gly
                405                 410                 415

Gly Gly Ser Gly Gly Gly Gly Ser Gly Gly Gly Gly Ser Asp Ile Val
            420                 425                 430

Leu Thr Gln Ser Pro Ala Ile Leu Ser Ala Ser Pro Gly Glu Lys Val
        435                 440                 445

Thr Met Thr Cys Arg Ala Ser Ser Ser Val Asn Tyr Met Asp Trp Tyr
    450                 455                 460

Gln Lys Lys Pro Gly Ser Ser Pro Lys Pro Trp Ile Tyr Ala Thr Ser
465                 470                 475                 480

Asn Leu Ala Ser Gly Val Pro Ala Arg Phe Ser Gly Ser Gly Ser Gly
                485                 490                 495
```

```
Thr Ser Tyr Ser Leu Thr Ile Ser Arg Val Glu Ala Glu Asp Ala Ala
            500                 505                 510

Thr Tyr Tyr Cys Gln Gln Trp Ser Phe Asn Pro Pro Thr Phe Gly Gly
        515                 520                 525

Gly Thr Lys Leu Glu Ile Lys Ala Ala Ala Thr Thr Thr Pro Ala Pro
    530                 535                 540

Arg Pro Pro Thr Pro Ala Pro Thr Ile Ala Ser Gln Pro Leu Ser Leu
545                 550                 555                 560

Arg Pro Glu Ala Cys Arg Pro Ala Ala Gly Gly Ala Val His Thr Arg
                565                 570                 575

Gly Leu Asp Phe Ala Cys Asp Ile Tyr Ile Trp Ala Pro Leu Ala Gly
            580                 585                 590

Thr Cys Gly Val Leu Leu Leu Ser Leu Val Ile Thr Leu Tyr Cys Lys
        595                 600                 605

Arg Gly Arg Lys Lys Leu Leu Tyr Ile Phe Lys Gln Pro Phe Met Arg
    610                 615                 620

Pro Val Gln Thr Thr Gln Glu Glu Asp Gly Cys Ser Cys Arg Phe Pro
625                 630                 635                 640

Glu Glu Glu Glu Gly Gly Cys Glu Leu Arg Val Lys Phe Ser Arg Ser
                645                 650                 655

Ala Asp Ala Pro Ala Tyr Gln Gln Gly Gln Asn Gln Leu Tyr Asn Glu
            660                 665                 670

Leu Asn Leu Gly Arg Arg Glu Glu Tyr Asp Val Leu Asp Lys Arg Arg
        675                 680                 685

Gly Arg Asp Pro Glu Met Gly Gly Lys Pro Arg Arg Lys Asn Pro Gln
    690                 695                 700

Glu Gly Leu Tyr Asn Glu Leu Gln Lys Asp Lys Met Ala Glu Ala Tyr
705                 710                 715                 720

Ser Glu Ile Gly Met Lys Gly Glu Arg Arg Arg Gly Lys Gly His Asp
                725                 730                 735

Gly Leu Tyr Gln Gly Leu Ser Thr Ala Thr Lys Asp Thr Tyr Asp Ala
            740                 745                 750

Leu His Met Gln Ala Leu Pro Pro Arg
        755                 760
```

<210> SEQ ID NO 37
<211> LENGTH: 732
<212> TYPE: DNA
<213> ORGANISM: Artificial
<220> FEATURE:
<223> OTHER INFORMATION: mesothelin-reactive scFv binding domain (LTG1904)

<400> SEQUENCE: 37

```
gaggtccagc tggtacagtc tggggggaggc ttggtacagc ctggggggtc cctgagactc      60

tcctgtgcag cctctggatt cacctttgat gattatgcca tgcactgggt ccggcaagct     120

ccagggaagg gcctggagtg ggtctcaggt attagttgga atagtggtag cataggctat     180

gcggactctg tgaagggccg attcaccatc tccagagaca acgccaagaa ctccctgtat     240

ctgcaaatga acagtctgag agctgaggac acggccttgt attactgtgc aaaagattta     300

tcgtcagtgg ctggaccctt taactactgg ggccagggca ccctggtcac cgtctcctca     360

ggaggtggcg ggtctggtgg aggcggtagc ggcggtggcg gatcctcttc tgagctgact     420

caggaccctg ctgtgtctgt ggccttggga cagacagtca ggatcacatg ccaaggagac     480
```

-continued

```
agcctcagaa gctattatgc aagctggtac cagcagaagc caggacaggc ccctgtactt    540

gtcatctatg gtaaaaacaa ccggccctca gggatcccag accgattctc tggctccagc    600

tcaggaaaca cagcttcctt gaccatcact ggggctcagg cggaggatga ggctgactat    660

tactgtaact cccgggacag cagtggtaac catctggtat tcggcggagg cacccagctg    720

accgtcctcg gt                                                        732
```

<210> SEQ ID NO 38
<211> LENGTH: 244
<212> TYPE: PRT
<213> ORGANISM: Artificial
<220> FEATURE:
<223> OTHER INFORMATION: mesothelin-reactive scFv binding domain (LTG1904)

<400> SEQUENCE: 38

```
Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Leu Ser Ser Val Ala Gly Pro Phe Asn Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Ser Ser Glu Leu Thr Gln Asp Pro Ala
    130                 135                 140

Val Ser Val Ala Leu Gly Gln Thr Val Arg Ile Thr Cys Gln Gly Asp
145                 150                 155                 160

Ser Leu Arg Ser Tyr Tyr Ala Ser Trp Tyr Gln Gln Lys Pro Gly Gln
                165                 170                 175

Ala Pro Val Leu Val Ile Tyr Gly Lys Asn Asn Arg Pro Ser Gly Ile
            180                 185                 190

Pro Asp Arg Phe Ser Gly Ser Ser Ser Gly Asn Thr Ala Ser Leu Thr
        195                 200                 205

Ile Thr Gly Ala Gln Ala Glu Asp Glu Ala Asp Tyr Tyr Cys Asn Ser
    210                 215                 220

Arg Asp Ser Ser Gly Asn His Leu Val Phe Gly Gly Gly Thr Gln Leu
225                 230                 235                 240

Thr Val Leu Gly
```

<210> SEQ ID NO 39
<211> LENGTH: 1476
<212> TYPE: DNA
<213> ORGANISM: Artificial
<220> FEATURE:
<223> OTHER INFORMATION: CAR LTG1904 (LP-LTG1904-CD8 TM-41BB-CD3zeta)

<400> SEQUENCE: 39

```
atgctgctgc tggtgaccag cctgctgctg tgcgaactgc cgcatccggc gtttctgctg     60
```

```
attccggagg tccagctggt acagtctggg ggaggcttgg tacagcctgg ggggtccctg    120

agactctcct gtgcagcctc tggattcacc tttgatgatt atgccatgca ctgggtccgg    180

caagctccag ggaagggcct ggagtgggtc tcaggtatta gttggaatag tggtagcata    240

ggctatgcgg actctgtgaa gggccgattc accatctcca gagacaacgc caagaactcc    300

ctgtatctgc aaatgaacag tctgagagct gaggacacgg ccttgtatta ctgtgcaaaa    360

gatttatcgt cagtggctgg accctttaac tactggggcc agggcaccct ggtcaccgtc    420

tcctcaggag gtggcgggtc tggtggaggc ggtagcggcg gtggcggatc ctcttctgag    480

ctgactcagg accctgctgt gtctgtggcc ttgggacaga cagtcaggat cacatgccaa    540

ggagacagcc tcagaagcta ttatgcaagc tggtaccagc agaagccagg acaggcccct    600

gtacttgtca tctatggtaa aaacaaccgg ccctcaggga tcccagaccg attctctggc    660

tccagctcag gaaacacagc ttccttgacc atcactgggg ctcaggcgga ggatgaggct    720

gactattact gtaactcccg ggacagcagt ggtaaccatc tggtattcgg cggaggcacc    780

cagctgaccg tcctcggtgc ggccgcaact accacccctg cccctcggcc gccgactccg    840

gccccaacca tcgcaagcca acccctctcc ttgcgccccg aagcttgccg cccggccgcg    900

ggtggagccg tgcatacccg gggctggac tttgcctgcg atatctacat ttgggccccg    960

ctggccggca cttgcggcgt gctcctgctg tcgctggtca tcaccctta ctgcaagagg   1020

ggccggaaga agctgcttta catcttcaag cagccgttca tgcggcccgt gcagacgact   1080

caggaagagg acggatgctc gtgcagattc cctgaggagg aagagggggg atgcgaactg   1140

cgcgtcaagt tctcacggtc cgccgacgcc cccgcatatc aacagggcca gaatcagctc   1200

tacaacgagc tgaacctggg aaggagagag gagtacgacg tgctggacaa gcgacgcgga   1260

cgcgacccgg agatgggggg gaaaccacgg cggaaaaacc ctcaggaagg actgtacaac   1320

gaactccaga aagacaagat ggcggaagcc tactcagaaa tcgggatgaa gggagagcgg   1380

aggaggggaa agggtcacga cgggctgtac cagggactga gcaccgccac taaggatacc   1440

tacgatgcct tgcatatgca agcactccca ccccgg                             1476
```

<210> SEQ ID NO 40
<211> LENGTH: 492
<212> TYPE: PRT
<213> ORGANISM: Artificial
<220> FEATURE:
<223> OTHER INFORMATION: CAR LTG1904 (LP-LTG1904-CD8 TM-41BB-CD3zeta)

<400> SEQUENCE: 40

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Gln Ser Gly Gly Gly
            20                  25                  30

Leu Val Gln Pro Gly Gly Ser Leu Arg Leu Ser Cys Ala Ala Ser Gly
        35                  40                  45

Phe Thr Phe Asp Asp Tyr Ala Met His Trp Val Arg Gln Ala Pro Gly
    50                  55                  60

Lys Gly Leu Glu Trp Val Ser Gly Ile Ser Trp Asn Ser Gly Ser Ile
65                  70                  75                  80

Gly Tyr Ala Asp Ser Val Lys Gly Arg Phe Thr Ile Ser Arg Asp Asn
                85                  90                  95

Ala Lys Asn Ser Leu Tyr Leu Gln Met Asn Ser Leu Arg Ala Glu Asp
            100                 105                 110
```

```
Thr Ala Leu Tyr Tyr Cys Ala Lys Asp Leu Ser Ser Val Ala Gly Pro
        115                 120                 125

Phe Asn Tyr Trp Gly Gln Gly Thr Leu Val Thr Val Ser Ser Gly Gly
    130                 135                 140

Gly Gly Ser Gly Gly Gly Gly Ser Gly Gly Gly Gly Ser Ser Ser Glu
145                 150                 155                 160

Leu Thr Gln Asp Pro Ala Val Ser Val Ala Leu Gly Gln Thr Val Arg
                165                 170                 175

Ile Thr Cys Gln Gly Asp Ser Leu Arg Ser Tyr Tyr Ala Ser Trp Tyr
            180                 185                 190

Gln Gln Lys Pro Gly Gln Ala Pro Val Leu Val Ile Tyr Gly Lys Asn
        195                 200                 205

Asn Arg Pro Ser Gly Ile Pro Asp Arg Phe Ser Gly Ser Ser Ser Gly
    210                 215                 220

Asn Thr Ala Ser Leu Thr Ile Thr Gly Ala Gln Ala Glu Asp Glu Ala
225                 230                 235                 240

Asp Tyr Tyr Cys Asn Ser Arg Asp Ser Ser Gly Asn His Leu Val Phe
                245                 250                 255

Gly Gly Gly Thr Gln Leu Thr Val Leu Gly Ala Ala Ala Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490
```

<210> SEQ ID NO 41
<211> LENGTH: 339
<212> TYPE: DNA
<213> ORGANISM: Artificial
<220> FEATURE:

-continued

<223> OTHER INFORMATION: CD33-reactive single chain binding domain VH-4
(LTG1906)

<400> SEQUENCE: 41
gaggtgcagc tggtggagtc tgggggaggc ttggtacagc ctggagggtc cctgagactc 60
tcctgtgcag cctctggatt caccttcagt agctatggca tgagctgggt ccgccaggct 120
ccaagacaag ggcttgagtg ggtggccaac ataaagcaag atggaagtga gaaatactat 180
gcggactcag tgaagggccg attcaccatc tccagagaca attccaagaa cacgctgtat 240
ctgcaaatga acagcctgag agccgaggac acagccacgt attactgtgc gaaagaaaat 300
gtggactggg gccagggcac cctggtcacc gtctcctca 339

<210> SEQ ID NO 42
<211> LENGTH: 113
<212> TYPE: PRT
<213> ORGANISM: Artificial
<220> FEATURE:
<223> OTHER INFORMATION: CD33-reactive single chain binding domain VH-4
(LTG1906)

<400> SEQUENCE: 42

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Gly Met Ser Trp Val Arg Gln Ala Pro Arg Gln Gly Leu Glu Trp Val
35 40 45

Ala Asn Ile Lys Gln Asp Gly Ser Glu Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Thr Tyr Tyr Cys
85 90 95

Ala Lys Glu Asn Val Asp Trp Gly Gln Gly Thr Leu Val Thr Val Ser
100 105 110

Ser

<210> SEQ ID NO 43
<211> LENGTH: 1083
<212> TYPE: DNA
<213> ORGANISM: Artificial
<220> FEATURE:
<223> OTHER INFORMATION: CAR LTG1906 (LP-VH4-CD8 TM-41BB-CD3zeta)

<400> SEQUENCE: 43
atgctgctgc tggtgaccag cctgctgctg tgcgaactgc cgcatccggc gtttctgctg 60
attccggagg tgcagctggt ggagtctggg ggaggcttgg tacagcctgg agggtccctg 120
agactctcct gtgcagcctc tggattcacc ttcagtagct atggcatgag ctgggtccgc 180
caggctccaa gacaagggct tgagtgggtg gccaacataa agcaagatgg aagtgagaaa 240
tactatgcgg actcagtgaa gggccgattc accatctcca gagacaattc caagaacacg 300
ctgtatctgc aaatgaacag cctgagagcc gaggacacag ccacgtatta ctgtgcgaaa 360
gaaaatgtgg actggggcca gggcaccctg gtcaccgtct cctcagcggc cgcaactacc 420
acccctgccc ctcggccgcc gactccggcc ccaaccatcg caagccaacc cctctccttg 480
cgccccgaag cttgccgccc ggccgcgggt ggagccgtgc atacccgggg gctggacttt 540

-continued

```
gcctgcgata tctacatttg ggccccgctg gccggcactt gcggcgtgct cctgctgtcg    600
ctggtcatca ccctttactg caagaggggc cggaagaagc tgctttacat cttcaagcag    660
ccgttcatgc ggcccgtgca gacgactcag gaagaggacg gatgctcgtg cagattccct    720
gaggaggaag aggggggatg cgaactgcgc gtcaagttct cacggtccgc cgacgccccc    780
gcatatcaac agggccagaa tcagctctac aacgagctga acctgggaag gagagaggag    840
tacgacgtgc tggacaagcg acgcggacgc gacccggaga tgggggggaa accacggcgg    900
aaaaaccctc aggaaggact gtacaacgaa ctccagaaag acaagatggc ggaagcctac    960
tcagaaatcg ggatgaaggg agagcggagg aggggaaagg gtcacgacgg gctgtaccag   1020
ggactgagca ccgccactaa ggatacctac gatgccttgc atatgcaagc actcccaccc   1080
cgg                                                                 1083

<210> SEQ ID NO 44
<211> LENGTH: 361
<212> TYPE: PRT
<213> ORGANISM: Artificial
<220> FEATURE:
<223> OTHER INFORMATION: CAR LTG1906 (LP-VH4-CD8 TM-41BB-CD3zeta)

<400> SEQUENCE: 44

Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Gly Met Ser Trp Val Arg Gln Ala Pro Arg
    50                  55                  60

Gln Gly Leu Glu Trp Val Ala Asn Ile Lys Gln Asp Gly Ser Glu Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Thr Tyr Tyr Cys Ala Lys Glu Asn Val Asp Trp Gly Gln Gly
        115                 120                 125

Thr Leu Val Thr Val Ser Ser Ala Ala Ala Thr Thr Thr Pro Ala Pro
    130                 135                 140

Arg Pro Pro Thr Pro Ala Pro Thr Ile Ala Ser Gln Pro Leu Ser Leu
145                 150                 155                 160

Arg Pro Glu Ala Cys Arg Pro Ala Ala Gly Gly Ala Val His Thr Arg
                165                 170                 175

Gly Leu Asp Phe Ala Cys Asp Ile Tyr Ile Trp Ala Pro Leu Ala Gly
            180                 185                 190

Thr Cys Gly Val Leu Leu Leu Ser Leu Val Ile Thr Leu Tyr Cys Lys
        195                 200                 205

Arg Gly Arg Lys Lys Leu Leu Tyr Ile Phe Lys Gln Pro Phe Met Arg
    210                 215                 220

Pro Val Gln Thr Thr Gln Glu Glu Asp Gly Cys Ser Cys Arg Phe Pro
225                 230                 235                 240

Glu Glu Glu Glu Gly Gly Cys Glu Leu Arg Val Lys Phe Ser Arg Ser
                245                 250                 255

Ala Asp Ala Pro Ala Tyr Gln Gln Gly Gln Asn Gln Leu Tyr Asn Glu
```

```
            260                 265                 270

Leu Asn Leu Gly Arg Arg Glu Glu Tyr Asp Val Leu Asp Lys Arg Arg
        275                 280                 285

Gly Arg Asp Pro Glu Met Gly Gly Lys Pro Arg Arg Lys Asn Pro Gln
    290                 295                 300

Glu Gly Leu Tyr Asn Glu Leu Gln Lys Asp Lys Met Ala Glu Ala Tyr
305                 310                 315                 320

Ser Glu Ile Gly Met Lys Gly Glu Arg Arg Arg Gly Lys Gly His Asp
                325                 330                 335

Gly Leu Tyr Gln Gly Leu Ser Thr Ala Thr Lys Asp Thr Tyr Asp Ala
            340                 345                 350

Leu His Met Gln Ala Leu Pro Pro Arg
        355                 360


<210> SEQ ID NO 45
<211> LENGTH: 797
<212> TYPE: DNA
<213> ORGANISM: Artificial
<220> FEATURE:
<223> OTHER INFORMATION: TSLPR-reactive scFv binding domain (LTG1789)

<400> SEQUENCE: 45

atggcactgc ccgtgaccgc cctgcttctg ccgcttgcac ttctgctgca cgccgctagg      60

ccccaagtca ccctcaaaga gtcagggcca ggaatcctca agccctcaca gactctgtct     120

cttacttgct cattcagcgg attcagcctt tccacctctg gtatgggcgt ggggtggatt     180

aggcaaccta gcggaaaggg gcttgaatgg ctggcccaca tctggtggga cgacgacaag     240

tactacaacc cctcactgaa gtcccagctc actatttcca aagatacttc ccggaatcag     300

gtgttcctca agattacctc tgtcgacacc gctgataccg ccacttacta ttgttcacgc     360

agaccgagag gtaccatgga cgcaatggac tactggggac agggcaccag cgtgaccgtg     420

tcatctggcg gtggagggtc aggaggtgga ggtagcggag gcggtgggtc cgacattgtc     480

atgacccagg ccgccagcag cctgagcgct tcactgggcg acagggtgac catcagctgt     540

cgcgcatcac aagatatctc taagtatctt aattggtacc agcaaaagcc ggatggaacc     600

gtgaagctgc tgatctacta cacctcacgg ctgcattctg gagtgcctag ccgctttagc     660

ggatctgggt ccggtactga ctacagcctc accattagaa accttgaaca ggaggacatc     720

gcaacttatt tctgccaaca ggtctatact ctgccgtgga ccttcggcgg aggtaccaaa     780

ctggagatta agtccgg                                                    797


<210> SEQ ID NO 46
<211> LENGTH: 265
<212> TYPE: PRT
<213> ORGANISM: Artificial
<220> FEATURE:
<223> OTHER INFORMATION: TSLPR-reactive scFv binding domain (LTG1789)

<400> SEQUENCE: 46

Met Ala Leu Pro Val Thr Ala Leu Leu Leu Pro Leu Ala Leu Leu Leu
1               5                   10                  15

His Ala Ala Arg Pro Gln Val Thr Leu Lys Glu Ser Gly Pro Gly Ile
            20                  25                  30

Leu Lys Pro Ser Gln Thr Leu Ser Leu Thr Cys Ser Phe Ser Gly Phe
        35                  40                  45

Ser Leu Ser Thr Ser Gly Met Gly Val Gly Trp Ile Arg Gln Pro Ser
    50                  55                  60
```

```
Gly Lys Gly Leu Glu Trp Leu Ala His Ile Trp Trp Asp Asp Asp Lys
65                  70                  75                  80

Tyr Tyr Asn Pro Ser Leu Lys Ser Gln Leu Thr Ile Ser Lys Asp Thr
                85                  90                  95

Ser Arg Asn Gln Val Phe Leu Lys Ile Thr Ser Val Asp Thr Ala Asp
            100                 105                 110

Thr Ala Thr Tyr Tyr Cys Ser Arg Arg Pro Arg Gly Thr Met Asp Ala
        115                 120                 125

Met Asp Tyr Trp Gly Gln Gly Thr Ser Val Thr Val Ser Ser Gly Gly
    130                 135                 140

Gly Gly Ser Gly Gly Gly Gly Ser Gly Gly Gly Gly Ser Asp Ile Val
145                 150                 155                 160

Met Thr Gln Ala Ala Ser Ser Leu Ser Ala Ser Leu Gly Asp Arg Val
                165                 170                 175

Thr Ile Ser Cys Arg Ala Ser Gln Asp Ile Ser Lys Tyr Leu Asn Trp
            180                 185                 190

Tyr Gln Gln Lys Pro Asp Gly Thr Val Lys Leu Leu Ile Tyr Tyr Thr
        195                 200                 205

Ser Arg Leu His Ser Gly Val Pro Ser Arg Phe Ser Gly Ser Gly Ser
    210                 215                 220

Gly Thr Asp Tyr Ser Leu Thr Ile Arg Asn Leu Glu Gln Glu Asp Ile
225                 230                 235                 240

Ala Thr Tyr Phe Cys Gln Gln Val Tyr Thr Leu Pro Trp Thr Phe Gly
                245                 250                 255

Gly Gly Thr Lys Leu Glu Ile Lys Ser
            260                 265
```

<210> SEQ ID NO 47
<211> LENGTH: 1170
<212> TYPE: DNA
<213> ORGANISM: Artificial
<220> FEATURE:
<223> OTHER INFORMATION: CAR LTG1789 (LP-3G11-CD8 TM-41BB-CD3zeta)

<400> SEQUENCE: 47

```
atggcactgc ccgtgaccgc cctgcttctg ccgcttgcac ttctgctgca cgccgctagg     60

ccccaagtca ccctcaaaga gtcagggcca ggaatcctca agccctcaca gactctgtct    120

cttacttgct cattcagcgg attcagcctt tccacctctg gtatgggcgt ggggtggatt    180

aggcaaccta gcggaaaggg gcttgaatgg ctggcccaca tctggtggga cgacgacaag    240

tactacaacc cctcactgaa gtcccagctc actatttcca aagatacttc ccggaatcag    300

gtgttcctca agattacctc tgtcgacacc gctgataccg ccacttacta ttgttcacgc    360

agaccgagag gtaccatgga cgcaatggac tactggggac agggcaccag cgtgaccgtg    420

tcatctggcg gtggagggtc aggaggtgga ggtagcggag gcggtgggtc cgacattgtc    480

atgacccagg ccgccagcag cctgagcgct tcactgggcg acagggtgac catcagctgt    540

cgcgcatcac aagatatctc taagtatctt aattggtacc agcaaaagcc ggatggaacc    600

gtgaagctgc tgatctacta cacctcacgg ctgcattctg gagtgcctag ccgctttagc    660

ggcacttgcg gcgtgctcct gctgtcgctg gtcatcaccc tttactgcaa gaggggccgg    720

aagaagctgc tttacatctt caagcagccg ttcatgcggc ccgtgcagac gactcaggaa    780

gaggacggat gctcgtgcag attccctgag gaggaagagg ggggatgcga actgcgcgtc    840

aagttctcac ggtccgccga cgcccccgca tatcaacagg gccagaatca gctctacaac    900
```

-continued gagctgaacc tgggaaggag agaggagtac gacgtgctgg acaagcgacg cggacgcgac 960
ccggagatgg gggggaaacc acggcggaaa aaccctcagg aaggactgta caacgaactc 1020
cagaaagaca agatggcgga agcctactca gaaatcggga tgaagggaga gcggaggagg 1080
ggaaagggtc acgacgggct gtaccaggga ctgagcaccg ccactaagga tacctacgat 1140
gccttgcata tgcaagcact cccaccccgg 1170

<210> SEQ ID NO 48
<211> LENGTH: 490
<212> TYPE: PRT
<213> ORGANISM: Artificial
<220> FEATURE:
<223> OTHER INFORMATION: CAR LTG1789 (LP-3G11-CD8 TM-41BB-CD3zeta)

<400> SEQUENCE: 48

Met Ala Leu Pro Val Thr Ala Leu Leu Leu Pro Leu Ala Leu Leu Leu
1 5 10 15

His Ala Ala Arg Pro Gln Val Thr Leu Lys Glu Ser Gly Pro Gly Ile
20 25 30

Leu Lys Pro Ser Gln Thr Leu Ser Leu Thr Cys Ser Phe Ser Gly Phe
35 40 45

Ser Leu Ser Thr Ser Gly Met Gly Val Gly Trp Ile Arg Gln Pro Ser
50 55 60

Gly Lys Gly Leu Glu Trp Leu Ala His Ile Trp Trp Asp Asp Asp Lys
65 70 75 80

Tyr Tyr Asn Pro Ser Leu Lys Ser Gln Leu Thr Ile Ser Lys Asp Thr
85 90 95

Ser Arg Asn Gln Val Phe Leu Lys Ile Thr Ser Val Asp Thr Ala Asp
100 105 110

Thr Ala Thr Tyr Tyr Cys Ser Arg Arg Pro Arg Gly Thr Met Asp Ala
115 120 125

Met Asp Tyr Trp Gly Gln Gly Thr Ser Val Thr Val Ser Ser Gly Gly
130 135 140

Gly Gly Ser Gly Gly Gly Gly Ser Gly Gly Gly Gly Ser Asp Ile Val
145 150 155 160

Met Thr Gln Ala Ala Ser Ser Leu Ser Ala Ser Leu Gly Asp Arg Val
165 170 175

Thr Ile Ser Cys Arg Ala Ser Gln Asp Ile Ser Lys Tyr Leu Asn Trp
180 185 190

Tyr Gln Gln Lys Pro Asp Gly Thr Val Lys Leu Leu Ile Tyr Tyr Thr
195 200 205

Ser Arg Leu His Ser Gly Val Pro Ser Arg Phe Ser Gly Ser Gly Ser
210 215 220

Gly Thr Asp Tyr Ser Leu Thr Ile Arg Asn Leu Glu Gln Glu Asp Ile
225 230 235 240

Ala Thr Tyr Phe Cys Gln Gln Val Tyr Thr Leu Pro Trp Thr Phe Gly
245 250 255

Gly Gly Thr Lys Leu Glu Ile Lys Ala Ala Ala Thr Thr Thr Pro Ala
260 265 270

Pro Arg Pro Pro Thr Pro Ala Pro Thr Ile Ala Ser Gln Pro Leu Ser
275 280 285

Leu Arg Pro Glu Ala Cys Arg Pro Ala Ala Gly Gly Ala Val His Thr
290 295 300

Arg Gly Leu Asp Phe Ala Cys Asp Ile Tyr Ile Trp Ala Pro Leu Ala

-continued

```
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490


<210> SEQ ID NO 49
<211> LENGTH: 1467
<212> TYPE: DNA
<213> ORGANISM: Artificial
<220> FEATURE:
<223> OTHER INFORMATION: CAR LTG1563 (LP-CD19-TNFRSF19TM-41BB-CD3zeta)

<400> SEQUENCE: 49

atgctgctgc tggtcaccag cctgctgctg tgcgagctcc ctcaccccgc ctttctgctt     60

atcccggaca ttcagatgac acagaccacc tcgagcttgt ccgcgtcgct gggcgatcgc    120

gtgaccatct cctgccgggc ctcccaagac atttcaaagt atctcaactg gtaccagcag    180

aagccggacg gaaccgtgaa actgctgatc taccatacca gccgcctgca ctccggcgtg    240

ccgtcccgct tctccggatc gggttccgga actgactact cactgactat ctccaacttg    300

gaacaagagg acatcgccac ttacttctgt caacaaggaa ataccettcc ctacaccttc    360

ggggggggta ccaagctgga gatcactggg ggcggaggct ccggtggagg cggatccggc    420

ggtggaggga gcgaagtcaa gctgcaggaa tcaggaccag gactcgtggc gccatcccag    480

tccctgtcgg tgacctgtac tgtctccgga gtcagcctcc ccgattacgg agtgtcatgg    540

attaggcaac cccaagaaa agggctggaa tggctcggag tgatctgggg ctccgaaacc    600

acctactaca actcggcgct gaagtcccgg ctgaccatca tcaaggacaa ctccaagagc    660

caagtgttct tgaagatgaa cagcttgcag accgacgata ccgcaatcta ctactgtgcc    720

aagcactatt actacggggg gtcttacgcc atggactact ggggacaggg cacctccgtg    780

actgtgtcgt ccgcggccgc gcccgcccct cggcccccga ctcctgcccc gacgatcgct    840

tcccaacctc tctcgctgcg cccggaagca tgccggcccg ccgccggtgg cgctgtccac    900

actcgcggac tggactttga taccgcactg gcggccgtga tctgtagcgc cctggccacc    960

gtgctgctgg cgctgctcat cctttgcgtg atctactgca agcggcagcc taggcgaaag   1020
```

-continued

```
aagctcctct acattttcaa gcaacccttc atgcgccccg tgcaaaccac ccaggaggag   1080

gatggatgct catgccggtt ccctgaggaa gaagagggcg gttgcgagct cagagtgaaa   1140

ttcagccggt cggctgacgc cccggcgtac cagcagggcc agaaccagct gtacaatgag   1200

ctcaacctgg ggcgccgcga agagtacgac gtgctggaca agaggagagg cagagatccg   1260

gaaatgggcg gaaagccaag gcggaagaac ccgcaggaag gtctttacaa cgaactgcag   1320

aaggacaaga tggccgaggc ctactccgag attgggatga agggagaaag acggagggga   1380

aagggacatg acggacttta ccagggcctg agcactgcca cgaaggacac ctatgatgcc   1440

ctgcacatgc aggcgctgcc gcctcgg                                       1467
```

```
<210> SEQ ID NO 50
<211> LENGTH: 489
<212> TYPE: PRT
<213> ORGANISM: Artificial
<220> FEATURE:
<223> OTHER INFORMATION: CAR LTG1563 (LP-CD19-TNFRSF19TM-41BB-CD3zeta)

<400> SEQUENCE: 50

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Gly Gly Gly Ser Gly Gly Gly Gly Ser Gly Gly Gly Gly Ser
    130                 135                 140

Glu Val Lys Leu Gln Glu Ser Gly Pro Gly Leu Val Ala Pro Ser Gln
145                 150                 155                 160

Ser Leu Ser Val Thr Cys Thr Val Ser Gly Val Ser Leu Pro Asp Tyr
                165                 170                 175

Gly Val Ser Trp Ile Arg Gln Pro Pro Arg Lys Gly Leu Glu Trp Leu
            180                 185                 190

Gly Val Ile Trp Gly Ser Glu Thr Thr Tyr Tyr Asn Ser Ala Leu Lys
        195                 200                 205

Ser Arg Leu Thr Ile Ile Lys Asp Asn Ser Lys Ser Gln Val Phe Leu
    210                 215                 220

Lys Met Asn Ser Leu Gln Thr Asp Asp Thr Ala Ile Tyr Tyr Cys Ala
225                 230                 235                 240

Lys His Tyr Tyr Tyr Gly Gly Ser Tyr Ala Met Asp Tyr Trp Gly Gln
                245                 250                 255

Gly Thr Ser Val Thr Val Ser Ser Ala Ala Ala Pro Ala Pro Arg Pro
            260                 265                 270

Pro Thr Pro Ala Pro Thr Ile Ala Ser Gln Pro Leu Ser Leu Arg Pro
        275                 280                 285
```

```
Glu Ala Cys Arg Pro Ala Ala Gly Gly Ala Val His Thr Arg Gly Leu
    290                 295                 300

Asp Phe Asp Thr Ala Leu Ala Ala Val Ile Cys Ser Ala Leu Ala Thr
305                 310                 315                 320

Val Leu Leu Ala Leu Leu Ile Leu Cys Val Ile Tyr Cys Lys Arg Gln
                325                 330                 335

Pro Arg Arg Lys Lys Leu Leu Tyr Ile Phe Lys Gln Pro Phe Met Arg
            340                 345                 350

Pro Val Gln Thr Thr Gln Glu Glu Asp Gly Cys Ser Cys Arg Phe Pro
        355                 360                 365

Glu Glu Glu Glu Gly Gly Cys Glu Leu Arg Val Lys Phe Ser Arg Ser
    370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485
```

<210> SEQ ID NO 51
<211> LENGTH: 2280
<212> TYPE: DNA
<213> ORGANISM: Artificial
<220> FEATURE:
<223> OTHER INFORMATION: CAR LTG2228 (LP-CD20_CD19-CD8TM-CD28-CD3zeta)

<400> SEQUENCE: 51

```
atgctccttc tcgtgacctc cctgcttctc tgcgaactgc cccatcctgc cttcctgctg     60

attcccgagg tgcagttgca acagtcagga gctgaactgg tcaagccagg agccagcgtg    120

aagatgagct gcaaggcctc cggttacacc ttcacctcct acaacatgca ctgggtgaaa    180

cagaccccgg gacaagggct cgaatggatt ggcgccatct accccgggaa tggcgatact    240

tcgtacaacc agaagttcaa gggaaaggcc accctgaccg ccgacaagag ctcctccacc    300

gcgtatatgc agttgagctc cctgacctcc gaggactccg ccgactacta ctgcgcacgg    360

tccaactact atggaagctc gtactggttc ttcgatgtct gggggggccgg caccactgtg    420

accgtcagct ccgggggcgg aggatccggt ggaggcggaa gcgggggtgg aggatccgac    480

attgtgctga ctcagtcccc ggcaatcctg tcggcctcac cgggcgaaaa ggtcacgatg    540

acttgtagag cgtcgtccag cgtgaactac atggattggt accaaaagaa gcctggatcg    600

tcacccaagc cttggatcta cgctacatct aacctggcct ccggcgtgcc agcgcggttc    660

agcgggtccg gctcgggcac ctcatactcg ctgaccatct cccgcgtgga ggctgaggac    720

gccgcgacct actactgcca gcagtggtcc ttcaacccgc cgacttttgg aggcggtact    780

aagctggaga tcaaaggagg cggcggcagc ggcgggggag ggtccggagg gggtggttct    840

ggtggaggag gatcgggagg cggtggcagc gacattcaga tgactcagac cacctcctcc    900
```

```
ctgtccgcct ccctgggcga ccgcgtgacc atctcatgcc gcgccagcca ggacatctcg    960
aagtacctca actggtacca gcagaagccc gacggaaccg tgaagctcct gatctaccac   1020
acctcccggc tgcacagcgg agtgccgtct agattctcgg gttcggggtc gggaactgac   1080
tactccctta ctatttccaa cctggagcag gaggatattg ccacctactt ctgccaacaa   1140
ggaaacaccc tgccgtacac ttttggcggg ggaaccaagc tggaaatcac tggcagcaca   1200
tccggttccg ggaagcccgg ctccggagag ggcagcacca agggggaagt caagctgcag   1260
gaatcaggac ctggcctggt ggccccgagc cagtcactgt ccgtgacttg tactgtgtcc   1320
ggagtgtcgc tcccggatta cggagtgtcc tggatcaggc agccacctcg gaaaggattg   1380
gaatggctcg gagtcatctg gggttccgaa accacctatt acaactcggc actgaaatcc   1440
aggctcacca ttatcaagga taactccaag tcacaagtgt tcctgaagat gaatagcctg   1500
cagactgacg acacggcgat ctactattgc gccaagcact actactacgg cggatcctac   1560
gctatggact actggggcca ggggaccagc gtgaccgtgt catccgcggc cgcgactacc   1620
actcctgcac cacggccacc taccccagcc cccaccattg caagccagcc actttcactg   1680
cgccccgaag cgtgtagacc agctgctgga ggagccgtgc atacccgagg gctggacttc   1740
gcctgtgaca tctacatctg ggccccattg gctggaactt gcggcgtgct gctcttgtct   1800
ctggtcatta ccctgtactg ccggtcgaag aggtccagac tcttgcactc cgactacatg   1860
aacatgactc ctagaaggcc cggacccact agaaagcact accagccgta cgcccctcct   1920
cgggatttcg ccgcataccg gtccagagtg aagttcagcc gctcagccga tgcaccggcc   1980
taccagcagg gacagaacca gctctacaac gagctcaacc tgggtcggcg ggaagaatat   2040
gacgtgctgg acaaacggcg cggcagagat ccggagatgg ggggaaagcc gaggaggaag   2100
aaccctcaag agggcctgta caacgaactg cagaaggaca agatggcgga agcctactcc   2160
gagatcggca tgaagggaga acgccggaga gggaagggtc atgacggact gtaccagggc   2220
ctgtcaactg ccactaagga cacttacgat gcgctccata tgcaagcttt gcccccgcgg   2280
```

<210> SEQ ID NO 52
<211> LENGTH: 760
<212> TYPE: PRT
<213> ORGANISM: Artificial
<220> FEATURE:
<223> OTHER INFORMATION: CAR LTG2228 (LP-CD20_CD19-CD8TM-CD28-CD3zeta)

<400> SEQUENCE: 52

```
Met Leu Leu Leu Val Thr Ser Leu Leu Leu Cys Glu Leu Pro His Pro
1               5                   10                  15

Ala Phe Leu Leu Ile Pro Glu Val Gln Leu Gln Gln Ser Gly Ala Glu
            20                  25                  30

Leu Val Lys Pro Gly Ala Ser Val Lys Met Ser Cys Lys Ala Ser Gly
        35                  40                  45

Tyr Thr Phe Thr Ser Tyr Asn Met His Trp Val Lys Gln Thr Pro Gly
    50                  55                  60

Gln Gly Leu Glu Trp Ile Gly Ala Ile Tyr Pro Gly Asn Gly Asp Thr
65                  70                  75                  80

Ser Tyr Asn Gln Lys Phe Lys Gly Lys Ala Thr Leu Thr Ala Asp Lys
                85                  90                  95

Ser Ser Ser Thr Ala Tyr Met Gln Leu Ser Ser Leu Thr Ser Glu Asp
            100                 105                 110

Ser Ala Asp Tyr Tyr Cys Ala Arg Ser Asn Tyr Tyr Gly Ser Ser Tyr
```

-continued

```
        115                 120                 125

Trp Phe Phe Asp Val Trp Gly Ala Gly Thr Thr Val Thr Val Ser Ser
    130                 135                 140

Gly Gly Gly Gly Ser Gly Gly Gly Gly Ser Gly Gly Gly Gly Ser Asp
145                 150                 155                 160

Ile Val Leu Thr Gln Ser Pro Ala Ile Leu Ser Ala Ser Pro Gly Glu
                165                 170                 175

Lys Val Thr Met Thr Cys Arg Ala Ser Ser Ser Val Asn Tyr Met Asp
            180                 185                 190

Trp Tyr Gln Lys Lys Pro Gly Ser Ser Pro Lys Pro Trp Ile Tyr Ala
        195                 200                 205

Thr Ser Asn Leu Ala Ser Gly Val Pro Ala Arg Phe Ser Gly Ser Gly
    210                 215                 220

Ser Gly Thr Ser Tyr Ser Leu Thr Ile Ser Arg Val Glu Ala Glu Asp
225                 230                 235                 240

Ala Ala Thr Tyr Tyr Cys Gln Gln Trp Ser Phe Asn Pro Pro Thr Phe
                245                 250                 255

Gly Gly Gly Thr Lys Leu Glu Ile Lys Gly Gly Gly Gly Ser Gly Gly
            260                 265                 270

Gly Gly Ser Gly Gly Gly Gly Ser Gly Gly Gly Gly Ser Gly Gly Gly
        275                 280                 285

Gly Ser Asp Ile Gln Met Thr Gln Thr Thr Ser Ser Leu Ser Ala Ser
    290                 295                 300

Leu Gly Asp Arg Val Thr Ile Ser Cys Arg Ala Ser Gln Asp Ile Ser
305                 310                 315                 320

Lys Tyr Leu Asn Trp Tyr Gln Gln Lys Pro Asp Gly Thr Val Lys Leu
                325                 330                 335

Leu Ile Tyr His Thr Ser Arg Leu His Ser Gly Val Pro Ser Arg Phe
            340                 345                 350

Ser Gly Ser Gly Ser Gly Thr Asp Tyr Ser Leu Thr Ile Ser Asn Leu
        355                 360                 365

Glu Gln Glu Asp Ile Ala Thr Tyr Phe Cys Gln Gln Gly Asn Thr Leu
    370                 375                 380

Pro Tyr Thr Phe Gly Gly Gly Thr Lys Leu Glu Ile Thr Gly Ser Thr
385                 390                 395                 400

Ser Gly Ser Gly Lys Pro Gly Ser Gly Glu Gly Ser Thr Lys Gly Glu
                405                 410                 415

Val Lys Leu Gln Glu Ser Gly Pro Gly Leu Val Ala Pro Ser Gln Ser
            420                 425                 430

Leu Ser Val Thr Cys Thr Val Ser Gly Val Ser Leu Pro Asp Tyr Gly
        435                 440                 445

Val Ser Trp Ile Arg Gln Pro Pro Arg Lys Gly Leu Glu Trp Leu Gly
    450                 455                 460

Val Ile Trp Gly Ser Glu Thr Thr Tyr Tyr Asn Ser Ala Leu Lys Ser
465                 470                 475                 480

Arg Leu Thr Ile Ile Lys Asp Asn Ser Lys Ser Gln Val Phe Leu Lys
                485                 490                 495

Met Asn Ser Leu Gln Thr Asp Asp Thr Ala Ile Tyr Tyr Cys Ala Lys
            500                 505                 510

His Tyr Tyr Tyr Gly Gly Ser Tyr Ala Met Asp Tyr Trp Gly Gln Gly
        515                 520                 525

Thr Ser Val Thr Val Ser Ser Ala Ala Ala Thr Thr Thr Pro Ala Pro
    530                 535                 540
```

-continued

Arg Pro Pro Thr Pro Ala Pro Thr Ile Ala Ser Gln Pro Leu Ser Leu
545 550 555 560

Arg Pro Glu Ala Cys Arg Pro Ala Ala Gly Gly Ala Val His Thr Arg
565 570 575

Gly Leu Asp Phe Ala Cys Asp Ile Tyr Ile Trp Ala Pro Leu Ala Gly
580 585 590

Thr Cys Gly Val Leu Leu Leu Ser Leu Val Ile Thr Leu Tyr Cys Arg
595 600 605

Ser Lys Arg Ser Arg Leu Leu His Ser Asp Tyr Met Asn Met Thr Pro
610 615 620

Arg Arg Pro Gly Pro Thr Arg Lys His Tyr Gln Pro Tyr Ala Pro Pro
625 630 635 640

Arg Asp Phe Ala Ala Tyr Arg Ser Arg Val Lys Phe Ser Arg Ser Ala
645 650 655

Asp Ala Pro Ala Tyr Gln Gln Gly Gln Asn Gln Leu Tyr Asn Glu Leu
660 665 670

Asn Leu Gly Arg Arg Glu Glu Tyr Asp Val Leu Asp Lys Arg Arg Gly
675 680 685

Arg Asp Pro Glu Met Gly Gly Lys Pro Arg Arg Lys Asn Pro Gln Glu
690 695 700

Gly Leu Tyr Asn Glu Leu Gln Lys Asp Lys Met Ala Glu Ala Tyr Ser
705 710 715 720

Glu Ile Gly Met Lys Gly Glu Arg Arg Arg Gly Lys Gly His Asp Gly
725 730 735

Leu Tyr Gln Gly Leu Ser Thr Ala Thr Lys Asp Thr Tyr Asp Ala Leu
740 745 750

His Met Gln Ala Leu Pro Pro Arg
755 760

<210> SEQ ID NO 53
<211> LENGTH: 3858
<212> TYPE: DNA
<213> ORGANISM: Artificial
<220> FEATURE:
<223> OTHER INFORMATION: synthetic oligonucleotide

<400> SEQUENCE: 53
atgctccttc tcgtgacctc cctgcttctc tgcgaactgc cccatcctgc cttcctgctg 60
attcccgagg tgcagttgca acagtcagga gctgaactgg tcaagccagg agccagcgtg 120
aagatgagct gcaaggcctc cggttacacc ttcacctcct acaacatgca ctgggtgaaa 180
cagaccccgg gacaagggct cgaatggatt ggcgccatct accccgggaa tggcgatact 240
tcgtacaacc agaagttcaa gggaaaggcc accctgaccg ccgacaagag ctcctccacc 300
gcgtatatgc agttgagctc cctgacctcc gaggactccg ccgactacta ctgcgcacgg 360
tccaactact atggaagctc gtactggttc ttcgatgtct gggggggccgg caccactgtg 420 accgtcagct ccgggggcgg aggatccggt ggaggcggaa gcgggggtgg aggatccgac 480
attgtgctga ctcagtcccc ggcaatcctg tcggcctcac cgggcgaaaa ggtcacgatg 540
acttgtagag cgtcgtccag cgtgaactac atggattggt accaaaagaa gcctggatcg 600
tcacccaagc cttggatcta cgctacatct aacctggcct ccggcgtgcc agcgcggttc 660
agcgggtccg gctcgggcac ctcatactcg ctgaccatct cccgcgtgga ggctgaggac 720
gccgcgacct actactgcca gcagtggtcc ttcaacccgc cgacttttgg aggcggtact 780

-continued

```
aagctggaga tcaaaggagg cggcggcagc ggcgggggag ggtccggagg gggtggttct    840
ggtggaggag gatcgggagg cggtggcagc gacattcaga tgactcagac cacctcctcc    900
ctgtccgcct ccctgggcga ccgcgtgacc atctcatgcc gcgccagcca ggacatctcg    960
aagtacctca actggtacca gcagaagccc gacggaaccg tgaagctcct gatctaccac   1020
acctcccggc tgcacagcgg agtgccgtct agattctcgg gttcggggtc gggaactgac   1080
tactccctta ctatttccaa cctggagcag gaggatattg ccacctactt ctgccaacaa   1140
ggaaacaccc tgccgtacac ttttggcggg ggaaccaagc tggaaatcac tggcagcaca   1200
tccggttccg ggaagcccgg ctccggagag ggcagcacca agggggaagt caagctgcag   1260
gaatcaggac ctggcctggt ggccccgagc cagtcactgt ccgtgacttg tactgtgtcc   1320
ggagtgtcgc tcccggatta cggagtgtcc tggatcaggc agccacctcg gaaaggattg   1380
gaatggctcg gagtcatctg gggttccgaa accacctatt acaactcggc actgaaatcc   1440
aggctcacca ttatcaagga taactccaag tcacaagtgt tcctgaagat gaatagcctg   1500
cagactgacg acacggcgat ctactattgc gccaagcact actactacgg cggatcctac   1560
gctatggact actggggcca ggggaccagc gtgaccgtgt catccgcggc cgcgactacc   1620
actcctgcac cacggccacc taccccagcc cccaccattg caagccagcc actttcactg   1680
cgccccgaag cgtgtagacc agctgctgga ggagccgtgc atacccgagg gctggacttc   1740
gcctgtgaca tctacatctg ggccccattg gctggaactt gcggcgtgct gctcttgtct   1800
ctggtcatta ccctgtactg ccggtcgaag aggtccagac tcttgcactc cgactacatg   1860
aacatgactc ctagaaggcc cggacccact agaaagcact accagccgta cgcccctcct   1920
cgggatttcg ccgcataccg gtccagagtg aagttcagcc gctcagccga tgcaccggcc   1980
taccagcagg gacagaacca gctctacaac gagctcaacc tgggtcggcg ggaagaatat   2040
gacgtgctgg acaaacggcg cggcagagat ccggagatgg ggggaaagcc gaggaggaag   2100
aaccctcaag agggcctgta caacgaactg cagaaggaca agatggcgga agcctactcc   2160
gagatcggca tgaagggaga acgccggaga gggaagggtc atgacggact gtaccagggc   2220
ctgtcaactg ccactaagga cacttacgat gcgctccata tgcaagcttt gccccccgcgg   2280
cgcgcgaaac gcggcagcgg cgcgaccaac tttagcctgc tgaaacaggc gggcgatgtg   2340
gaagaaaacc cgggcccgcg agcaaagagg aatattatgc ttctattagt gacttccctt   2400
ttgctgtgcg agttgccaca ccccgccttc ctgcttattc cccaggtaca gctccagcag   2460
agtggcccag ggctcgtgaa gccaagccag acgctgtccc tgacttgtgc aatttcaggg   2520
gattcagttt catcaaatag cgcggcgtgg aattggattc gacaatctcc ttcccgaggg   2580
ttggaatggc ttggacgaac atattacaga tccaaatggt ataacgacta tgcggtatca   2640
gtaaagtcaa gaataaccat taaccccgac acaagcaaga accaattctc tttgcagctt   2700
aactctgtca cgccagaaga cacggcagtc tattattgcg ctcgcgaggt aacgggtgac   2760
ctggaagacg cttttgacat ttgggggcag ggtacgatgg tgacagtcag ttcagggggc   2820
ggtgggagtg ggggaggggg tagcgggggg ggagggtcag acattcagat gacccagtcc   2880
ccttcatcct tgtctgcctc cgtcggtgac agggtgacaa taacatgcag agcaagccaa   2940
acaatctgga gctatctcaa ctggtaccag cagcgaccag gaaaagcgcc aaacctgctg   3000
atttacgctg cttcctccct ccaatcaggc gtgcctagta gatttagcgg taggggctcc   3060
ggcaccgatt ttacgctcac tataagctct cttcaagcag aagattttgc gacttattac   3120
tgccagcagt cctatagtat acctcagact ttcggacagg gtaccaagtt ggagattaag   3180
```

-continued

```
gctagcgcaa ccactacgcc tgctccgcgg cctccaacgc ccgcgcccac gatagctagt   3240

cagccgttgt ctctccgacc agaggcgtgt agaccggccg ctggcggagc cgtacatact   3300

cgcggactcg acttcgcttg cgacatctac atttgggcac ccttggctgg gacctgtggg   3360

gtgctgttgc tgtccttggt tattacgttg tactgcaaga ggggccggaa gaagctgctt   3420

tacatcttca agcagccgtt catgcggccc gtgcagacga ctcaggaaga ggacggatgc   3480

tcgtgcagat tccctgagga ggaagagggg ggatgcgaac tgagagtcaa attttccagg   3540

tccgcagatg cccccgcgta ccagcaaggc cagaaccaac tttacaacga actgaacctg   3600

ggtcgccggg aggaatatga tgtgctggat aaacgaaggg ggagggaccc tgagatggga   3660

gggaaacctc gcaggaaaaa cccgcaggaa ggtttgtaca acgagttgca gaaggataag   3720

atggctgagg cttactctga aatagggatg aagggagaga gacggagagg aaaaggccat   3780

gatggccttt accagggctt gagcacagca acaaaggata cttacgacgc tcttcacatg   3840

caagctctgc caccacgg                                                 3858
```

<210> SEQ ID NO 54
<211> LENGTH: 1286
<212> TYPE: PRT
<213> ORGANISM: Artificial
<220> FEATURE:
<223> OTHER INFORMATION: synthetic polypeptide

<400> SEQUENCE: 54

```
Met Leu Leu Leu Val Thr Ser Leu Leu Leu Cys Glu Leu Pro His Pro
1               5                   10                  15

Ala Phe Leu Leu Ile Pro Glu Val Gln Leu Gln Gln Ser Gly Ala Glu
            20                  25                  30

Leu Val Lys Pro Gly Ala Ser Val Lys Met Ser Cys Lys Ala Ser Gly
        35                  40                  45

Tyr Thr Phe Thr Ser Tyr Asn Met His Trp Val Lys Gln Thr Pro Gly
    50                  55                  60

Gln Gly Leu Glu Trp Ile Gly Ala Ile Tyr Pro Gly Asn Gly Asp Thr
65                  70                  75                  80

Ser Tyr Asn Gln Lys Phe Lys Gly Lys Ala Thr Leu Thr Ala Asp Lys
                85                  90                  95

Ser Ser Ser Thr Ala Tyr Met Gln Leu Ser Ser Leu Thr Ser Glu Asp
            100                 105                 110

Ser Ala Asp Tyr Tyr Cys Ala Arg Ser Asn Tyr Tyr Gly Ser Ser Tyr
        115                 120                 125

Trp Phe Phe Asp Val Trp Gly Ala Gly Thr Thr Val Thr Val Ser Ser
    130                 135                 140

Gly Gly Gly Gly Ser Gly Gly Gly Gly Ser Gly Gly Gly Gly Ser Asp
145                 150                 155                 160

Ile Val Leu Thr Gln Ser Pro Ala Ile Leu Ser Ala Ser Pro Gly Glu
                165                 170                 175

Lys Val Thr Met Thr Cys Arg Ala Ser Ser Ser Val Asn Tyr Met Asp
            180                 185                 190

Trp Tyr Gln Lys Lys Pro Gly Ser Ser Pro Lys Pro Trp Ile Tyr Ala
        195                 200                 205

Thr Ser Asn Leu Ala Ser Gly Val Pro Ala Arg Phe Ser Gly Ser Gly
    210                 215                 220

Ser Gly Thr Ser Tyr Ser Leu Thr Ile Ser Arg Val Glu Ala Glu Asp
225                 230                 235                 240
```

```
Ala Ala Thr Tyr Tyr Cys Gln Gln Trp Ser Phe Asn Pro Pro Thr Phe
                245                 250                 255

Gly Gly Gly Thr Lys Leu Glu Ile Lys Gly Gly Gly Gly Ser Gly Gly
            260                 265                 270

Gly Gly Ser Gly Gly Gly Gly Ser Gly Gly Gly Gly Ser Gly Gly Gly
        275                 280                 285

Gly Ser Asp Ile Gln Met Thr Gln Thr Thr Ser Ser Leu Ser Ala Ser
    290                 295                 300

Leu Gly Asp Arg Val Thr Ile Ser Cys Arg Ala Ser Gln Asp Ile Ser
305                 310                 315                 320

Lys Tyr Leu Asn Trp Tyr Gln Gln Lys Pro Asp Gly Thr Val Lys Leu
                325                 330                 335

Leu Ile Tyr His Thr Ser Arg Leu His Ser Gly Val Pro Ser Arg Phe
            340                 345                 350

Ser Gly Ser Gly Ser Gly Thr Asp Tyr Ser Leu Thr Ile Ser Asn Leu
        355                 360                 365

Glu Gln Glu Asp Ile Ala Thr Tyr Phe Cys Gln Gln Gly Asn Thr Leu
    370                 375                 380

Pro Tyr Thr Phe Gly Gly Gly Thr Lys Leu Glu Ile Thr Gly Ser Thr
385                 390                 395                 400

Ser Gly Ser Gly Lys Pro Gly Ser Gly Glu Gly Ser Thr Lys Gly Glu
                405                 410                 415

Val Lys Leu Gln Glu Ser Gly Pro Gly Leu Val Ala Pro Ser Gln Ser
            420                 425                 430

Leu Ser Val Thr Cys Thr Val Ser Gly Val Ser Leu Pro Asp Tyr Gly
        435                 440                 445

Val Ser Trp Ile Arg Gln Pro Pro Arg Lys Gly Leu Glu Trp Leu Gly
    450                 455                 460

Val Ile Trp Gly Ser Glu Thr Thr Tyr Tyr Asn Ser Ala Leu Lys Ser
465                 470                 475                 480

Arg Leu Thr Ile Ile Lys Asp Asn Ser Lys Ser Gln Val Phe Leu Lys
                485                 490                 495

Met Asn Ser Leu Gln Thr Asp Asp Thr Ala Ile Tyr Tyr Cys Ala Lys
            500                 505                 510

His Tyr Tyr Tyr Gly Gly Ser Tyr Ala Met Asp Tyr Trp Gly Gln Gly
        515                 520                 525

Thr Ser Val Thr Val Ser Ser Ala Ala Ala Thr Thr Thr Pro Ala Pro
    530                 535                 540

Arg Pro Pro Thr Pro Ala Pro Thr Ile Ala Ser Gln Pro Leu Ser Leu
545                 550                 555                 560

Arg Pro Glu Ala Cys Arg Pro Ala Ala Gly Gly Ala Val His Thr Arg
                565                 570                 575

Gly Leu Asp Phe Ala Cys Asp Ile Tyr Ile Trp Ala Pro Leu Ala Gly
            580                 585                 590

Thr Cys Gly Val Leu Leu Leu Ser Leu Val Ile Thr Leu Tyr Cys Arg
        595                 600                 605

Ser Lys Arg Ser Arg Leu Leu His Ser Asp Tyr Met Asn Met Thr Pro
    610                 615                 620

Arg Arg Pro Gly Pro Thr Arg Lys His Tyr Gln Pro Tyr Ala Pro Pro
625                 630                 635                 640

Arg Asp Phe Ala Ala Tyr Arg Ser Arg Val Lys Phe Ser Arg Ser Ala
                645                 650                 655
```

-continued

```
Asp Ala Pro Ala Tyr Gln Gln Gly Gln Asn Gln Leu Tyr Asn Glu Leu
            660                 665                 670

Asn Leu Gly Arg Arg Glu Glu Tyr Asp Val Leu Asp Lys Arg Arg Gly
        675                 680                 685

Arg Asp Pro Glu Met Gly Gly Lys Pro Arg Arg Lys Asn Pro Gln Glu
    690                 695                 700

Gly Leu Tyr Asn Glu Leu Gln Lys Asp Lys Met Ala Glu Ala Tyr Ser
705                 710                 715                 720

Glu Ile Gly Met Lys Gly Glu Arg Arg Arg Gly Lys Gly His Asp Gly
                725                 730                 735

Leu Tyr Gln Gly Leu Ser Thr Ala Thr Lys Asp Thr Tyr Asp Ala Leu
            740                 745                 750

His Met Gln Ala Leu Pro Pro Arg Arg Ala Lys Arg Gly Ser Gly Ala
        755                 760                 765

Thr Asn Phe Ser Leu Leu Lys Gln Ala Gly Asp Val Glu Glu Asn Pro
    770                 775                 780

Gly Pro Arg Ala Lys Arg Asn Ile Met Leu Leu Leu Val Thr Ser Leu
785                 790                 795                 800

Leu Leu Cys Glu Leu Pro His Pro Ala Phe Leu Leu Ile Pro Gln Val
                805                 810                 815

Gln Leu Gln Gln Ser Gly Pro Gly Leu Val Lys Pro Ser Gln Thr Leu
            820                 825                 830

Ser Leu Thr Cys Ala Ile Ser Gly Asp Ser Val Ser Ser Asn Ser Ala
        835                 840                 845

Ala Trp Asn Trp Ile Arg Gln Ser Pro Ser Arg Gly Leu Glu Trp Leu
    850                 855                 860

Gly Arg Thr Tyr Tyr Arg Ser Lys Trp Tyr Asn Asp Tyr Ala Val Ser
865                 870                 875                 880

Val Lys Ser Arg Ile Thr Ile Asn Pro Asp Thr Ser Lys Asn Gln Phe
                885                 890                 895

Ser Leu Gln Leu Asn Ser Val Thr Pro Glu Asp Thr Ala Val Tyr Tyr
            900                 905                 910

Cys Ala Arg Glu Val Thr Gly Asp Leu Glu Asp Ala Phe Asp Ile Trp
        915                 920                 925

Gly Gln Gly Thr Met Val Thr Val Ser Ser Gly Gly Gly Gly Ser Gly
    930                 935                 940

Gly Gly Gly Ser Gly Gly Gly Gly Ser Asp Ile Gln Met Thr Gln Ser
945                 950                 955                 960

Pro Ser Ser Leu Ser Ala Ser Val Gly Asp Arg Val Thr Ile Thr Cys
                965                 970                 975

Arg Ala Ser Gln Thr Ile Trp Ser Tyr Leu Asn Trp Tyr Gln Gln Arg
            980                 985                 990

Pro Gly Lys Ala Pro Asn Leu Leu  Ile Tyr Ala Ala Ser  Ser Leu Gln
        995                 1000                 1005

Ser Gly  Val Pro Ser Arg Phe  Ser Gly Arg Gly Ser  Gly Thr Asp
    1010                 1015                 1020

Phe Thr  Leu Thr Ile Ser Ser  Leu Gln Ala Glu Asp  Phe Ala Thr
    1025                 1030                 1035

Tyr Tyr  Cys Gln Gln Ser Tyr  Ser Ile Pro Gln Thr  Phe Gly Gln
    1040                 1045                 1050

Gly Thr  Lys Leu Glu Ile Lys  Ala Ser Ala Thr Thr  Thr Pro Ala
    1055                 1060                 1065

Pro Arg  Pro Pro Thr Pro Ala  Pro Thr Ile Ala Ser  Gln Pro Leu
```

1070 1075 1080

Ser Leu Arg Pro Glu Ala Cys Arg Pro Ala Ala Gly Gly Ala Val
1085 1090 1095

His Thr Arg Gly Leu Asp Phe Ala Cys Asp Ile Tyr Ile Trp Ala
1100 1105 1110

Pro Leu Ala Gly Thr Cys Gly Val Leu Leu Leu Ser Leu Val Ile
1115 1120 1125

Thr Leu Tyr Cys Lys Arg Gly Arg Lys Lys Leu Leu Tyr Ile Phe
1130 1135 1140

Lys Gln Pro Phe Met Arg Pro Val Gln Thr Thr Gln Glu Glu Asp
1145 1150 1155

Gly Cys Ser Cys Arg Phe Pro Glu Glu Glu Glu Gly Gly Cys Glu
1160 1165 1170

Leu Arg Val Lys Phe Ser Arg Ser Ala Asp Ala Pro Ala Tyr Gln
1175 1180 1185

Gln Gly Gln Asn Gln Leu Tyr Asn Glu Leu Asn Leu Gly Arg Arg
1190 1195 1200

Glu Glu Tyr Asp Val Leu Asp Lys Arg Arg Gly Arg Asp Pro Glu
1205 1210 1215

Met Gly Gly Lys Pro Arg Arg Lys Asn Pro Gln Glu Gly Leu Tyr
1220 1225 1230

Asn Glu Leu Gln Lys Asp Lys Met Ala Glu Ala Tyr Ser Glu Ile
1235 1240 1245

Gly Met Lys Gly Glu Arg Arg Arg Gly Lys Gly His Asp Gly Leu
1250 1255 1260

Tyr Gln Gly Leu Ser Thr Ala Thr Lys Asp Thr Tyr Asp Ala Leu
1265 1270 1275

His Met Gln Ala Leu Pro Pro Arg
1280 1285

<210> SEQ ID NO 55
<211> LENGTH: 3852
<212> TYPE: DNA
<213> ORGANISM: Artificial
<220> FEATURE:
<223> OTHER INFORMATION: synthetic oligonucleotide

<400> SEQUENCE: 55
atgctccttc tcgtgacctc cctgcttctc tgcgaactgc cccatcctgc cttcctgctg 60
attcccgagg tgcagttgca acagtcagga gctgaactgg tcaagccagg agccagcgtg 120
aagatgagct gcaaggcctc cggttacacc ttcacctcct acaacatgca ctgggtgaaa 180
cagaccccgg gacaagggct cgaatggatt ggcgccatct accccgggaa tggcgatact 240
tcgtacaacc agaagttcaa gggaaaggcc accctgaccg ccgacaagag ctcctccacc 300
gcgtatatgc agttgagctc cctgacctcc gaggactccg ccgactacta ctgcgcacgg 360
tccaactact atggaagctc gtactggttc ttcgatgtct gggggggccgg caccactgtg 420 accgtcagct ccgggggcgg aggatccggt ggaggcggaa gcgggggtgg aggatccgac 480
attgtgctga ctcagtcccc ggcaatcctg tcggcctcac cgggcgaaaa ggtcacgatg 540
acttgtagag cgtcgtccag cgtgaactac atggattggt accaaaagaa gcctggatcg 600
tcacccaagc cttggatcta cgctacatct aacctggcct ccggcgtgcc agcgcggttc 660
agcgggtccg gctcgggcac ctcatactcg ctgaccatct cccgcgtgga ggctgaggac 720
gccgcgacct actactgcca gcagtggtcc ttcaacccgc cgacttttgg aggcggtact 780

```
aagctggaga tcaaaggagg cggcggcagc ggcgggggag ggtccggagg gggtggttct    840
ggtggaggag gatcgggagg cggtggcagc gacattcaga tgactcagac cacctcctcc    900
ctgtccgcct ccctgggcga ccgcgtgacc atctcatgcc gcgccagcca ggacatctcg    960
aagtacctca actggtacca gcagaagccc gacggaaccg tgaagctcct gatctaccac   1020
acctcccggc tgcacagcgg agtgccgtct agattctcgg gttcggggtc gggaactgac   1080
tactccctta ctatttccaa cctggagcag gaggatattg ccacctactt ctgccaacaa   1140
ggaaacaccc tgccgtacac ttttggcggg ggaaccaagc tggaaatcac tggcagcaca   1200
tccggttccg ggaagcccgg ctccggagag ggcagcacca agggggaagt caagctgcag   1260
gaatcaggac ctggcctggt ggccccgagc cagtcactgt ccgtgacttg tactgtgtcc   1320
ggagtgtcgc tcccggatta cggagtgtcc tggatcaggc agccacctcg gaaaggattg   1380
gaatggctcg gagtcatctg gggttccgaa accacctatt acaactcggc actgaaatcc   1440
aggctcacca ttatcaagga taactccaag tcacaagtgt tcctgaagat gaatagcctg   1500
cagactgacg acacggcgat ctactattgc gccaagcact actactacgg cggatcctac   1560
gctatggact actggggcca ggggaccagc gtgaccgtgt catccgcggc cgcgactacc   1620
actcctgcac cacggccacc taccccagcc cccaccattg caagccagcc actttcactg   1680
cgccccgaag cgtgtagacc agctgctgga ggagccgtgc atacccgagg gctggacttc   1740
gcctgtgaca tctacatctg ggccccattg gctggaactt gcggcgtgct gctcttgtct   1800
ctggtcatta ccctgtactg ccggtcgaag aggtccagac tcttgcactc cgactacatg   1860
aacatgactc ctagaaggcc cggacccact agaaagcact accagccgta cgcccctcct   1920
cgggatttcg ccgcataccg gtccagagtg aagttcagcc gctcagccga tgcaccggcc   1980
taccagcagg gacagaacca gctctacaac gagctcaacc tgggtcggcg ggaagaatat   2040
gacgtgctgg acaaacggcg cggcagagat ccggagatgg ggggaaagcc gaggaggaag   2100
aaccctcaag agggcctgta caacgaactg cagaaggaca agatggcgga agcctactcc   2160
gagatcggca tgaagggaga acgccggaga gggaagggtc atgacggact gtaccagggc   2220
ctgtcaactg ccactaagga cacttacgat gcgctccata tgcaagcttt gcccccgcgg   2280
cgcgcgaaac gcggcagcgg cgcgaccaac tttagcctgc tgaaacaggc gggcgatgtg   2340
gaagaaaacc cgggcccgcg agcaaagagg aatattatgt tgctgctcgt gacctcgctc   2400
cttctgtgcg agctgcccca tccggctttt ctgctcatcc ctcaagtgca gctgcagcag   2460
tccggtcctg gactggtcaa gccgtcccag actctgagcc tgacttgcgc aattagcggg   2520
gactcagtct cgtccaattc ggcggcctgg aactggatcc ggcagtcacc atcaaggggc   2580
ctggaatggc tcgggcgcac ttactaccgg tccaaatggt ataccgacta cgccgtgtcc   2640
gtgaagaatc ggatcaccat taaccccgac acctcgaaga accagttctc actccaactg   2700
aacagcgtga cccccgagga taccgcggtg tactactgcg cacaagaagt ggaaccgcag   2760
gacgccttcg acatttgggg acagggaacg atggtcacag tgtcgtccgg tggaggaggt   2820
tccggaggcg gtggatctgg aggcggaggt tcggatatcc agatgaccca gagcccctcc   2880
tcggtgtccg catccgtggg cgataaggtc accattacct gtagagcgtc ccaggacgtg   2940
tccggatggc tggcctggta ccagcagaag ccaggcttgg ctcctcaact gctgatcttc   3000
ggcgccagca ctcttcaggg ggaagtgcca tcacgcttct ccggatccgg ttccggcacc   3060
gacttcaccc tgaccatcag cagcctccag cctgaggact tcgccactta ctactgccaa   3120
```

-continued

```
caggccaagt acttccccta taccttcgga agaggcacta agctggaaat caaggctagc   3180

gcaaccacta cgcctgctcc gcggcctcca acgcccgcgc ccacgatagc tagtcagccg   3240

ttgtctctcc gaccagaggc gtgtagaccg gccgctggcg gagccgtaca tactcgcgga   3300

ctcgacttcg cttgcgacat ctacatttgg gcacccttgg ctgggacctg tggggtgctg   3360

ttgctgtcct tggttattac gttgtactgc aagaggggcc ggaagaagct gctttacatc   3420

ttcaagcagc cgttcatgcg gcccgtgcag acgactcagg aagaggacgg atgctcgtgc   3480

agattccctg aggaggaaga ggggggatgc gaactgagag tcaaattttc caggtccgca   3540

gatgcccccg cgtaccagca aggccagaac caactttaca acgaactgaa cctgggtcgc   3600

cgggaggaat atgatgtgct ggataaacga agggggaggg accctgagat gggagggaaa   3660

cctcgcagga aaaacccgca ggaaggtttg tacaacgagt tgcagaagga taagatggct   3720

gaggcttact ctgaaatagg gatgaaggga gagagacgga gaggaaaagg ccatgatggc   3780

ctttaccagg gcttgagcac agcaacaaag gatacttacg acgctcttca catgcaagct   3840

ctgccaccac gg                                                       3852


<210> SEQ ID NO 56
<211> LENGTH: 1284
<212> TYPE: PRT
<213> ORGANISM: Artificial
<220> FEATURE:
<223> OTHER INFORMATION: synthetic polypeptide

<400> SEQUENCE: 56

Met Leu Leu Leu Val Thr Ser Leu Leu Leu Cys Glu Leu Pro His Pro
1               5                   10                  15

Ala Phe Leu Leu Ile Pro Glu Val Gln Leu Gln Gln Ser Gly Ala Glu
            20                  25                  30

Leu Val Lys Pro Gly Ala Ser Val Lys Met Ser Cys Lys Ala Ser Gly
        35                  40                  45

Tyr Thr Phe Thr Ser Tyr Asn Met His Trp Val Lys Gln Thr Pro Gly
    50                  55                  60

Gln Gly Leu Glu Trp Ile Gly Ala Ile Tyr Pro Gly Asn Gly Asp Thr
65                  70                  75                  80

Ser Tyr Asn Gln Lys Phe Lys Gly Lys Ala Thr Leu Thr Ala Asp Lys
                85                  90                  95

Ser Ser Ser Thr Ala Tyr Met Gln Leu Ser Ser Leu Thr Ser Glu Asp
            100                 105                 110

Ser Ala Asp Tyr Tyr Cys Ala Arg Ser Asn Tyr Tyr Gly Ser Ser Tyr
        115                 120                 125

Trp Phe Phe Asp Val Trp Gly Ala Gly Thr Thr Val Thr Val Ser Ser
    130                 135                 140

Gly Gly Gly Gly Ser Gly Gly Gly Gly Ser Gly Gly Gly Gly Ser Asp
145                 150                 155                 160

Ile Val Leu Thr Gln Ser Pro Ala Ile Leu Ser Ala Ser Pro Gly Glu
                165                 170                 175

Lys Val Thr Met Thr Cys Arg Ala Ser Ser Ser Val Asn Tyr Met Asp
            180                 185                 190

Trp Tyr Gln Lys Lys Pro Gly Ser Ser Pro Lys Pro Trp Ile Tyr Ala
        195                 200                 205

Thr Ser Asn Leu Ala Ser Gly Val Pro Ala Arg Phe Ser Gly Ser Gly
    210                 215                 220

Ser Gly Thr Ser Tyr Ser Leu Thr Ile Ser Arg Val Glu Ala Glu Asp
```

-continued

```
225                 230                 235                 240

Ala Ala Thr Tyr Tyr Cys Gln Gln Trp Ser Phe Asn Pro Pro Thr Phe
                245                 250                 255

Gly Gly Gly Thr Lys Leu Glu Ile Lys Gly Gly Gly Gly Ser Gly Gly
            260                 265                 270

Gly Gly Ser Gly Gly Gly Gly Ser Gly Gly Gly Gly Ser Gly Gly Gly
        275                 280                 285

Gly Ser Asp Ile Gln Met Thr Gln Thr Thr Ser Ser Leu Ser Ala Ser
    290                 295                 300

Leu Gly Asp Arg Val Thr Ile Ser Cys Arg Ala Ser Gln Asp Ile Ser
305                 310                 315                 320

Lys Tyr Leu Asn Trp Tyr Gln Gln Lys Pro Asp Gly Thr Val Lys Leu
                325                 330                 335

Leu Ile Tyr His Thr Ser Arg Leu His Ser Gly Val Pro Ser Arg Phe
            340                 345                 350

Ser Gly Ser Gly Ser Gly Thr Asp Tyr Ser Leu Thr Ile Ser Asn Leu
        355                 360                 365

Glu Gln Glu Asp Ile Ala Thr Tyr Phe Cys Gln Gln Gly Asn Thr Leu
    370                 375                 380

Pro Tyr Thr Phe Gly Gly Gly Thr Lys Leu Glu Ile Thr Gly Ser Thr
385                 390                 395                 400

Ser Gly Ser Gly Lys Pro Gly Ser Gly Glu Gly Ser Thr Lys Gly Glu
                405                 410                 415

Val Lys Leu Gln Glu Ser Gly Pro Gly Leu Val Ala Pro Ser Gln Ser
            420                 425                 430

Leu Ser Val Thr Cys Thr Val Ser Gly Val Ser Leu Pro Asp Tyr Gly
        435                 440                 445

Val Ser Trp Ile Arg Gln Pro Pro Arg Lys Gly Leu Glu Trp Leu Gly
    450                 455                 460

Val Ile Trp Gly Ser Glu Thr Thr Tyr Tyr Asn Ser Ala Leu Lys Ser
465                 470                 475                 480

Arg Leu Thr Ile Ile Lys Asp Asn Ser Lys Ser Gln Val Phe Leu Lys
                485                 490                 495

Met Asn Ser Leu Gln Thr Asp Asp Thr Ala Ile Tyr Tyr Cys Ala Lys
            500                 505                 510

His Tyr Tyr Tyr Gly Gly Ser Tyr Ala Met Asp Tyr Trp Gly Gln Gly
        515                 520                 525

Thr Ser Val Thr Val Ser Ser Ala Ala Ala Thr Thr Thr Pro Ala Pro
    530                 535                 540

Arg Pro Pro Thr Pro Ala Pro Thr Ile Ala Ser Gln Pro Leu Ser Leu
545                 550                 555                 560

Arg Pro Glu Ala Cys Arg Pro Ala Ala Gly Gly Ala Val His Thr Arg
                565                 570                 575

Gly Leu Asp Phe Ala Cys Asp Ile Tyr Ile Trp Ala Pro Leu Ala Gly
            580                 585                 590

Thr Cys Gly Val Leu Leu Leu Ser Leu Val Ile Thr Leu Tyr Cys Arg
        595                 600                 605

Ser Lys Arg Ser Arg Leu Leu His Ser Asp Tyr Met Asn Met Thr Pro
    610                 615                 620

Arg Arg Pro Gly Pro Thr Arg Lys His Tyr Gln Pro Tyr Ala Pro Pro
625                 630                 635                 640

Arg Asp Phe Ala Ala Tyr Arg Ser Arg Val Lys Phe Ser Arg Ser Ala
                645                 650                 655
```

-continued

Asp Ala Pro Ala Tyr Gln Gln Gly Gln Asn Gln Leu Tyr Asn Glu Leu
660 665 670

Asn Leu Gly Arg Arg Glu Glu Tyr Asp Val Leu Asp Lys Arg Arg Gly
675 680 685

Arg Asp Pro Glu Met Gly Gly Lys Pro Arg Arg Lys Asn Pro Gln Glu
690 695 700

Gly Leu Tyr Asn Glu Leu Gln Lys Asp Lys Met Ala Glu Ala Tyr Ser
705 710 715 720

Glu Ile Gly Met Lys Gly Glu Arg Arg Arg Gly Lys Gly His Asp Gly
725 730 735

Leu Tyr Gln Gly Leu Ser Thr Ala Thr Lys Asp Thr Tyr Asp Ala Leu
740 745 750

His Met Gln Ala Leu Pro Pro Arg Arg Ala Lys Arg Gly Ser Gly Ala
755 760 765

Thr Asn Phe Ser Leu Leu Lys Gln Ala Gly Asp Val Glu Glu Asn Pro
770 775 780

Gly Pro Arg Ala Lys Arg Asn Ile Met Leu Leu Leu Val Thr Ser Leu
785 790 795 800

Leu Leu Cys Glu Leu Pro His Pro Ala Phe Leu Leu Ile Pro Gln Val
805 810 815

Gln Leu Gln Gln Ser Gly Pro Gly Leu Val Lys Pro Ser Gln Thr Leu
820 825 830

Ser Leu Thr Cys Ala Ile Ser Gly Asp Ser Val Ser Ser Asn Ser Ala
835 840 845

Ala Trp Asn Trp Ile Arg Gln Ser Pro Ser Arg Gly Leu Glu Trp Leu
850 855 860

Gly Arg Thr Tyr Tyr Arg Ser Lys Trp Tyr Thr Asp Tyr Ala Val Ser
865 870 875 880

Val Lys Asn Arg Ile Thr Ile Asn Pro Asp Thr Ser Lys Asn Gln Phe
885 890 895

Ser Leu Gln Leu Asn Ser Val Thr Pro Glu Asp Thr Ala Val Tyr Tyr
900 905 910

Cys Ala Gln Glu Val Glu Pro Gln Asp Ala Phe Asp Ile Trp Gly Gln
915 920 925

Gly Thr Met Val Thr Val Ser Ser Gly Gly Gly Gly Ser Gly Gly Gly
930 935 940

Gly Ser Gly Gly Gly Gly Ser Asp Ile Gln Met Thr Gln Ser Pro Ser
945 950 955 960

Ser Val Ser Ala Ser Val Gly Asp Lys Val Thr Ile Thr Cys Arg Ala
965 970 975

Ser Gln Asp Val Ser Gly Trp Leu Ala Trp Tyr Gln Gln Lys Pro Gly
980 985 990

Leu Ala Pro Gln Leu Leu Ile Phe Gly Ala Ser Thr Leu Gln Gly Glu
995 1000 1005

Val Pro Ser Arg Phe Ser Gly Ser Gly Ser Gly Thr Asp Phe Thr
1010 1015 1020

Leu Thr Ile Ser Ser Leu Gln Pro Glu Asp Phe Ala Thr Tyr Tyr
1025 1030 1035

Cys Gln Gln Ala Lys Tyr Phe Pro Tyr Thr Phe Gly Arg Gly Thr
1040 1045 1050

Lys Leu Glu Ile Lys Ala Ser Ala Thr Thr Thr Pro Ala Pro Arg
1055 1060 1065

```
Pro Pro  Thr Pro Ala Pro Thr  Ile Ala Ser Gln Pro  Leu Ser Leu
    1070                 1075                 1080

Arg Pro  Glu Ala Cys Arg Pro  Ala Ala Gly Gly Ala  Val His Thr
    1085                 1090                 1095

Arg Gly  Leu Asp Phe Ala Cys  Asp Ile Tyr Ile Trp  Ala Pro Leu
    1100                 1105                 1110

Ala Gly  Thr Cys Gly Val Leu  Leu Leu Ser Leu Val  Ile Thr Leu
    1115                 1120                 1125

Tyr Cys  Lys Arg Gly Arg Lys  Lys Leu Leu Tyr Ile  Phe Lys Gln
    1130                 1135                 1140

Pro Phe  Met Arg Pro Val Gln  Thr Thr Gln Glu Glu  Asp Gly Cys
    1145                 1150                 1155

Ser Cys  Arg Phe Pro Glu Glu  Glu Glu Gly Gly Cys  Glu Leu Arg
    1160                 1165                 1170

Val Lys  Phe Ser Arg Ser Ala  Asp Ala Pro Ala Tyr  Gln Gln Gly
    1175                 1180                 1185

Gln Asn  Gln Leu Tyr Asn Glu  Leu Asn Leu Gly Arg  Arg Glu Glu
    1190                 1195                 1200

Tyr Asp  Val Leu Asp Lys Arg  Arg Gly Arg Asp Pro  Glu Met Gly
    1205                 1210                 1215

Gly Lys  Pro Arg Arg Lys Asn  Pro Gln Glu Gly Leu  Tyr Asn Glu
    1220                 1225                 1230

Leu Gln  Lys Asp Lys Met Ala  Glu Ala Tyr Ser Glu  Ile Gly Met
    1235                 1240                 1245

Lys Gly  Glu Arg Arg Arg Gly  Lys Gly His Asp Gly  Leu Tyr Gln
    1250                 1255                 1260

Gly Leu  Ser Thr Ala Thr Lys  Asp Thr Tyr Asp Ala  Leu His Met
    1265                 1270                 1275

Gln Ala  Leu Pro Pro Arg
    1280
```

<210> SEQ ID NO 57

<400> SEQUENCE: 57

000

<210> SEQ ID NO 58

<400> SEQUENCE: 58

000

<210> SEQ ID NO 59
<211> LENGTH: 3855
<212> TYPE: DNA
<213> ORGANISM: Artificial
<220> FEATURE:
<223> OTHER INFORMATION: synthetic oligonucleotide

<400> SEQUENCE: 59

```
atgcttcttt tggtgacttc ccttttgctg tgcgagttgc cacaccccgc cttcctgctt     60

attccccagg tacagctcca gcagagtggc ccagggctcg tgaagccaag ccagacgctg    120

tccctgactt gtgcaatttc aggggattca gtttcatcaa atagcgcggc gtggaattgg    180

attcgacaat ctccttcccg agggttggaa tggcttggac gaacatatta cagatccaaa    240

tggtataacg actatgcggt atcagtaaag tcaagaataa ccattaaccc cgacacaagc    300
```

-continued

```
aagaaccaat tctctttgca gcttaactct gtcacgccag aagacacggc agtctattat    360
tgcgctcgcg aggtaacggg tgacctggaa gacgcttttg acatttgggg gcagggtacg    420
atggtgacag tcagttcagg gggcggtggg agtgggggag gggggtagcgg ggggggaggg    480
tcagacattc agatgaccca gtccccttca tccttgtctg cctccgtcgg tgacagggtg    540
acaataacat gcagagcaag ccaaacaatc tggagctatc tcaactggta ccagcagcga    600
ccaggaaaag cgccaaacct gctgatttac gctgcttcct ccctccaatc aggcgtgcct    660
agtagattta gcggtagggg ctccggcacc gattttacgc tcactataag ctctcttcaa    720
gcagaagatt ttgcgactta ttactgccag cagtcctata gtatacctca gactttcgga    780
cagggtacca agttggagat taaggcggcc gctaccacaa cccctgcgcc ccggcctcct    840
acccccgcac ccacgattgc ttctcaacct ctttcactcc gacctgaggc ttgtagacct    900
gcagccgggg gtgccgtcca cacacgggga ctcgacttcg cttgtgatat atatatttgg    960
gcgcccctgg ccggcacttg tggagttctt ttgctctctc ttgttatcac attgtactgc   1020
aagcgaggta ggaagaaatt gctttacatt tttaagcagc cgttcatgcg accagtacag   1080
actactcaag aagaagatgg gtgctcttgt cggttcccgg aagaagaaga gggtggttgc   1140
gagttgaggg tgaagttctc ccgctctgcc gacgcaccgg catatcagca gggacaaaac   1200
cagctctaca acgaattgaa cctgggtcgg cgggaagaat atgacgtgct cgataagcgg   1260
cggggtcgcg acccagaaat gggaggcaaa ccgcgcagga aaaatccaca ggagggactt   1320
tataacgaac ttcaaaagga taagatggca gaggcataca gcgaaatcgg gatgaaaggc   1380
gagagaagaa gggggaaagg gcacgatggt ctttaccagg ggctttctac cgcgacgaag   1440
gatacctacg atgctctcca tatgcaagca cttcctccta gacgggcaaa gcggggctca   1500
ggggcgacta acttttcact gttgaagcag gccggggatg tggaggagaa tcctggtcct   1560
agagctaagc gagtagacat ggccctgccc gtcactgcgc tgcttcttcc acttgcgctt   1620
ctgctgcacg cagcgcgccc ggaagtccag ctccagcaaa gcggagccga actcgtgaag   1680
ccgggggcct ccgtgaagat gagctgcaag gcatccggct acaccttcac tagctacaac   1740
atgcactggg tgaagcagac tccgggtcaa gggctggagt ggattggggc gatctacccg   1800
ggcaacggcg acacctccta caaccaaaag ttcaagggga aggctactct tacggcggac   1860
aagtcgtcca gcaccgcata catgcaactc tcctccctga cctccgagga ctcggcggac   1920
tactactgcg cccggagcaa ctactacggt tcctcctact ggttcttcga cgtgtggggt   1980
gccggaacta ctgtgactgt gtcctccggt ggtggcggat caggcggcgg gggatccggc   2040
ggtggaggat ccgacattgt gctgactcag tcccccgcaa tcctttcggc ctcccccgga   2100
gagaaggtca cgatgacttg cagggcttcg tcctccgtga actacatgga ttggtaccaa   2160
aagaagcccg ggtcgtcgcc taagccgtgg atctacgcta cctcaaacct ggcttccggc   2220
gtccctgcgc ggttcagcgg ctcggggagc ggtacctcat actcactcac catctcccgg   2280
gtggaggccg aagatgcggc cacctattat tgccaacagt ggtccttcaa tccgcccacc   2340
ttcggggggg gaaccaagct cgagatcaag gggggtggcg gctcaggggg aggcggaagc   2400
ggagggggtg gctcgggcgg cggcggttcc ggcggcggag ggtccgatat ccaaatgacc   2460
cagactacta gctcgttgag cgcctcgctc ggcgacagag tgaccattag ctgcagggca   2520
tcccaggaca tttcaaagta cctgaactgg taccaacaga agcccgacgg aactgtgaag   2580
ctcctgatct accacacctc ccggctgcac tccggagtcc cgtcgagatt ttccggctcc   2640
ggaagcggaa ccgattattc gctcaccatt tctaacctgg aacaggagga cattgccact   2700
```

```
tacttctgtc aacaaggaaa cactctgcct tacacctttg gtggcggaac caagttggaa   2760

attaccggct ccacctccgg atccggaaag cctggatccg gagagggatc aaccaaggga   2820

gaagtgaagc tgcaggagag cgggcccggc cttgtcgccc cgagccagtc cttgtccgtg   2880

acctgtactg tctccggagt cagcctgccg gactacgggg tgtcctggat ccgccagccg   2940

cctcgcaagg gcctggagtg gctcggcgtg atctggggat ccgaaacgac ttactacaac   3000

tcggccctca agtcgaggct cactattatc aaggacaact cgaagtccca ggtgttcctc   3060

aagatgaact cgctgcaaac cgacgacaca gcgatctact actgtgcaaa gcattactac   3120

tacggaggca gctacgcaat ggactactgg ggacagggaa cctccgtgac tgtctctagc   3180

gctagcgcga ccactacgcc cgcccccgc ccacctaccc ccgccccgac cattgcgagc    3240

caaccgttgt cactccgccc ggaagcctgc cgccccgccg ctggcggagc cgtgcacacc   3300

cggggactgg acttcgcatg cgacatctac atttgggccc cgctggctgg aacctgtgga   3360

gtcctgctgc tctccctcgt gatcactctg tactgccggt cgaagcgctc aagactgctg   3420

cactcagact acatgaacat gactcctcgg cggccggggc cgactcggaa gcactaccag   3480

ccttacgcac ccccgagaga tttcgcggcc taccgctccc gggtcaagtt ttcccggtct   3540

gccgacgctc cggcgtacca gcaggggcag aaccagctct acaatgagct gaatctgggt   3600

cggagagaag agtacgatgt gctggataag cggagaggca gagatccaga aatgggagga   3660

aagcctcgga gaaagaaccc acaggaggga ctgtataatg agctgcagaa ggacaaaatg   3720

gccgaagcct acagcgagat cggcatgaag ggagagcggc gcagagggaa gggacatgac   3780

ggcctgtacc agggtctgag caccgcgact aaggacacct acgatgccct tcatatgcaa   3840

gcactccctc cgcgc                                                    3855
```

<210> SEQ ID NO 60
<211> LENGTH: 1285
<212> TYPE: PRT
<213> ORGANISM: Artificial
<220> FEATURE:
<223> OTHER INFORMATION: synthetic polypeptide

<400> SEQUENCE: 60

```
Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys Pro Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Arg Glu Val Thr Gly Asp
        115                 120                 125

Leu Glu Asp Ala Phe Asp Ile Trp Gly Gln Gly Thr Met Val Thr Val
    130                 135                 140

Ser Ser Gly Gly Gly Gly Ser Gly Gly Gly Gly Ser Gly Gly Gly Gly
```

-continued

```
145                 150                 155                 160

Ser Asp Ile Gln Met Thr Gln Ser Pro Ser Ser Leu Ser Ala Ser Val
                165                 170                 175

Gly Asp Arg Val Thr Ile Thr Cys Arg Ala Ser Gln Thr Ile Trp Ser
            180                 185                 190

Tyr Leu Asn Trp Tyr Gln Gln Arg Pro Gly Lys Ala Pro Asn Leu Leu
        195                 200                 205

Ile Tyr Ala Ala Ser Ser Leu Gln Ser Gly Val Pro Ser Arg Phe Ser
    210                 215                 220

Gly Arg Gly Ser Gly Thr Asp Phe Thr Leu Thr Ile Ser Ser Leu Gln
225                 230                 235                 240

Ala Glu Asp Phe Ala Thr Tyr Tyr Cys Gln Gln Ser Tyr Ser Ile Pro
                245                 250                 255

Gln Thr Phe Gly Gln Gly Thr Lys Leu Glu Ile Lys Ala Ala Ala Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Lys Arg Gly Arg Lys Lys Leu Leu Tyr Ile Phe Lys
            340                 345                 350

Gln Pro Phe Met Arg Pro Val Gln Thr Thr Gln Glu Glu Asp Gly Cys
        355                 360                 365

Ser Cys Arg Phe Pro Glu Glu Glu Glu Gly Gly Cys Glu Leu Arg Val
    370                 375                 380

Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg Arg Ala
                485                 490                 495

Lys Arg Gly Ser Gly Ala Thr Asn Phe Ser Leu Leu Lys Gln Ala Gly
            500                 505                 510

Asp Val Glu Glu Asn Pro Gly Pro Arg Ala Lys Arg Val Asp Met Ala
        515                 520                 525

Leu Pro Val Thr Ala Leu Leu Leu Pro Leu Ala Leu Leu Leu His Ala
    530                 535                 540

Ala Arg Pro Glu Val Gln Leu Gln Gln Ser Gly Ala Glu Leu Val Lys
545                 550                 555                 560

Pro Gly Ala Ser Val Lys Met Ser Cys Lys Ala Ser Gly Tyr Thr Phe
                565                 570                 575
```

```
Thr Ser Tyr Asn Met His Trp Val Lys Gln Thr Pro Gly Gln Gly Leu
            580                 585                 590

Glu Trp Ile Gly Ala Ile Tyr Pro Gly Asn Gly Asp Thr Ser Tyr Asn
        595                 600                 605

Gln Lys Phe Lys Gly Lys Ala Thr Leu Thr Ala Asp Lys Ser Ser Ser
    610                 615                 620

Thr Ala Tyr Met Gln Leu Ser Ser Leu Thr Ser Glu Asp Ser Ala Asp
625                 630                 635                 640

Tyr Tyr Cys Ala Arg Ser Asn Tyr Tyr Gly Ser Ser Tyr Trp Phe Phe
                645                 650                 655

Asp Val Trp Gly Ala Gly Thr Thr Val Thr Val Ser Ser Gly Gly Gly
            660                 665                 670

Gly Ser Gly Gly Gly Gly Ser Gly Gly Gly Gly Ser Asp Ile Val Leu
        675                 680                 685

Thr Gln Ser Pro Ala Ile Leu Ser Ala Ser Pro Gly Glu Lys Val Thr
    690                 695                 700

Met Thr Cys Arg Ala Ser Ser Ser Val Asn Tyr Met Asp Trp Tyr Gln
705                 710                 715                 720

Lys Lys Pro Gly Ser Ser Pro Lys Pro Trp Ile Tyr Ala Thr Ser Asn
                725                 730                 735

Leu Ala Ser Gly Val Pro Ala Arg Phe Ser Gly Ser Gly Ser Gly Thr
            740                 745                 750

Ser Tyr Ser Leu Thr Ile Ser Arg Val Glu Ala Glu Asp Ala Ala Thr
        755                 760                 765

Tyr Tyr Cys Gln Gln Trp Ser Phe Asn Pro Pro Thr Phe Gly Gly Gly
    770                 775                 780

Thr Lys Leu Glu Ile Lys Gly Gly Gly Gly Ser Gly Gly Gly Gly Ser
785                 790                 795                 800

Gly Gly Gly Gly Ser Gly Gly Gly Gly Ser Gly Gly Gly Gly Ser Asp
                805                 810                 815

Ile Gln Met Thr Gln Thr Thr Ser Ser Leu Ser Ala Ser Leu Gly Asp
            820                 825                 830

Arg Val Thr Ile Ser Cys Arg Ala Ser Gln Asp Ile Ser Lys Tyr Leu
        835                 840                 845

Asn Trp Tyr Gln Gln Lys Pro Asp Gly Thr Val Lys Leu Leu Ile Tyr
    850                 855                 860

His Thr Ser Arg Leu His Ser Gly Val Pro Ser Arg Phe Ser Gly Ser
865                 870                 875                 880

Gly Ser Gly Thr Asp Tyr Ser Leu Thr Ile Ser Asn Leu Glu Gln Glu
                885                 890                 895

Asp Ile Ala Thr Tyr Phe Cys Gln Gln Gly Asn Thr Leu Pro Tyr Thr
            900                 905                 910

Phe Gly Gly Gly Thr Lys Leu Glu Ile Thr Gly Ser Thr Ser Gly Ser
        915                 920                 925

Gly Lys Pro Gly Ser Gly Glu Gly Ser Thr Lys Gly Glu Val Lys Leu
    930                 935                 940

Gln Glu Ser Gly Pro Gly Leu Val Ala Pro Ser Gln Ser Leu Ser Val
945                 950                 955                 960

Thr Cys Thr Val Ser Gly Val Ser Leu Pro Asp Tyr Gly Val Ser Trp
                965                 970                 975

Ile Arg Gln Pro Pro Arg Lys Gly Leu Glu Trp Leu Gly Val Ile Trp
            980                 985                 990
```

```
Gly Ser Glu Thr Thr Tyr Tyr Asn  Ser Ala Leu Lys Ser  Arg Leu Thr
        995                 1000                 1005

Ile Ile  Lys Asp Asn Ser Lys  Ser Gln Val Phe Leu  Lys Met Asn
    1010                 1015                 1020

Ser Leu  Gln Thr Asp Asp Thr  Ala Ile Tyr Tyr Cys  Ala Lys His
    1025                 1030                 1035

Tyr Tyr  Tyr Gly Gly Ser Tyr  Ala Met Asp Tyr Trp  Gly Gln Gly
    1040                 1045                 1050

Thr Ser  Val Thr Val Ser Ser  Ala Ser Ala Thr Thr  Thr Pro Ala
    1055                 1060                 1065

Pro Arg  Pro Pro Thr Pro Ala  Pro Thr Ile Ala Ser  Gln Pro Leu
    1070                 1075                 1080

Ser Leu  Arg Pro Glu Ala Cys  Arg Pro Ala Ala Gly  Gly Ala Val
    1085                 1090                 1095

His Thr  Arg Gly Leu Asp Phe  Ala Cys Asp Ile Tyr  Ile Trp Ala
    1100                 1105                 1110

Pro Leu  Ala Gly Thr Cys Gly  Val Leu Leu Leu Ser  Leu Val Ile
    1115                 1120                 1125

Thr Leu  Tyr Cys Arg Ser Lys  Arg Ser Arg Leu Leu  His Ser Asp
    1130                 1135                 1140

Tyr Met  Asn Met Thr Pro Arg  Arg Pro Gly Pro Thr  Arg Lys His
    1145                 1150                 1155

Tyr Gln  Pro Tyr Ala Pro Pro  Arg Asp Phe Ala Ala  Tyr Arg Ser
    1160                 1165                 1170

Arg Val  Lys Phe Ser Arg Ser  Ala Asp Ala Pro Ala  Tyr Gln Gln
    1175                 1180                 1185

Gly Gln  Asn Gln Leu Tyr Asn  Glu Leu Asn Leu Gly  Arg Arg Glu
    1190                 1195                 1200

Glu Tyr  Asp Val Leu Asp Lys  Arg Arg Gly Arg Asp  Pro Glu Met
    1205                 1210                 1215

Gly Gly  Lys Pro Arg Arg Lys  Asn Pro Gln Glu Gly  Leu Tyr Asn
    1220                 1225                 1230

Glu Leu  Gln Lys Asp Lys Met  Ala Glu Ala Tyr Ser  Glu Ile Gly
    1235                 1240                 1245

Met Lys  Gly Glu Arg Arg Arg  Gly Lys Gly His Asp  Gly Leu Tyr
    1250                 1255                 1260

Gln Gly  Leu Ser Thr Ala Thr  Lys Asp Thr Tyr Asp  Ala Leu His
    1265                 1270                 1275

Met Gln  Ala Leu Pro Pro Arg
    1280                 1285


<210> SEQ ID NO 61
<211> LENGTH: 3849
<212> TYPE: DNA
<213> ORGANISM: Artificial
<220> FEATURE:
<223> OTHER INFORMATION: synthetic oligonucleotide

<400> SEQUENCE: 61

atgttgctgc tcgtgacctc gctccttctg tgcgagctgc cccatccggc ttttctgctc     60

atccctcaag tgcagctgca gcagtccggt cctggactgg tcaagccgtc ccagactctg    120

agcctgactt gcgcaattag cggggactca gtctcgtcca attcggcggc ctggaactgg    180

atccggcagt caccatcaag ggcctggaa tggctcgggc gcacttacta ccggtccaaa    240

tggtataccg actacgccgt gtccgtgaag aatcggatca ccattaaccc cgacacctcg    300
```

aagaaccagt tctcactcca actgaacagc gtgacccccg aggataccgc ggtgtactac 360
tgcgcacaag aagtggaacc gcaggacgcc ttcgacattt ggggacaggg aacgatggtc 420
acagtgtcgt ccggtggagg aggttccgga ggcggtggat ctggaggcgg aggttcggat 480
atccagatga cccagagccc ctcctcggtg tccgcatccg tgggcgataa ggtcaccatt 540
acctgtagag cgtcccagga cgtgtccgga tggctggcct ggtaccagca gaagccaggc 600
ttggctcctc aactgctgat cttcggcgcc agcactcttc agggggaagt gccatcacgc 660
ttctccggat ccggttccgg caccgacttc accctgacca tcagcagcct ccagcctgag 720
gacttcgcca cttactactg ccaacaggcc aagtacttcc cctatacctt cggaagaggc 780
actaagctgg aaatcaaggc ggccgctacc acaacccctg cgccccggcc tcctaccccc 840
gcacccacga ttgcttctca acctctttca ctccgacctg aggcttgtag acctgcagcc 900
gggggtgccg tccacacacg gggactcgac ttcgcttgtg atatatatat ttgggcgccc 960
ctggccggca cttgtggagt tcttttgctc tctcttgtta tcacattgta ctgcaagcga 1020
ggtaggaaga aattgcttta catttttaag cagccgttca tgcgaccagt acagactact 1080
caagaagaag atgggtgctc ttgtcggttc ccggaagaag aagagggtgg ttgcgagttg 1140
agggtgaagt tctcccgctc tgccgacgca ccggcatatc agcagggaca aaaccagctc 1200
tacaacgaat tgaacctggg tcggcgggaa gaatatgacg tgctcgataa gcggcggggt 1260
cgcgacccag aaatgggagg caaaccgcgc aggaaaaatc cacaggaggg actttataac 1320
gaacttcaaa aggataagat ggcagaggca tacagcgaaa tcgggatgaa aggcgagaga 1380
agaaggggga aagggcacga tggtctttac caggggcttt ctaccgcgac gaaggatacc 1440
tacgatgctc tccatatgca agcacttcct cctagacggg caaagcgggg ctcaggggcg 1500
actaactttt cactgttgaa gcaggccggg gatgtggagg agaatcctgg tcctagagct 1560
aagcgagtag acatggccct gcccgtcact gcgctgcttc ttccacttgc gcttctgctg 1620
cacgcagcgc gcccggaagt ccagctccag caaagcggag ccgaactcgt gaagccgggg 1680
gcctccgtga agatgagctg caaggcatcc ggctacacct tcactagcta caacatgcac 1740
tgggtgaagc agactccggg tcaagggctg gagtggattg gggcgatcta cccgggcaac 1800
ggcgacacct cctacaacca aaagttcaag gggaaggcta ctcttacggc ggacaagtcg 1860
tccagcaccg catacatgca actctcctcc ctgacctccg aggactcggc ggactactac 1920
tgcgcccgga gcaactacta cggttcctcc tactggttct tcgacgtgtg gggtgccgga 1980
actactgtga ctgtgtcctc cggtggtggc ggatcaggcg gcgggggatc cggcggtgga 2040
ggatccgaca ttgtgctgac tcagtccccc gcaatccttt cggcctcccc cggagagaag 2100
gtcacgatga cttgcagggc ttcgtcctcc gtgaactaca tggattggta ccaaaagaag 2160
cccgggtcgt cgcctaagcc gtggatctac gctacctcaa acctggcttc cggcgtccct 2220
gcgcggttca gcggctcggg gagcggtacc tcatactcac tcaccatctc ccgggtggag 2280
gccgaagatg cggccaccta ttattgccaa cagtggtcct tcaatccgcc caccttcggg 2340
gggggaacca agctcgagat caaggggggt ggcggctcag gggaggcgg aagcggaggg 2400
ggtggctcgg gcggcggcgg ttccggcggc ggagggtccg atatccaaat gacccagact 2460
actagctcgt tgagcgcctc gctcggcgac agagtgacca ttagctgcag ggcatcccag 2520
gacatttcaa agtacctgaa ctggtaccaa cagaagcccg acggaactgt gaagctcctg 2580
atctaccaca cctcccggct gcactccgga gtcccgtcga gatttccgg ctccggaagc 2640

-continued

```
ggaaccgatt attcgctcac catttctaac ctggaacagg aggacattgc cacttacttc   2700

tgtcaacaag gaaacactct gccttacacc tttggtggcg gaaccaagtt ggaaattacc   2760

ggctccacct ccggatccgg aaagcctgga tccggagagg gatcaaccaa gggagaagtg   2820

aagctgcagg agagcgggcc cggccttgtc gccccgagcc agtccttgtc cgtgacctgt   2880

actgtctccg gagtcagcct gccggactac ggggtgtcct ggatccgcca gccgcctcgc   2940

aagggcctgg agtggctcgg cgtgatctgg ggatccgaaa cgacttacta caactcggcc   3000

ctcaagtcga ggctcactat tatcaaggac aactcgaagt cccaggtgtt cctcaagatg   3060

aactcgctgc aaaccgacga cacagcgatc tactactgtg caaagcatta ctactacgga   3120

ggcagctacg caatggacta ctggggacag ggaacctccg tgactgtctc tagcgctagc   3180

gcgaccacta cgcccgcccc ccgcccacct acccccgccc cgaccattgc gagccaaccg   3240

ttgtcactcc gcccggaagc ctgccgcccc gccgctggcg gagccgtgca cacccgggga   3300

ctggacttcg catgcgacat ctacatttgg gccccgctgg ctggaacctg tggagtcctg   3360

ctgctctccc tcgtgatcac tctgtactgc cggtcgaagc gctcaagact gctgcactca   3420

gactacatga acatgactcc tcggcggccg gggccgactc ggaagcacta ccagccttac   3480

gcacccccga gagatttcgc ggcctaccgc tcccgggtca agttttcccg gtctgccgac   3540

gctccggcgt accagcaggg gcagaaccag ctctacaatg agctgaatct gggtcggaga   3600

gaagagtacg atgtgctgga taagcggaga ggcagagatc cagaaatggg aggaaagcct   3660

cggagaaaga acccacagga gggactgtat aatgagctgc agaaggacaa aatggccgaa   3720

gcctacagcg agatcggcat gaagggagag cggcgcagag ggaagggaca tgacggcctg   3780

taccagggtc tgagcaccgc gactaaggac acctacgatg cccttcatat gcaagcactc   3840

cctccgcgc                                                           3849
```

<210> SEQ ID NO 62
<211> LENGTH: 1283
<212> TYPE: PRT
<213> ORGANISM: Artificial
<220> FEATURE:
<223> OTHER INFORMATION: synthetic polypeptide

<400> SEQUENCE: 62

```
Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys Pro Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Thr Asp Tyr Ala Val Ser Val Lys Asn Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Gln Glu Val Glu Pro Gln
        115                 120                 125

Asp Ala Phe Asp Ile Trp Gly Gln Gly Thr Met Val Thr Val Ser Ser
    130                 135                 140
```

-continued

```
Gly Gly Gly Gly Ser Gly Gly Gly Gly Ser Gly Gly Gly Gly Ser Asp
145                 150                 155                 160

Ile Gln Met Thr Gln Ser Pro Ser Ser Val Ser Ala Ser Val Gly Asp
                165                 170                 175

Lys Val Thr Ile Thr Cys Arg Ala Ser Gln Asp Val Ser Gly Trp Leu
            180                 185                 190

Ala Trp Tyr Gln Gln Lys Pro Gly Leu Ala Pro Gln Leu Leu Ile Phe
        195                 200                 205

Gly Ala Ser Thr Leu Gln Gly Glu Val Pro Ser Arg Phe Ser Gly Ser
    210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Tyr Phe Pro Tyr Thr
                245                 250                 255

Phe Gly Arg Gly Thr Lys Leu Glu Ile Lys Ala Ala Ala Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg Arg Ala Lys Arg
                485                 490                 495

Gly Ser Gly Ala Thr Asn Phe Ser Leu Leu Lys Gln Ala Gly Asp Val
            500                 505                 510

Glu Glu Asn Pro Gly Pro Arg Ala Lys Arg Val Asp Met Ala Leu Pro
        515                 520                 525

Val Thr Ala Leu Leu Leu Pro Leu Ala Leu Leu Leu His Ala Ala Arg
    530                 535                 540

Pro Glu Val Gln Leu Gln Gln Ser Gly Ala Glu Leu Val Lys Pro Gly
545                 550                 555                 560

Ala Ser Val Lys Met Ser Cys Lys Ala Ser Gly Tyr Thr Phe Thr Ser
```

-continued

```
                565                 570                 575

Tyr Asn Met His Trp Val Lys Gln Thr Pro Gly Gln Gly Leu Glu Trp
            580                 585                 590

Ile Gly Ala Ile Tyr Pro Gly Asn Gly Asp Thr Ser Tyr Asn Gln Lys
        595                 600                 605

Phe Lys Gly Lys Ala Thr Leu Thr Ala Asp Lys Ser Ser Ser Thr Ala
    610                 615                 620

Tyr Met Gln Leu Ser Ser Leu Thr Ser Glu Asp Ser Ala Asp Tyr Tyr
625                 630                 635                 640

Cys Ala Arg Ser Asn Tyr Tyr Gly Ser Ser Tyr Trp Phe Phe Asp Val
                645                 650                 655

Trp Gly Ala Gly Thr Thr Val Thr Val Ser Ser Gly Gly Gly Gly Ser
            660                 665                 670

Gly Gly Gly Gly Ser Gly Gly Gly Gly Ser Asp Ile Val Leu Thr Gln
        675                 680                 685

Ser Pro Ala Ile Leu Ser Ala Ser Pro Gly Glu Lys Val Thr Met Thr
    690                 695                 700

Cys Arg Ala Ser Ser Ser Val Asn Tyr Met Asp Trp Tyr Gln Lys Lys
705                 710                 715                 720

Pro Gly Ser Ser Pro Lys Pro Trp Ile Tyr Ala Thr Ser Asn Leu Ala
                725                 730                 735

Ser Gly Val Pro Ala Arg Phe Ser Gly Ser Gly Ser Gly Thr Ser Tyr
            740                 745                 750

Ser Leu Thr Ile Ser Arg Val Glu Ala Glu Asp Ala Ala Thr Tyr Tyr
        755                 760                 765

Cys Gln Gln Trp Ser Phe Asn Pro Pro Thr Phe Gly Gly Gly Thr Lys
    770                 775                 780

Leu Glu Ile Lys Gly Gly Gly Gly Ser Gly Gly Gly Gly Ser Gly Gly
785                 790                 795                 800

Gly Gly Ser Gly Gly Gly Gly Ser Gly Gly Gly Gly Ser Asp Ile Gln
                805                 810                 815

Met Thr Gln Thr Thr Ser Ser Leu Ser Ala Ser Leu Gly Asp Arg Val
            820                 825                 830

Thr Ile Ser Cys Arg Ala Ser Gln Asp Ile Ser Lys Tyr Leu Asn Trp
        835                 840                 845

Tyr Gln Gln Lys Pro Asp Gly Thr Val Lys Leu Leu Ile Tyr His Thr
    850                 855                 860

Ser Arg Leu His Ser Gly Val Pro Ser Arg Phe Ser Gly Ser Gly Ser
865                 870                 875                 880

Gly Thr Asp Tyr Ser Leu Thr Ile Ser Asn Leu Glu Gln Glu Asp Ile
                885                 890                 895

Ala Thr Tyr Phe Cys Gln Gln Gly Asn Thr Leu Pro Tyr Thr Phe Gly
            900                 905                 910

Gly Gly Thr Lys Leu Glu Ile Thr Gly Ser Thr Ser Gly Ser Gly Lys
        915                 920                 925

Pro Gly Ser Gly Glu Gly Ser Thr Lys Gly Glu Val Lys Leu Gln Glu
    930                 935                 940

Ser Gly Pro Gly Leu Val Ala Pro Ser Gln Ser Leu Ser Val Thr Cys
945                 950                 955                 960

Thr Val Ser Gly Val Ser Leu Pro Asp Tyr Gly Val Ser Trp Ile Arg
                965                 970                 975

Gln Pro Pro Arg Lys Gly Leu Glu Trp Leu Gly Val Ile Trp Gly Ser
            980                 985                 990
```

```
Glu Thr Thr Tyr Tyr Asn Ser Ala  Leu Lys Ser Arg Leu  Thr Ile Ile
        995                  1000                 1005

Lys Asp  Asn Ser Lys Ser Gln  Val Phe Leu Lys Met  Asn Ser Leu
    1010                 1015                 1020

Gln Thr  Asp Asp Thr Ala Ile  Tyr Tyr Cys Ala Lys  His Tyr Tyr
    1025                 1030                 1035

Tyr Gly  Gly Ser Tyr Ala Met  Asp Tyr Trp Gly Gln  Gly Thr Ser
    1040                 1045                 1050

Val Thr  Val Ser Ser Ala Ser  Ala Thr Thr Thr Pro  Ala Pro Arg
    1055                 1060                 1065

Pro Pro  Thr Pro Ala Pro Thr  Ile Ala Ser Gln Pro  Leu Ser Leu
    1070                 1075                 1080

Arg Pro  Glu Ala Cys Arg Pro  Ala Ala Gly Gly Ala  Val His Thr
    1085                 1090                 1095

Arg Gly  Leu Asp Phe Ala Cys  Asp Ile Tyr Ile Trp  Ala Pro Leu
    1100                 1105                 1110

Ala Gly  Thr Cys Gly Val Leu  Leu Leu Ser Leu Val  Ile Thr Leu
    1115                 1120                 1125

Tyr Cys  Arg Ser Lys Arg Ser  Arg Leu Leu His Ser  Asp Tyr Met
    1130                 1135                 1140

Asn Met  Thr Pro Arg Arg Pro  Gly Pro Thr Arg Lys  His Tyr Gln
    1145                 1150                 1155

Pro Tyr  Ala Pro Pro Arg Asp  Phe Ala Ala Tyr Arg  Ser Arg Val
    1160                 1165                 1170

Lys Phe  Ser Arg Ser Ala Asp  Ala Pro Ala Tyr Gln  Gln Gly Gln
    1175                 1180                 1185

Asn Gln  Leu Tyr Asn Glu Leu  Asn Leu Gly Arg Arg  Glu Glu Tyr
    1190                 1195                 1200

Asp Val  Leu Asp Lys Arg Arg  Gly Arg Asp Pro Glu  Met Gly Gly
    1205                 1210                 1215

Lys Pro  Arg Arg Lys Asn Pro  Gln Glu Gly Leu Tyr  Asn Glu Leu
    1220                 1225                 1230

Gln Lys  Asp Lys Met Ala Glu  Ala Tyr Ser Glu Ile  Gly Met Lys
    1235                 1240                 1245

Gly Glu  Arg Arg Arg Gly Lys  Gly His Asp Gly Leu  Tyr Gln Gly
    1250                 1255                 1260

Leu Ser  Thr Ala Thr Lys Asp  Thr Tyr Asp Ala Leu  His Met Gln
    1265                 1270                 1275

Ala Leu  Pro Pro Arg
    1280
```

<210> SEQ ID NO 63

<400> SEQUENCE: 63

000

<210> SEQ ID NO 64

<400> SEQUENCE: 64

000

<210> SEQ ID NO 65
<211> LENGTH: 1476
<212> TYPE: DNA

<213> ORGANISM: Artificial
<220> FEATURE:
<223> OTHER INFORMATION: synthetic oligonucleotide

<400> SEQUENCE: 65
atgcttcttt tggtgacttc ccttttgctg tgcgagttgc cacaccccgc cttcctgctt 60
attccccagg tacagcttca acagagtggg ccgggactgg tgaaacactc ccaaacactt 120
tctctgacgt gcgctatatc aggtgactct gtttcatcta attctgctgc gtggaactgg 180
attcgacaat ctcccagtcg cgggttggaa tggctgggac gaacatatta tcggtctaag 240
tggtataacg attatgctgt atctgttaaa tctcgaatta cgattaatcc tgacacctcc 300
aagaaccagt tctccctcca gttgaactca gtcacaccgg aagacactgc ggtctactat 360
tgcgctcaag aagtcgagcc acatgatgca ttcgacatct ggggccaggg aacgatggtc 420
accgtcagca gtggcggcgg cggatctggg ggtggcggtt ctggcggtgg aggatcagac 480
atacaaatga cgcagagtcc ctcaagtgtg tacgcgagtg tgggggataa ggtaactatt 540
acgtgcagag cgtcacagga tgttagtgga tggcttgcct ggtatcagca gaagccaggc 600
cttgctccac agctccttat cagtggtgct tctacacttc agggcgaggt tccgagtaga 660
ttctctggtt ctggatctgg tactgacttc actcttacaa tttcttcttt gcaaccagaa 720
gactttgcga cttattactg ccaacaggcc aaatacttcc cttatacatt tggccaaggt 780
accaagttgg agataaaggc ggccgcaact accacccctg cccctcggcc gccgactccg 840
gccccaacca tcgcaagcca acccctctcc ttgcgccccg aagcttgccg cccggccgcg 900
ggtggagccg tgcatacccg ggggctggac tttgcctgcg atatctacat ttgggccccg 960
ctggccggca cttgcggcgt gctcctgctg tcgctggtca tcacccttta ctgcaagagg 1020
ggccggaaga agctgcttta catcttcaag cagccgttca tgcggcccgt gcagacgact 1080
caggaagagg acggatgctc gtgcagattc cctgaggagg aagagggggg atgcgaactg 1140
cgcgtcaagt tctcacggtc cgccgacgcc cccgcatatc aacagggcca gaatcagctc 1200
tacaacgagc tgaacctggg aaggagagag gagtacgacg tgctggacaa gcgacgcgga 1260
cgcgacccgg agatgggggg gaaaccacgg cggaaaaacc ctcaggaagg actgtacaac 1320
gaactccaga aagacaagat ggcggaagcc tactcagaaa tcgggatgaa gggagagcgg 1380
aggaggggaa agggtcacga cgggctgtac cagggactga gcaccgccac taaggatacc 1440
tacgatgcct tgcatatgca agcactccca ccccgg 1476

<210> SEQ ID NO 66
<211> LENGTH: 492
<212> TYPE: PRT
<213> ORGANISM: Artificial
<220> FEATURE:
<223> OTHER INFORMATION: synthetic polypeptide

<400> SEQUENCE: 66

Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys His Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys

-continued

```
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Gln Glu Val Glu Pro His
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Gly Ser Gly Gly Gly Gly Ser Asp
145                 150                 155                 160

Ile Gln Met Thr Gln Ser Pro Ser Ser Val Tyr Ala Ser Val Gly Asp
                165                 170                 175

Lys Val Thr Ile Thr Cys Arg Ala Ser Gln Asp Val Ser Gly Trp Leu
            180                 185                 190

Ala Trp Tyr Gln Gln Lys Pro Gly Leu Ala Pro Gln Leu Leu Ile Ser
        195                 200                 205

Gly Ala Ser Thr Leu Gln Gly Glu Val Pro Ser Arg Phe Ser Gly Ser
    210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Tyr Phe Pro Tyr Thr
                245                 250                 255

Phe Gly Gln Gly Thr Lys Leu Glu Ile Lys Ala Ala Ala Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490
```

<210> SEQ ID NO 67
<211> LENGTH: 1476
<212> TYPE: DNA
<213> ORGANISM: Artificial
<220> FEATURE:
<223> OTHER INFORMATION: synthetic oligonucleotide

<400> SEQUENCE: 67
atgttgctgc tcgtgacctc gctccttctg tgcgagctgc cccatccggc ttttctgctc 60
atccctcaag tgcagctgca gcagtccggt cctggactgg tcaagccgtc ccagactctg 120
agcctgactt gcgcaattag cggggactca gtctcgtcca attcggcggc ctggaactgg 180
atccggcagt caccatcaag ggcctggaa tggctcgggc gcacttacta ccggtccaaa 240
tggtataccg actacgccgt gtccgtgaag aatcggatca ccattaaccc cgacacctcg 300
aagaaccagt tctcactcca actgaacagc gtgacccccg aggataccgc ggtgtactac 360
tgcgcacaag aagtggaacc gcaggacgcc ttcgacattt ggggacaggg aacgatggtc 420
acagtgtcgt ccggtggagg aggttccgga ggcggtggat ctggaggcgg aggttcggat 480
atccagatga cccagagccc ctcctcggtg tccgcatccg tgggcgataa ggtcaccatt 540
acctgtagag cgtcccagga cgtgtccgga tggctggcct ggtaccagca gaagccaggc 600
ttggctcctc aactgctgat cttcggcgcc agcactcttc agggggaagt gccatcacgc 660
ttctccggat ccggttccgg caccgacttc accctgacca tcagcagcct ccagcctgag 720
gacttcgcca cttactactg ccaacaggcc aagtacttcc cctatacctt cggaagaggc 780
actaagctgg aaatcaaggc ggccgcaact accacccctg cccctcggcc gccgactccg 840
gccccaacca tcgcaagcca acccctctcc ttgcgccccg aagcttgccg cccggccgcg 900
ggtggagccg tgcatacccg ggggctggac tttgcctgcg atatctacat ttgggccccg 960
ctggccggca cttgcggcgt gctcctgctg tcgctggtca tcacccttta ctgcaagagg 1020
ggccggaaga agctgcttta catcttcaag cagccgttca tgcggcccgt gcagacgact 1080
caggaagagg acggatgctc gtgcagattc cctgaggagg aagagggggg atgcgaactg 1140
cgcgtcaagt tctcacggtc cgccgacgcc cccgcatatc aacagggcca gaatcagctc 1200
tacaacgagc tgaacctggg aaggagagag gagtacgacg tgctggacaa gcgacgcgga 1260
cgcgacccgg agatgggggg gaaaccacgg cggaaaaacc ctcaggaagg actgtacaac 1320
gaactccaga aagacaagat ggcggaagcc tactcagaaa tcgggatgaa gggagagcgg 1380
aggaggggaa agggtcacga cggctgtac cagggactga gcaccgccac taaggatacc 1440
tacgatgcct tgcatatgca agcactccca ccccgg 1476

<210> SEQ ID NO 68
<211> LENGTH: 492
<212> TYPE: PRT
<213> ORGANISM: Artificial
<220> FEATURE:
<223> OTHER INFORMATION: synthetic polypeptide

<400> SEQUENCE: 68

Met Leu Leu Leu Val Thr Ser Leu Leu Leu Cys Glu Leu Pro His Pro
1 5 10 15

Ala Phe Leu Leu Ile Pro Gln Val Gln Leu Gln Gln Ser Gly Pro Gly
20 25 30

Leu Val Lys Pro Ser Gln Thr Leu Ser Leu Thr Cys Ala Ile Ser Gly
35 40 45

-continued

```
Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Thr Asp Tyr Ala Val Ser Val Lys Asn Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Gln Glu Val Glu Pro Gln
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Gly Ser Gly Gly Gly Gly Ser Asp
145                 150                 155                 160

Ile Gln Met Thr Gln Ser Pro Ser Ser Val Ser Ala Ser Val Gly Asp
                165                 170                 175

Lys Val Thr Ile Thr Cys Arg Ala Ser Gln Asp Val Ser Gly Trp Leu
            180                 185                 190

Ala Trp Tyr Gln Gln Lys Pro Gly Leu Ala Pro Gln Leu Leu Ile Phe
        195                 200                 205

Gly Ala Ser Thr Leu Gln Gly Glu Val Pro Ser Arg Phe Ser Gly Ser
    210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Tyr Phe Pro Tyr Thr
                245                 250                 255

Phe Gly Arg Gly Thr Lys Leu Glu Ile Lys Ala Ala Ala Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460
```

Gly His Asp Gly Leu Tyr Gln Gly Leu Ser Thr Ala Thr Lys Asp Thr
465 470 475 480

Tyr Asp Ala Leu His Met Gln Ala Leu Pro Pro Arg
485 490

<210> SEQ ID NO 69
<211> LENGTH: 1476
<212> TYPE: DNA
<213> ORGANISM: Artificial
<220> FEATURE:
<223> OTHER INFORMATION: synthetic oligonucleotide

<400> SEQUENCE: 69
atgttgctgc tcgtgacctc gctccttctg tgcgagctgc cccatccggc ttttctgctc 60
atccctcaag tgcagctgca gcagtccggt cctggactgg tcaagccgtc ccagactctg 120
agcctgactt gcgccattag cgggaactca gtctcgtcca attcggcggc ctggaactgg 180
atccggcagt caccatcaag ggcctggaa tggctcgggc gcacttacta ccggtccaaa 240
tggtataacg actacgccgt gtccgtgaag tcccggatca ccattaaccc cgacacctcg 300
aagaaccagt tctcactcca actgaacagc gtgacccccg aggataccgc ggtgtactac 360
tgcgcacaag aagtggaacc gcaggacgcc ttcgacattt ggggacaggg aacgatggtc 420
acagtgtcgt ccggtggagg aggttccgga ggcggtggat ctggaggcgg aggttcggat 480
atccagatga cccagagccc ctcctcggtg tccgcatccg tgggcgataa ggtcaccatt 540
acctgtagag cgtcccagga cgtgtccgga tggctggcct ggtaccagca gaagccaggc 600
ttggctcctc aactgctgat ctttggcgcc agcactcttc agggggaggt gccatcacgc 660
ttctccggag gtggttccgg caccgacttc accctgacca tcagcagcct ccagcctgag 720
gacttcgcca cttactactg ccaacaggcc aagtacttcc cctatacctt cggacaaggc 780
actaagctgg aaatcaaggc ggccgcaact accacccctg cccctcggcc gccgactccg 840
gccccaacca tcgcaagcca acccctctcc ttgcgccccg aagcttgccg cccggccgcg 900
ggtggagccg tgcatacccg gggctggac tttgcctgcg atatctacat ttgggccccg 960
ctggccggca cttgcggcgt gctcctgctg tcgctggtca tcacccttta ctgcaagagg 1020
ggccggaaga agctgcttta catcttcaag cagccgttca tgcggcccgt gcagacgact 1080
caggaagagg acggatgctc gtgcagattc cctgaggagg aagaggggg atgcgaactg 1140 cgcgtcaagt tctcacggtc cgccgacgcc cccgcatatc aacagggcca gaatcagctc 1200
tacaacgagc tgaacctggg aaggagagag gagtacgacg tgctggacaa gcgacgcgga 1260
cgcgacccgg agatgggggg gaaaccacgg cggaaaaacc ctcaggaagg actgtacaac 1320
gaactccaga aagacaagat ggcggaagcc tactcagaaa tcgggatgaa gggagagcgg 1380
aggaggggaa agggtcacga cgggctgtac cagggactga gcaccgccac taaggatacc 1440
tacgatgcct tgcatatgca agcactccca ccccgg 1476

<210> SEQ ID NO 70
<211> LENGTH: 492
<212> TYPE: PRT
<213> ORGANISM: Artificial
<220> FEATURE:
<223> OTHER INFORMATION: synthetic polypeptide

<400> SEQUENCE: 70

Met Leu Leu Leu Val Thr Ser Leu Leu Leu Cys Glu Leu Pro His Pro
1 5 10 15

-continued

```
Ala Phe Leu Leu Ile Pro Gln Val Gln Leu Gln Gln Ser Gly Pro Gly
            20                  25                  30

Leu Val Lys Pro Ser Gln Thr Leu Ser Leu Thr Cys Ala Ile Ser Gly
        35                  40                  45

Asn Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Gln Glu Val Glu Pro Gln
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Gly Ser Gly Gly Gly Gly Ser Asp
145                 150                 155                 160

Ile Gln Met Thr Gln Ser Pro Ser Ser Val Ser Ala Ser Val Gly Asp
                165                 170                 175

Lys Val Thr Ile Thr Cys Arg Ala Ser Gln Asp Val Ser Gly Trp Leu
            180                 185                 190

Ala Trp Tyr Gln Gln Lys Pro Gly Leu Ala Pro Gln Leu Leu Ile Phe
        195                 200                 205

Gly Ala Ser Thr Leu Gln Gly Glu Val Pro Ser Arg Phe Ser Gly Gly
    210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Tyr Phe Pro Tyr Thr
                245                 250                 255

Phe Gly Gln Gly Thr Lys Leu Glu Ile Lys Ala Ala Ala Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
```

```
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490


<210> SEQ ID NO 71

<400> SEQUENCE: 71

000


<210> SEQ ID NO 72

<400> SEQUENCE: 72

000


<210> SEQ ID NO 73
<211> LENGTH: 2280
<212> TYPE: DNA
<213> ORGANISM: Artificial
<220> FEATURE:
<223> OTHER INFORMATION: synthetic oligonucleotide

<400> SEQUENCE: 73

atgctccttc tcgtgacctc cctgcttctc tgcgaactgc cccatcctgc cttcctgctg     60

attcccgagg tgcagttgca acagtcagga gctgaactgg tcaagccagg agccagcgtg    120

aagatgagct gcaaggcctc cggttacacc ttcacctcct acaacatgca ctgggtgaaa    180

cagaccccgg gacaagggct cgaatggatt ggcgccatct accccgggaa tggcgatact    240

tcgtacaacc agaagttcaa gggaaaggcc accctgaccg ccgacaagag ctcctccacc    300

gcgtatatgc agttgagctc cctgacctcc gaggactccg ccgactacta ctgcgcacgg    360

tccaactact atggaagctc gtactggttc ttcgatgtct gggggggccgg caccactgtg    420

accgtcagct ccgggggcgg aggatccggt ggaggcggaa gcgggggtgg aggatccgac    480

attgtgctga ctcagtcccc ggcaatcctg tcggcctcac cgggcgaaaa ggtcacgatg    540

acttgtagag cgtcgtccag cgtgaactac atggattggt accaaaagaa gcctggatcg    600

tcacccaagc cttggatcta cgctacatct aacctggcct ccggcgtgcc agcgcggttc    660

agcgggtccg gctcgggcac ctcatactcg ctgaccatct cccgcgtgga ggctgaggac    720

gccgcgacct actactgcca gcagtggtcc ttcaacccgc cgacttttgg aggcggtact    780

aagctggaga tcaaaggagg cggcggcagc ggcgggggag ggtccggagg gggtggttct    840

ggtggaggag gatcgggagg cggtggcagc gacattcaga tgactcagac cacctcctcc    900

ctgtccgcct ccctgggcga ccgcgtgacc atctcatgcc gcgccagcca ggacatctcg    960

aagtacctca actggtacca gcagaagccc gacggaaccg tgaagctcct gatctaccac   1020

acctcccggc tgcacagcgg agtgccgtct agattctcgg gttcggggtc gggaactgac   1080

tactccctta ctatttccaa cctggagcag gaggatattg ccacctactt ctgccaacaa   1140

ggaaacaccc tgccgtacac ttttggcggg ggaaccaagc tggaaatcac tggcagcaca   1200

tccggttccg ggaagcccgg ctccggagag ggcagcacca agggggaagt caagctgcag   1260

gaatcaggac ctggcctggt ggccccgagc cagtcactgt ccgtgacttg tactgtgtcc   1320
```

ggagtgtcgc tcccggatta cggagtgtcc tggatcaggc agccacctcg gaaaggattg 1380
gaatggctcg gagtcatctg gggttccgaa accacctatt acaactcggc actgaaatcc 1440
aggctcacca ttatcaagga taactccaag tcacaagtgt tcctgaagat gaatagcctg 1500
cagactgacg acacggcgat ctactattgc gccaagcact actactacgg cggatcctac 1560
gctatggact actggggcca ggggaccagc gtgaccgtgt catccgcggc cgcgactacc 1620
actcctgcac cacggccacc taccccagcc cccaccattg caagccagcc actttcactg 1680
cgccccgaag cgtgtagacc agctgctgga ggagccgtgc atacccgagg gctggacttc 1740
gcctgtgaca tctacatctg ggccccattg gctggaactt gcggcgtgct gctcttgtct 1800
ctggtcatta ccctgtactg ccggtcgaag aggtccagac tcttgcactc cgactacatg 1860
aacatgactc ctagaaggcc cggacccact agaaagcact accagccgta cgcccctcct 1920
cgggatttcg ccgcataccg gtccagagtg aagttcagcc gctcagccga tgcaccggcc 1980
taccagcagg gacagaacca gctctacaac gagctcaacc tgggtcggcg ggaagaatat 2040
gacgtgctgg acaaacggcg cggcagagat ccggagatgg ggggaaagcc gaggaggaag 2100
aaccctcaag agggcctgta caacgaactg cagaaggaca agatggcgga agcctactcc 2160
gagatcggca tgaagggaga acgccggaga gggaagggtc atgacggact gtaccagggc 2220
ctgtcaactg ccactaagga cacttacgat gcgctccata tgcaagcttt gccccccgcgg 2280

<210> SEQ ID NO 74
<211> LENGTH: 760
<212> TYPE: PRT
<213> ORGANISM: Artificial
<220> FEATURE:
<223> OTHER INFORMATION: synthetic polypeptide

<400> SEQUENCE: 74

Met Leu Leu Leu Val Thr Ser Leu Leu Leu Cys Glu Leu Pro His Pro
1 5 10 15

Ala Phe Leu Leu Ile Pro Glu Val Gln Leu Gln Gln Ser Gly Ala Glu
20 25 30

Leu Val Lys Pro Gly Ala Ser Val Lys Met Ser Cys Lys Ala Ser Gly
35 40 45

Tyr Thr Phe Thr Ser Tyr Asn Met His Trp Val Lys Gln Thr Pro Gly
50 55 60

Gln Gly Leu Glu Trp Ile Gly Ala Ile Tyr Pro Gly Asn Gly Asp Thr
65 70 75 80

Ser Tyr Asn Gln Lys Phe Lys Gly Lys Ala Thr Leu Thr Ala Asp Lys
85 90 95

Ser Ser Ser Thr Ala Tyr Met Gln Leu Ser Ser Leu Thr Ser Glu Asp
100 105 110

Ser Ala Asp Tyr Tyr Cys Ala Arg Ser Asn Tyr Tyr Gly Ser Ser Tyr
115 120 125

Trp Phe Phe Asp Val Trp Gly Ala Gly Thr Thr Val Thr Val Ser Ser
130 135 140

Gly Gly Gly Gly Ser Gly Gly Gly Gly Ser Gly Gly Gly Gly Ser Asp
145 150 155 160

Ile Val Leu Thr Gln Ser Pro Ala Ile Leu Ser Ala Ser Pro Gly Glu
165 170 175

Lys Val Thr Met Thr Cys Arg Ala Ser Ser Ser Val Asn Tyr Met Asp
180 185 190

Trp Tyr Gln Lys Lys Pro Gly Ser Ser Pro Lys Pro Trp Ile Tyr Ala

```
        195                 200                 205

Thr Ser Asn Leu Ala Ser Gly Val Pro Ala Arg Phe Ser Gly Ser Gly
    210                 215                 220

Ser Gly Thr Ser Tyr Ser Leu Thr Ile Ser Arg Val Glu Ala Glu Asp
225                 230                 235                 240

Ala Ala Thr Tyr Tyr Cys Gln Gln Trp Ser Phe Asn Pro Pro Thr Phe
                245                 250                 255

Gly Gly Gly Thr Lys Leu Glu Ile Lys Gly Gly Gly Gly Ser Gly Gly
            260                 265                 270

Gly Gly Ser Gly Gly Gly Gly Ser Gly Gly Gly Gly Ser Gly Gly Gly
        275                 280                 285

Gly Ser Asp Ile Gln Met Thr Gln Thr Thr Ser Ser Leu Ser Ala Ser
    290                 295                 300

Leu Gly Asp Arg Val Thr Ile Ser Cys Arg Ala Ser Gln Asp Ile Ser
305                 310                 315                 320

Lys Tyr Leu Asn Trp Tyr Gln Gln Lys Pro Asp Gly Thr Val Lys Leu
                325                 330                 335

Leu Ile Tyr His Thr Ser Arg Leu His Ser Gly Val Pro Ser Arg Phe
            340                 345                 350

Ser Gly Ser Gly Ser Gly Thr Asp Tyr Ser Leu Thr Ile Ser Asn Leu
        355                 360                 365

Glu Gln Glu Asp Ile Ala Thr Tyr Phe Cys Gln Gln Gly Asn Thr Leu
    370                 375                 380

Pro Tyr Thr Phe Gly Gly Gly Thr Lys Leu Glu Ile Thr Gly Ser Thr
385                 390                 395                 400

Ser Gly Ser Gly Lys Pro Gly Ser Gly Glu Gly Ser Thr Lys Gly Glu
                405                 410                 415

Val Lys Leu Gln Glu Ser Gly Pro Gly Leu Val Ala Pro Ser Gln Ser
            420                 425                 430

Leu Ser Val Thr Cys Thr Val Ser Gly Val Ser Leu Pro Asp Tyr Gly
        435                 440                 445

Val Ser Trp Ile Arg Gln Pro Pro Arg Lys Gly Leu Glu Trp Leu Gly
    450                 455                 460

Val Ile Trp Gly Ser Glu Thr Thr Tyr Tyr Asn Ser Ala Leu Lys Ser
465                 470                 475                 480

Arg Leu Thr Ile Ile Lys Asp Asn Ser Lys Ser Gln Val Phe Leu Lys
                485                 490                 495

Met Asn Ser Leu Gln Thr Asp Asp Thr Ala Ile Tyr Tyr Cys Ala Lys
            500                 505                 510

His Tyr Tyr Tyr Gly Gly Ser Tyr Ala Met Asp Tyr Trp Gly Gln Gly
        515                 520                 525

Thr Ser Val Thr Val Ser Ser Ala Ala Ala Thr Thr Thr Pro Ala Pro
    530                 535                 540

Arg Pro Pro Thr Pro Ala Pro Thr Ile Ala Ser Gln Pro Leu Ser Leu
545                 550                 555                 560

Arg Pro Glu Ala Cys Arg Pro Ala Ala Gly Gly Ala Val His Thr Arg
                565                 570                 575

Gly Leu Asp Phe Ala Cys Asp Ile Tyr Ile Trp Ala Pro Leu Ala Gly
            580                 585                 590

Thr Cys Gly Val Leu Leu Leu Ser Leu Val Ile Thr Leu Tyr Cys Arg
        595                 600                 605

Ser Lys Arg Ser Arg Leu Leu His Ser Asp Tyr Met Asn Met Thr Pro
    610                 615                 620
```

Arg Arg Pro Gly Pro Thr Arg Lys His Tyr Gln Pro Tyr Ala Pro Pro
625 630 635 640

Arg Asp Phe Ala Ala Tyr Arg Ser Arg Val Lys Phe Ser Arg Ser Ala
645 650 655

Asp Ala Pro Ala Tyr Gln Gln Gly Gln Asn Gln Leu Tyr Asn Glu Leu
660 665 670

Asn Leu Gly Arg Arg Glu Glu Tyr Asp Val Leu Asp Lys Arg Arg Gly
675 680 685

Arg Asp Pro Glu Met Gly Gly Lys Pro Arg Arg Lys Asn Pro Gln Glu
690 695 700

Gly Leu Tyr Asn Glu Leu Gln Lys Asp Lys Met Ala Glu Ala Tyr Ser
705 710 715 720

Glu Ile Gly Met Lys Gly Glu Arg Arg Arg Gly Lys Gly His Asp Gly
725 730 735

Leu Tyr Gln Gly Leu Ser Thr Ala Thr Lys Asp Thr Tyr Asp Ala Leu
740 745 750

His Met Gln Ala Leu Pro Pro Arg
755 760

<210> SEQ ID NO 75
<211> LENGTH: 1482
<212> TYPE: DNA
<213> ORGANISM: Artificial
<220> FEATURE:
<223> OTHER INFORMATION: synthetic oligonucleotide

<400> SEQUENCE: 75
atgcttcttt tggtgacttc ccttttgctg tgcgagttgc cacaccccgc cttcctgctt 60
attccccagg tacagctcca gcagagtggc ccagggctcg tgaagccaag ccagacgctg 120
tccctgactt gtgcaatttc aggggattca gtttcatcaa atagcgcggc gtggaattgg 180
attcgacaat ctccttcccg agggttggaa tggcttggac gaacatatta cagatccaaa 240
tggtataacg actatgcggt atcagtaaag tcaagaataa ccattaaccc cgacacaagc 300
aagaaccaat tctctttgca gcttaactct gtcacgccag aagacacggc agtctattat 360
tgcgctcgcg aggtaacggg tgacctggaa gacgcttttg acatttgggg gcagggtacg 420
atggtgacag tcagttcagg gggcggtggg agtgggggag gggtagcgg ggggggaggg 480 tcagacattc agatgaccca gtccccttca tccttgtctg cctccgtcgg tgacagggtg 540
acaataacat gcagagcaag ccaaacaatc tggagctatc tcaactggta ccagcagcga 600
ccaggaaaag cgccaaacct gctgatttac gctgcttcct ccctccaatc aggcgtgcct 660
agtagattta gcggtagggg ctccggcacc gattttacgc tcactataag ctctcttcaa 720
gcagaagatt ttgcgactta ttactgccag cagtcctata gtatacctca gactttcgga 780
cagggtacca agttggagat taaggcggcc gcaactacca cccctgcccc tcggccgccg 840
actccggccc caaccatcgc aagccaaccc ctctccttgc gccccgaagc ttgccgcccg 900
gccgcgggtg gagccgtgca tacccggggg ctggactttg cctgcgatat ctacatttgg 960
gccccgctgg ccggcacttg cggcgtgctc ctgctgtcgc tggtcatcac cctttactgc 1020
aagaggggcc ggaagaagct gctttacatc ttcaagcagc cgttcatgcg gcccgtgcag 1080
acgactcagg aagaggacgg atgctcgtgc agattccctg aggaggaaga gggggggatgc 1140 gaactgcgcg tcaagttctc acggtccgcc gacgcccccg catatcaaca gggccagaat 1200
cagctctaca acgagctgaa cctgggaagg agagaggagt acgacgtgct ggacaagcga 1260
cgcggacgcg acccggagat gggggggaaa ccacggcgga aaaaccctca ggaaggactg 1320
tacaacgaac tccagaaaga caagatggcg gaagcctact cagaaatcgg gatgaaggga 1380
gagcggagga ggggaaaggg tcacgacggg ctgtaccagg gactgagcac cgccactaag 1440
gatacctacg atgccttgca tatgcaagca ctcccacccc gg 1482

<210> SEQ ID NO 76
<211> LENGTH: 494
<212> TYPE: PRT
<213> ORGANISM: Artificial
<220> FEATURE:
<223> OTHER INFORMATION: synthetic polypeptide

<400> SEQUENCE: 76

Met Leu Leu Leu Val Thr Ser Leu Leu Leu Cys Glu Leu Pro His Pro
1 5 10 15

Ala Phe Leu Leu Ile Pro Gln Val Gln Leu Gln Gln Ser Gly Pro Gly
20 25 30

Leu Val Lys Pro Ser Gln Thr Leu Ser Leu Thr Cys Ala Ile Ser Gly
35 40 45

Asp Ser Val Ser Ser Asn Ser Ala Ala Trp Asn Trp Ile Arg Gln Ser
50 55 60

Pro Ser Arg Gly Leu Glu Trp Leu Gly Arg Thr Tyr Tyr Arg Ser Lys
65 70 75 80

Trp Tyr Asn Asp Tyr Ala Val Ser Val Lys Ser Arg Ile Thr Ile Asn
85 90 95

Pro Asp Thr Ser Lys Asn Gln Phe Ser Leu Gln Leu Asn Ser Val Thr
100 105 110

Pro Glu Asp Thr Ala Val Tyr Tyr Cys Ala Arg Glu Val Thr Gly Asp
115 120 125

Leu Glu Asp Ala Phe Asp Ile Trp Gly Gln Gly Thr Met Val Thr Val
130 135 140

Ser Ser Gly Gly Gly Gly Ser Gly Gly Gly Gly Ser Gly Gly Gly Gly
145 150 155 160

Ser Asp Ile Gln Met Thr Gln Ser Pro Ser Ser Leu Ser Ala Ser Val
165 170 175

Gly Asp Arg Val Thr Ile Thr Cys Arg Ala Ser Gln Thr Ile Trp Ser
180 185 190

Tyr Leu Asn Trp Tyr Gln Gln Arg Pro Gly Lys Ala Pro Asn Leu Leu
195 200 205

Ile Tyr Ala Ala Ser Ser Leu Gln Ser Gly Val Pro Ser Arg Phe Ser
210 215 220

Gly Arg Gly Ser Gly Thr Asp Phe Thr Leu Thr Ile Ser Ser Leu Gln
225 230 235 240

Ala Glu Asp Phe Ala Thr Tyr Tyr Cys Gln Gln Ser Tyr Ser Ile Pro
245 250 255

Gln Thr Phe Gly Gln Gly Thr Lys Leu Glu Ile Lys Ala Ala Ala Thr
260 265 270

Thr Thr Pro Ala Pro Arg Pro Pro Thr Pro Ala Pro Thr Ile Ala Ser
275 280 285

Gln Pro Leu Ser Leu Arg Pro Glu Ala Cys Arg Pro Ala Ala Gly Gly
290 295 300

Ala Val His Thr Arg Gly Leu Asp Phe Ala Cys Asp Ile Tyr Ile Trp
305 310 315 320

-continued

```
Ala Pro Leu Ala Gly Thr Cys Gly Val Leu Leu Leu Ser Leu Val Ile
                325                 330                 335

Thr Leu Tyr Cys Lys Arg Gly Arg Lys Lys Leu Leu Tyr Ile Phe Lys
            340                 345                 350

Gln Pro Phe Met Arg Pro Val Gln Thr Thr Gln Glu Glu Asp Gly Cys
        355                 360                 365

Ser Cys Arg Phe Pro Glu Glu Glu Glu Gly Gly Cys Glu Leu Arg Val
    370                 375                 380

Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490


<210> SEQ ID NO 77
<211> LENGTH: 66
<212> TYPE: DNA
<213> ORGANISM: Artificial
<220> FEATURE:
<223> OTHER INFORMATION: GMCSF leader peptide

<400> SEQUENCE: 77

atgcttcttt tggtgacttc ccttttgctg tgcgagttgc cacaccccgc cttcctgctt      60

attccc                                                                 66


<210> SEQ ID NO 78
<211> LENGTH: 22
<212> TYPE: PRT
<213> ORGANISM: Artificial
<220> FEATURE:
<223> OTHER INFORMATION: GMCSF leader peptide

<400> SEQUENCE: 78

Met Leu Leu Leu Val Thr Ser Leu Leu Leu Cys Glu Leu Pro His Pro
1               5                   10                  15

Ala Phe Leu Leu Ile Pro
            20


<210> SEQ ID NO 79
<211> LENGTH: 63
<212> TYPE: DNA
<213> ORGANISM: Artificial
<220> FEATURE:
<223> OTHER INFORMATION: CD8a leader peptide

<400> SEQUENCE: 79

atggccctgc ccgtcactgc gctgcttctt ccacttgcgc ttctgctgca cgcagcgcgc      60

ccg                                                                    63


<210> SEQ ID NO 80
```

<211> LENGTH: 21
<212> TYPE: PRT
<213> ORGANISM: Artificial
<220> FEATURE:
<223> OTHER INFORMATION: CD8a leader peptide

<400> SEQUENCE: 80

Met Ala Leu Pro Val Thr Ala Leu Leu Leu Pro Leu Ala Leu Leu Leu
1 5 10 15

His Ala Ala Arg Pro
20

<210> SEQ ID NO 81
<211> LENGTH: 216
<212> TYPE: DNA
<213> ORGANISM: Artificial
<220> FEATURE:
<223> OTHER INFORMATION: CD8 hinge and transmembrane domain

<400> SEQUENCE: 81
gcggccgcta ccacaacccc tgcgccccgg cctcctaccc ccgcacccac gattgcttct 60
caacctcttt cactccgacc tgaggcttgt agacctgcag ccgggggtgc cgtccacaca 120
cggggactcg acttcgcttg tgatatatat atttgggcgc cctggccgg cacttgtgga 180 gttcttttgc tctctcttgt tatcacattg tactgc 216

<210> SEQ ID NO 82
<211> LENGTH: 72
<212> TYPE: PRT
<213> ORGANISM: Artificial
<220> FEATURE:
<223> OTHER INFORMATION: CD8 hinge and transmembrane domain

<400> SEQUENCE: 82

Ala Ala Ala Thr Thr Thr Pro Ala Pro Arg Pro Pro Thr Pro Ala Pro
1 5 10 15

Thr Ile Ala Ser Gln Pro Leu Ser Leu Arg Pro Glu Ala Cys Arg Pro
20 25 30

Ala Ala Gly Gly Ala Val His Thr Arg Gly Leu Asp Phe Ala Cys Asp
35 40 45

Ile Tyr Ile Trp Ala Pro Leu Ala Gly Thr Cys Gly Val Leu Leu Leu
50 55 60

Ser Leu Val Ile Thr Leu Tyr Cys
65 70

<210> SEQ ID NO 83
<211> LENGTH: 126
<212> TYPE: DNA
<213> ORGANISM: Artificial
<220> FEATURE:
<223> OTHER INFORMATION: 4-1BB/CD137 costimulatory domain

<400> SEQUENCE: 83
aagcgaggta ggaagaaatt gctttacatt tttaagcagc cgttcatgcg accagtacag 60
actactcaag aagaagatgg gtgctcttgt cggttcccgg aagaagaaga gggtggttgc 120
gagttg 126

<210> SEQ ID NO 84
<211> LENGTH: 42
<212> TYPE: PRT
<213> ORGANISM: Artificial
<220> FEATURE:

<223> OTHER INFORMATION: 4-1BB/CD137 costimulatory domain

<400> SEQUENCE: 84

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 85
<211> LENGTH: 123
<212> TYPE: DNA
<213> ORGANISM: Artificial
<220> FEATURE:
<223> OTHER INFORMATION: CD28 costimulatory domain

<400> SEQUENCE: 85

```
cggtcgaagc gctcaagact gctgcactca gactacatga acatgactcc tcggcggccg      60

gggccgactc ggaagcacta ccagccttac gcacccccga gagatttcgc ggcctaccgc     120

tcc                                                                   123
```

<210> SEQ ID NO 86
<211> LENGTH: 41
<212> TYPE: PRT
<213> ORGANISM: Artificial
<220> FEATURE:
<223> OTHER INFORMATION: CD28 costimulatory domain

<400> SEQUENCE: 86

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 87
<211> LENGTH: 336
<212> TYPE: DNA
<213> ORGANISM: Artificial
<220> FEATURE:
<223> OTHER INFORMATION: synthetic oligonucleotide

<400> SEQUENCE: 87

```
agggtgaagt tctcccgctc tgccgacgca ccggcatatc agcagggaca aaaccagctc      60

tacaacgaat tgaacctggg tcggcgggaa gaatatgacg tgctcgataa gcggcggggt     120

cgcgacccag aaatgggagg caaaccgcgc aggaaaaatc cacaggaggg actttataac     180

gaacttcaaa aggataagat ggcagaggca tacagcgaaa tcgggatgaa aggcgagaga     240

agaaggggga aagggcacga tggtctttac caggggcttt ctaccgcgac gaaggatacc     300

tacgatgctc tccatatgca agcacttcct cctaga                               336
```

<210> SEQ ID NO 88
<211> LENGTH: 112
<212> TYPE: PRT
<213> ORGANISM: Artificial
<220> FEATURE:
<223> OTHER INFORMATION: synthetic polypeptide

<400> SEQUENCE: 88

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 89
<211> LENGTH: 91
<212> TYPE: DNA
<213> ORGANISM: Artificial
<220> FEATURE:
<223> OTHER INFORMATION: synthetic oligonucleotide

<400> SEQUENCE: 89

```
cgggcaaagc ggggctcagg ggcgactaac ttttcactgt tgaagcaggc cggggatgtg     60

gaggagaatc ctggtcctag agctaagcga g                                    91
```

<210> SEQ ID NO 90
<211> LENGTH: 30
<212> TYPE: PRT
<213> ORGANISM: Artificial
<220> FEATURE:
<223> OTHER INFORMATION: synthetic polypeptide

<400> SEQUENCE: 90

```
Arg Ala Lys Arg Gly Ser Gly Ala Thr Asn Phe Ser Leu Leu Lys Gln
1               5                   10                  15

Ala Gly Asp Val Glu Glu Asn Pro Gly Pro Arg Ala Lys Arg
            20                  25                  30
```

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95
<211> LENGTH: 366
<212> TYPE: DNA
<213> ORGANISM: Artificial
<220> FEATURE:
<223> OTHER INFORMATION: synthetic oligonucleotide

<400> SEQUENCE: 95
caggtacagc ttcaacagag tgggccggga ctggtgaaac actcccaaac actttctctg 60
acgtgcgcta tatcaggtga ctctgtttca tctaattctg ctgcgtggaa ctggattcga 120
caatctccca gtcgcgggtt ggaatggctg ggacgaacat attatcggtc taagtggtat 180
aacgattatg ctgtatctgt taaatctcga attacgatta atcctgacac ctccaagaac 240
cagttctccc tccagttgaa ctcagtcaca ccggaagaca ctgcggtcta ctattgcgct 300
caagaagtcg agccacatga tgcattcgac atctggggcc agggaacgat ggtcaccgtc 360
agcagt 366

<210> SEQ ID NO 96
<211> LENGTH: 122
<212> TYPE: PRT
<213> ORGANISM: Artificial
<220> FEATURE:
<223> OTHER INFORMATION: synthetic polypeptide

<400> SEQUENCE: 96

Gln Val Gln Leu Gln Gln Ser Gly Pro Gly Leu Val Lys His Ser Gln
1 5 10 15

Thr Leu Ser Leu Thr Cys Ala Ile Ser Gly Asp Ser Val Ser Ser Asn
20 25 30

Ser Ala Ala Trp Asn Trp Ile Arg Gln Ser Pro Ser Arg Gly Leu Glu
35 40 45

Trp Leu Gly Arg Thr Tyr Tyr Arg Ser Lys Trp Tyr Asn Asp Tyr Ala
50 55 60

Val Ser Val Lys Ser Arg Ile Thr Ile Asn Pro Asp Thr Ser Lys Asn
65 70 75 80

Gln Phe Ser Leu Gln Leu Asn Ser Val Thr Pro Glu Asp Thr Ala Val
85 90 95

Tyr Tyr Cys Ala Gln Glu Val Glu Pro His Asp Ala Phe Asp Ile Trp
100 105 110

Gly Gln Gly Thr Met Val Thr Val Ser Ser
115 120

<210> SEQ ID NO 97
<211> LENGTH: 321
<212> TYPE: DNA
<213> ORGANISM: Artificial
<220> FEATURE:
<223> OTHER INFORMATION: synthetic oligonucleotide

<400> SEQUENCE: 97
gacatacaaa tgacgcagag tccctcaagt gtgtacgcga gtgtggggga taaggtaact 60
attacgtgca gagcgtcaca ggatgttagt ggatggcttg cctggtatca gcagaagcca 120
ggccttgctc cacagctcct tatcagtggt gcttctacac ttcagggcga ggttccgagt 180
agattctctg gttctggatc tggtactgac ttcactctta caatttcttc tttgcaacca 240
gaagactttg cgacttatta ctgccaacag gccaaatact tcccttatac atttggccaa 300

-continued

```
ggtaccaagt tggagataaa g                                              321


<210> SEQ ID NO 98
<211> LENGTH: 107
<212> TYPE: PRT
<213> ORGANISM: Artificial
<220> FEATURE:
<223> OTHER INFORMATION: synthetic polypeptide

<400> SEQUENCE: 98

Asp Ile Gln Met Thr Gln Ser Pro Ser Ser Val Tyr Ala Ser Val Gly
1               5                   10                  15

Asp Lys Val Thr Ile Thr Cys Arg Ala Ser Gln Asp Val Ser Gly Trp
            20                  25                  30

Leu Ala Trp Tyr Gln Gln Lys Pro Gly Leu Ala Pro Gln Leu Leu Ile
        35                  40                  45

Ser Gly Ala Ser Thr Leu Gln Gly Glu Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Lys Tyr Phe Pro Tyr
                85                  90                  95

Thr Phe Gly Gln Gly Thr Lys Leu Glu Ile Lys
            100                 105


<210> SEQ ID NO 99
<211> LENGTH: 366
<212> TYPE: DNA
<213> ORGANISM: Artificial
<220> FEATURE:
<223> OTHER INFORMATION: synthetic oligonucleotide

<400> SEQUENCE: 99

caagtgcagc tgcagcagtc cggtcctgga ctggtcaagc cgtcccagac tctgagcctg      60

acttgcgcaa ttagcgggga ctcagtctcg tccaattcgg cggcctggaa ctggatccgg     120

cagtcaccat caaggggcct ggaatggctc gggcgcactt actaccggtc caaatggtat     180

accgactacg ccgtgtccgt gaagaatcgg atcaccatta accccgacac ctcgaagaac     240

cagttctcac tccaactgaa cagcgtgacc cccgaggata ccgcggtgta ctactgcgca     300

caagaagtgg aaccgcagga cgccttcgac atttggggac agggaacgat ggtcacagtg     360

tcgtcc                                                                366


<210> SEQ ID NO 100
<211> LENGTH: 122
<212> TYPE: PRT
<213> ORGANISM: Artificial
<220> FEATURE:
<223> OTHER INFORMATION: synthetic polypeptide

<400> SEQUENCE: 100

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Thr Asp Tyr Ala
    50                  55                  60
```

-continued

Val Ser Val Lys Asn Arg Ile Thr Ile Asn Pro Asp Thr Ser Lys Asn
65 70 75 80

Gln Phe Ser Leu Gln Leu Asn Ser Val Thr Pro Glu Asp Thr Ala Val
85 90 95

Tyr Tyr Cys Ala Gln Glu Val Glu Pro Gln Asp Ala Phe Asp Ile Trp
100 105 110

Gly Gln Gly Thr Met Val Thr Val Ser Ser
115 120

<210> SEQ ID NO 101
<211> LENGTH: 321
<212> TYPE: DNA
<213> ORGANISM: Artificial
<220> FEATURE:
<223> OTHER INFORMATION: synthetic oligonucleotide

<400> SEQUENCE: 101
gatatccaga tgacccagag cccctcctcg gtgtccgcat ccgtgggcga taaggtcacc 60
attacctgta gagcgtccca ggacgtgtcc ggatggctgg cctggtacca gcagaagcca 120
ggcttggctc ctcaactgct gatcttcggc gccagcactc ttcaggggga agtgccatca 180
cgcttctccg gatccggttc cggcaccgac ttcaccctga ccatcagcag cctccagcct 240
gaggacttcg ccacttacta ctgccaacag gccaagtact tcccctatac cttcggaaga 300
ggcactaagc tggaaatcaa g 321

<210> SEQ ID NO 102
<211> LENGTH: 107
<212> TYPE: PRT
<213> ORGANISM: Artificial
<220> FEATURE:
<223> OTHER INFORMATION: synthetic polypeptide

<400> SEQUENCE: 102

Asp Ile Gln Met Thr Gln Ser Pro Ser Ser Val Ser Ala Ser Val Gly
1 5 10 15

Asp Lys Val Thr Ile Thr Cys Arg Ala Ser Gln Asp Val Ser Gly Trp
20 25 30

Leu Ala Trp Tyr Gln Gln Lys Pro Gly Leu Ala Pro Gln Leu Leu Ile
35 40 45

Phe Gly Ala Ser Thr Leu Gln Gly Glu Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ala Lys Tyr Phe Pro Tyr
85 90 95

Thr Phe Gly Arg Gly Thr Lys Leu Glu Ile Lys
100 105

<210> SEQ ID NO 103
<211> LENGTH: 366
<212> TYPE: DNA
<213> ORGANISM: Artificial
<220> FEATURE:
<223> OTHER INFORMATION: synthetic oligonucleotide

<400> SEQUENCE: 103
caagtgcagc tgcagcagtc cggtcctgga ctggtcaagc cgtcccagac tctgagcctg 60
acttgcgcca ttagcgggaa ctcagtctcg tccaattcgg cggcctggaa ctggatccgg 120
cagtcaccat caaggggcct ggaatggctc gggcgcactt actaccggtc caaatggtat 180
aacgactacg ccgtgtccgt gaagtcccgg atcaccatta accccgacac ctcgaagaac 240
cagttctcac tccaactgaa cagcgtgacc cccgaggata ccgcggtgta ctactgcgca 300
caagaagtgg aaccgcagga cgccttcgac atttggggac agggaacgat ggtcacagtg 360
tcgtcc 366

<210> SEQ ID NO 104
<211> LENGTH: 122
<212> TYPE: PRT
<213> ORGANISM: Artificial
<220> FEATURE:
<223> OTHER INFORMATION: synthetic polypeptide

<400> SEQUENCE: 104

Gln Val Gln Leu Gln Gln Ser Gly Pro Gly Leu Val Lys Pro Ser Gln
1 5 10 15

Thr Leu Ser Leu Thr Cys Ala Ile Ser Gly Asn Ser Val Ser Ser Asn
20 25 30

Ser Ala Ala Trp Asn Trp Ile Arg Gln Ser Pro Ser Arg Gly Leu Glu
35 40 45

Trp Leu Gly Arg Thr Tyr Tyr Arg Ser Lys Trp Tyr Asn Asp Tyr Ala
50 55 60

Val Ser Val Lys Ser Arg Ile Thr Ile Asn Pro Asp Thr Ser Lys Asn
65 70 75 80

Gln Phe Ser Leu Gln Leu Asn Ser Val Thr Pro Glu Asp Thr Ala Val
85 90 95

Tyr Tyr Cys Ala Gln Glu Val Glu Pro Gln Asp Ala Phe Asp Ile Trp
100 105 110

Gly Gln Gly Thr Met Val Thr Val Ser Ser
115 120

<210> SEQ ID NO 105
<211> LENGTH: 321
<212> TYPE: DNA
<213> ORGANISM: Artificial
<220> FEATURE:
<223> OTHER INFORMATION: synthetic oligonucleotide

<400> SEQUENCE: 105
gatatccaga tgacccagag cccctcctcg gtgtccgcat ccgtgggcga taaggtcacc 60
attacctgta gagcgtccca ggacgtgtcc ggatggctgg cctggtacca gcagaagcca 120
ggcttggctc ctcaactgct gatctttggc gccagcactc ttcaggggga ggtgccatca 180
cgcttctccg gaggtggttc cggcaccgac ttcaccctga ccatcagcag cctccagcct 240
gaggacttcg ccacttacta ctgccaacag gccaagtact tcccctatac cttcggacaa 300
ggcactaagc tggaaatcaa g 321

<210> SEQ ID NO 106
<211> LENGTH: 107
<212> TYPE: PRT
<213> ORGANISM: Artificial
<220> FEATURE:
<223> OTHER INFORMATION: synthetic polypeptide

<400> SEQUENCE: 106

Asp Ile Gln Met Thr Gln Ser Pro Ser Ser Val Ser Ala Ser Val Gly
1 5 10 15

Asp Lys Val Thr Ile Thr Cys Arg Ala Ser Gln Asp Val Ser Gly Trp
            20                  25                  30

Leu Ala Trp Tyr Gln Gln Lys Pro Gly Leu Ala Pro Gln Leu Leu Ile
        35                  40                  45

Phe Gly Ala Ser Thr Leu Gln Gly Glu Val Pro Ser Arg Phe Ser Gly
    50                  55                  60

Gly Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Lys Tyr Phe Pro Tyr
                85                  90                  95

Thr Phe Gly Gln Gly Thr Lys Leu Glu Ile Lys
            100                 105

<210> SEQ ID NO 107
<211> LENGTH: 18
<212> TYPE: PRT
<213> ORGANISM: Artificial
<220> FEATURE:
<223> OTHER INFORMATION: Whitlow linker

<400> SEQUENCE: 107

Gly Ser Thr Ser Gly Ser Gly Lys Pro Gly Ser Gly Glu Gly Ser Thr
1               5                   10                  15

Lys Gly

<210> SEQ ID NO 108
<211> LENGTH: 25
<212> TYPE: PRT
<213> ORGANISM: Artificial
<220> FEATURE:
<223> OTHER INFORMATION: flexible interchain linker

<400> SEQUENCE: 108

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 109
<211> LENGTH: 3711
<212> TYPE: DNA
<213> ORGANISM: Artificial
<220> FEATURE:
<223> OTHER INFORMATION: LTG 2948 DuoCAR D93 CAR2019 ICOZz 2A CAR22z

<400> SEQUENCE: 109
atgctccttc tcgtgacctc cctgcttctc tgcgaactgc cccatcctgc cttcctgctg      60
attcccgagg tgcagttgca acagtcagga gctgaactgg tcaagccagg agccagcgtg     120
aagatgagct gcaaggcctc cggttacacc ttcacctcct acaacatgca ctgggtgaaa     180
cagaccccgg gacaagggct cgaatggatt ggcgccatct accccgggaa tggcgatact     240
tcgtacaacc agaagttcaa gggaaaggcc accctgaccg ccgacaagag ctcctccacc     300
gcgtatatgc agttgagctc cctgacctcc gaggactccg ccgactacta ctgcgcacgg     360
tccaactact atggaagctc gtactggttc ttcgatgtct gggggggccgg caccactgtg     420 accgtcagct ccgggggcgg aggatccggt ggaggcggaa gcgggggtgg aggatccgac     480
attgtgctga ctcagtcccc ggcaatcctg tcggcctcac cgggcgaaaa ggtcacgatg     540
acttgtagag cgtcgtccag cgtgaactac atggattggt accaaaagaa gcctggatcg     600

-continued

```
tcacccaagc cttggatcta cgctacatct aacctggcct ccggcgtgcc agcgcggttc    660
agcgggtccg gctcgggcac ctcatactcg ctgaccatct cccgcgtgga ggctgaggac    720
gccgcgacct actactgcca gcagtggtcc ttcaacccgc cgacttttgg aggcggtact    780
aagctggaga tcaaaggagg cggcggcagc ggcgggggag ggtccggagg gggtggttct    840
ggtggaggag gatcgggagg cggtggcagc gacattcaga tgactcagac cacctcctcc    900
ctgtccgcct ccctgggcga ccgcgtgacc atctcatgcc gcgccagcca ggacatctcg    960
aagtacctca actggtacca gcagaagccc gacggaaccg tgaagctcct gatctaccac   1020
acctcccggc tgcacagcgg agtgccgtct agattctcgg gttcggggtc gggaactgac   1080
tactccctta ctatttccaa cctggagcag gaggatattg ccacctactt ctgccaacaa   1140
ggaaacaccc tgccgtacac ttttggcggg ggaaccaagc tggaaatcac tggcagcaca   1200
tccggttccg ggaagcccgg ctccggagag ggcagcacca agggggaagt caagctgcag   1260
gaatcaggac ctggcctggt ggccccgagc cagtcactgt ccgtgacttg tactgtgtcc   1320
ggagtgtcgc tcccggatta cggagtgtcc tggatcaggc agccacctcg gaaaggattg   1380
gaatggctcg gagtcatctg gggttccgaa accacctatt acaactcggc actgaaatcc   1440
aggctcacca ttatcaagga taactccaag tcacaagtgt tcctgaagat gaatagcctg   1500
cagactgacg acacggcgat ctactattgc gccaagcact actactacgg cggatcctac   1560
gctatggact actggggcca ggggaccagc gtgaccgtgt catccgcggc cgcaacgacc   1620
actcctgcac cacggccacc taccccagcc cccaccattg caagccagcc actttcactg   1680
cgccccgaag cgtgtagacc agctgctgga ggagccgtgc atacccgagg gctggacttc   1740
gcctgtgaca tctacatctg ggccccattg gctggaactt gcggcgtgct gctcttgtct   1800
ctggtcatta ccctgtactg ctggctgaca aaaaagaagt attcatctag tgtacatgat   1860
ccgaacggtg aatacatgtt catgcgcgcg gtgaacacgg ccaagaagag cagactgacc   1920
gacgtaaccc ttagagtgaa gtttagccgc tcagccgatg caccggccta ccagcaggga   1980
cagaaccagc tctacaacga gctcaacctg ggtcggcggg aagaatatga cgtgctggac   2040
aaacggcgcg gcagagatcc ggagatgggg ggaaagccga ggaggaagaa ccctcaagag   2100
ggcctgtaca acgaactgca gaaggacaag atggcggaag cctactccga gatcggcatg   2160
aagggagaac gccggagagg gaagggtcat gacggactgt accagggcct gtcaactgcc   2220
actaaggaca cttacgatgc gctccatatg caagctttgc cccgcggcg cgcgaaacgc   2280
ggcagcggcg cgaccaactt tagcctgctg aaacaggcgg gcgatgtgga agaaaacccg   2340
ggcccgcgag caaagaggaa tattatggct ctgcctgtta cggcactgct ccttccgctt   2400
gcattgttgt tgcacgcagc gcggccccaa gtgcagctgc agcagtccgg tcctggactg   2460
gtcaagccgt cccagactct gagcctgact tgcgcaatta gcggggactc agtctcgtcc   2520
aattcggcgg cctggaactg gatccggcag tcaccatcaa ggggcctgga atggctcggg   2580
cgcacttact accggtccaa atggtatacc gactacgccg tgtccgtgaa gaatcggatc   2640
accattaacc ccgacacctc gaagaaccag ttctcactcc aactgaacag cgtgaccccc   2700
gaggataccg cggtgtacta ctgcgcacaa gaagtggaac cgcaggacgc cttcgacatt   2760
tggggacagg gaacgatggt cacagtgtcg tccggtggag gaggttccgg aggcggtgga   2820
tctggaggcg gaggttcgga tatccagatg acccagagcc cctcctcggt gtccgcatcc   2880
gtgggcgata aggtcaccat tacctgtaga gcgtcccagg acgtgtccgg atggctggcc   2940
tggtaccagc agaagccagg cttggctcct caactgctga tcttcggcgc cagcactctt   3000
```

-continued

```
caggggaag tgccatcacg cttctccgga tccggttccg gcaccgactt caccctgacc   3060

atcagcagcc tccagcctga ggacttcgcc acttactact gccaacaggc caagtacttc   3120

ccctatacct tcggaagagg cactaagctg gaaatcaagg ctagcgcaac cactacgcct   3180

gctccgcggc ctccaacgcc cgcgcccacg atagctagtc agccgttgtc tctccgacca   3240

gaggcgtgta gaccggccgc tggcggagcc gtacatactc gcggactcga cttcgcttgc   3300

gacatctaca tttgggcacc cttggctggg acctgtgggg tgctgttgct gtccttggtt   3360

attacgttgt actgcagagt caaattttcc aggtccgcag atgcccccgc gtaccagcaa   3420

ggccagaacc aactttacaa cgaactgaac ctgggtcgcc gggaggaata tgatgtgctg   3480

gataaacgaa gggggaggga ccctgagatg ggagggaaac ctcgcaggaa aaacccgcag   3540

gaaggtttgt acaacgagtt gcagaaggat aagatggctg aggcttactc tgaaataggg   3600

atgaagggag agagacggag aggaaaaggc catgatggcc tttaccaggg cttaagcaca   3660

gcaacaaagg atacttacga cgctcttcac atgcaagctc tgccaccacg g            3711
```

<210> SEQ ID NO 110
<211> LENGTH: 1237
<212> TYPE: PRT
<213> ORGANISM: Artificial
<220> FEATURE:
<223> OTHER INFORMATION: LTG 2948 DuoCAR D93 CAR2019 ICOZz 2A CAR22z

<400> SEQUENCE: 110

```
Met Leu Leu Leu Val Thr Ser Leu Leu Leu Cys Glu Leu Pro His Pro
1               5                   10                  15

Ala Phe Leu Leu Ile Pro Glu Val Gln Leu Gln Gln Ser Gly Ala Glu
            20                  25                  30

Leu Val Lys Pro Gly Ala Ser Val Lys Met Ser Cys Lys Ala Ser Gly
        35                  40                  45

Tyr Thr Phe Thr Ser Tyr Asn Met His Trp Val Lys Gln Thr Pro Gly
    50                  55                  60

Gln Gly Leu Glu Trp Ile Gly Ala Ile Tyr Pro Gly Asn Gly Asp Thr
65                  70                  75                  80

Ser Tyr Asn Gln Lys Phe Lys Gly Lys Ala Thr Leu Thr Ala Asp Lys
                85                  90                  95

Ser Ser Ser Thr Ala Tyr Met Gln Leu Ser Ser Leu Thr Ser Glu Asp
            100                 105                 110

Ser Ala Asp Tyr Tyr Cys Ala Arg Ser Asn Tyr Tyr Gly Ser Ser Tyr
        115                 120                 125

Trp Phe Phe Asp Val Trp Gly Ala Gly Thr Thr Val Thr Val Ser Ser
    130                 135                 140

Gly Gly Gly Gly Ser Gly Gly Gly Gly Ser Gly Gly Gly Gly Ser Asp
145                 150                 155                 160

Ile Val Leu Thr Gln Ser Pro Ala Ile Leu Ser Ala Ser Pro Gly Glu
                165                 170                 175

Lys Val Thr Met Thr Cys Arg Ala Ser Ser Ser Val Asn Tyr Met Asp
            180                 185                 190

Trp Tyr Gln Lys Lys Pro Gly Ser Ser Pro Lys Pro Trp Ile Tyr Ala
        195                 200                 205

Thr Ser Asn Leu Ala Ser Gly Val Pro Ala Arg Phe Ser Gly Ser Gly
    210                 215                 220

Ser Gly Thr Ser Tyr Ser Leu Thr Ile Ser Arg Val Glu Ala Glu Asp
225                 230                 235                 240
```

-continued

```
Ala Ala Thr Tyr Tyr Cys Gln Gln Trp Ser Phe Asn Pro Pro Thr Phe
                245                 250                 255

Gly Gly Gly Thr Lys Leu Glu Ile Lys Gly Gly Gly Gly Ser Gly Gly
            260                 265                 270

Gly Gly Ser Gly Gly Gly Gly Ser Gly Gly Gly Gly Ser Gly Gly Gly
        275                 280                 285

Gly Ser Asp Ile Gln Met Thr Gln Thr Thr Ser Ser Leu Ser Ala Ser
    290                 295                 300

Leu Gly Asp Arg Val Thr Ile Ser Cys Arg Ala Ser Gln Asp Ile Ser
305                 310                 315                 320

Lys Tyr Leu Asn Trp Tyr Gln Gln Lys Pro Asp Gly Thr Val Lys Leu
                325                 330                 335

Leu Ile Tyr His Thr Ser Arg Leu His Ser Gly Val Pro Ser Arg Phe
            340                 345                 350

Ser Gly Ser Gly Ser Gly Thr Asp Tyr Ser Leu Thr Ile Ser Asn Leu
        355                 360                 365

Glu Gln Glu Asp Ile Ala Thr Tyr Phe Cys Gln Gln Gly Asn Thr Leu
    370                 375                 380

Pro Tyr Thr Phe Gly Gly Gly Thr Lys Leu Glu Ile Thr Gly Ser Thr
385                 390                 395                 400

Ser Gly Ser Gly Lys Pro Gly Ser Gly Glu Gly Ser Thr Lys Gly Glu
                405                 410                 415

Val Lys Leu Gln Glu Ser Gly Pro Gly Leu Val Ala Pro Ser Gln Ser
            420                 425                 430

Leu Ser Val Thr Cys Thr Val Ser Gly Val Ser Leu Pro Asp Tyr Gly
        435                 440                 445

Val Ser Trp Ile Arg Gln Pro Pro Arg Lys Gly Leu Glu Trp Leu Gly
    450                 455                 460

Val Ile Trp Gly Ser Glu Thr Thr Tyr Tyr Asn Ser Ala Leu Lys Ser
465                 470                 475                 480

Arg Leu Thr Ile Ile Lys Asp Asn Ser Lys Ser Gln Val Phe Leu Lys
                485                 490                 495

Met Asn Ser Leu Gln Thr Asp Asp Thr Ala Ile Tyr Tyr Cys Ala Lys
            500                 505                 510

His Tyr Tyr Tyr Gly Gly Ser Tyr Ala Met Asp Tyr Trp Gly Gln Gly
        515                 520                 525

Thr Ser Val Thr Val Ser Ser Ala Ala Ala Thr Thr Thr Pro Ala Pro
    530                 535                 540

Arg Pro Pro Thr Pro Ala Pro Thr Ile Ala Ser Gln Pro Leu Ser Leu
545                 550                 555                 560

Arg Pro Glu Ala Cys Arg Pro Ala Ala Gly Gly Ala Val His Thr Arg
                565                 570                 575

Gly Leu Asp Phe Ala Cys Asp Ile Tyr Ile Trp Ala Pro Leu Ala Gly
            580                 585                 590

Thr Cys Gly Val Leu Leu Leu Ser Leu Val Ile Thr Leu Tyr Cys Trp
        595                 600                 605

Leu Thr Lys Lys Lys Tyr Ser Ser Ser Val His Asp Pro Asn Gly Glu
    610                 615                 620

Tyr Met Phe Met Arg Ala Val Asn Thr Ala Lys Lys Ser Arg Leu Thr
625                 630                 635                 640

Asp Val Thr Leu Arg Val Lys Phe Ser Arg Ser Ala Asp Ala Pro Ala
                645                 650                 655
```

```
Tyr Gln Gln Gly Gln Asn Gln Leu Tyr Asn Glu Leu Asn Leu Gly Arg
            660                 665                 670

Arg Glu Glu Tyr Asp Val Leu Asp Lys Arg Arg Gly Arg Asp Pro Glu
        675                 680                 685

Met Gly Gly Lys Pro Arg Arg Lys Asn Pro Gln Glu Gly Leu Tyr Asn
    690                 695                 700

Glu Leu Gln Lys Asp Lys Met Ala Glu Ala Tyr Ser Glu Ile Gly Met
705                 710                 715                 720

Lys Gly Glu Arg Arg Arg Gly Lys Gly His Asp Gly Leu Tyr Gln Gly
                725                 730                 735

Leu Ser Thr Ala Thr Lys Asp Thr Tyr Asp Ala Leu His Met Gln Ala
            740                 745                 750

Leu Pro Pro Arg Arg Ala Lys Arg Gly Ser Gly Ala Thr Asn Phe Ser
        755                 760                 765

Leu Leu Lys Gln Ala Gly Asp Val Glu Glu Asn Pro Gly Pro Arg Ala
    770                 775                 780

Lys Arg Asn Ile Met Ala Leu Pro Val Thr Ala Leu Leu Leu Pro Leu
785                 790                 795                 800

Ala Leu Leu Leu His Ala Ala Arg Pro Gln Val Gln Leu Gln Gln Ser
                805                 810                 815

Gly Pro Gly Leu Val Lys Pro Ser Gln Thr Leu Ser Leu Thr Cys Ala
            820                 825                 830

Ile Ser Gly Asp Ser Val Ser Ser Asn Ser Ala Ala Trp Asn Trp Ile
        835                 840                 845

Arg Gln Ser Pro Ser Arg Gly Leu Glu Trp Leu Gly Arg Thr Tyr Tyr
    850                 855                 860

Arg Ser Lys Trp Tyr Thr Asp Tyr Ala Val Ser Val Lys Asn Arg Ile
865                 870                 875                 880

Thr Ile Asn Pro Asp Thr Ser Lys Asn Gln Phe Ser Leu Gln Leu Asn
                885                 890                 895

Ser Val Thr Pro Glu Asp Thr Ala Val Tyr Tyr Cys Ala Gln Glu Val
            900                 905                 910

Glu Pro Gln Asp Ala Phe Asp Ile Trp Gly Gln Gly Thr Met Val Thr
        915                 920                 925

Val Ser Ser Gly Gly Gly Gly Ser Gly Gly Gly Gly Ser Gly Gly Gly
    930                 935                 940

Gly Ser Asp Ile Gln Met Thr Gln Ser Pro Ser Ser Val Ser Ala Ser
945                 950                 955                 960

Val Gly Asp Lys Val Thr Ile Thr Cys Arg Ala Ser Gln Asp Val Ser
                965                 970                 975

Gly Trp Leu Ala Trp Tyr Gln Gln Lys Pro Gly Leu Ala Pro Gln Leu
            980                 985                 990

Leu Ile Phe Gly Ala Ser Thr Leu  Gln Gly Glu Val Pro  Ser Arg Phe
        995                 1000                1005

Ser Gly  Ser Gly Ser Gly Thr  Asp Phe Thr Leu Thr  Ile Ser Ser
    1010                1015                1020

Leu Gln  Pro Glu Asp Phe Ala  Thr Tyr Tyr Cys Gln  Gln Ala Lys
    1025                1030                1035

Tyr Phe  Pro Tyr Thr Phe Gly  Arg Gly Thr Lys Leu  Glu Ile Lys
    1040                1045                1050

Ala Ser  Ala Thr Thr Thr Pro  Ala Pro Arg Pro Pro  Thr Pro Ala
    1055                1060                1065

Pro Thr  Ile Ala Ser Gln Pro  Leu Ser Leu Arg Pro  Glu Ala Cys
```

-continued 1070 1075 1080

Arg Pro Ala Ala Gly Gly Ala Val His Thr Arg Gly Leu Asp Phe
1085 1090 1095

Ala Cys Asp Ile Tyr Ile Trp Ala Pro Leu Ala Gly Thr Cys Gly
1100 1105 1110

Val Leu Leu Leu Ser Leu Val Ile Thr Leu Tyr Cys Arg Val Lys
1115 1120 1125

Phe Ser Arg Ser Ala Asp Ala Pro Ala Tyr Gln Gln Gly Gln Asn
1130 1135 1140

Gln Leu Tyr Asn Glu Leu Asn Leu Gly Arg Arg Glu Glu Tyr Asp
1145 1150 1155

Val Leu Asp Lys Arg Arg Gly Arg Asp Pro Glu Met Gly Gly Lys
1160 1165 1170

Pro Arg Arg Lys Asn Pro Gln Glu Gly Leu Tyr Asn Glu Leu Gln
1175 1180 1185

Lys Asp Lys Met Ala Glu Ala Tyr Ser Glu Ile Gly Met Lys Gly
1190 1195 1200

Glu Arg Arg Arg Gly Lys Gly His Asp Gly Leu Tyr Gln Gly Leu
1205 1210 1215

Ser Thr Ala Thr Lys Asp Thr Tyr Asp Ala Leu His Met Gln Ala
1220 1225 1230

Leu Pro Pro Arg
1235

<210> SEQ ID NO 111
<211> LENGTH: 3717
<212> TYPE: PRT
<213> ORGANISM: Artificial
<220> FEATURE:
<223> OTHER INFORMATION: LTG 2949 DuoCAR D94 CAR2019 OX40z 2A CAR22z

<400> SEQUENCE: 111

Ala Thr Gly Cys Thr Cys Cys Thr Thr Cys Thr Cys Gly Thr Gly Ala
1 5 10 15

Cys Cys Thr Cys Cys Cys Thr Gly Cys Thr Thr Cys Thr Cys Thr Gly
20 25 30

Cys Gly Ala Ala Cys Thr Gly Cys Cys Cys Cys Ala Thr Cys Cys Thr
35 40 45

Gly Cys Cys Thr Thr Cys Cys Thr Gly Cys Thr Gly Ala Thr Thr Cys
50 55 60

Cys Cys Gly Ala Gly Gly Thr Gly Cys Ala Gly Thr Thr Gly Cys Ala
65 70 75 80

Ala Cys Ala Gly Thr Cys Ala Gly Gly Ala Gly Cys Thr Gly Ala Ala
85 90 95

Cys Thr Gly Gly Thr Cys Ala Ala Gly Cys Cys Ala Gly Gly Ala Gly
100 105 110

Cys Cys Ala Gly Cys Gly Thr Gly Ala Ala Gly Ala Thr Gly Ala Gly
115 120 125

Cys Thr Gly Cys Ala Ala Gly Gly Cys Cys Thr Cys Cys Gly Gly Thr
130 135 140

Thr Ala Cys Ala Cys Cys Thr Thr Cys Ala Cys Cys Thr Cys Cys Thr
145 150 155 160

Ala Cys Ala Ala Cys Ala Thr Gly Cys Ala Cys Thr Gly Gly Gly Thr
165 170 175

Gly Ala Ala Ala Cys Ala Gly Ala Cys Cys Cys Cys Gly Gly Gly Ala

-continued

```
            180                 185                 190

Cys Ala Ala Gly Gly Gly Cys Thr Cys Gly Ala Ala Thr Gly Gly Ala
        195                 200                 205

Thr Thr Gly Gly Cys Gly Cys Cys Ala Thr Cys Thr Ala Cys Cys Cys
    210                 215                 220

Cys Gly Gly Gly Ala Ala Thr Gly Gly Cys Gly Ala Thr Ala Cys Thr
225                 230                 235                 240

Thr Cys Gly Thr Ala Cys Ala Ala Cys Cys Ala Gly Ala Ala Gly Thr
                245                 250                 255

Thr Cys Ala Ala Gly Gly Gly Ala Ala Ala Gly Gly Cys Cys Ala Cys
            260                 265                 270

Cys Cys Thr Gly Ala Cys Cys Gly Cys Cys Gly Ala Cys Ala Ala Gly
        275                 280                 285

Ala Gly Cys Thr Cys Cys Thr Cys Cys Ala Cys Cys Gly Cys Gly Thr
    290                 295                 300

Ala Thr Ala Thr Gly Cys Ala Gly Thr Thr Gly Ala Gly Cys Thr Cys
305                 310                 315                 320

Cys Cys Thr Gly Ala Cys Cys Thr Cys Cys Gly Ala Gly Gly Ala Cys
                325                 330                 335

Thr Cys Cys Gly Cys Cys Gly Ala Cys Thr Ala Cys Thr Ala Cys Thr
            340                 345                 350

Gly Cys Gly Cys Ala Cys Gly Gly Thr Cys Cys Ala Ala Cys Thr Ala
        355                 360                 365

Cys Thr Ala Thr Gly Gly Ala Ala Gly Cys Thr Cys Gly Thr Ala Cys
    370                 375                 380

Thr Gly Gly Thr Thr Cys Thr Thr Cys Gly Ala Thr Gly Thr Cys Thr
385                 390                 395                 400

Gly Gly Gly Gly Gly Gly Cys Cys Gly Gly Cys Ala Cys Cys Ala Cys
                405                 410                 415

Thr Gly Thr Gly Ala Cys Cys Gly Thr Cys Ala Gly Cys Thr Cys Cys
            420                 425                 430

Gly Gly Gly Gly Gly Cys Gly Gly Ala Gly Gly Ala Thr Cys Cys Gly
        435                 440                 445

Gly Thr Gly Gly Ala Gly Gly Cys Gly Gly Ala Ala Gly Cys Gly Gly
    450                 455                 460

Gly Gly Gly Thr Gly Gly Ala Gly Gly Ala Thr Cys Cys Gly Ala Cys
465                 470                 475                 480

Ala Thr Thr Gly Thr Gly Cys Thr Gly Ala Cys Thr Cys Ala Gly Thr
                485                 490                 495

Cys Cys Cys Cys Gly Gly Cys Ala Ala Thr Cys Cys Thr Gly Thr Cys
            500                 505                 510

Gly Gly Cys Cys Thr Cys Ala Cys Cys Gly Gly Gly Cys Gly Ala Ala
        515                 520                 525

Ala Ala Gly Gly Thr Cys Ala Cys Gly Ala Thr Gly Ala Cys Thr Thr
    530                 535                 540

Gly Thr Ala Gly Ala Gly Cys Gly Thr Cys Gly Thr Cys Cys Ala Gly
545                 550                 555                 560

Cys Gly Thr Gly Ala Ala Cys Thr Ala Cys Ala Thr Gly Gly Ala Thr
                565                 570                 575

Thr Gly Gly Thr Ala Cys Cys Ala Ala Ala Gly Ala Ala Gly Cys
            580                 585                 590

Cys Thr Gly Gly Ala Thr Cys Gly Thr Cys Ala Cys Cys Cys Ala Ala
        595                 600                 605
```

```
Gly Cys Cys Thr Thr Gly Gly Ala Thr Cys Thr Ala Cys Gly Cys Thr
    610                 615                 620

Ala Cys Ala Thr Cys Thr Ala Ala Cys Cys Thr Gly Gly Cys Cys Thr
625                 630                 635                 640

Cys Cys Gly Gly Cys Gly Thr Gly Cys Cys Ala Gly Cys Gly Cys Gly
                645                 650                 655

Gly Thr Thr Cys Ala Gly Cys Gly Gly Gly Thr Cys Cys Gly Gly Cys
            660                 665                 670

Thr Cys Gly Gly Gly Cys Ala Cys Cys Thr Cys Ala Thr Ala Cys Thr
        675                 680                 685

Cys Gly Cys Thr Gly Ala Cys Cys Ala Thr Cys Thr Cys Cys Cys Gly
    690                 695                 700

Cys Gly Thr Gly Gly Ala Gly Gly Cys Thr Gly Ala Gly Gly Ala Cys
705                 710                 715                 720

Gly Cys Cys Gly Cys Gly Ala Cys Cys Thr Ala Cys Thr Ala Cys Thr
                725                 730                 735

Gly Cys Cys Ala Gly Cys Ala Gly Thr Gly Gly Thr Cys Cys Thr Thr
            740                 745                 750

Cys Ala Ala Cys Cys Cys Gly Cys Cys Gly Ala Cys Thr Thr Thr Thr
        755                 760                 765

Gly Gly Ala Gly Gly Cys Gly Gly Thr Ala Cys Thr Ala Ala Gly Cys
    770                 775                 780

Thr Gly Gly Ala Gly Ala Thr Cys Ala Ala Ala Gly Gly Ala Gly Gly
785                 790                 795                 800

Cys Gly Gly Cys Gly Gly Cys Ala Gly Cys Gly Gly Cys Gly Gly Gly
                805                 810                 815

Gly Gly Ala Gly Gly Gly Thr Cys Cys Gly Gly Ala Gly Gly Gly Gly
            820                 825                 830

Gly Thr Gly Gly Thr Thr Cys Thr Gly Gly Thr Gly Gly Ala Gly Gly
        835                 840                 845

Ala Gly Gly Ala Thr Cys Gly Gly Gly Ala Gly Gly Cys Gly Gly Thr
    850                 855                 860

Gly Gly Cys Ala Gly Cys Gly Ala Cys Ala Thr Thr Cys Ala Gly Ala
865                 870                 875                 880

Thr Gly Ala Cys Thr Cys Ala Gly Ala Cys Cys Ala Cys Cys Thr Cys
                885                 890                 895

Cys Thr Cys Cys Cys Thr Gly Thr Cys Cys Gly Cys Cys Thr Cys Cys
            900                 905                 910

Cys Thr Gly Gly Gly Cys Gly Ala Cys Cys Gly Cys Gly Thr Gly Ala
        915                 920                 925

Cys Cys Ala Thr Cys Thr Cys Ala Thr Gly Cys Cys Gly Cys Gly Cys
    930                 935                 940

Cys Ala Gly Cys Cys Ala Gly Gly Ala Cys Ala Thr Cys Thr Cys Gly
945                 950                 955                 960

Ala Ala Gly Thr Ala Cys Cys Thr Cys Ala Ala Cys Thr Gly Gly Thr
                965                 970                 975

Ala Cys Cys Ala Gly Cys Ala Gly Ala Ala Gly Cys Cys Cys Gly Ala
            980                 985                 990

Cys Gly Gly Ala Ala Cys Cys Gly  Thr Gly Ala Ala Gly  Cys Thr Cys
        995                 1000                1005

Cys Thr  Gly Ala Thr Cys Thr  Ala Cys Cys Ala Cys  Ala Cys Cys
    1010                1015                1020
```

-continued

```
Thr Cys  Cys Cys Gly Gly Cys  Thr Gly Cys Ala Cys  Ala Gly Cys
    1025                 1030                 1035

Gly Gly  Ala Gly Thr Gly Cys  Cys Gly Thr Cys Thr  Ala Gly Ala
    1040                 1045                 1050

Thr Thr  Cys Thr Cys Gly Gly  Gly Thr Thr Cys Gly  Gly Gly Gly
    1055                 1060                 1065

Thr Cys  Gly Gly Gly Ala Ala  Cys Thr Gly Ala Cys  Thr Ala Cys
    1070                 1075                 1080

Thr Cys  Cys Cys Thr Thr Ala  Cys Thr Ala Thr Thr  Thr Cys Cys
    1085                 1090                 1095

Ala Ala  Cys Cys Thr Gly Gly  Ala Gly Cys Ala Gly  Gly Ala Gly
    1100                 1105                 1110

Gly Ala  Thr Ala Thr Thr Gly  Cys Cys Ala Cys Cys  Thr Ala Cys
    1115                 1120                 1125

Thr Thr  Cys Thr Gly Cys Cys  Ala Ala Cys Ala Ala  Gly Gly Ala
    1130                 1135                 1140

Ala Ala  Cys Ala Cys Cys Cys  Thr Gly Cys Cys Gly  Thr Ala Cys
    1145                 1150                 1155

Ala Cys  Thr Thr Thr Thr Gly  Gly Cys Gly Gly Gly  Gly Gly Ala
    1160                 1165                 1170

Ala Cys  Cys Ala Ala Gly Cys  Thr Gly Gly Ala Ala  Ala Thr Cys
    1175                 1180                 1185

Ala Cys  Thr Gly Gly Cys Ala  Gly Cys Ala Cys Ala  Thr Cys Cys
    1190                 1195                 1200

Gly Gly  Thr Thr Cys Cys Gly  Gly Gly Ala Ala Gly  Cys Cys Cys
    1205                 1210                 1215

Gly Gly  Cys Thr Cys Cys Gly  Gly Ala Gly Ala Gly  Gly Gly Cys
    1220                 1225                 1230

Ala Gly  Cys Ala Cys Cys Ala  Ala Gly Gly Gly Gly  Gly Ala Ala
    1235                 1240                 1245

Gly Thr  Cys Ala Ala Gly Cys  Thr Gly Cys Ala Gly  Gly Ala Ala
    1250                 1255                 1260

Thr Cys  Ala Gly Gly Ala Cys  Cys Thr Gly Gly Cys  Cys Thr Gly
    1265                 1270                 1275

Gly Thr  Gly Gly Cys Cys Cys  Cys Gly Ala Gly Cys  Cys Ala Gly
    1280                 1285                 1290

Thr Cys  Ala Cys Thr Gly Thr  Cys Cys Gly Thr Gly  Ala Cys Thr
    1295                 1300                 1305

Thr Gly  Thr Ala Cys Thr Gly  Thr Gly Thr Cys Cys  Gly Gly Ala
    1310                 1315                 1320

Gly Thr  Gly Thr Cys Gly Cys  Thr Cys Cys Cys Gly  Gly Ala Thr
    1325                 1330                 1335

Thr Ala  Cys Gly Gly Ala Gly  Thr Gly Thr Cys Cys  Thr Gly Gly
    1340                 1345                 1350

Ala Thr  Cys Ala Gly Gly Cys  Ala Gly Cys Cys Ala  Cys Cys Thr
    1355                 1360                 1365

Cys Gly  Gly Ala Ala Ala Gly  Gly Ala Thr Thr Gly  Gly Ala Ala
    1370                 1375                 1380

Thr Gly  Gly Cys Thr Cys Gly  Gly Ala Gly Thr Cys  Ala Thr Cys
    1385                 1390                 1395

Thr Gly  Gly Gly Gly Thr Thr  Cys Cys Gly Ala Ala  Ala Cys Cys
    1400                 1405                 1410

Ala Cys  Cys Thr Ala Thr Thr  Ala Cys Ala Ala Cys  Thr Cys Gly
```

-continued 1415 1420 1425

Gly Cys Ala Cys Thr Gly Ala Ala Ala Thr Cys Cys Ala Gly Gly
1430 1435 1440

Cys Thr Cys Ala Cys Cys Ala Thr Thr Ala Thr Cys Ala Ala Gly
1445 1450 1455

Gly Ala Thr Ala Ala Cys Thr Cys Cys Ala Ala Gly Thr Cys Ala
1460 1465 1470

Cys Ala Ala Gly Thr Gly Thr Thr Cys Cys Thr Gly Ala Ala Gly
1475 1480 1485

Ala Thr Gly Ala Ala Thr Ala Gly Cys Cys Thr Gly Cys Ala Gly
1490 1495 1500

Ala Cys Thr Gly Ala Cys Gly Ala Cys Ala Cys Gly Gly Cys Gly
1505 1510 1515

Ala Thr Cys Thr Ala Cys Thr Ala Thr Thr Gly Cys Gly Cys Cys
1520 1525 1530

Ala Ala Gly Cys Ala Cys Thr Ala Cys Thr Ala Cys Thr Ala Cys
1535 1540 1545

Gly Gly Cys Gly Gly Ala Thr Cys Cys Thr Ala Cys Gly Cys Thr
1550 1555 1560

Ala Thr Gly Gly Ala Cys Thr Ala Cys Thr Gly Gly Gly Gly Cys
1565 1570 1575

Cys Ala Gly Gly Gly Gly Ala Cys Cys Ala Gly Cys Gly Thr Gly
1580 1585 1590

Ala Cys Cys Gly Thr Gly Thr Cys Ala Thr Cys Cys Gly Cys Gly
1595 1600 1605

Gly Cys Cys Gly Cys Ala Ala Cys Gly Ala Cys Cys Ala Cys Thr
1610 1615 1620

Cys Cys Ala Gly Cys Ala Cys Cys Gly Ala Gly Ala Cys Cys Gly
1625 1630 1635

Cys Cys Ala Ala Cys Cys Cys Cys Cys Gly Cys Gly Cys Cys Thr
1640 1645 1650

Ala Cys Cys Ala Thr Cys Gly Cys Ala Ala Gly Thr Cys Ala Ala
1655 1660 1665

Cys Cys Ala Cys Thr Thr Thr Cys Thr Cys Thr Cys Ala Gly Gly
1670 1675 1680

Cys Cys Thr Gly Ala Ala Gly Cys Gly Thr Gly Cys Cys Gly Ala
1685 1690 1695

Cys Cys Thr Gly Cys Ala Gly Cys Thr Gly Gly Thr Gly Gly Gly
1700 1705 1710

Gly Cys Ala Gly Thr Ala Cys Ala Thr Ala Cys Cys Ala Gly Gly
1715 1720 1725

Gly Gly Thr Thr Thr Gly Gly Ala Cys Thr Thr Cys Gly Cys Ala
1730 1735 1740

Thr Gly Thr Gly Ala Cys Gly Thr Gly Gly Cys Gly Gly Cys Ala
1745 1750 1755

Ala Thr Thr Cys Thr Cys Gly Gly Cys Cys Thr Gly Gly Gly Ala
1760 1765 1770

Cys Thr Thr Gly Thr Cys Cys Thr Thr Gly Gly Thr Cys Thr Gly
1775 1780 1785

Cys Thr Thr Gly Gly Thr Cys Cys Gly Cys Thr Cys Gly Cys Ala
1790 1795 1800

Ala Thr Ala Cys Thr Thr Cys Thr Gly Gly Cys Cys Thr Thr Gly
1805 1810 1815

```
Thr Ala  Cys Cys Thr Gly Cys  Thr Cys Cys Gly Cys  Ala Gly Ala
    1820                 1825                 1830

Gly Ala  Cys Cys Ala Ala Ala  Gly Ala Cys Thr Thr  Cys Cys Gly
    1835                 1840                 1845

Cys Cys  Cys Gly Ala Cys Gly  Cys Cys Cys Ala Cys  Ala Ala Gly
    1850                 1855                 1860

Cys Cys  Cys Cys Cys Ala Gly  Gly Ala Gly Gly Ala  Gly Gly Thr
    1865                 1870                 1875

Thr Cys  Cys Thr Thr Cys Ala  Gly Ala Ala Cys Gly  Cys Cys Thr
    1880                 1885                 1890

Ala Thr  Ala Cys Ala Ala Gly  Ala Ala Gly Ala Ala  Cys Ala Ala
    1895                 1900                 1905

Gly Cys  Ala Gly Ala Thr Gly  Cys Cys Cys Ala Cys  Thr Cys Thr
    1910                 1915                 1920

Ala Cys  Cys Cys Thr Gly Gly  Cys Thr Ala Ala Ala  Ala Thr Cys
    1925                 1930                 1935

Ala Gly  Gly Gly Thr Gly Ala  Ala Gly Thr Thr Thr  Ala Gly Cys
    1940                 1945                 1950

Cys Gly  Cys Thr Cys Ala Gly  Cys Cys Gly Ala Thr  Gly Cys Ala
    1955                 1960                 1965

Cys Cys  Gly Gly Cys Cys Thr  Ala Cys Cys Ala Gly  Cys Ala Gly
    1970                 1975                 1980

Gly Gly  Ala Cys Ala Gly Ala  Ala Cys Cys Ala Gly  Cys Thr Cys
    1985                 1990                 1995

Thr Ala  Cys Ala Ala Cys Gly  Ala Gly Cys Thr Cys  Ala Ala Cys
    2000                 2005                 2010

Cys Thr  Gly Gly Gly Thr Cys  Gly Gly Cys Gly Gly  Gly Ala Ala
    2015                 2020                 2025

Gly Ala  Ala Thr Ala Thr Gly  Ala Cys Gly Thr Gly  Cys Thr Gly
    2030                 2035                 2040

Gly Ala  Cys Ala Ala Ala Cys  Gly Gly Cys Gly Cys  Gly Gly Cys
    2045                 2050                 2055

Ala Gly  Ala Gly Ala Thr Cys  Cys Gly Gly Ala Gly  Ala Thr Gly
    2060                 2065                 2070

Gly Gly  Gly Gly Gly Ala Ala  Ala Gly Cys Cys Gly  Ala Gly Gly
    2075                 2080                 2085

Ala Gly  Gly Ala Ala Gly Ala  Ala Cys Cys Cys Thr  Cys Ala Ala
    2090                 2095                 2100

Gly Ala  Gly Gly Gly Cys Cys  Thr Gly Thr Ala Cys  Ala Ala Cys
    2105                 2110                 2115

Gly Ala  Ala Cys Thr Gly Cys  Ala Gly Ala Ala Gly  Gly Ala Cys
    2120                 2125                 2130

Ala Ala  Gly Ala Thr Gly Gly  Cys Gly Gly Ala Ala  Gly Cys Cys
    2135                 2140                 2145

Thr Ala  Cys Thr Cys Cys Gly  Ala Gly Ala Thr Cys  Gly Gly Cys
    2150                 2155                 2160

Ala Thr  Gly Ala Ala Gly Gly  Gly Ala Gly Ala Ala  Cys Gly Cys
    2165                 2170                 2175

Cys Gly  Gly Ala Gly Ala Gly  Gly Gly Ala Ala Gly  Gly Gly Thr
    2180                 2185                 2190

Cys Ala  Thr Gly Ala Cys Gly  Gly Ala Cys Thr Gly  Thr Ala Cys
    2195                 2200                 2205
```

-continued

Cys Ala Gly Gly Gly Cys Cys Thr Gly Thr Cys Ala Ala Cys Thr
2210 2215 2220

Gly Cys Cys Ala Cys Thr Ala Ala Gly Gly Ala Cys Ala Cys Thr
2225 2230 2235

Thr Ala Cys Gly Ala Thr Gly Cys Gly Cys Thr Cys Cys Ala Thr
2240 2245 2250

Ala Thr Gly Cys Ala Ala Gly Cys Thr Thr Thr Gly Cys Cys Cys
2255 2260 2265

Cys Cys Gly Cys Gly Gly Cys Gly Cys Gly Cys Gly Ala Ala Ala
2270 2275 2280

Cys Gly Cys Gly Gly Cys Ala Gly Cys Gly Gly Cys Gly Cys Gly
2285 2290 2295

Ala Cys Cys Ala Ala Cys Thr Thr Thr Ala Gly Cys Cys Thr Gly
2300 2305 2310

Cys Thr Gly Ala Ala Ala Cys Ala Gly Gly Cys Gly Gly Gly Cys
2315 2320 2325

Gly Ala Thr Gly Thr Gly Gly Ala Ala Gly Ala Ala Ala Ala Cys
2330 2335 2340

Cys Cys Gly Gly Gly Cys Cys Cys Gly Cys Gly Ala Gly Cys Ala
2345 2350 2355

Ala Ala Gly Ala Gly Gly Ala Ala Thr Ala Thr Thr Ala Thr Gly
2360 2365 2370

Gly Cys Thr Cys Thr Gly Cys Cys Thr Gly Thr Thr Ala Cys Gly
2375 2380 2385

Gly Cys Ala Cys Thr Gly Cys Thr Cys Cys Thr Thr Cys Cys Gly
2390 2395 2400

Cys Thr Thr Gly Cys Ala Thr Thr Gly Thr Thr Gly Thr Thr Gly
2405 2410 2415

Cys Ala Cys Gly Cys Ala Gly Cys Gly Cys Gly Gly Cys Cys Cys
2420 2425 2430

Cys Ala Ala Gly Thr Gly Cys Ala Gly Cys Thr Gly Cys Ala Gly
2435 2440 2445

Cys Ala Gly Thr Cys Cys Gly Gly Thr Cys Cys Thr Gly Gly Ala
2450 2455 2460

Cys Thr Gly Gly Thr Cys Ala Ala Gly Cys Cys Gly Thr Cys Cys
2465 2470 2475

Cys Ala Gly Ala Cys Thr Cys Thr Gly Ala Gly Cys Cys Thr Gly
2480 2485 2490

Ala Cys Thr Thr Gly Cys Gly Cys Ala Ala Thr Thr Ala Gly Cys
2495 2500 2505

Gly Gly Gly Gly Ala Cys Thr Cys Ala Gly Thr Cys Thr Cys Gly
2510 2515 2520

Thr Cys Cys Ala Ala Thr Thr Cys Gly Gly Cys Gly Gly Cys Cys
2525 2530 2535

Thr Gly Gly Ala Ala Cys Thr Gly Gly Ala Thr Cys Cys Gly Gly
2540 2545 2550

Cys Ala Gly Thr Cys Ala Cys Cys Ala Thr Cys Ala Ala Gly Gly
2555 2560 2565

Gly Gly Cys Cys Thr Gly Gly Ala Ala Thr Gly Gly Cys Thr Cys
2570 2575 2580

Gly Gly Gly Cys Gly Cys Ala Cys Thr Thr Ala Cys Thr Ala Cys
2585 2590 2595

Cys Gly Gly Thr Cys Cys Ala Ala Ala Thr Gly Gly Thr Ala Thr 2600 2605 2610

Ala Cys Cys Gly Ala Cys Thr Ala Cys Gly Cys Cys Gly Thr Gly
2615 2620 2625

Thr Cys Cys Gly Thr Gly Ala Ala Gly Ala Ala Thr Cys Gly Gly
2630 2635 2640

Ala Thr Cys Ala Cys Cys Ala Thr Thr Ala Ala Cys Cys Cys Cys
2645 2650 2655

Gly Ala Cys Ala Cys Cys Thr Cys Gly Ala Ala Gly Ala Ala Cys
2660 2665 2670

Cys Ala Gly Thr Thr Cys Thr Cys Ala Cys Thr Cys Cys Ala Ala
2675 2680 2685

Cys Thr Gly Ala Ala Cys Ala Gly Cys Gly Thr Gly Ala Cys Cys
2690 2695 2700

Cys Cys Cys Gly Ala Gly Gly Ala Thr Ala Cys Cys Gly Cys Gly
2705 2710 2715

Gly Thr Gly Thr Ala Cys Thr Ala Cys Thr Gly Cys Gly Cys Ala
2720 2725 2730

Cys Ala Ala Gly Ala Ala Gly Thr Gly Gly Ala Ala Cys Cys Gly
2735 2740 2745

Cys Ala Gly Gly Ala Cys Gly Cys Cys Thr Thr Cys Gly Ala Cys
2750 2755 2760

Ala Thr Thr Thr Gly Gly Gly Gly Ala Cys Ala Gly Gly Gly Ala
2765 2770 2775

Ala Cys Gly Ala Thr Gly Gly Thr Cys Ala Cys Ala Gly Thr Gly
2780 2785 2790

Thr Cys Gly Thr Cys Cys Gly Gly Thr Gly Gly Ala Gly Gly Ala
2795 2800 2805

Gly Gly Thr Thr Cys Cys Gly Gly Ala Gly Gly Cys Gly Gly Thr
2810 2815 2820

Gly Gly Ala Thr Cys Thr Gly Gly Ala Gly Gly Cys Gly Gly Ala
2825 2830 2835

Gly Gly Thr Thr Cys Gly Gly Ala Thr Ala Thr Cys Cys Ala Gly
2840 2845 2850

Ala Thr Gly Ala Cys Cys Cys Ala Gly Ala Gly Cys Cys Cys Cys
2855 2860 2865

Thr Cys Cys Thr Cys Gly Gly Thr Gly Thr Cys Cys Gly Cys Ala
2870 2875 2880

Thr Cys Cys Gly Thr Gly Gly Gly Cys Gly Ala Thr Ala Ala Gly
2885 2890 2895

Gly Thr Cys Ala Cys Cys Ala Thr Thr Ala Cys Cys Thr Gly Thr
2900 2905 2910

Ala Gly Ala Gly Cys Gly Thr Cys Cys Cys Ala Gly Gly Ala Cys
2915 2920 2925

Gly Thr Gly Thr Cys Cys Gly Gly Ala Thr Gly Gly Cys Thr Gly
2930 2935 2940

Gly Cys Cys Thr Gly Gly Thr Ala Cys Cys Ala Gly Cys Ala Gly
2945 2950 2955

Ala Ala Gly Cys Cys Ala Gly Gly Cys Thr Thr Gly Gly Cys Thr
2960 2965 2970

Cys Cys Thr Cys Ala Ala Cys Thr Gly Cys Thr Gly Ala Thr Cys
2975 2980 2985

Thr Thr Cys Gly Gly Cys Gly Cys Cys Ala Gly Cys Ala Cys Thr
2990 2995 3000

-continued

```
Cys Thr  Thr Cys Ala Gly Gly  Gly Gly Gly Ala Ala  Gly Thr Gly
    3005                 3010                 3015

Cys Cys  Ala Thr Cys Ala Cys  Gly Cys Thr Thr Cys  Thr Cys Cys
    3020                 3025                 3030

Gly Gly  Ala Thr Cys Cys Gly  Gly Thr Thr Cys Cys  Gly Gly Cys
    3035                 3040                 3045

Ala Cys  Cys Gly Ala Cys Thr  Thr Cys Ala Cys Cys  Cys Thr Gly
    3050                 3055                 3060

Ala Cys  Cys Ala Thr Cys Ala  Gly Cys Ala Gly Cys  Cys Thr Cys
    3065                 3070                 3075

Cys Ala  Gly Cys Cys Thr Gly  Ala Gly Gly Ala Cys  Thr Thr Cys
    3080                 3085                 3090

Gly Cys  Cys Ala Cys Thr Thr  Ala Cys Thr Ala Cys  Thr Gly Cys
    3095                 3100                 3105

Cys Ala  Ala Cys Ala Gly Gly  Cys Cys Ala Ala Gly  Thr Ala Cys
    3110                 3115                 3120

Thr Thr  Cys Cys Cys Cys Thr  Ala Thr Ala Cys Cys  Thr Thr Cys
    3125                 3130                 3135

Gly Gly  Ala Ala Gly Ala Gly  Gly Cys Ala Cys Thr  Ala Ala Gly
    3140                 3145                 3150

Cys Thr  Gly Gly Ala Ala Ala  Thr Cys Ala Ala Gly  Gly Cys Thr
    3155                 3160                 3165

Ala Gly  Cys Gly Cys Ala Ala  Cys Cys Ala Cys Thr  Ala Cys Gly
    3170                 3175                 3180

Cys Cys  Thr Gly Cys Thr Cys  Cys Gly Cys Gly Gly  Cys Cys Thr
    3185                 3190                 3195

Cys Cys  Ala Ala Cys Gly Cys  Cys Cys Gly Cys Gly  Cys Cys Cys
    3200                 3205                 3210

Ala Cys  Gly Ala Thr Ala Gly  Cys Thr Ala Gly Thr  Cys Ala Gly
    3215                 3220                 3225

Cys Cys  Gly Thr Thr Gly Thr  Cys Thr Cys Thr Cys  Cys Gly Ala
    3230                 3235                 3240

Cys Cys  Ala Gly Ala Gly Gly  Cys Gly Thr Gly Thr  Ala Gly Ala
    3245                 3250                 3255

Cys Cys  Gly Gly Cys Cys Gly  Cys Thr Gly Gly Cys  Gly Gly Ala
    3260                 3265                 3270

Gly Cys  Cys Gly Thr Ala Cys  Ala Thr Ala Cys Thr  Cys Gly Cys
    3275                 3280                 3285

Gly Gly  Ala Cys Thr Cys Gly  Ala Cys Thr Thr Cys  Gly Cys Thr
    3290                 3295                 3300

Thr Gly  Cys Gly Ala Cys Ala  Thr Cys Thr Ala Cys  Ala Thr Thr
    3305                 3310                 3315

Thr Gly  Gly Gly Cys Ala Cys  Cys Cys Thr Thr Gly  Gly Cys Thr
    3320                 3325                 3330

Gly Gly  Gly Ala Cys Cys Thr  Gly Thr Gly Gly Gly  Gly Thr Gly
    3335                 3340                 3345

Cys Thr  Gly Thr Thr Gly Cys  Thr Gly Thr Cys Cys  Thr Thr Gly
    3350                 3355                 3360

Gly Thr  Thr Ala Thr Thr Ala  Cys Gly Thr Thr Gly  Thr Ala Cys
    3365                 3370                 3375

Thr Gly  Cys Ala Gly Ala Gly  Thr Cys Ala Ala Ala  Thr Thr Thr
    3380                 3385                 3390
```

Thr Cys Cys Ala Gly Gly Thr Cys Cys Gly Cys Ala Gly Ala Thr
3395 3400 3405

Gly Cys Cys Cys Cys Cys Gly Cys Gly Thr Ala Cys Cys Ala Gly
3410 3415 3420

Cys Ala Ala Gly Gly Cys Cys Ala Gly Ala Ala Cys Cys Ala Ala
3425 3430 3435

Cys Thr Thr Thr Ala Cys Ala Ala Cys Gly Ala Ala Cys Thr Gly
3440 3445 3450

Ala Ala Cys Cys Thr Gly Gly Gly Thr Cys Gly Cys Cys Gly Gly
3455 3460 3465

Gly Ala Gly Gly Ala Ala Thr Ala Thr Gly Ala Thr Gly Thr Gly
3470 3475 3480

Cys Thr Gly Gly Ala Thr Ala Ala Ala Cys Gly Ala Ala Gly Gly
3485 3490 3495

Gly Gly Gly Ala Gly Gly Gly Ala Cys Cys Cys Thr Gly Ala Gly
3500 3505 3510

Ala Thr Gly Gly Gly Ala Gly Gly Gly Ala Ala Ala Cys Cys Thr
3515 3520 3525

Cys Gly Cys Ala Gly Gly Ala Ala Ala Ala Ala Cys Cys Cys Gly
3530 3535 3540

Cys Ala Gly Gly Ala Ala Gly Gly Thr Thr Thr Gly Thr Ala Cys
3545 3550 3555

Ala Ala Cys Gly Ala Gly Thr Thr Gly Cys Ala Gly Ala Ala Gly
3560 3565 3570

Gly Ala Thr Ala Ala Gly Ala Thr Gly Gly Cys Thr Gly Ala Gly
3575 3580 3585

Gly Cys Thr Thr Ala Cys Thr Cys Thr Gly Ala Ala Ala Thr Ala
3590 3595 3600

Gly Gly Gly Ala Thr Gly Ala Ala Gly Gly Gly Ala Gly Ala Gly
3605 3610 3615

Ala Gly Ala Cys Gly Gly Ala Gly Ala Gly Gly Ala Ala Ala Ala
3620 3625 3630

Gly Gly Cys Cys Ala Thr Gly Ala Thr Gly Gly Cys Cys Thr Thr
3635 3640 3645

Thr Ala Cys Cys Ala Gly Gly Gly Cys Thr Thr Ala Ala Gly Cys
3650 3655 3660

Ala Cys Ala Gly Cys Ala Ala Cys Ala Ala Ala Gly Gly Ala Thr
3665 3670 3675

Ala Cys Thr Thr Ala Cys Gly Ala Cys Gly Cys Thr Cys Thr Thr
3680 3685 3690

Cys Ala Cys Ala Thr Gly Cys Ala Ala Gly Cys Thr Cys Thr Gly
3695 3700 3705

Cys Cys Ala Cys Cys Ala Cys Gly Gly
3710 3715

<210> SEQ ID NO 112
<211> LENGTH: 1239
<212> TYPE: PRT
<213> ORGANISM: Artificial
<220> FEATURE:
<223> OTHER INFORMATION: LTG 2949 DuoCAR D94 CAR2019 OX40z 2A CAR22z

<400> SEQUENCE: 112

Met Leu Leu Leu Val Thr Ser Leu Leu Leu Cys Glu Leu Pro His Pro
1 5 10 15

-continued

```
Ala Phe Leu Leu Ile Pro Glu Val Gln Leu Gln Gln Ser Gly Ala Glu
            20                  25                  30

Leu Val Lys Pro Gly Ala Ser Val Lys Met Ser Cys Lys Ala Ser Gly
        35                  40                  45

Tyr Thr Phe Thr Ser Tyr Asn Met His Trp Val Lys Gln Thr Pro Gly
    50                  55                  60

Gln Gly Leu Glu Trp Ile Gly Ala Ile Tyr Pro Gly Asn Gly Asp Thr
65                  70                  75                  80

Ser Tyr Asn Gln Lys Phe Lys Gly Lys Ala Thr Leu Thr Ala Asp Lys
                85                  90                  95

Ser Ser Ser Thr Ala Tyr Met Gln Leu Ser Ser Leu Thr Ser Glu Asp
            100                 105                 110

Ser Ala Asp Tyr Tyr Cys Ala Arg Ser Asn Tyr Tyr Gly Ser Ser Tyr
        115                 120                 125

Trp Phe Phe Asp Val Trp Gly Ala Gly Thr Thr Val Thr Val Ser Ser
    130                 135                 140

Gly Gly Gly Gly Ser Gly Gly Gly Gly Ser Gly Gly Gly Gly Ser Asp
145                 150                 155                 160

Ile Val Leu Thr Gln Ser Pro Ala Ile Leu Ser Ala Ser Pro Gly Glu
                165                 170                 175

Lys Val Thr Met Thr Cys Arg Ala Ser Ser Ser Val Asn Tyr Met Asp
            180                 185                 190

Trp Tyr Gln Lys Lys Pro Gly Ser Ser Pro Lys Pro Trp Ile Tyr Ala
        195                 200                 205

Thr Ser Asn Leu Ala Ser Gly Val Pro Ala Arg Phe Ser Gly Ser Gly
    210                 215                 220

Ser Gly Thr Ser Tyr Ser Leu Thr Ile Ser Arg Val Glu Ala Glu Asp
225                 230                 235                 240

Ala Ala Thr Tyr Tyr Cys Gln Gln Trp Ser Phe Asn Pro Pro Thr Phe
                245                 250                 255

Gly Gly Gly Thr Lys Leu Glu Ile Lys Gly Gly Gly Gly Ser Gly Gly
            260                 265                 270

Gly Gly Ser Gly Gly Gly Gly Ser Gly Gly Gly Gly Ser Gly Gly Gly
        275                 280                 285

Gly Ser Asp Ile Gln Met Thr Gln Thr Thr Ser Ser Leu Ser Ala Ser
    290                 295                 300

Leu Gly Asp Arg Val Thr Ile Ser Cys Arg Ala Ser Gln Asp Ile Ser
305                 310                 315                 320

Lys Tyr Leu Asn Trp Tyr Gln Gln Lys Pro Asp Gly Thr Val Lys Leu
                325                 330                 335

Leu Ile Tyr His Thr Ser Arg Leu His Ser Gly Val Pro Ser Arg Phe
            340                 345                 350

Ser Gly Ser Gly Ser Gly Thr Asp Tyr Ser Leu Thr Ile Ser Asn Leu
        355                 360                 365

Glu Gln Glu Asp Ile Ala Thr Tyr Phe Cys Gln Gln Gly Asn Thr Leu
    370                 375                 380

Pro Tyr Thr Phe Gly Gly Gly Thr Lys Leu Glu Ile Thr Gly Ser Thr
385                 390                 395                 400

Ser Gly Ser Gly Lys Pro Gly Ser Gly Glu Gly Ser Thr Lys Gly Glu
                405                 410                 415

Val Lys Leu Gln Glu Ser Gly Pro Gly Leu Val Ala Pro Ser Gln Ser
            420                 425                 430

Leu Ser Val Thr Cys Thr Val Ser Gly Val Ser Leu Pro Asp Tyr Gly
```

```
        435                 440                 445

Val Ser Trp Ile Arg Gln Pro Pro Arg Lys Gly Leu Glu Trp Leu Gly
    450                 455                 460

Val Ile Trp Gly Ser Glu Thr Thr Tyr Tyr Asn Ser Ala Leu Lys Ser
465                 470                 475                 480

Arg Leu Thr Ile Ile Lys Asp Asn Ser Lys Ser Gln Val Phe Leu Lys
                485                 490                 495

Met Asn Ser Leu Gln Thr Asp Asp Thr Ala Ile Tyr Tyr Cys Ala Lys
            500                 505                 510

His Tyr Tyr Tyr Gly Gly Ser Tyr Ala Met Asp Tyr Trp Gly Gln Gly
        515                 520                 525

Thr Ser Val Thr Val Ser Ser Ala Ala Ala Thr Thr Thr Pro Ala Pro
    530                 535                 540

Arg Pro Pro Thr Pro Ala Pro Thr Ile Ala Ser Gln Pro Leu Ser Leu
545                 550                 555                 560

Arg Pro Glu Ala Cys Arg Pro Ala Ala Gly Gly Ala Val His Thr Arg
                565                 570                 575

Gly Leu Asp Phe Ala Cys Asp Val Ala Ala Ile Leu Gly Leu Gly Leu
            580                 585                 590

Val Leu Gly Leu Leu Gly Pro Leu Ala Ile Leu Leu Ala Leu Tyr Leu
        595                 600                 605

Leu Arg Arg Asp Gln Arg Leu Pro Pro Asp Ala His Lys Pro Pro Gly
    610                 615                 620

Gly Gly Ser Phe Arg Thr Pro Ile Gln Glu Glu Gln Ala Asp Ala His
625                 630                 635                 640

Ser Thr Leu Ala Lys Ile Arg Val Lys Phe Ser Arg Ser Ala Asp Ala
                645                 650                 655

Pro Ala Tyr Gln Gln Gly Gln Asn Gln Leu Tyr Asn Glu Leu Asn Leu
            660                 665                 670

Gly Arg Arg Glu Glu Tyr Asp Val Leu Asp Lys Arg Arg Gly Arg Asp
        675                 680                 685

Pro Glu Met Gly Gly Lys Pro Arg Arg Lys Asn Pro Gln Glu Gly Leu
    690                 695                 700

Tyr Asn Glu Leu Gln Lys Asp Lys Met Ala Glu Ala Tyr Ser Glu Ile
705                 710                 715                 720

Gly Met Lys Gly Glu Arg Arg Arg Gly Lys Gly His Asp Gly Leu Tyr
                725                 730                 735

Gln Gly Leu Ser Thr Ala Thr Lys Asp Thr Tyr Asp Ala Leu His Met
            740                 745                 750

Gln Ala Leu Pro Pro Arg Arg Ala Lys Arg Gly Ser Gly Ala Thr Asn
        755                 760                 765

Phe Ser Leu Leu Lys Gln Ala Gly Asp Val Glu Glu Asn Pro Gly Pro
    770                 775                 780

Arg Ala Lys Arg Asn Ile Met Ala Leu Pro Val Thr Ala Leu Leu Leu
785                 790                 795                 800

Pro Leu Ala Leu Leu Leu His Ala Ala Arg Pro Gln Val Gln Leu Gln
                805                 810                 815

Gln Ser Gly Pro Gly Leu Val Lys Pro Ser Gln Thr Leu Ser Leu Thr
            820                 825                 830

Cys Ala Ile Ser Gly Asp Ser Val Ser Ser Asn Ser Ala Ala Trp Asn
        835                 840                 845

Trp Ile Arg Gln Ser Pro Ser Arg Gly Leu Glu Trp Leu Gly Arg Thr
    850                 855                 860
```

```
Tyr Tyr Arg Ser Lys Trp Tyr Thr Asp Tyr Ala Val Ser Val Lys Asn
865                 870                 875                 880

Arg Ile Thr Ile Asn Pro Asp Thr Ser Lys Asn Gln Phe Ser Leu Gln
                885                 890                 895

Leu Asn Ser Val Thr Pro Glu Asp Thr Ala Val Tyr Tyr Cys Ala Gln
            900                 905                 910

Glu Val Glu Pro Gln Asp Ala Phe Asp Ile Trp Gly Gln Gly Thr Met
        915                 920                 925

Val Thr Val Ser Ser Gly Gly Gly Gly Ser Gly Gly Gly Gly Ser Gly
    930                 935                 940

Gly Gly Gly Ser Asp Ile Gln Met Thr Gln Ser Pro Ser Ser Val Ser
945                 950                 955                 960

Ala Ser Val Gly Asp Lys Val Thr Ile Thr Cys Arg Ala Ser Gln Asp
                965                 970                 975

Val Ser Gly Trp Leu Ala Trp Tyr Gln Gln Lys Pro Gly Leu Ala Pro
            980                 985                 990

Gln Leu Leu Ile Phe Gly Ala Ser  Thr Leu Gln Gly Glu  Val Pro Ser
        995                 1000                1005

Arg Phe  Ser Gly Ser Gly Ser  Gly Thr Asp Phe Thr  Leu Thr Ile
    1010                1015                1020

Ser Ser  Leu Gln Pro Glu Asp  Phe Ala Thr Tyr Tyr  Cys Gln Gln
    1025                1030                1035

Ala Lys  Tyr Phe Pro Tyr Thr  Phe Gly Arg Gly Thr  Lys Leu Glu
    1040                1045                1050

Ile Lys  Ala Ser Ala Thr Thr  Thr Pro Ala Pro Arg  Pro Pro Thr
    1055                1060                1065

Pro Ala  Pro Thr Ile Ala Ser  Gln Pro Leu Ser Leu  Arg Pro Glu
    1070                1075                1080

Ala Cys  Arg Pro Ala Ala Gly  Gly Ala Val His Thr  Arg Gly Leu
    1085                1090                1095

Asp Phe  Ala Cys Asp Ile Tyr  Ile Trp Ala Pro Leu  Ala Gly Thr
    1100                1105                1110

Cys Gly  Val Leu Leu Leu Ser  Leu Val Ile Thr Leu  Tyr Cys Arg
    1115                1120                1125

Val Lys  Phe Ser Arg Ser Ala  Asp Ala Pro Ala Tyr  Gln Gln Gly
    1130                1135                1140

Gln Asn  Gln Leu Tyr Asn Glu  Leu Asn Leu Gly Arg  Arg Glu Glu
    1145                1150                1155

Tyr Asp  Val Leu Asp Lys Arg  Arg Gly Arg Asp Pro  Glu Met Gly
    1160                1165                1170

Gly Lys  Pro Arg Arg Lys Asn  Pro Gln Glu Gly Leu  Tyr Asn Glu
    1175                1180                1185

Leu Gln  Lys Asp Lys Met Ala  Glu Ala Tyr Ser Glu  Ile Gly Met
    1190                1195                1200

Lys Gly  Glu Arg Arg Arg Gly  Lys Gly His Asp Gly  Leu Tyr Gln
    1205                1210                1215

Gly Leu  Ser Thr Ala Thr Lys  Asp Thr Tyr Asp Ala  Leu His Met
    1220                1225                1230

Gln Ala  Leu Pro Pro Arg
    1235
```

<210> SEQ ID NO 113
<211> LENGTH: 3828

<212> TYPE: DNA
<213> ORGANISM: Artificial
<220> FEATURE:
<223> OTHER INFORMATION: LTG 2950 DuoCAR D95 CAR2019 OX40z 2A CAR22 ICOSz

<400> SEQUENCE: 113

```
atgctccttc tcgtgacctc cctgcttctc tgcgaactgc cccatcctgc cttcctgctg     60
attcccgagg tgcagttgca acagtcagga gctgaactgg tcaagccagg agccagcgtg    120
aagatgagct gcaaggcctc cggttacacc ttcacctcct acaacatgca ctgggtgaaa    180
cagaccccgg gacaagggct cgaatggatt ggcgccatct accccgggaa tggcgatact    240
tcgtacaacc agaagttcaa gggaaaggcc accctgaccg ccgacaagag ctcctccacc    300
gcgtatatgc agttgagctc cctgacctcc gaggactccg ccgactacta ctgcgcacgg    360
tccaactact atggaagctc gtactggttc ttcgatgtct gggggggccgg caccactgtg    420
accgtcagct ccgggggcgg aggatccggt ggaggcggaa gcgggggtgg aggatccgac    480
attgtgctga ctcagtcccc ggcaatcctg tcggcctcac cgggcgaaaa ggtcacgatg    540
acttgtagag cgtcgtccag cgtgaactac atggattggt accaaaagaa gcctggatcg    600
tcacccaagc cttggatcta cgctacatct aacctggcct ccggcgtgcc agcgcggttc    660
agcgggtccg gctcgggcac ctcatactcg ctgaccatct cccgcgtgga ggctgaggac    720
gccgcgacct actactgcca gcagtggtcc ttcaacccgc cgacttttgg aggcggtact    780
aagctggaga tcaaaggagg cggcggcagc ggcgggggag ggtccggagg gggtggttct    840
ggtggaggag gatcgggagg cggtggcagc gacattcaga tgactcagac cacctcctcc    900
ctgtccgcct ccctgggcga ccgcgtgacc atctcatgcc gcgccagcca ggacatctcg    960
aagtacctca actggtacca gcagaagccc gacggaaccg tgaagctcct gatctaccac   1020
acctcccggc tgcacagcgg agtgccgtct agattctcgg gttcggggtc gggaactgac   1080
tactccctta ctatttccaa cctggagcag gaggatattg ccacctactt ctgccaacaa   1140
ggaaacaccc tgccgtacac ttttggcggg ggaaccaagc tggaaatcac tggcagcaca   1200
tccggttccg ggaagcccgg ctccggagag ggcagcacca agggggaagt caagctgcag   1260
gaatcaggac ctggcctggt ggccccgagc cagtcactgt ccgtgacttg tactgtgtcc   1320
ggagtgtcgc tcccggatta cggagtgtcc tggatcaggc agccacctcg gaaaggattg   1380
gaatggctcg gagtcatctg ggttccgaa accacctatt acaactcggc actgaaatcc   1440
aggctcacca ttatcaagga taactccaag tcacaagtgt tcctgaagat gaatagcctg   1500
cagactgacg acacggcgat ctactattgc gccaagcact actactacgg cggatcctac   1560
gctatggact actggggcca ggggaccagc gtgaccgtgt catccgcggc cgcaacgacc   1620
actccagcac cgagaccgcc aacccccgcg cctaccatcg caagtcaacc actttctctc   1680
aggcctgaag cgtgccgacc tgcagctggt ggggcagtac ataccagggg tttggacttc   1740
gcatgtgacg tggcggcaat tctcggcctg ggacttgtcc ttggtctgct tggtccgctc   1800
gcaatacttc tggccttgta cctgctccgc agagaccaaa gacttccgcc cgacgcccac   1860
aagcccccag gaggaggttc cttcagaacg cctatacaag aagaacaagc agatgcccac   1920
tctaccctgg ctaaaatcag ggtgaagttt agccgctcag ccgatgcacc ggcctaccag   1980
cagggacaga accagctcta caacgagctc aacctgggtc ggcgggaaga atatgacgtg   2040
ctggacaaac ggcgcggcag agatccggag atgggggggaa agccgaggag gaagaaccct   2100
caagagggcc tgtacaacga actgcagaag gacaagatgg cggaagccta ctccgagatc   2160
```

```
ggcatgaagg gagaacgccg gagagggaag ggtcatgacg gactgtacca gggcctgtca   2220

actgccacta aggacactta cgatgcgctc catatgcaag ctttgccccc gcggcgcgcg   2280

aaacgcggca gcggcgcgac caactttagc ctgctgaaac aggcgggcga tgtggaagaa   2340

aacccgggcc cgcgagcaaa gaggaatatt atggctctgc ctgttacggc actgctcctt   2400

ccgcttgcat tgttgttgca cgcagcgcgg ccccaagtgc agctgcagca gtccggtcct   2460

ggactggtca agccgtccca gactctgagc ctgacttgcg caattagcgg ggactcagtc   2520

tcgtccaatt cggcggcctg gaactggatc cggcagtcac catcaagggg cctggaatgg   2580

ctcgggcgca cttactaccg gtccaaatgg tataccgact acgccgtgtc cgtgaagaat   2640

cggatcacca ttaaccccga cacctcgaag aaccagttct cactccaact gaacagcgtg   2700

acccccgagg ataccgcggt gtactactgc gcacaagaag tggaaccgca ggacgccttc   2760

gacatttggg gacagggaac gatggtcaca gtgtcgtccg gtggaggagg ttccggaggc   2820

ggtggatctg gaggcggagg ttcggatatc cagatgaccc agagcccctc ctcggtgtcc   2880

gcatccgtgg gcgataaggt caccattacc tgtagagcgt cccaggacgt gtccggatgg   2940

ctggcctggt accagcagaa gccaggcttg gctcctcaac tgctgatctt cggcgccagc   3000

actcttcagg gggaagtgcc atcacgcttc tccggatccg gttccggcac cgacttcacc   3060

ctgaccatca gcagcctcca gcctgaggac ttcgccactt actactgcca acaggccaag   3120

tacttcccct ataccttcgg aagaggcact aagctggaaa tcaaggctag cgcaaccact   3180

acgcctgctc cgcggcctcc aacgcccgcg cccacgatag ctagtcagcc gttgtctctc   3240

cgaccagagg cgtgtagacc ggccgctggc ggagccgtac atactcgcgg actcgacttc   3300

gcttgcgaca tctacatttg ggcacccttg gctgggacct gtggggtgct gttgctgtcc   3360

ttggttatta cgttgtactg ctggctgaca aaaaagaagt attcatctag tgtacatgat   3420

ccgaacggtg aatacatgtt catgcgcgcg gtgaacacgg ccaagaagag cagactgacc   3480

gacgtaaccc ttagagtcaa attttccagg tccgcagatg cccccgcgta ccagcaaggc   3540

cagaaccaac tttacaacga actgaacctg ggtcgccggg aggaatatga tgtgctggat   3600

aaacgaaggg ggagggaccc tgagatggga gggaaacctc gcaggaaaaa cccgcaggaa   3660

ggtttgtaca acgagttgca gaaggataag atggctgagg cttactctga aatagggatg   3720

aagggagaga gacggagagg aaaaggccat gatggccttt accagggctt gagcacagca   3780

acaaaggata cttacgacgc tcttcacatg caagctctgc caccacgg               3828
```

<210> SEQ ID NO 114
<211> LENGTH: 1276
<212> TYPE: PRT
<213> ORGANISM: Artificial
<220> FEATURE:
<223> OTHER INFORMATION: LTG 2950 DuoCAR D95 CAR2019 OX40z 2A CAR22 ICOSz

<400> SEQUENCE: 114

```
Met Leu Leu Leu Val Thr Ser Leu Leu Leu Cys Glu Leu Pro His Pro
1               5                   10                  15

Ala Phe Leu Leu Ile Pro Glu Val Gln Leu Gln Gln Ser Gly Ala Glu
            20                  25                  30

Leu Val Lys Pro Gly Ala Ser Val Lys Met Ser Cys Lys Ala Ser Gly
        35                  40                  45

Tyr Thr Phe Thr Ser Tyr Asn Met His Trp Val Lys Gln Thr Pro Gly
    50                  55                  60
```

-continued

```
Gln Gly Leu Glu Trp Ile Gly Ala Ile Tyr Pro Gly Asn Gly Asp Thr
65                  70                  75                  80

Ser Tyr Asn Gln Lys Phe Lys Gly Lys Ala Thr Leu Thr Ala Asp Lys
                85                  90                  95

Ser Ser Ser Thr Ala Tyr Met Gln Leu Ser Ser Leu Thr Ser Glu Asp
            100                 105                 110

Ser Ala Asp Tyr Tyr Cys Ala Arg Ser Asn Tyr Tyr Gly Ser Ser Tyr
        115                 120                 125

Trp Phe Phe Asp Val Trp Gly Ala Gly Thr Thr Val Thr Val Ser Ser
    130                 135                 140

Gly Gly Gly Gly Ser Gly Gly Gly Gly Ser Gly Gly Gly Gly Ser Asp
145                 150                 155                 160

Ile Val Leu Thr Gln Ser Pro Ala Ile Leu Ser Ala Ser Pro Gly Glu
                165                 170                 175

Lys Val Thr Met Thr Cys Arg Ala Ser Ser Ser Val Asn Tyr Met Asp
            180                 185                 190

Trp Tyr Gln Lys Lys Pro Gly Ser Ser Pro Lys Pro Trp Ile Tyr Ala
        195                 200                 205

Thr Ser Asn Leu Ala Ser Gly Val Pro Ala Arg Phe Ser Gly Ser Gly
    210                 215                 220

Ser Gly Thr Ser Tyr Ser Leu Thr Ile Ser Arg Val Glu Ala Glu Asp
225                 230                 235                 240

Ala Ala Thr Tyr Tyr Cys Gln Gln Trp Ser Phe Asn Pro Pro Thr Phe
                245                 250                 255

Gly Gly Gly Thr Lys Leu Glu Ile Lys Gly Gly Gly Gly Ser Gly Gly
            260                 265                 270

Gly Gly Ser Gly Gly Gly Gly Ser Gly Gly Gly Gly Ser Gly Gly Gly
        275                 280                 285

Gly Ser Asp Ile Gln Met Thr Gln Thr Thr Ser Ser Leu Ser Ala Ser
    290                 295                 300

Leu Gly Asp Arg Val Thr Ile Ser Cys Arg Ala Ser Gln Asp Ile Ser
305                 310                 315                 320

Lys Tyr Leu Asn Trp Tyr Gln Gln Lys Pro Asp Gly Thr Val Lys Leu
                325                 330                 335

Leu Ile Tyr His Thr Ser Arg Leu His Ser Gly Val Pro Ser Arg Phe
            340                 345                 350

Ser Gly Ser Gly Ser Gly Thr Asp Tyr Ser Leu Thr Ile Ser Asn Leu
        355                 360                 365

Glu Gln Glu Asp Ile Ala Thr Tyr Phe Cys Gln Gln Gly Asn Thr Leu
    370                 375                 380

Pro Tyr Thr Phe Gly Gly Gly Thr Lys Leu Glu Ile Thr Gly Ser Thr
385                 390                 395                 400

Ser Gly Ser Gly Lys Pro Gly Ser Gly Glu Gly Ser Thr Lys Gly Glu
                405                 410                 415

Val Lys Leu Gln Glu Ser Gly Pro Gly Leu Val Ala Pro Ser Gln Ser
            420                 425                 430

Leu Ser Val Thr Cys Thr Val Ser Gly Val Ser Leu Pro Asp Tyr Gly
        435                 440                 445

Val Ser Trp Ile Arg Gln Pro Pro Arg Lys Gly Leu Glu Trp Leu Gly
    450                 455                 460

Val Ile Trp Gly Ser Glu Thr Thr Tyr Tyr Asn Ser Ala Leu Lys Ser
465                 470                 475                 480
```

-continued

```
Arg Leu Thr Ile Ile Lys Asp Asn Ser Lys Ser Gln Val Phe Leu Lys
                485                 490                 495

Met Asn Ser Leu Gln Thr Asp Asp Thr Ala Ile Tyr Tyr Cys Ala Lys
            500                 505                 510

His Tyr Tyr Tyr Gly Gly Ser Tyr Ala Met Asp Tyr Trp Gly Gln Gly
        515                 520                 525

Thr Ser Val Thr Val Ser Ser Ala Ala Ala Thr Thr Thr Pro Ala Pro
    530                 535                 540

Arg Pro Pro Thr Pro Ala Pro Thr Ile Ala Ser Gln Pro Leu Ser Leu
545                 550                 555                 560

Arg Pro Glu Ala Cys Arg Pro Ala Ala Gly Gly Ala Val His Thr Arg
                565                 570                 575

Gly Leu Asp Phe Ala Cys Asp Val Ala Ala Ile Leu Gly Leu Gly Leu
            580                 585                 590

Val Leu Gly Leu Leu Gly Pro Leu Ala Ile Leu Leu Ala Leu Tyr Leu
        595                 600                 605

Leu Arg Arg Asp Gln Arg Leu Pro Pro Asp Ala His Lys Pro Pro Gly
    610                 615                 620

Gly Gly Ser Phe Arg Thr Pro Ile Gln Glu Glu Gln Ala Asp Ala His
625                 630                 635                 640

Ser Thr Leu Ala Lys Ile Arg Val Lys Phe Ser Arg Ser Ala Asp Ala
                645                 650                 655

Pro Ala Tyr Gln Gln Gly Gln Asn Gln Leu Tyr Asn Glu Leu Asn Leu
            660                 665                 670

Gly Arg Arg Glu Glu Tyr Asp Val Leu Asp Lys Arg Arg Gly Arg Asp
        675                 680                 685

Pro Glu Met Gly Gly Lys Pro Arg Arg Lys Asn Pro Gln Glu Gly Leu
    690                 695                 700

Tyr Asn Glu Leu Gln Lys Asp Lys Met Ala Glu Ala Tyr Ser Glu Ile
705                 710                 715                 720

Gly Met Lys Gly Glu Arg Arg Arg Gly Lys Gly His Asp Gly Leu Tyr
                725                 730                 735

Gln Gly Leu Ser Thr Ala Thr Lys Asp Thr Tyr Asp Ala Leu His Met
            740                 745                 750

Gln Ala Leu Pro Pro Arg Arg Ala Lys Arg Gly Ser Gly Ala Thr Asn
        755                 760                 765

Phe Ser Leu Leu Lys Gln Ala Gly Asp Val Glu Glu Asn Pro Gly Pro
    770                 775                 780

Arg Ala Lys Arg Asn Ile Met Ala Leu Pro Val Thr Ala Leu Leu Leu
785                 790                 795                 800

Pro Leu Ala Leu Leu Leu His Ala Ala Arg Pro Gln Val Gln Leu Gln
                805                 810                 815

Gln Ser Gly Pro Gly Leu Val Lys Pro Ser Gln Thr Leu Ser Leu Thr
            820                 825                 830

Cys Ala Ile Ser Gly Asp Ser Val Ser Ser Asn Ser Ala Ala Trp Asn
        835                 840                 845

Trp Ile Arg Gln Ser Pro Ser Arg Gly Leu Glu Trp Leu Gly Arg Thr
    850                 855                 860

Tyr Tyr Arg Ser Lys Trp Tyr Thr Asp Tyr Ala Val Ser Val Lys Asn
865                 870                 875                 880

Arg Ile Thr Ile Asn Pro Asp Thr Ser Lys Asn Gln Phe Ser Leu Gln
                885                 890                 895

Leu Asn Ser Val Thr Pro Glu Asp Thr Ala Val Tyr Tyr Cys Ala Gln
```

```
            900                 905                 910

Glu Val Glu Pro Gln Asp Ala Phe Asp Ile Trp Gly Gln Gly Thr Met
        915                 920                 925

Val Thr Val Ser Ser Gly Gly Gly Gly Ser Gly Gly Gly Gly Ser Gly
    930                 935                 940

Gly Gly Gly Ser Asp Ile Gln Met Thr Gln Ser Pro Ser Ser Val Ser
945                 950                 955                 960

Ala Ser Val Gly Asp Lys Val Thr Ile Thr Cys Arg Ala Ser Gln Asp
                965                 970                 975

Val Ser Gly Trp Leu Ala Trp Tyr Gln Gln Lys Pro Gly Leu Ala Pro
            980                 985                 990

Gln Leu Leu Ile Phe Gly Ala Ser  Thr Leu Gln Gly Glu  Val Pro Ser
        995                 1000                1005

Arg Phe  Ser Gly Ser Gly Ser  Gly Thr Asp Phe Thr  Leu Thr Ile
    1010                 1015                 1020

Ser Ser  Leu Gln Pro Glu Asp  Phe Ala Thr Tyr Tyr  Cys Gln Gln
    1025                 1030                 1035

Ala Lys  Tyr Phe Pro Tyr Thr  Phe Gly Arg Gly Thr  Lys Leu Glu
    1040                 1045                 1050

Ile Lys  Ala Ser Ala Thr Thr  Thr Pro Ala Pro Arg  Pro Pro Thr
    1055                 1060                 1065

Pro Ala  Pro Thr Ile Ala Ser  Gln Pro Leu Ser Leu  Arg Pro Glu
    1070                 1075                 1080

Ala Cys  Arg Pro Ala Ala Gly  Gly Ala Val His Thr  Arg Gly Leu
    1085                 1090                 1095

Asp Phe  Ala Cys Asp Ile Tyr  Ile Trp Ala Pro Leu  Ala Gly Thr
    1100                 1105                 1110

Cys Gly  Val Leu Leu Leu Ser  Leu Val Ile Thr Leu  Tyr Cys Trp
    1115                 1120                 1125

Leu Thr  Lys Lys Lys Tyr Ser  Ser Ser Val His Asp  Pro Asn Gly
    1130                 1135                 1140

Glu Tyr  Met Phe Met Arg Ala  Val Asn Thr Ala Lys  Lys Ser Arg
    1145                 1150                 1155

Leu Thr  Asp Val Thr Leu Arg  Val Lys Phe Ser Arg  Ser Ala Asp
    1160                 1165                 1170

Ala Pro  Ala Tyr Gln Gln Gly  Gln Asn Gln Leu Tyr  Asn Glu Leu
    1175                 1180                 1185

Asn Leu  Gly Arg Arg Glu Glu  Tyr Asp Val Leu Asp  Lys Arg Arg
    1190                 1195                 1200

Gly Arg  Asp Pro Glu Met Gly  Gly Lys Pro Arg Arg  Lys Asn Pro
    1205                 1210                 1215

Gln Glu  Gly Leu Tyr Asn Glu  Leu Gln Lys Asp Lys  Met Ala Glu
    1220                 1225                 1230

Ala Tyr  Ser Glu Ile Gly Met  Lys Gly Glu Arg Arg  Arg Gly Lys
    1235                 1240                 1245

Gly His  Asp Gly Leu Tyr Gln  Gly Leu Ser Thr Ala  Thr Lys Asp
    1250                 1255                 1260

Thr Tyr  Asp Ala Leu His Met  Gln Ala Leu Pro Pro  Arg
    1265                 1270                 1275


<210> SEQ ID NO 115
<211> LENGTH: 3855
<212> TYPE: DNA
<213> ORGANISM: Artificial
```

<220> FEATURE:
<223> OTHER INFORMATION: LTG 2951 DuoCAR D96 CAR2019 27z 2A CAR22 ICOSz

<400> SEQUENCE: 115

```
atgctccttc tcgtgacctc cctgcttctc tgcgaactgc cccatcctgc cttcctgctg     60
attcccgagg tgcagttgca acagtcagga gctgaactgg tcaagccagg agccagcgtg    120
aagatgagct gcaaggcctc cggttacacc ttcacctcct acaacatgca ctgggtgaaa    180
cagaccccgg gacaagggct cgaatggatt ggcgccatct accccgggaa tggcgatact    240
tcgtacaacc agaagttcaa gggaaaggcc accctgaccg ccgacaagag ctcctccacc    300
gcgtatatgc agttgagctc cctgacctcc gaggactccg ccgactacta ctgcgcacgg    360
tccaactact atggaagctc gtactggttc ttcgatgtct gggggggccgg caccactgtg    420
accgtcagct ccgggggcgg aggatccggt ggaggcggaa gcgggggtgg aggatccgac    480
attgtgctga ctcagtcccc ggcaatcctg tcggcctcac cgggcgaaaa ggtcacgatg    540
acttgtagag cgtcgtccag cgtgaactac atggattggt accaaaagaa gcctggatcg    600
tcacccaagc cttggatcta cgctacatct aacctggcct ccggcgtgcc agcgcggttc    660
agcgggtccg gctcgggcac ctcatactcg ctgaccatct cccgcgtgga ggctgaggac    720
gccgcgacct actactgcca gcagtggtcc ttcaacccgc cgacttttgg aggcggtact    780
aagctggaga tcaaaggagg cggcggcagc ggcgggggag ggtccggagg gggtggttct    840
ggtggaggag gatcgggagg cggtggcagc gacattcaga tgactcagac cacctcctcc    900
ctgtccgcct ccctgggcga ccgcgtgacc atctcatgcc gcgccagcca ggacatctcg    960
aagtacctca actggtacca gcagaagccc gacggaaccg tgaagctcct gatctaccac   1020
acctcccggc tgcacagcgg agtgccgtct agattctcgg gttcggggtc gggaactgac   1080
tactccctta ctatttccaa cctggagcag gaggatattg ccacctactt ctgccaacaa   1140
ggaaacaccc tgccgtacac ttttggcggg ggaaccaagc tggaaatcac tggcagcaca   1200
tccggttccg ggaagcccgg ctccggagag ggcagcacca aggggggaagt caagctgcag   1260
gaatcaggac ctggcctggt ggccccgagc cagtcactgt ccgtgacttg tactgtgtcc   1320
ggagtgtcgc tcccggatta cggagtgtcc tggatcaggc agccacctcg gaaaggattg   1380
gaatggctcg gagtcatctg ggttccgaa accacctatt acaactcggc actgaaatcc   1440
aggctcacca ttatcaagga taactccaag tcacaagtgt tcctgaagat gaatagcctg   1500
cagactgacg acacggcgat ctactattgc gccaagcact actactacgg cggatcctac   1560
gctatggact actggggcca ggggaccagc gtgaccgtgt catccgcggc cgcgactacc   1620
actcctgcac cacggccacc taccccagcc cccaccattg caagccagcc actttcactg   1680
cgccccgaag cgtgtagacc agctgctgga ggagccgtgc atacccgagg gctggacttc   1740
gcctgtgaca tctacatctg ggccccattg gctggaactt gcggcgtgct gctcttgtct   1800
ctggtcatta ccctgtactg ccaacggcgc aaataccgct ccaataaagg cgaaagtccg   1860
gtagaacccg cagaaccttg ccactacagt tgtcccagag aagaagaggg ttctacaata   1920
cctattcaag aggactatag gaaaccagag cccgcatgta gtcccagagt gaagttcagc   1980
cgctcagccg atgcaccggc ctaccagcag ggacagaacc agctctacaa cgagctcaac   2040
ctgggtcggc gggaagaata tgacgtgctg gacaaacggc gcggcagaga tccggagatg   2100
gggggaaagc cgaggaggaa gaaccctcaa gagggcctgt acaacgaact gcagaaggac   2160
aagatggcgg aagcctactc cgagatcggc atgaagggag aacgccggag agggaagggt   2220
```

-continued

```
catgacggac tgtaccaggg cctgtcaact gccactaagg acacttacga tgcgctccat   2280

atgcaagctt tgcccccgcg gcgcgcgaaa cgcggcagcg gcgcgaccaa ctttagcctg   2340

ctgaaacagg cgggcgatgt ggaagaaaac ccgggcccgc gagcaaagag gaatattatg   2400

gctctgcctg ttacggcact gctccttccg cttgcattgt tgttgcacgc agcgcggccc   2460

caagtgcagc tgcagcagtc cggtcctgga ctggtcaagc cgtcccagac tctgagcctg   2520

acttgcgcaa ttagcgggga ctcagtctcg tccaattcgg cggcctggaa ctggatccgg   2580

cagtcaccat caaggggcct ggaatggctc gggcgcactt actaccggtc caaatggtat   2640

accgactacg ccgtgtccgt gaagaatcgg atcaccatta accccgacac ctcgaagaac   2700

cagttctcac tccaactgaa cagcgtgacc cccgaggata ccgcggtgta ctactgcgca   2760

caagaagtgg aaccgcagga cgccttcgac atttggggac agggaacgat ggtcacagtg   2820

tcgtccggtg gaggaggttc cggaggcggt ggatctggag gcggaggttc ggatatccag   2880

atgacccaga gcccctcctc ggtgtccgca tccgtgggcg ataaggtcac cattacctgt   2940

agagcgtccc aggacgtgtc cggatggctg gcctggtacc agcagaagcc aggcttggct   3000

cctcaactgc tgatcttcgg cgccagcact cttcaggggg aagtgccatc acgcttctcc   3060

ggatccggtt ccggcaccga cttcaccctg accatcagca gcctccagcc tgaggacttc   3120

gccacttact actgccaaca ggccaagtac ttcccctata ccttcggaag aggcactaag   3180

ctggaaatca aggctagcgc aaccactacg cctgctccgc ggcctccaac gcccgcgccc   3240

acgatagcta gtcagccgtt gtctctccga ccagaggcgt gtagaccggc cgctggcgga   3300

gccgtacata ctcgcggact cgacttcgct tgcgacatct acatttgggc acccttggct   3360

gggacctgtg ggtgctgtt gctgtccttg gttattacgt tgtactgctg gctgacaaaa   3420

aagaagtatt catctagtgt acatgatccg aacggtgaat acatgttcat gcgcgcggtg   3480

aacacggcca agaagagcag actgaccgac gtaaccctta gagtcaaatt ttccaggtcc   3540

gcagatgccc ccgcgtacca gcaaggccag aaccaacttt acaacgaact gaacctgggt   3600

cgccgggagg aatatgatgt gctggataaa cgaagggga gggaccctga gatgggaggg   3660

aaacctcgca ggaaaaaccc gcaggaaggt ttgtacaacg agttgcagaa ggataagatg   3720

gctgaggctt actctgaaat agggatgaag ggagagagac ggagaggaaa aggccatgat   3780

ggcctttacc agggcttgag cacagcaaca aaggatactt acgacgctct tcacatgcaa   3840

gctctgccac cacgg                                                   3855
```

<210> SEQ ID NO 116
<211> LENGTH: 1285
<212> TYPE: PRT
<213> ORGANISM: Artificial
<220> FEATURE:
<223> OTHER INFORMATION: LTG2951 DuoCAR D96 CAR2019 27z 2A CAR22 ICOSz

<400> SEQUENCE: 116

```
Met Leu Leu Leu Val Thr Ser Leu Leu Leu Cys Glu Leu Pro His Pro
1               5                   10                  15

Ala Phe Leu Leu Ile Pro Glu Val Gln Leu Gln Gln Ser Gly Ala Glu
            20                  25                  30

Leu Val Lys Pro Gly Ala Ser Val Lys Met Ser Cys Lys Ala Ser Gly
        35                  40                  45

Tyr Thr Phe Thr Ser Tyr Asn Met His Trp Val Lys Gln Thr Pro Gly
    50                  55                  60

Gln Gly Leu Glu Trp Ile Gly Ala Ile Tyr Pro Gly Asn Gly Asp Thr
```

65 70 75 80

Ser Tyr Asn Gln Lys Phe Lys Gly Lys Ala Thr Leu Thr Ala Asp Lys
85 90 95

Ser Ser Ser Thr Ala Tyr Met Gln Leu Ser Ser Leu Thr Ser Glu Asp
100 105 110

Ser Ala Asp Tyr Tyr Cys Ala Arg Ser Asn Tyr Tyr Gly Ser Ser Tyr
115 120 125

Trp Phe Phe Asp Val Trp Gly Ala Gly Thr Thr Val Thr Val Ser Ser
130 135 140

Gly Gly Gly Gly Ser Gly Gly Gly Gly Ser Gly Gly Gly Gly Ser Asp
145 150 155 160

Ile Val Leu Thr Gln Ser Pro Ala Ile Leu Ser Ala Ser Pro Gly Glu
165 170 175

Lys Val Thr Met Thr Cys Arg Ala Ser Ser Ser Val Asn Tyr Met Asp
180 185 190

Trp Tyr Gln Lys Lys Pro Gly Ser Ser Pro Lys Pro Trp Ile Tyr Ala
195 200 205

Thr Ser Asn Leu Ala Ser Gly Val Pro Ala Arg Phe Ser Gly Ser Gly
210 215 220

Ser Gly Thr Ser Tyr Ser Leu Thr Ile Ser Arg Val Glu Ala Glu Asp
225 230 235 240

Ala Ala Thr Tyr Tyr Cys Gln Gln Trp Ser Phe Asn Pro Pro Thr Phe
245 250 255

Gly Gly Gly Thr Lys Leu Glu Ile Lys Gly Gly Gly Gly Ser Gly Gly
260 265 270

Gly Gly Ser Gly Gly Gly Gly Ser Gly Gly Gly Gly Ser Gly Gly Gly
275 280 285

Gly Ser Asp Ile Gln Met Thr Gln Thr Thr Ser Ser Leu Ser Ala Ser
290 295 300

Leu Gly Asp Arg Val Thr Ile Ser Cys Arg Ala Ser Gln Asp Ile Ser
305 310 315 320

Lys Tyr Leu Asn Trp Tyr Gln Gln Lys Pro Asp Gly Thr Val Lys Leu
325 330 335

Leu Ile Tyr His Thr Ser Arg Leu His Ser Gly Val Pro Ser Arg Phe
340 345 350

Ser Gly Ser Gly Ser Gly Thr Asp Tyr Ser Leu Thr Ile Ser Asn Leu
355 360 365

Glu Gln Glu Asp Ile Ala Thr Tyr Phe Cys Gln Gln Gly Asn Thr Leu
370 375 380

Pro Tyr Thr Phe Gly Gly Gly Thr Lys Leu Glu Ile Thr Gly Ser Thr
385 390 395 400

Ser Gly Ser Gly Lys Pro Gly Ser Gly Glu Gly Ser Thr Lys Gly Glu
405 410 415

Val Lys Leu Gln Glu Ser Gly Pro Gly Leu Val Ala Pro Ser Gln Ser
420 425 430

Leu Ser Val Thr Cys Thr Val Ser Gly Val Ser Leu Pro Asp Tyr Gly
435 440 445

Val Ser Trp Ile Arg Gln Pro Pro Arg Lys Gly Leu Glu Trp Leu Gly
450 455 460

Val Ile Trp Gly Ser Glu Thr Thr Tyr Tyr Asn Ser Ala Leu Lys Ser
465 470 475 480

Arg Leu Thr Ile Ile Lys Asp Asn Ser Lys Ser Gln Val Phe Leu Lys
485 490 495

```
Met Asn Ser Leu Gln Thr Asp Asp Thr Ala Ile Tyr Tyr Cys Ala Lys
            500                 505                 510

His Tyr Tyr Tyr Gly Gly Ser Tyr Ala Met Asp Tyr Trp Gly Gln Gly
        515                 520                 525

Thr Ser Val Thr Val Ser Ser Ala Ala Ala Thr Thr Thr Pro Ala Pro
    530                 535                 540

Arg Pro Pro Thr Pro Ala Pro Thr Ile Ala Ser Gln Pro Leu Ser Leu
545                 550                 555                 560

Arg Pro Glu Ala Cys Arg Pro Ala Ala Gly Gly Ala Val His Thr Arg
                565                 570                 575

Gly Leu Asp Phe Ala Cys Asp Ile Tyr Ile Trp Ala Pro Leu Ala Gly
            580                 585                 590

Thr Cys Gly Val Leu Leu Leu Ser Leu Val Ile Thr Leu Tyr Cys Gln
        595                 600                 605

Arg Arg Lys Tyr Arg Ser Asn Lys Gly Glu Ser Pro Val Glu Pro Ala
    610                 615                 620

Glu Pro Cys His Tyr Ser Cys Pro Arg Glu Glu Glu Gly Ser Thr Ile
625                 630                 635                 640

Pro Ile Gln Glu Asp Tyr Arg Lys Pro Glu Pro Ala Cys Ser Pro Arg
                645                 650                 655

Val Lys Phe Ser Arg Ser Ala Asp Ala Pro Ala Tyr Gln Gln Gly Gln
            660                 665                 670

Asn Gln Leu Tyr Asn Glu Leu Asn Leu Gly Arg Arg Glu Glu Tyr Asp
        675                 680                 685

Val Leu Asp Lys Arg Arg Gly Arg Asp Pro Glu Met Gly Gly Lys Pro
    690                 695                 700

Arg Arg Lys Asn Pro Gln Glu Gly Leu Tyr Asn Glu Leu Gln Lys Asp
705                 710                 715                 720

Lys Met Ala Glu Ala Tyr Ser Glu Ile Gly Met Lys Gly Glu Arg Arg
                725                 730                 735

Arg Gly Lys Gly His Asp Gly Leu Tyr Gln Gly Leu Ser Thr Ala Thr
            740                 745                 750

Lys Asp Thr Tyr Asp Ala Leu His Met Gln Ala Leu Pro Pro Arg Arg
        755                 760                 765

Ala Lys Arg Gly Ser Gly Ala Thr Asn Phe Ser Leu Leu Lys Gln Ala
    770                 775                 780

Gly Asp Val Glu Glu Asn Pro Gly Pro Arg Ala Lys Arg Asn Ile Met
785                 790                 795                 800

Ala Leu Pro Val Thr Ala Leu Leu Leu Pro Leu Ala Leu Leu Leu His
                805                 810                 815

Ala Ala Arg Pro Gln Val Gln Leu Gln Gln Ser Gly Pro Gly Leu Val
            820                 825                 830

Lys Pro Ser Gln Thr Leu Ser Leu Thr Cys Ala Ile Ser Gly Asp Ser
        835                 840                 845

Val Ser Ser Asn Ser Ala Ala Trp Asn Trp Ile Arg Gln Ser Pro Ser
    850                 855                 860

Arg Gly Leu Glu Trp Leu Gly Arg Thr Tyr Tyr Arg Ser Lys Trp Tyr
865                 870                 875                 880

Thr Asp Tyr Ala Val Ser Val Lys Asn Arg Ile Thr Ile Asn Pro Asp
                885                 890                 895

Thr Ser Lys Asn Gln Phe Ser Leu Gln Leu Asn Ser Val Thr Pro Glu
            900                 905                 910
```

-continued

```
Asp Thr Ala Val Tyr Tyr Cys Ala Gln Glu Val Glu Pro Gln Asp Ala
        915                 920                 925

Phe Asp Ile Trp Gly Gln Gly Thr Met Val Thr Val Ser Ser Gly Gly
    930                 935                 940

Gly Gly Ser Gly Gly Gly Gly Ser Gly Gly Gly Gly Ser Asp Ile Gln
945                 950                 955                 960

Met Thr Gln Ser Pro Ser Ser Val Ser Ala Ser Val Gly Asp Lys Val
                965                 970                 975

Thr Ile Thr Cys Arg Ala Ser Gln Asp Val Ser Gly Trp Leu Ala Trp
            980                 985                 990

Tyr Gln Gln Lys Pro Gly Leu Ala  Pro Gln Leu Leu Ile  Phe Gly Ala
        995                 1000                1005

Ser Thr  Leu Gln Gly Glu Val  Pro Ser Arg Phe Ser  Gly Ser Gly
    1010                1015                1020

Ser Gly  Thr Asp Phe Thr Leu  Thr Ile Ser Ser Leu  Gln Pro Glu
    1025                1030                1035

Asp Phe  Ala Thr Tyr Tyr Cys  Gln Gln Ala Lys Tyr  Phe Pro Tyr
    1040                1045                1050

Thr Phe  Gly Arg Gly Thr Lys  Leu Glu Ile Lys Ala  Ser Ala Thr
    1055                1060                1065

Thr Thr  Pro Ala Pro Arg Pro  Pro Thr Pro Ala Pro  Thr Ile Ala
    1070                1075                1080

Ser Gln  Pro Leu Ser Leu Arg  Pro Glu Ala Cys Arg  Pro Ala Ala
    1085                1090                1095

Gly Gly  Ala Val His Thr Arg  Gly Leu Asp Phe Ala  Cys Asp Ile
    1100                1105                1110

Tyr Ile  Trp Ala Pro Leu Ala  Gly Thr Cys Gly Val  Leu Leu Leu
    1115                1120                1125

Ser Leu  Val Ile Thr Leu Tyr  Cys Trp Leu Thr Lys  Lys Lys Tyr
    1130                1135                1140

Ser Ser  Ser Val His Asp Pro  Asn Gly Glu Tyr Met  Phe Met Arg
    1145                1150                1155

Ala Val  Asn Thr Ala Lys Lys  Ser Arg Leu Thr Asp  Val Thr Leu
    1160                1165                1170

Arg Val  Lys Phe Ser Arg Ser  Ala Asp Ala Pro Ala  Tyr Gln Gln
    1175                1180                1185

Gly Gln  Asn Gln Leu Tyr Asn  Glu Leu Asn Leu Gly  Arg Arg Glu
    1190                1195                1200

Glu Tyr  Asp Val Leu Asp Lys  Arg Arg Gly Arg Asp  Pro Glu Met
    1205                1210                1215

Gly Gly  Lys Pro Arg Arg Lys  Asn Pro Gln Glu Gly  Leu Tyr Asn
    1220                1225                1230

Glu Leu  Gln Lys Asp Lys Met  Ala Glu Ala Tyr Ser  Glu Ile Gly
    1235                1240                1245

Met Lys  Gly Glu Arg Arg Arg  Gly Lys Gly His Asp  Gly Leu Tyr
    1250                1255                1260

Gln Gly  Leu Ser Thr Ala Thr  Lys Asp Thr Tyr Asp  Ala Leu His
    1265                1270                1275

Met Gln  Ala Leu Pro Pro Arg
    1280                1285
```

<210> SEQ ID NO 117
<211> LENGTH: 2268
<212> TYPE: DNA

<213> ORGANISM: Artificial
<220> FEATURE:
<223> OTHER INFORMATION: D088 CAR2019 ICOSz

<400> SEQUENCE: 117

```
atgctccttc tcgtgacctc cctgcttctc tgcgaactgc cccatcctgc cttcctgctg     60
attcccgagg tgcagttgca acagtcagga gctgaactgg tcaagccagg agccagcgtg    120
aagatgagct gcaaggcctc cggttacacc ttcacctcct acaacatgca ctgggtgaaa    180
cagaccccgg gacaagggct cgaatggatt ggcgccatct accccgggaa tggcgatact    240
tcgtacaacc agaagttcaa gggaaaggcc accctgaccg ccgacaagag ctcctccacc    300
gcgtatatgc agttgagctc cctgacctcc gaggactccg ccgactacta ctgcgcacgg    360
tccaactact atggaagctc gtactggttc ttcgatgtct gggggggccgg caccactgtg    420
accgtcagct ccgggggcgg aggatccggt ggaggcggaa gcgggggtgg aggatccgac    480
attgtgctga ctcagtcccc ggcaatcctg tcggcctcac cgggcgaaaa ggtcacgatg    540
acttgtagag cgtcgtccag cgtgaactac atggattggt accaaaagaa gcctggatcg    600
tcacccaagc cttggatcta cgctacatct aacctggcct ccggcgtgcc agcgcggttc    660
agcgggtccg gctcgggcac ctcatactcg ctgaccatct cccgcgtgga ggctgaggac    720
gccgcgacct actactgcca gcagtggtcc ttcaacccgc cgacttttgg aggcggtact    780
aagctggaga tcaaaggagg cggcggcagc ggcgggggag ggtccggagg gggtggttct    840
ggtggaggag gatcgggagg cggtggcagc gacattcaga tgactcagac cacctcctcc    900
ctgtccgcct ccctgggcga ccgcgtgacc atctcatgcc gcgccagcca ggacatctcg    960
aagtacctca actggtacca gcagaagccc gacggaaccg tgaagctcct gatctaccac   1020
acctcccggc tgcacagcgg agtgccgtct agattctcgg gttcggggtc gggaactgac   1080
tactccctta ctatttccaa cctggagcag gaggatattg ccacctactt ctgccaacaa   1140
ggaaacaccc tgccgtacac ttttggcggg ggaaccaagc tggaaatcac tggcagcaca   1200
tccggttccg ggaagcccgg ctccggagag ggcagcacca agggggaagt caagctgcag   1260
gaatcaggac ctggcctggt ggccccgagc cagtcactgt ccgtgacttg tactgtgtcc   1320
ggagtgtcgc tcccggatta cggagtgtcc tggatcaggc agccacctcg gaaaggattg   1380
gaatggctcg gagtcatctg gggttccgaa accacctatt acaactcggc actgaaatcc   1440
aggctcacca ttatcaagga taactccaag tcacaagtgt tcctgaagat gaatagcctg   1500
cagactgacg acacggcgat ctactattgc gccaagcact actactacgg cggatcctac   1560
gctatggact actggggcca ggggaccagc gtgaccgtgt catccgcggc cgcgactacc   1620
actcctgcac cacggccacc taccccagcc cccaccattg caagccagcc actttcactg   1680
cgccccgaag cgtgtagacc agctgctgga ggagccgtgc atacccgagg gctggacttc   1740
gcctgtgaca tctacatctg ggccccattg gctggaactt gcggcgtgct gctcttgtct   1800
ctggtcatta ccctgtactg ctggctgaca aaaaagaagt attcatctag tgtacatgat   1860
ccgaacggtg aatacatgtt catgcgcgcg gtgaacacgg ccaagaagag cagactgacc   1920
gacgtaaccc ttagagtgaa gttcagccgc tcagccgatg caccggccta ccagcaggga   1980
cagaaccagc tctacaacga gctcaacctg ggtcggcggg aagaatatga cgtgctggac   2040
aaacggcgcg gcagagatcc ggagatgggg ggaaagccga ggaggaagaa ccctcaagag   2100
ggcctgtaca acgaactgca gaaggacaag atggcggaag cctactccga gatcggcatg   2160
aagggagaac gccggagagg gaagggtcat gacggactgt accagggcct gtcaactgcc   2220
```

-continued actaaggaca cttacgatgc gctccatatg caagctttgc ccccgcgg 2268

<210> SEQ ID NO 118
<211> LENGTH: 756
<212> TYPE: PRT
<213> ORGANISM: Artificial
<220> FEATURE:
<223> OTHER INFORMATION: D088 CAR2019 ICOSz

<400> SEQUENCE: 118

Met Leu Leu Leu Val Thr Ser Leu Leu Leu Cys Glu Leu Pro His Pro
1 5 10 15

Ala Phe Leu Leu Ile Pro Glu Val Gln Leu Gln Gln Ser Gly Ala Glu
20 25 30

Leu Val Lys Pro Gly Ala Ser Val Lys Met Ser Cys Lys Ala Ser Gly
35 40 45

Tyr Thr Phe Thr Ser Tyr Asn Met His Trp Val Lys Gln Thr Pro Gly
50 55 60

Gln Gly Leu Glu Trp Ile Gly Ala Ile Tyr Pro Gly Asn Gly Asp Thr
65 70 75 80

Ser Tyr Asn Gln Lys Phe Lys Gly Lys Ala Thr Leu Thr Ala Asp Lys
85 90 95

Ser Ser Ser Thr Ala Tyr Met Gln Leu Ser Ser Leu Thr Ser Glu Asp
100 105 110

Ser Ala Asp Tyr Tyr Cys Ala Arg Ser Asn Tyr Tyr Gly Ser Ser Tyr
115 120 125

Trp Phe Phe Asp Val Trp Gly Ala Gly Thr Thr Val Thr Val Ser Ser
130 135 140

Gly Gly Gly Gly Ser Gly Gly Gly Gly Ser Gly Gly Gly Gly Ser Asp
145 150 155 160

Ile Val Leu Thr Gln Ser Pro Ala Ile Leu Ser Ala Ser Pro Gly Glu
165 170 175

Lys Val Thr Met Thr Cys Arg Ala Ser Ser Ser Val Asn Tyr Met Asp
180 185 190

Trp Tyr Gln Lys Lys Pro Gly Ser Ser Pro Lys Pro Trp Ile Tyr Ala
195 200 205

Thr Ser Asn Leu Ala Ser Gly Val Pro Ala Arg Phe Ser Gly Ser Gly
210 215 220

Ser Gly Thr Ser Tyr Ser Leu Thr Ile Ser Arg Val Glu Ala Glu Asp
225 230 235 240

Ala Ala Thr Tyr Tyr Cys Gln Gln Trp Ser Phe Asn Pro Pro Thr Phe
245 250 255

Gly Gly Gly Thr Lys Leu Glu Ile Lys Gly Gly Gly Gly Ser Gly Gly
260 265 270

Gly Gly Ser Gly Gly Gly Gly Ser Gly Gly Gly Gly Ser Gly Gly Gly
275 280 285

Gly Ser Asp Ile Gln Met Thr Gln Thr Thr Ser Ser Leu Ser Ala Ser
290 295 300

Leu Gly Asp Arg Val Thr Ile Ser Cys Arg Ala Ser Gln Asp Ile Ser
305 310 315 320

Lys Tyr Leu Asn Trp Tyr Gln Gln Lys Pro Asp Gly Thr Val Lys Leu
325 330 335

Leu Ile Tyr His Thr Ser Arg Leu His Ser Gly Val Pro Ser Arg Phe
340 345 350

-continued

```
Ser Gly Ser Gly Ser Gly Thr Asp Tyr Ser Leu Thr Ile Ser Asn Leu
        355                 360                 365

Glu Gln Glu Asp Ile Ala Thr Tyr Phe Cys Gln Gln Gly Asn Thr Leu
    370                 375                 380

Pro Tyr Thr Phe Gly Gly Gly Thr Lys Leu Glu Ile Thr Gly Ser Thr
385                 390                 395                 400

Ser Gly Ser Gly Lys Pro Gly Ser Gly Glu Gly Ser Thr Lys Gly Glu
                405                 410                 415

Val Lys Leu Gln Glu Ser Gly Pro Gly Leu Val Ala Pro Ser Gln Ser
            420                 425                 430

Leu Ser Val Thr Cys Thr Val Ser Gly Val Ser Leu Pro Asp Tyr Gly
        435                 440                 445

Val Ser Trp Ile Arg Gln Pro Pro Arg Lys Gly Leu Glu Trp Leu Gly
    450                 455                 460

Val Ile Trp Gly Ser Glu Thr Thr Tyr Tyr Asn Ser Ala Leu Lys Ser
465                 470                 475                 480

Arg Leu Thr Ile Ile Lys Asp Asn Ser Lys Ser Gln Val Phe Leu Lys
                485                 490                 495

Met Asn Ser Leu Gln Thr Asp Asp Thr Ala Ile Tyr Tyr Cys Ala Lys
            500                 505                 510

His Tyr Tyr Tyr Gly Gly Ser Tyr Ala Met Asp Tyr Trp Gly Gln Gly
        515                 520                 525

Thr Ser Val Thr Val Ser Ser Ala Ala Ala Thr Thr Thr Pro Ala Pro
    530                 535                 540

Arg Pro Pro Thr Pro Ala Pro Thr Ile Ala Ser Gln Pro Leu Ser Leu
545                 550                 555                 560

Arg Pro Glu Ala Cys Arg Pro Ala Ala Gly Gly Ala Val His Thr Arg
                565                 570                 575

Gly Leu Asp Phe Ala Cys Asp Ile Tyr Ile Trp Ala Pro Leu Ala Gly
            580                 585                 590

Thr Cys Gly Val Leu Leu Leu Ser Leu Val Ile Thr Leu Tyr Cys Trp
        595                 600                 605

Leu Thr Lys Lys Lys Tyr Ser Ser Ser Val His Asp Pro Asn Gly Glu
    610                 615                 620

Tyr Met Phe Met Arg Ala Val Asn Thr Ala Lys Lys Ser Arg Leu Thr
625                 630                 635                 640

Asp Val Thr Leu Arg Val Lys Phe Ser Arg Ser Ala Asp Ala Pro Ala
                645                 650                 655

Tyr Gln Gln Gly Gln Asn Gln Leu Tyr Asn Glu Leu Asn Leu Gly Arg
            660                 665                 670

Arg Glu Glu Tyr Asp Val Leu Asp Lys Arg Arg Gly Arg Asp Pro Glu
        675                 680                 685

Met Gly Gly Lys Pro Arg Arg Lys Asn Pro Gln Glu Gly Leu Tyr Asn
    690                 695                 700

Glu Leu Gln Lys Asp Lys Met Ala Glu Ala Tyr Ser Glu Ile Gly Met
705                 710                 715                 720

Lys Gly Glu Arg Arg Arg Gly Lys Gly His Asp Gly Leu Tyr Gln Gly
                725                 730                 735

Leu Ser Thr Ala Thr Lys Asp Thr Tyr Asp Ala Leu His Met Gln Ala
            740                 745                 750

Leu Pro Pro Arg
        755
```

<210> SEQ ID NO 119
<211> LENGTH: 1461
<212> TYPE: DNA
<213> ORGANISM: Artificial
<220> FEATURE:
<223> OTHER INFORMATION: D089 CAR22 ICOSz

<400> SEQUENCE: 119

```
atgttgctgc tcgtgacctc gctccttctg tgcgagctgc cccatccggc ttttctgctc      60

atccctcaag tgcagctgca gcagtccggt cctggactgg tcaagccgtc ccagactctg     120

agcctgactt gcgcaattag cggggactca gtctcgtcca attcggcggc ctggaactgg     180

atccggcagt caccatcaag gggcctggaa tggctcgggc gcacttacta ccggtccaaa     240

tggtataccg actacgccgt gtccgtgaag aatcggatca ccattaaccc cgacacctcg     300

aagaaccagt tctcactcca actgaacagc gtgacccccg aggataccgc ggtgtactac     360

tgcgcacaag aagtggaacc gcaggacgcc ttcgacattt ggggacaggg aacgatggtc     420

acagtgtcgt ccggtggagg aggttccgga ggcggtggat ctggaggcgg aggttcggat     480

atccagatga cccagagccc ctcctcggtg tccgcatccg tgggcgataa ggtcaccatt     540

acctgtagag cgtcccagga cgtgtccgga tggctggcct ggtaccagca gaagccaggc     600

ttggctcctc aactgctgat cttcggcgcc agcactcttc agggggaagt gccatcacgc     660

ttctccggat ccggttccgg caccgacttc accctgacca tcagcagcct ccagcctgag     720

gacttcgcca cttactactg ccaacaggcc aagtacttcc cctatacctt cggaagaggc     780

actaagctgg aaatcaaggc ggccgcgact accactcctg caccacggcc acctacccca     840

gcccccacca ttgcaagcca gccactttca ctgcgccccg aagcgtgtag accagctgct     900

ggaggagccg tgcatacccg agggctggac ttcgcctgtg acatctacat ctgggcccca     960

ttggctggaa cttgcggcgt gctgctcttg tctctggtca ttaccctgta ctgctggctg    1020

acaaaaaaga agtattcatc tagtgtacat gatccgaacg gtgaatacat gttcatgcgc    1080

gcggtgaaca cggccaagaa gagcagactg accgacgtaa cccttagagt gaagttcagc    1140

cgctcagccg atgcaccggc ctaccagcag ggacagaacc agctctacaa cgagctcaac    1200

ctgggtcggc gggaagaata tgacgtgctg gacaaacggc gcggcagaga tccggagatg    1260

gggggaaagc cgaggaggaa gaaccctcaa gagggcctgt acaacgaact gcagaaggac    1320

aagatggcgg aagcctactc cgagatcggc atgaagggag aacgccggag agggaagggt    1380

catgacggac tgtaccaggg cctgtcaact gccactaagg acacttacga tgcgctccat    1440

atgcaagctt tgcccccgcg g                                              1461
```

<210> SEQ ID NO 120
<211> LENGTH: 487
<212> TYPE: PRT
<213> ORGANISM: Artificial
<220> FEATURE:
<223> OTHER INFORMATION: D089 CAR22 ICOSz

<400> SEQUENCE: 120

```
Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys Pro Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
```

-continued

```
    50                  55                  60

Pro Ser Arg Gly Leu Glu Trp Leu Gly Arg Thr Tyr Tyr Arg Ser Lys
65                  70                  75                  80

Trp Tyr Thr Asp Tyr Ala Val Ser Val Lys Asn Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Gln Glu Val Glu Pro Gln
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Gly Ser Gly Gly Gly Gly Ser Asp
145                 150                 155                 160

Ile Gln Met Thr Gln Ser Pro Ser Ser Val Ser Ala Ser Val Gly Asp
                165                 170                 175

Lys Val Thr Ile Thr Cys Arg Ala Ser Gln Asp Val Ser Gly Trp Leu
            180                 185                 190

Ala Trp Tyr Gln Gln Lys Pro Gly Leu Ala Pro Gln Leu Leu Ile Phe
        195                 200                 205

Gly Ala Ser Thr Leu Gln Gly Glu Val Pro Ser Arg Phe Ser Gly Ser
    210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Tyr Phe Pro Tyr Thr
                245                 250                 255

Phe Gly Arg Gly Thr Lys Leu Glu Ile Lys Ala Ala Ala Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Trp Leu Thr Lys Lys Lys Tyr Ser Ser Ser Val His Asp Pro
            340                 345                 350

Asn Gly Glu Tyr Met Phe Met Arg Ala Val Asn Thr Ala Lys Lys Ser
        355                 360                 365

Arg Leu Thr Asp Val Thr Leu Arg Val Lys Phe Ser Arg Ser Ala Asp
    370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
        435                 440                 445

Ile Gly Met Lys Gly Glu Arg Arg Gly Lys Gly His Asp Gly Leu
    450                 455                 460

Tyr Gln Gly Leu Ser Thr Ala Thr Lys Asp Thr Tyr Asp Ala Leu His
465                 470                 475                 480
```

Met Gln Ala Leu Pro Pro Arg
485

<210> SEQ ID NO 121
<211> LENGTH: 2274
<212> TYPE: DNA
<213> ORGANISM: Artificial
<220> FEATURE:
<223> OTHER INFORMATION: D090 CAR2019 OX40z

<400> SEQUENCE: 121
atgctccttc tcgtgacctc cctgcttctc tgcgaactgc cccatcctgc cttcctgctg 60
attcccgagg tgcagttgca acagtcagga gctgaactgg tcaagccagg agccagcgtg 120
aagatgagct gcaaggcctc cggttacacc ttcacctcct acaacatgca ctgggtgaaa 180
cagaccccgg gacaagggct cgaatggatt ggcgccatct accccgggaa tggcgatact 240
tcgtacaacc agaagttcaa gggaaaggcc accctgaccg ccgacaagag ctcctccacc 300
gcgtatatgc agttgagctc cctgacctcc gaggactccg ccgactacta ctgcgcacgg 360
tccaactact atggaagctc gtactggttc ttcgatgtct gggggggccgg caccactgtg 420 accgtcagct ccgggggcgg aggatccggt ggaggcggaa gcgggggtgg aggatccgac 480
attgtgctga ctcagtcccc ggcaatcctg tcggcctcac cgggcgaaaa ggtcacgatg 540
acttgtagag cgtcgtccag cgtgaactac atggattggt accaaaagaa gcctggatcg 600
tcacccaagc cttggatcta cgctacatct aacctggcct ccggcgtgcc agcgcggttc 660
agcgggtccg gctcgggcac ctcatactcg ctgaccatct cccgcgtgga ggctgaggac 720
gccgcgacct actactgcca gcagtggtcc ttcaacccgc cgacttttgg aggcggtact 780
aagctggaga tcaaaggagg cggcggcagc ggcgggggag ggtccggagg gggtggttct 840
ggtggaggag gatcgggagg cggtggcagc gacattcaga tgactcagac cacctcctcc 900
ctgtccgcct ccctgggcga ccgcgtgacc atctcatgcc gcgccagcca ggacatctcg 960
aagtacctca actggtacca gcagaagccc gacggaaccg tgaagctcct gatctaccac 1020
acctcccggc tgcacagcgg agtgccgtct agattctcgg gttcggggtc gggaactgac 1080
tactccctta ctatttccaa cctggagcag gaggatattg ccacctactt ctgccaacaa 1140
ggaaacaccc tgccgtacac ttttggcggg ggaaccaagc tggaaatcac tggcagcaca 1200
tccggttccg ggaagcccgg ctccggagag ggcagcacca agggggaagt caagctgcag 1260
gaatcaggac ctggcctggt ggccccgagc cagtcactgt ccgtgacttg tactgtgtcc 1320
ggagtgtcgc tcccggatta cggagtgtcc tggatcaggc agccacctcg gaaaggattg 1380
gaatggctcg gagtcatctg gggttccgaa accacctatt acaactcggc actgaaatcc 1440
aggctcacca ttatcaagga taactccaag tcacaagtgt tcctgaagat gaatagcctg 1500
cagactgacg acacggcgat ctactattgc gccaagcact actactacgg cggatcctac 1560
gctatggact actggggcca ggggaccagc gtgaccgtgt catccgcggc cgcaacgacc 1620
actccagcac cgagaccgcc aacccccgcg cctaccatcg caagtcaacc actttctctc 1680
aggcctgaag cgtgccgacc tgcagctggt ggggcagtac ataccagggg tttggacttc 1740
gcatgtgacg tggcggcaat tctcggcctg ggacttgtcc ttggtctgct tggtccgctc 1800
gcaatacttc tggccttgta cctgctccgc agagaccaaa gacttccgcc cgacgcccac 1860
aagcccccag gaggaggttc cttcagaacg cctatacaag aagaacaagc agatgcccac 1920
tctaccctgg ctaaaatcag ggtgaagttt agccggtcag ctgatgcacc tgcatatcag 1980

```
cagggacaga accagctgta caatgagctg aacctcggac gaagagagga gtacgacgtg   2040

ttggacaaaa gacgaggtag agaccccgag atgggcggca agccgagaag aaaaaaccca   2100

caagaagggc tttataatga gcttcagaaa gataagatgg cagaggccta cagtgagatt   2160

ggcatgaagg gcgaaagaag gaggggcaaa ggacacgacg gtctctacca aggcctcagc   2220

acggctacca aagatacgta tgacgcattg catatgcagg cattgccgcc ccgc         2274


<210> SEQ ID NO 122
<211> LENGTH: 758
<212> TYPE: PRT
<213> ORGANISM: Artificial
<220> FEATURE:
<223> OTHER INFORMATION: D090 CAR2019 OX40z

<400> SEQUENCE: 122

Met Leu Leu Leu Val Thr Ser Leu Leu Leu Cys Glu Leu Pro His Pro
1               5                   10                  15

Ala Phe Leu Leu Ile Pro Glu Val Gln Leu Gln Gln Ser Gly Ala Glu
            20                  25                  30

Leu Val Lys Pro Gly Ala Ser Val Lys Met Ser Cys Lys Ala Ser Gly
        35                  40                  45

Tyr Thr Phe Thr Ser Tyr Asn Met His Trp Val Lys Gln Thr Pro Gly
    50                  55                  60

Gln Gly Leu Glu Trp Ile Gly Ala Ile Tyr Pro Gly Asn Gly Asp Thr
65                  70                  75                  80

Ser Tyr Asn Gln Lys Phe Lys Gly Lys Ala Thr Leu Thr Ala Asp Lys
                85                  90                  95

Ser Ser Ser Thr Ala Tyr Met Gln Leu Ser Ser Leu Thr Ser Glu Asp
            100                 105                 110

Ser Ala Asp Tyr Tyr Cys Ala Arg Ser Asn Tyr Tyr Gly Ser Ser Tyr
        115                 120                 125

Trp Phe Phe Asp Val Trp Gly Ala Gly Thr Thr Val Thr Val Ser Ser
    130                 135                 140

Gly Gly Gly Gly Ser Gly Gly Gly Gly Ser Gly Gly Gly Gly Ser Asp
145                 150                 155                 160

Ile Val Leu Thr Gln Ser Pro Ala Ile Leu Ser Ala Ser Pro Gly Glu
                165                 170                 175

Lys Val Thr Met Thr Cys Arg Ala Ser Ser Ser Val Asn Tyr Met Asp
            180                 185                 190

Trp Tyr Gln Lys Lys Pro Gly Ser Ser Pro Lys Pro Trp Ile Tyr Ala
        195                 200                 205

Thr Ser Asn Leu Ala Ser Gly Val Pro Ala Arg Phe Ser Gly Ser Gly
    210                 215                 220

Ser Gly Thr Ser Tyr Ser Leu Thr Ile Ser Arg Val Glu Ala Glu Asp
225                 230                 235                 240

Ala Ala Thr Tyr Tyr Cys Gln Gln Trp Ser Phe Asn Pro Pro Thr Phe
                245                 250                 255

Gly Gly Gly Thr Lys Leu Glu Ile Lys Gly Gly Gly Gly Ser Gly Gly
            260                 265                 270

Gly Gly Ser Gly Gly Gly Gly Ser Gly Gly Gly Gly Ser Gly Gly Gly
        275                 280                 285

Gly Ser Asp Ile Gln Met Thr Gln Thr Thr Ser Ser Leu Ser Ala Ser
    290                 295                 300

Leu Gly Asp Arg Val Thr Ile Ser Cys Arg Ala Ser Gln Asp Ile Ser
```

-continued

```
305                 310                 315                 320

Lys Tyr Leu Asn Trp Tyr Gln Gln Lys Pro Asp Gly Thr Val Lys Leu
                325                 330                 335

Leu Ile Tyr His Thr Ser Arg Leu His Ser Gly Val Pro Ser Arg Phe
            340                 345                 350

Ser Gly Ser Gly Ser Gly Thr Asp Tyr Ser Leu Thr Ile Ser Asn Leu
        355                 360                 365

Glu Gln Glu Asp Ile Ala Thr Tyr Phe Cys Gln Gln Gly Asn Thr Leu
    370                 375                 380

Pro Tyr Thr Phe Gly Gly Gly Thr Lys Leu Glu Ile Thr Gly Ser Thr
385                 390                 395                 400

Ser Gly Ser Gly Lys Pro Gly Ser Gly Glu Gly Ser Thr Lys Gly Glu
                405                 410                 415

Val Lys Leu Gln Glu Ser Gly Pro Gly Leu Val Ala Pro Ser Gln Ser
            420                 425                 430

Leu Ser Val Thr Cys Thr Val Ser Gly Val Ser Leu Pro Asp Tyr Gly
        435                 440                 445

Val Ser Trp Ile Arg Gln Pro Pro Arg Lys Gly Leu Glu Trp Leu Gly
    450                 455                 460

Val Ile Trp Gly Ser Glu Thr Thr Tyr Tyr Asn Ser Ala Leu Lys Ser
465                 470                 475                 480

Arg Leu Thr Ile Ile Lys Asp Asn Ser Lys Ser Gln Val Phe Leu Lys
                485                 490                 495

Met Asn Ser Leu Gln Thr Asp Asp Thr Ala Ile Tyr Tyr Cys Ala Lys
            500                 505                 510

His Tyr Tyr Tyr Gly Gly Ser Tyr Ala Met Asp Tyr Trp Gly Gln Gly
        515                 520                 525

Thr Ser Val Thr Val Ser Ser Ala Ala Ala Thr Thr Thr Pro Ala Pro
    530                 535                 540

Arg Pro Pro Thr Pro Ala Pro Thr Ile Ala Ser Gln Pro Leu Ser Leu
545                 550                 555                 560

Arg Pro Glu Ala Cys Arg Pro Ala Ala Gly Gly Ala Val His Thr Arg
                565                 570                 575

Gly Leu Asp Phe Ala Cys Asp Val Ala Ala Ile Leu Gly Leu Gly Leu
            580                 585                 590

Val Leu Gly Leu Leu Gly Pro Leu Ala Ile Leu Leu Ala Leu Tyr Leu
        595                 600                 605

Leu Arg Arg Asp Gln Arg Leu Pro Pro Asp Ala His Lys Pro Pro Gly
    610                 615                 620

Gly Gly Ser Phe Arg Thr Pro Ile Gln Glu Glu Gln Ala Asp Ala His
625                 630                 635                 640

Ser Thr Leu Ala Lys Ile Arg Val Lys Phe Ser Arg Ser Ala Asp Ala
                645                 650                 655

Pro Ala Tyr Gln Gln Gly Gln Asn Gln Leu Tyr Asn Glu Leu Asn Leu
            660                 665                 670

Gly Arg Arg Glu Glu Tyr Asp Val Leu Asp Lys Arg Arg Gly Arg Asp
        675                 680                 685

Pro Glu Met Gly Gly Lys Pro Arg Arg Lys Asn Pro Gln Glu Gly Leu
    690                 695                 700

Tyr Asn Glu Leu Gln Lys Asp Lys Met Ala Glu Ala Tyr Ser Glu Ile
705                 710                 715                 720

Gly Met Lys Gly Glu Arg Arg Arg Gly Lys Gly His Asp Gly Leu Tyr
                725                 730                 735
```

Gln Gly Leu Ser Thr Ala Thr Lys Asp Thr Tyr Asp Ala Leu His Met
740 745 750

Gln Ala Leu Pro Pro Arg
755

<210> SEQ ID NO 123
<211> LENGTH: 2301
<212> TYPE: DNA
<213> ORGANISM: Artificial
<220> FEATURE:
<223> OTHER INFORMATION: D091 CAR2019 CD27z

<400> SEQUENCE: 123
atgctccttc tcgtgacctc cctgcttctc tgcgaactgc cccatcctgc cttcctgctg 60
attcccgagg tgcagttgca acagtcagga gctgaactgg tcaagccagg agccagcgtg 120
aagatgagct gcaaggcctc cggttacacc ttcacctcct acaacatgca ctgggtgaaa 180
cagaccccgg gacaagggct cgaatggatt ggcgccatct accccgggaa tggcgatact 240
tcgtacaacc agaagttcaa gggaaaggcc accctgaccg ccgacaagag ctcctccacc 300
gcgtatatgc agttgagctc cctgacctcc gaggactccg ccgactacta ctgcgcacgg 360
tccaactact atggaagctc gtactggttc ttcgatgtct gggggggccgg caccactgtg 420 accgtcagct ccgggggcgg aggatccggt ggaggcggaa gcgggggtgg aggatccgac 480
attgtgctga ctcagtcccc ggcaatcctg tcggcctcac cgggcgaaaa ggtcacgatg 540
acttgtagag cgtcgtccag cgtgaactac atggattggt accaaaagaa gcctggatcg 600
tcacccaagc cttggatcta cgctacatct aacctggcct ccggcgtgcc agcgcggttc 660
agcgggtccg gctcgggcac ctcatactcg ctgaccatct cccgcgtgga ggctgaggac 720
gccgcgacct actactgcca gcagtggtcc ttcaacccgc cgacttttgg aggcggtact 780
aagctggaga tcaaaggagg cggcggcagc ggcgggggag ggtccggagg gggtggttct 840
ggtggaggag gatcgggagg cggtggcagc gacattcaga tgactcagac cacctcctcc 900
ctgtccgcct ccctgggcga ccgcgtgacc atctcatgcc gcgccagcca ggacatctcg 960
aagtacctca actggtacca gcagaagccc gacggaaccg tgaagctcct gatctaccac 1020
acctcccggc tgcacagcgg agtgccgtct agattctcgg gttcggggtc gggaactgac 1080
tactccctta ctatttccaa cctggagcag gaggatattg ccacctactt ctgccaacaa 1140
ggaaacaccc tgccgtacac ttttggcggg ggaaccaagc tggaaatcac tggcagcaca 1200
tccggttccg ggaagcccgg ctccggagag ggcagcacca agggggaagt caagctgcag 1260
gaatcaggac ctggcctggt ggccccgagc cagtcactgt ccgtgacttg tactgtgtcc 1320
ggagtgtcgc tcccggatta cggagtgtcc tggatcaggc agccacctcg gaaaggattg 1380
gaatggctcg gagtcatctg ggttccgaa accacctatt acaactcggc actgaaatcc 1440
aggctcacca ttatcaagga taactccaag tcacaagtgt tcctgaagat gaatagcctg 1500
cagactgacg acacggcgat ctactattgc gccaagcact actactacgg cggatcctac 1560
gctatggact actggggcca ggggaccagc gtgaccgtgt catccgcggc cgcgactacc 1620
actcctgcac cacggccacc taccccagcc cccaccattg caagccagcc actttcactg 1680
cgccccgaag cgtgtagacc agctgctgga ggagccgtgc atacccgagg gctggacttc 1740
gcctgtgaca tctacatctg ggccccattg gctggaactt gcggcgtgct gctcttgtct 1800
ctggtcatta ccctgtactg ccaacggcgc aaataccgct ccaataaagg cgaaagtccg 1860

-continued

```
gtagaacccg cagaaccttg ccactacagt tgtcccagag aagaagaggg ttctacaata   1920

cctattcaag aggactatag gaaaccagag cccgcatgta gtcccagagt gaagttcagc   1980

cgctcagccg atgcaccggc ctaccagcag ggacagaacc agctctacaa cgagctcaac   2040

ctgggtcggc gggaagaata tgacgtgctg gacaaacggc gcggcagaga tccggagatg   2100

gggggaaagc cgaggaggaa gaaccctcaa gagggcctgt acaacgaact gcagaaggac   2160

aagatggcgg aagcctactc cgagatcggc atgaagggag aacgccggag agggaagggt   2220

catgacggac tgtaccaggg cctgtcaact gccactaagg acacttacga tgcgctccat   2280

atgcaagctt tgcccccgcg g                                             2301
```

<210> SEQ ID NO 124
<211> LENGTH: 767
<212> TYPE: PRT
<213> ORGANISM: Artificial
<220> FEATURE:
<223> OTHER INFORMATION: D091 CAR2019 CD27z

<400> SEQUENCE: 124

```
Met Leu Leu Leu Val Thr Ser Leu Leu Leu Cys Glu Leu Pro His Pro
1               5                   10                  15

Ala Phe Leu Leu Ile Pro Glu Val Gln Leu Gln Gln Ser Gly Ala Glu
            20                  25                  30

Leu Val Lys Pro Gly Ala Ser Val Lys Met Ser Cys Lys Ala Ser Gly
        35                  40                  45

Tyr Thr Phe Thr Ser Tyr Asn Met His Trp Val Lys Gln Thr Pro Gly
    50                  55                  60

Gln Gly Leu Glu Trp Ile Gly Ala Ile Tyr Pro Gly Asn Gly Asp Thr
65                  70                  75                  80

Ser Tyr Asn Gln Lys Phe Lys Gly Lys Ala Thr Leu Thr Ala Asp Lys
                85                  90                  95

Ser Ser Ser Thr Ala Tyr Met Gln Leu Ser Ser Leu Thr Ser Glu Asp
            100                 105                 110

Ser Ala Asp Tyr Tyr Cys Ala Arg Ser Asn Tyr Tyr Gly Ser Ser Tyr
        115                 120                 125

Trp Phe Phe Asp Val Trp Gly Ala Gly Thr Thr Val Thr Val Ser Ser
    130                 135                 140

Gly Gly Gly Gly Ser Gly Gly Gly Gly Ser Gly Gly Gly Gly Ser Asp
145                 150                 155                 160

Ile Val Leu Thr Gln Ser Pro Ala Ile Leu Ser Ala Ser Pro Gly Glu
                165                 170                 175

Lys Val Thr Met Thr Cys Arg Ala Ser Ser Ser Val Asn Tyr Met Asp
            180                 185                 190

Trp Tyr Gln Lys Lys Pro Gly Ser Ser Pro Lys Pro Trp Ile Tyr Ala
        195                 200                 205

Thr Ser Asn Leu Ala Ser Gly Val Pro Ala Arg Phe Ser Gly Ser Gly
    210                 215                 220

Ser Gly Thr Ser Tyr Ser Leu Thr Ile Ser Arg Val Glu Ala Glu Asp
225                 230                 235                 240

Ala Ala Thr Tyr Tyr Cys Gln Gln Trp Ser Phe Asn Pro Pro Thr Phe
                245                 250                 255

Gly Gly Gly Thr Lys Leu Glu Ile Lys Gly Gly Gly Gly Ser Gly Gly
            260                 265                 270

Gly Gly Ser Gly Gly Gly Gly Ser Gly Gly Gly Gly Ser Gly Gly Gly
        275                 280                 285
```

-continued

```
Gly Ser Asp Ile Gln Met Thr Gln Thr Thr Ser Ser Leu Ser Ala Ser
    290                 295                 300

Leu Gly Asp Arg Val Thr Ile Ser Cys Arg Ala Ser Gln Asp Ile Ser
305                 310                 315                 320

Lys Tyr Leu Asn Trp Tyr Gln Gln Lys Pro Asp Gly Thr Val Lys Leu
                325                 330                 335

Leu Ile Tyr His Thr Ser Arg Leu His Ser Gly Val Pro Ser Arg Phe
            340                 345                 350

Ser Gly Ser Gly Ser Gly Thr Asp Tyr Ser Leu Thr Ile Ser Asn Leu
        355                 360                 365

Glu Gln Glu Asp Ile Ala Thr Tyr Phe Cys Gln Gln Gly Asn Thr Leu
    370                 375                 380

Pro Tyr Thr Phe Gly Gly Gly Thr Lys Leu Glu Ile Thr Gly Ser Thr
385                 390                 395                 400

Ser Gly Ser Gly Lys Pro Gly Ser Gly Glu Gly Ser Thr Lys Gly Glu
                405                 410                 415

Val Lys Leu Gln Glu Ser Gly Pro Gly Leu Val Ala Pro Ser Gln Ser
            420                 425                 430

Leu Ser Val Thr Cys Thr Val Ser Gly Val Ser Leu Pro Asp Tyr Gly
        435                 440                 445

Val Ser Trp Ile Arg Gln Pro Pro Arg Lys Gly Leu Glu Trp Leu Gly
    450                 455                 460

Val Ile Trp Gly Ser Glu Thr Thr Tyr Tyr Asn Ser Ala Leu Lys Ser
465                 470                 475                 480

Arg Leu Thr Ile Ile Lys Asp Asn Ser Lys Ser Gln Val Phe Leu Lys
                485                 490                 495

Met Asn Ser Leu Gln Thr Asp Asp Thr Ala Ile Tyr Tyr Cys Ala Lys
            500                 505                 510

His Tyr Tyr Tyr Gly Gly Ser Tyr Ala Met Asp Tyr Trp Gly Gln Gly
        515                 520                 525

Thr Ser Val Thr Val Ser Ser Ala Ala Ala Thr Thr Thr Pro Ala Pro
    530                 535                 540

Arg Pro Pro Thr Pro Ala Pro Thr Ile Ala Ser Gln Pro Leu Ser Leu
545                 550                 555                 560

Arg Pro Glu Ala Cys Arg Pro Ala Ala Gly Gly Ala Val His Thr Arg
                565                 570                 575

Gly Leu Asp Phe Ala Cys Asp Ile Tyr Ile Trp Ala Pro Leu Ala Gly
            580                 585                 590

Thr Cys Gly Val Leu Leu Leu Ser Leu Val Ile Thr Leu Tyr Cys Gln
        595                 600                 605

Arg Arg Lys Tyr Arg Ser Asn Lys Gly Glu Ser Pro Val Glu Pro Ala
    610                 615                 620

Glu Pro Cys His Tyr Ser Cys Pro Arg Glu Glu Glu Gly Ser Thr Ile
625                 630                 635                 640

Pro Ile Gln Glu Asp Tyr Arg Lys Pro Glu Pro Ala Cys Ser Pro Arg
                645                 650                 655

Val Lys Phe Ser Arg Ser Ala Asp Ala Pro Ala Tyr Gln Gln Gly Gln
            660                 665                 670

Asn Gln Leu Tyr Asn Glu Leu Asn Leu Gly Arg Arg Glu Glu Tyr Asp
        675                 680                 685

Val Leu Asp Lys Arg Arg Gly Arg Asp Pro Glu Met Gly Gly Lys Pro
    690                 695                 700
```

-continued

```
Arg Arg Lys Asn Pro Gln Glu Gly Leu Tyr Asn Glu Leu Gln Lys Asp
705                 710                 715                 720

Lys Met Ala Glu Ala Tyr Ser Glu Ile Gly Met Lys Gly Glu Arg Arg
                725                 730                 735

Arg Gly Lys Gly His Asp Gly Leu Tyr Gln Gly Leu Ser Thr Ala Thr
            740                 745                 750

Lys Asp Thr Tyr Asp Ala Leu His Met Gln Ala Leu Pro Pro Arg
        755                 760                 765
```

<210> SEQ ID NO 125
<211> LENGTH: 1350
<212> TYPE: DNA
<213> ORGANISM: Artificial
<220> FEATURE:
<223> OTHER INFORMATION: D92 CAR22z

<400> SEQUENCE: 125

```
atgttgctgc tcgtgacctc gctccttctg tgcgagctgc cccatccggc ttttctgctc      60

atccctcaag tgcagctgca gcagtccggt cctggactgg tcaagccgtc ccagactctg     120

agcctgactt gcgcaattag cggggactca gtctcgtcca attcggcggc ctggaactgg     180

atccggcagt caccatcaag ggcctggaa tggctcgggc gcacttacta ccggtccaaa     240

tggtataccg actacgccgt gtccgtgaag aatcggatca ccattaaccc cgacacctcg     300

aagaaccagt tctcactcca actgaacagc gtgacccccg aggataccgc ggtgtactac     360

tgcgcacaag aagtggaacc gcaggacgcc ttcgacattt ggggacaggg aacgatggtc     420

acagtgtcgt ccggtggagg aggttccgga ggcggtggat ctggaggcgg aggttcggat     480

atccagatga cccagagccc ctcctcggtg tccgcatccg tgggcgataa ggtcaccatt     540

acctgtagag cgtcccagga cgtgtccgga tggctggcct ggtaccagca gaagccaggc     600

ttggctcctc aactgctgat cttcggcgcc agcactcttc aggggaagt gccatcacgc     660

ttctccggat ccggttccgg caccgacttc accctgacca tcagcagcct ccagcctgag     720

gacttcgcca cttactactg ccaacaggcc aagtacttcc cctatacctt cggaagaggc     780

actaagctgg aaatcaaggc ggccgcaacc actacaccag ctccgcggcc acccacccca     840

gcaccaacaa tagccagtca gcctttgtct ctgagacctg aggcttgtcg acccgctgca     900

ggtggggcag ttcatactcg ggtcttgat ttcgcctgcg atatatatat ttgggccccc     960

ctggcgggca cgtgtggggt gctccttctt tcactcgtaa ttactcttta ctgtagggtt    1020

aagttctcac gatccgccga tgcgccagca taccaacagg gacagaacca actttataat    1080

gagctgaatc ttggtcgcag ggaagaatat gatgtacttg ataaacgcag aggccgggat    1140

cccgagatgg gagggaaacc tcggagaaag aacccccagg agggcctgta taatgaattg    1200

caaaaagata aaatggctga agcttattca gagattggaa tgaaaggcga gcggagaaga    1260

ggaaaagggc acgacgggct ttaccaagga ctgtccaccg cgacaaagga cacgtacgac    1320

gcccttcata tgcaggcgct tcctccacga                                     1350
```

<210> SEQ ID NO 126
<211> LENGTH: 450
<212> TYPE: PRT
<213> ORGANISM: Artificial
<220> FEATURE:
<223> OTHER INFORMATION: D92 CAR22z

<400> SEQUENCE: 126

```
Met Leu Leu Leu Val Thr Ser Leu Leu Leu Cys Glu Leu Pro His Pro
```

-continued

```
1               5                   10                  15

Ala Phe Leu Leu Ile Pro Gln Val Gln Leu Gln Gln Ser Gly Pro Gly
            20                  25                  30

Leu Val Lys Pro Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Thr Asp Tyr Ala Val Ser Val Lys Asn Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Gln Glu Val Glu Pro Gln
        115                 120                 125

Asp Ala Phe Asp Ile Trp Gly Gln Gly Thr Met Val Thr Val Ser Ser
    130                 135                 140

Gly Gly Gly Gly Ser Gly Gly Gly Gly Ser Gly Gly Gly Gly Ser Asp
145                 150                 155                 160

Ile Gln Met Thr Gln Ser Pro Ser Ser Val Ser Ala Ser Val Gly Asp
                165                 170                 175

Lys Val Thr Ile Thr Cys Arg Ala Ser Gln Asp Val Ser Gly Trp Leu
            180                 185                 190

Ala Trp Tyr Gln Gln Lys Pro Gly Leu Ala Pro Gln Leu Leu Ile Phe
        195                 200                 205

Gly Ala Ser Thr Leu Gln Gly Glu Val Pro Ser Arg Phe Ser Gly Ser
    210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ala Lys Tyr Phe Pro Tyr Thr
                245                 250                 255

Phe Gly Arg Gly Thr Lys Leu Glu Ile Lys Ala Ala Ala Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Arg Val Lys Phe Ser Arg Ser Ala Asp Ala Pro Ala Tyr Gln
            340                 345                 350

Gln Gly Gln Asn Gln Leu Tyr Asn Glu Leu Asn Leu Gly Arg Arg Glu
        355                 360                 365

Glu Tyr Asp Val Leu Asp Lys Arg Arg Gly Arg Asp Pro Glu Met Gly
    370                 375                 380

Gly Lys Pro Arg Arg Lys Asn Pro Gln Glu Gly Leu Tyr Asn Glu Leu
385                 390                 395                 400

Gln Lys Asp Lys Met Ala Glu Ala Tyr Ser Glu Ile Gly Met Lys Gly
                405                 410                 415

Glu Arg Arg Arg Gly Lys Gly His Asp Gly Leu Tyr Gln Gly Leu Ser
            420                 425                 430
```

-continued

```
Thr Ala Thr Lys Asp Thr Tyr Asp Ala Leu His Met Gln Ala Leu Pro
        435                 440                 445

Pro Arg
    450
```

COMPOSITIONS AND METHODS FOR TREATING CANCER WITH DuoCARs

CROSS-REFERENCE TO RELATED APPLICATIONS

This U.S. Utility Patent application claims priority as a continuation of U.S. Utility application Ser. No. 16/692,957, filed Nov. 22, 2019, which is a continuation-in-part to PCT Application No. PCT/US2019/051734, filed Sep. 18, 2019, which in turn claims priority to U.S. Utility patent application Ser. No. 16/134,735, filed on Sep. 18, 2018, which is a continuation-in-part application of U.S. Utility patent application Ser. No. 16/078,269, filed Aug. 21, 2018, which in turn claims priority to PCT Application No. PCT/US2017/049923, filed Sep. 1, 2017, which in turn claims the benefit of priority under 35 U.S.C. Section 119 (e) to U.S. Provisional Patent Application No. 62/382,791 filed on Sep. 2, 2016, the entire contents of each of which are incorporated herein by reference.

SEQUENCE LISTING

The instant application contains a Sequence Listing, which has been submitted electronically in ASCII format and is hereby incorporated by reference in its entirety. Said ASCII copy, created on Nov. 23, 2021, is named Sequence_Listing.txt and is 367,000 bytes in size.

FIELD OF THE DISCLOSURE

This application relates to the field of cancer, particularly to a composition comprising at least two vectors encoding functional chimeric antigen receptors and methods of use of same in patient-specific immunotherapy.

BACKGROUND OF THE INVENTION

Cancer is one of the deadliest threats to human health. In the U.S. alone, cancer affects nearly 1.3 million new patients each year, and is the second leading cause of death after cardiovascular disease, accounting for approximately 1 in 4 deaths. Solid tumors are responsible for most of those deaths. Although there have been significant advances in the medical treatment of certain cancers, the overall 5-year survival rate for all cancers has improved only by about 10% in the past 20 years. Cancers, or malignant tumors, metastasize and grow rapidly in an uncontrolled manner, making treatment extremely difficult. One of the difficulties in modern cancer treatments is the amount of time that elapses between a biopsy and the diagnosis of cancer, and effective treatment of the patient. During this time, a patient's tumor may grow unimpeded, such that the disease has progressed further before treatment is applied. This negatively affects the prognosis and outcome of the cancer.

Chimeric Antigen Receptors (DuoCARs) are hybrid molecules comprising three essential units: (1) an extracellular antigen-binding motif, (2) linking/transmembrane motifs, and (3) intracellular T-cell signaling motifs (Long A H, Haso W M, Orentas R J. Lessons learned from a highly-active CD22-specific chimeric antigen receptor. Oncoimmunology. 2013; 2 (4): e23621). The antigen-binding motif of a CAR is commonly fashioned after a single chain Fragment variable (scFv), the minimal binding domain of an immunoglobulin (Ig) molecule. Alternate antigen-binding motifs, such as receptor ligands (i.e., IL-13 has been engineered to bind tumor expressed IL-13 receptor), intact immune receptors, library-derived peptides, and innate immune system effector molecules (such as NKG2D) also have been engineered. Alternate cell targets for CAR expression (such as NK or gamma-delta T cells) are also under development (Brown C E et al. Clin Cancer Res. 2012; 18 (8): 2199-209; Lehner M et al. PLOS One. 2012; 7 (2): e31210). There remains significant work with regard to defining the most active T-cell population to transduce with CAR vectors, determining the optimal culture and expansion techniques, and defining the molecular details of the CAR protein structure itself.

The linking motifs of a CAR can be a relatively stable structural domain, such as the constant domain of IgG, or designed to be an extended flexible linker. Structural motifs, such as those derived from IgG constant domains, can be used to extend the scFv binding domain away from the T-cell plasma membrane surface. This may be important for some tumor targets where the binding domain is particularly close to the tumor cell surface membrane (such as for the disialoganglioside GD2; Orentas et al., unpublished observations). To date, the signaling motifs used in CARs always include the CD3-3 chain because this core motif is the key signal for T cell activation. The first reported second-generation CARs featured CD28 signaling domains and the CD28 transmembrane sequence. This motif was used in third-generation CARs containing CD137 (4-1BB) signaling motifs as well (Zhao Y et al. J Immunol. 2009; 183 (9): 5563-74). With the advent of new technology, the activation of T cells with beads linked to anti-CD3 and anti-CD28 antibody, the presence of the canonical "signal 2" from CD28 was no longer required to be encoded by the CAR itself. Using bead activation, third-generation vectors were found to be not superior to second-generation vectors in in vitro assays, and they provided no clear benefit over second-generation vectors in mouse models of leukemia (Haso W, Lee D W, Shah N N, Stetler-Stevenson M, Yuan C M, Pastan I H, Dimitrov D S, Morgan R A, FitzGerald D J, Barrett D M, Wayne A S, Mackall C L, Orentas R J. Anti-CD22-chimeric antigen receptors targeting B cell precursor acute lymphoblastic leukemia. Blood. 2013; 121 (7): 1165-74; Kochenderfer J N et al. Blood. 2012; 119 (12): 2709-20). This is borne out by the clinical success of CD19-specific CARs that are in a second generation CD28/CD3-ζ (Lee D W et al. American Society of Hematology Annual Meeting. New Orleans, LA; Dec. 7-10, 2013) and a CD137/CD3-ζ signaling format (Porter D L et al. N Engl J Med. 2011; 365 (8): 725-33). In addition to CD137, other tumor necrosis factor receptor superfamily members such as OX40 also are able to provide important persistence signals in CAR-transduced T cells (Yvon E et al. Clin Cancer Res. 2009; 15 (18): 5852-60). Equally important are the culture conditions under which the CAR T-cell populations were cultured.

Current challenges in the more widespread and effective adaptation of CAR therapy for cancer relate to a paucity of compelling targets. Creating binders to cell surface antigens is now readily achievable, but discovering a cell surface antigen that is specific for tumor while sparing normal tissues remains a formidable challenge. One potential way to imbue greater target cell specificity to CAR-expressing T cells is to use combinatorial CAR approaches. In one system, the CD3-3 and CD28 signal units are split between two different CAR constructs expressed in the same cell; in another, two DuoCARs are expressed in the same T cell, but one has a lower affinity and thus requires the alternate CAR to be engaged first for full activity of the second (Lanitis E et al. Cancer Immunol Res. 2013; 1 (1): 43-53; Kloss C C et al. Nat Biotechnol. 2013; 31 (1): 71-5). A second challenge for the generation of a single scFv-based CAR as an immunotherapeutic agent is tumor cell heterogeneity. At least one group has developed a CAR strategy for glioblastoma whereby the effector cell population targets multiple antigens (HER2, IL-13Ra, EphA2) at the same time in the hope of avoiding the outgrowth of target antigen-negative populations (Hegde M et al. Mol Ther. 2013; 21 (11): 2087-101).

T-cell-based immunotherapy has become a new frontier in synthetic biology; multiple promoters and gene products are envisioned to steer these highly potent cells to the tumor microenvironment, where T cells can both evade negative regulatory signals and mediate effective tumor killing. The elimination of unwanted T cells through the drug-induced dimerization of inducible caspase 9 constructs with AP1903 demonstrates one way in which a powerful switch that can control T-cell populations can be initiated pharmacologically (Di Stasi A et al. N Engl J Med. 2011; 365 (18): 1673-83). The creation of effector T-cell populations that are immune to the negative regulatory effects of transforming growth factor-β by the expression of a decoy receptor further demonstrates that degree to which effector T cells can be engineered for optimal antitumor activity (Foster A E et al. J Immunother. 2008; 31 (5): 500-5).

Thus, while it appears that CARs can trigger T-cell activation in a manner similar to an endogenous T-cell receptor, a major impediment to the clinical application of CAR-based technology to date has been limited in vivo expansion of CAR+ T cells, rapid disappearance of the cells after infusion, disappointing clinical activity, relapse of the underlying medical disease or condition, and the undue length of time that elapses between diagnosis and timely treatment of cancer using such CAR+ T cells.

Accordingly, there is an urgent and long felt need in the art for discovering compositions and methods for treatment of cancer using a CAR-based therapy that can exhibit cancer-specific intended therapeutic attributes without the aforementioned short comings.

The present invention addresses these needs by providing compositions comprising at least two vectors encoding functional chimeric antigen receptors and methods of use of same in patient-specific immunotherapy that can be used to treat cancers and other diseases and/or conditions.

In particular, the present invention as disclosed and described herein provides an immunotherapy composition comprising one or more isolated nucleic acid molecules encoding at least two vectors, each vector encoding a functional DuoCAR, whereby the combination of vectors results in the expression of two or more non-identical binding domains, wherein each vector encoded binding domain(s) are covalently linked to a transmembrane domain and one or more non-identical intracellular signaling motifs, which immunotherapy composition may be used to transduce autologous lymphocytes to generate active patient-specific anti-tumor lymphocyte cell populations that can be infused directly back into the patient to promote in vivo expansion, persistence of patient-specific anti-tumor T-cells resulting in tumor stabilization, reduction, elimination, remission of cancer, or prevention or amelioration of relapse of cancer, or a combination thereof, in a patient-specific manner.

SUMMARY OF THE INVENTION

Novel adoptive immunotherapy compositions comprising two or more vector-transduced lymphocytes are provided herein as well as are methods of use of same in a patient-specific combination immunotherapy that can be used to treat cancers and other diseases and conditions.

Thus, in one aspect, lentiviral vectors expressing Duo chimeric antigen receptors (DuoCARs) are provided herein, as well as nucleic acid molecules encoding the lentiviral vectors expressing DuoCARs. Methods of using the disclosed lentiviral vectors expressing DuoCARs, host cells, and nucleic acid molecules are also provided, for example, to treat a cancer in a subject.

In one aspect, an immunotherapy composition is provided comprising one or more isolated nucleic acid molecules encoding at least two vectors (DuoCARs), each vector encoding a functional CAR, wherein at least one binding domain(s) in one of the vectors are non-identical, and whereby the combination of vectors results in the expression of two or more non-identical binding domains, wherein each vector encoded binding domain(s) are covalently linked to a transmembrane domain and one or more non-identical intracellular signaling motifs.

In one embodiment, an immunotherapy composition is provided comprising one or more isolated nucleic acid molecules encoding at least three vectors (TrioCARs), each vector encoding a functional CAR, whereby the combination of vectors results in the expression of two or more non-identical binding domains, wherein each vector encoded binding domain(s) are covalently linked to a transmembrane domain and one or more non-identical intracellular signaling motifs.

In one embodiment, an immunotherapy composition is provided comprising one or more isolated nucleic acid molecules encoding at least four vectors (QuatroCARs), each vector encoding a functional CAR, whereby the combination of vectors results in the expression of two or more non-identical binding domains, wherein each vector encoded binding domain(s) are covalently linked to a transmembrane domain and one or more non-identical intracellular signaling motifs.

In yet another embodiment, an immunotherapy composition is provided comprising one or more isolated nucleic acid molecules encoding at least two, three, four, five, six, seven, eight, nine, or ten vectors (e.g., an "nCAR"), each vector encoding a functional CAR, whereby the combination of vectors results in the expression of two or more non-identical binding domains, wherein each vector encoded binding domain(s) are covalently linked to a transmembrane domain and one or more non-identical intracellular signaling motifs, wherein each unique member of the nCAR set when assembled into a CAR product constitutes a unique CAR composition referred to herein as "nCAR" (e.g., DuoCAR, TrioCAR, QuatroCAR, PentaCAR, HexaCAR, HeptaCAR, OctaCAR, NonaCAR, and DecaCAR, etc.).

In one embodiment, an immunotherapy composition is provided comprising: (a) at least two vectors, each comprising nucleic acid sequences that are functional in cells; (b) wherein each vector encodes a functional CAR; (c) wherein each CAR comprises of at least one binding domain, a single transmembrane domain, and at least one intracellular signaling motif; (d) wherein the at least one binding domains in one of the vectors are non-identical; and (e) wherein the at least one binding domain, a single transmembrane domain, at least one linker domain, and at least one intracellular signaling motif are covalently linked in each said vector, wherein the combination of vectors are used to genetically modify one or more lymphocyte populations.

In another embodiment, an immunotherapy composition is provided comprising: (a) at least two vectors, each comprising nucleic acid sequences that are functional in cells; (b) wherein each vector encodes a functional CAR; (c) wherein each CAR comprises at least one binding domain, a single transmembrane domain, and at least one intracellular signaling motif; (d) wherein the at least one binding domain(s) in each vector are non-identical; (e) wherein the at least one signaling motif combinations are non-identical between each of the vectors; and (f) wherein the at least one binding domain, a single transmembrane domain, and at least one intracellular signaling motif are covalently linked in each said vector, wherein the combination of two or more vectors are used to genetically modify one or more lymphocyte populations.

In one embodiment, an immunotherapy composition is provided wherein each vector encodes more than one functional CAR.

In another embodiment, an immunotherapy composition is provided wherein one or more signaling motifs combinations are identical on one or more vectors.

In another embodiment, an immunotherapy composition is provided wherein one or more multiple binding domains are identical on one or more vectors.

In another embodiment, an immunotherapy composition is provided wherein the lymphocyte population(s) comprise autologous T-cells or a mixture of peripheral blood derived lymphocytes.

In another embodiment, an immunotherapy composition is provided wherein the at least one extracellular antigen binding domain of the CAR comprises at least one single chain variable fragment of an antibody that binds to the antigen.

In another embodiment, an immunotherapy composition is provided wherein the at least one extracellular antigen binding domain of the CAR comprises at least one heavy chain variable region of an antibody that binds to the antigen.

In another embodiment, an immunotherapy composition is provided wherein the at least one extracellular antigen binding domain of the CAR, the at least one intracellular signaling domain of the CAR, or both are connected to the transmembrane domain by a linker or spacer domain.

In another embodiment, an immunotherapy composition is provided wherein the extracellular antigen binding domain of the CAR is preceded by a leader peptide.

In another embodiment, an immunotherapy composition is provided wherein the extracellular antigen binding domain of the CAR targets an antigen comprising CD19, CD20, CD22, ROR1, TSLPR, mesothelin, CD33, CD38, CD123 (IL3RA), CD138, BCMA (CD269), GPC2, GPC3, FGFR4, c-Met, PSMA, Glycolipid F77, EGFRVIII, GD-2, NY-ESO-1, MAGE-A3, PRAME peptides in combination with MHC, or any combination thereof.

In another embodiment, an immunotherapy composition is provided wherein the extracellular antigen binding domain of the CAR comprises an anti-CD19 scFV antigen binding domain, an anti-CD20 scFV antigen binding domain, an anti-CD22 scFV antigen binding domain, an anti-ROR1 scFV antigen binding domain, an anti-TSLPR scFV antigen binding domain, an anti-mesothelin scFV antigen binding domain, an anti-CD33 scFV antigen binding domain, an anti-CD38 scFV antigen binding domain, an anti-CD123 (IL3RA) scFV antigen binding domain, an anti-CD138 scFV antigen binding domain, an anti-BCMA (CD269) scFV antigen binding domain, an anti-GPC2 scFV antigen binding domain, an anti-GPC3 scFV antigen binding domain, an anti-FGFR4 scFV antigen binding domain, an anti-c-Met scFV antigen binding domain, an anti-PMSA scFV antigen binding domain, an anti-glycolipid F77 scFV antigen binding domain, an anti-EGFRvIII scFV antigen binding domain, an anti-GD-2 scFV antigen binding domain, an anti-NY-ESO-1 TCR (including single chain TCR constructs) antigen binding domain, an anti-MAGE-A3 TCR, or an amino acid sequence with 85%, 90%, 95%, 96%, 97%, 98% or 99% identity thereof, or any combination thereof.

In another embodiment, an immunotherapy composition is provided wherein the linker or spacer domain of the CAR is derived from the extracellular domain of CD8, and is linked to the transmembrane domain.

In another embodiment, an immunotherapy composition is provided wherein the CAR further comprises a transmembrane domain that comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, CD271, TNFRSF19, Fc epsilon R, or any combination thereof.

In another embodiment, an immunotherapy composition is provided wherein the at least one intracellular signaling domain further comprises a CD3 zeta intracellular domain.

In another embodiment, an immunotherapy composition is provided wherein the at least one intracellular signaling domain is arranged on a C-terminal side relative to the CD3 zeta intracellular domain.

In another embodiment, an immunotherapy composition is provided wherein the at least one intracellular signaling domain comprises a costimulatory domain, a primary signaling domain, or any combination thereof.

In another embodiment, an immunotherapy composition is provided wherein the at least one costimulatory domain comprises a functional signaling domain of OX40, CD70, CD27, CD28, CD5, ICAM-1, LFA-1 (CD11a/CD18), ICOS (CD278), DAP10, DAP12, and 4-1BB (CD137), PD-1, GITR, CTLA-4, or any combination thereof.

In another embodiment, an immunotherapy composition is provided wherein a single vector is used to encode all chimeric antigen receptors (e.g., retroviral, adenoviral, SV40, herpes vector, POX vector, RNA, plasmid, cosmid, or any viral vector or non-viral vector), in combination with a CRISPR system for integration.

In another embodiment, an immunotherapy composition is provided wherein each vector is an RNA or DNA vector, alone or in combination with a transfection reagent or a method to deliver the RNA or DNA into the cell, a non-limiting example being electroporation.

In another embodiment, an immunotherapy composition is provided wherein at least one vector expresses a nucleic acid molecule that modulates the expression of a nucleic acid in the cell.

In another embodiment, an immunotherapy composition is provided wherein the nucleic acid molecule inhibits or deletes the expression of an endogenous gene.

In certain embodiments, an immunotherapy composition is provided wherein the active patient-specific autologous anti-tumor lymphocyte cell population is generated within one day, two days, three days, four days, five days, seven days, ten days, twelve days, fourteen days, twenty-one days, or one month of lymphocyte harvest or tumor biopsy and wherein the active patient-specific autologous anti-tumor lymphocyte cell population that can be infused back into a patient suffering from cancer and is capable of promoting in vivo expansion, persistence of patient-specific anti-tumor lymphocyte cells resulting in tumor stabilization, reduction, elimination, remission of cancer, or prevention or amelioration of relapse of cancer, or a combination thereof, in a patient-specific manner.

In one aspect, isolated nucleic acid molecules encoding the aforementioned chimeric antigen receptors are provided herein.

In one aspect of the DuoCARs used in the patient-specific autologous lymphocyte population(s) of the immunotherapy composition of the present invention, the DuoCARs are modified to express or contain a detectable marker for use in diagnosis, monitoring, and/or predicting the treatment outcome such as progression free survival of cancer patients or for monitoring the progress of such treatment. In one embodiment of the DuoCARs used in the patient-specific autologous anti-tumor lymphocyte cell population(s), the nucleic acid molecules encoding the disclosed DuoCARs can be contained in a vector, such as a viral or non-viral vector. The vector is a DNA vector, an RNA vector, a plasmid vector, a cosmid vector, a herpes virus vector, a measles virus vector, a lentiviral vector, adenoviral vector, or a retrovirus vector, or a combination thereof.

In certain embodiments of the DuoCARs used in the patient-specific autologous anti-tumor lymphocyte cell population(s), the two or more lentiviral vectors are pseudotyped with different viral glycoproteins (GPS) including for example, and not by way of limitation, amphotropic murine leukemia virus [MLV-A], a baboon endogenous virus (BaEV), GP164, gibbon ape leukemia virus [GALV], RD114, feline endogenous virus retroviral-derived GPs, and vesicular stomatitis virus [VSV], measles virus, fowl plague virus [FPV], Ebola virus [EboV], lymphocytic choriomeningitis virus [LCMV]) non retroviral-derived GPs, as well as chimeric variants thereof including, for example, and not by way of limitation, chimeric GPs encoding the extracellular and transmembrane domains of GALV or RD114 GPs fused to the cytoplasmic tail (designated TR) of MLV-A GP.

In certain embodiments of the DuoCARs used in the patient-specific autologous anti-tumor lymphocyte cell population(s), the vector further comprises a promoter wherein the promoter is an inducible promoter, a tissue specific promoter, a constitutive promoter, a suicide promoter or any combination thereof.

In yet another embodiment of the DuoCARs used in the patient-specific autologous anti-tumor lymphocyte cell population(s), the vector expressing the CAR can be further modified to include one or more operative elements to control the expression of CAR T cells, or to eliminate CAR-T cells by virtue of a suicide switch. The suicide switch can include, for example, an apoptosis inducing signaling cascade or a drug that induces cell death. In a preferred embodiment, the vector expressing the CAR can be further modified to express an enzyme such thymidine kinase (TK) or cytosine deaminase (CD).

In another aspect of the DuoCARs used in the patient-specific autologous anti-tumor lymphocyte cell population(s), host cells including the nucleic acid molecule(s) encoding the DuoCARs are also provided. In some embodiments, the host cell is a T cell, such as a primary T cell obtained from a subject. In one embodiment, the host cell is a CD8+ T cell. In one embodiment the host cell is a CD4+ T cell. In one embodiment the host cells are selected CD4+ and CD8+ lymphocytes purified directly from a patient product without regard to proportionality. In another embodiment the number of CD4+ and CD8+ T cells in the product are specific. In another embodiment specific subsets of T cells are utilized as identified by phenotypic markers including T naïve cells (Tn), T effector memory cells (Tem), T central memory cells (Tcm), T regulatory cells (Treg), induced T regulatory cells (iTreg), T suppressor cells (Ts), T stem cell memory cells (Tscm), Natural Killer (NK) cells, and lymphokine activated killer (LAK) cells.

In yet another embodiment, a pharmaceutical composition is provided comprising an anti-tumor effective amount of an immunotherapy composition comprising a population of patient-specific autologous anti-tumor lymphocyte cell population(s) of a human having a cancer, wherein the cells of the population include cells comprising nucleic acid molecules encoding at least two vectors, each vector encoding a functional CAR, whereby the combination of vectors results in the expression of two or more non-identical binding domains, wherein each vector encoded binding domain(s) are covalently linked to a transmembrane domain and one or more non-identical intracellular signaling motifs.

In yet another embodiment, a pharmaceutical composition is provided comprising an anti-tumor effective amount of an immunotherapy composition comprising a population of patient-specific autologous anti-tumor lymphocyte cell population(s) of a human having a cancer, wherein the cells of the population include cells comprising (a) nucleic acid molecules encoding two or more vectors; (b) wherein each vector encodes a functional CAR; (c) wherein each CAR comprises of at least one binding domain, at least one transmembrane domain, at least one linker domain, and at least one intracellular signaling motif; (d) wherein the at least one binding domains in one of the vectors are non-identical; and (e) wherein the at least one binding domain, a single transmembrane domain, at least one linker domain, and at least one intracellular signaling motif are covalently linked in each said vector, wherein the combination of vectors are used to genetically modify one or more lymphocyte populations.

In yet another embodiment, a pharmaceutical composition is provided comprising an anti-tumor effective amount of an immunotherapy composition comprising a population of patient-specific autologous anti-tumor lymphocyte cell population(s) of a human having a cancer, wherein the cells of the population include cells comprising (a) nucleic acid molecules encoding two or more vectors; (b) wherein each vector encodes a functional CAR; (c) wherein each CAR comprises at least one binding domain, at least one transmembrane domain, at least one linker domain, and at least one intracellular signaling motif; (d) wherein the at least one binding domain(s) in each vector are non-identical; (e) wherein the at least one signaling motif combinations are non-identical between each of the vectors; and (f) wherein the at least one binding domain, a single transmembrane domain, at least one linker domain, and at least one intracellular signaling motif are covalently linked in each said vector, wherein the combination of two or more vectors are used to genetically modify one or more lymphocyte populations.

In one embodiment, the cancer is a refractory cancer non-responsive to one or more chemotherapeutic agents. The cancer includes hematopoietic cancer, myelodysplastic syndrome, pancreatic cancer, head and neck cancer, cutaneous tumors, minimal residual disease (MRD) in acute lymphoblastic leukemia (ALL), acute myeloid leukemia (AML), lung cancer, breast cancer, ovarian cancer, prostate cancer, colon cancer, melanoma or other hematological cancer and solid tumors, or any combination thereof. In another embodiment, the cancer includes a hematological cancer such as leukemia (e.g., chronic lymphocytic leukemia (CLL), acute lymphocytic leukemia (ALL), acute myeloid leukemia (AML), or chronic myelogenous leukemia (CML), lymphoma (e.g., mantle cell lymphoma, non-Hodgkin's lymphoma or Hodgkin's lymphoma) or multiple myeloma, or any combination thereof.

In yet another embodiment, the cancer includes an adult carcinoma comprising coral and pharynx cancer (tongue, mouth, pharynx, head and neck), digestive system cancers (esophagus, stomach, small intestine, colon, rectum, anus, liver, intrahepatic bile duct, gallbladder, pancreas), respiratory system cancers (larynx, lung and bronchus), bones and joint cancers, soft tissue cancers, skin cancers (melanoma, basal and squamous cell carcinoma), pediatric tumors (neuroblastoma, rhabdomyosarcoma, osteosarcoma, Ewing's sarcoma), tumors of the central nervous system (brain, astrocytoma, glioblastoma, glioma), and cancers of the breast, the genital system (uterine cervix, uterine corpus, ovary, vulva, vagina, prostate, testis, penis, endometrium), the urinary system (urinary bladder, kidney and renal pelvis, ureter), the eye and orbit, the endocrine system (thyroid), and the brain and other nervous system, or any combination thereof.

In another aspect, a pharmaceutical composition is provided comprising an autologous lymphocyte cell population transduced with two or more lentiviral vectors encoding single or multiple chimeric antigen receptors (DuoCARs), thereby generating a patient-specific autologous anti-tumor lymphocyte cell population capable of promoting in vivo expansion, persistence of patient-specific anti-tumor T-cells resulting in tumor stabilization, reduction, elimination, remission of cancer, or prevention or amelioration of relapse of cancer, or a combination thereof, in a patient-specific manner.

In another aspect, a pharmaceutical composition is provided comprising an autologous T cell population transduced with one or more lentiviral vectors encoding single or multiple chimeric antigen receptors (DuoCARs) to generate an patient-specific autologous anti-tumor lymphocyte cell population capable of promoting in vivo expansion, persistence of patient-specific anti-tumor T-cells resulting in tumor stabilization, reduction, elimination, remission of cancer, or prevention or amelioration of relapse of cancer, or a combination thereof, in a patient-specific manner.

In another aspect, methods of making active patient-specific autologous anti-tumor Duo CAR-containing lymphocyte cells are provided. The methods include transducing a lymphocyte cell with two or more vectors or nucleic acid molecule encoding two or more chimeric antigen receptors (DuoCARs) that specifically bind an antigen, thereby making active patient-specific autologous anti-tumor Duo CAR-containing lymphocyte cells.

In yet another aspect, a method of generating a population of RNA-engineered lymphocyte cells is provided that comprises introducing an in vitro transcribed RNA or synthetic RNA of a nucleic acid molecule encoding a two or more chimeric antigen receptors (DuoCARs) into a cell population of a subject, thereby generating an patient-specific autologous anti-tumor lymphocyte cell population capable of promoting in vivo expansion, persistence of patient-specific anti-tumor T-cells resulting in tumor stabilization, reduction, elimination, remission of cancer, or prevention or amelioration of relapse of cancer, or a combination thereof, in a patient-specific manner.

In another aspect, a method is provided for treating a mammal having a disease, disorder or condition associated with an elevated expression of a tumor antigen, the method comprising administering to the subject a pharmaceutical composition comprising an anti-tumor effective amount of an autologous lymphocyte cell population transduced with one or more lentiviral vectors encoding single or multiple chimeric antigen receptors (DuoCARs) thereby generating an patient-specific autologous anti-tumor lymphocyte cell population capable of promoting in vivo expansion, persistence of patient-specific anti-tumor T-cells resulting in tumor stabilization, reduction, elimination, remission of cancer, or prevention or amelioration of relapse of cancer, or a combination thereof, in a patient-specific manner.

In another aspect, a method is provided for treating a mammal having a disease, disorder or condition associated with an elevated expression of a tumor antigen, the method comprising administering to the subject a pharmaceutical composition comprising an anti-tumor effective amount of an autologous lymphocyte cell population transduced with two or more lentiviral vectors encoding single or multiple chimeric antigen receptors (DuoCARs) to generate an patient-specific autologous anti-tumor lymphocyte cell population which can be infused directly back into the patient to promote in vivo expansion, persistence of patient-specific anti-tumor T-cells resulting in tumor stabilization, reduction, elimination, or remission of cancer, or prevention or amelioration of relapse of cancer, or any combination thereof, in a patient-specific manner.

In one embodiment, a method is provided for treating a mammal having a disease, disorder or condition associated with an elevated expression of a tumor antigen, the method comprising administering to the subject a pharmaceutical composition comprising at least two vectors, each vector encoding a functional CAR, whereby the combination of vectors results in the expression of two or more non-identical binding domains, wherein each vector encoded binding domain(s) are covalently linked to a transmembrane domain and one or more non-identical intracellular signaling motifs, and a pharmaceutically acceptable excipient, wherein the combination of vectors are used to genetically modify one or more lymphocyte populations.

In another embodiment, a method is provided for treating a mammal having a disease, disorder or condition associated with an elevated expression of a tumor antigen, the method comprising administering to the subject a pharmaceutical composition comprising (a) nucleic acid molecules encoding two or more vectors; (b) wherein each vector encodes a functional CAR; (c) wherein each CAR comprises of at least one binding domain, at least one transmembrane domain, and at least one intracellular signaling motif; (d) wherein the at least one binding domains in one of the vectors are non-identical; and (e) wherein the at least one binding domain, a single transmembrane domain, and at least one intracellular signaling motif are covalently linked in each said vector, wherein the combination of vectors are used to genetically modify one or more lymphocyte populations.

In yet another embodiment, a method is provided for treating a mammal having a disease, disorder or condition associated with an elevated expression of a tumor antigen, the method comprising administering to the subject a pharmaceutical composition comprising (a) nucleic acid molecules encoding two or more vectors; (b) wherein each vector encodes a functional CAR; (c) wherein each CAR comprises at least one binding domain, at least one transmembrane domain, and at least one intracellular signaling motif; (d) wherein the at least one binding domain(s) in each vector are non-identical; (e) wherein the at least one signaling motif combinations are non-identical between each of the vectors; and (f) wherein the at least one binding domain, a single transmembrane domain, and at least one intracellular signaling motif are covalently linked in each said vector, wherein the combination of two or more vectors are used to genetically modify one or more lymphocyte populations.

In certain embodiments, the genetically modified lymphocytes are autologous T cell lymphocytes, and wherein the autologous or allogeneic T cell lymphocytes are infused directly back into the patient so as to prevent or ameliorate relapse of malignant disease.

In certain other embodiments, the genetically modified lymphocytes are autologous T cell lymphocytes, and wherein the autologous lymphocytes are infused directly back into the patient to promote in vivo expansion, persistence of patient-specific anti-tumor T-cell lymphocytes resulting in tumor stabilization, reduction, elimination, or remission of cancer, or prevention or amelioration of relapse of cancer, or any combination thereof, in a patient-specific manner.

In yet another embodiment, the T cell has been preselected by virtue of expressing specific activation or memory-associated surface markers.

In yet another embodiment, the T cell is derived from a hematopoietic stem cell donor, and wherein the procedure is carried out in the context of hematopoietic stem cell transplantation.

In certain embodiments, a method is provided wherein the lymphocyte cell has been preselected by virtue of expressing specific activation or memory-associated surface markers.

In certain embodiments, a method is provided herein wherein the lymphocyte cell is a T cell and is derived from a hematopoietic stem cell donor, and wherein the procedure is carried out in the context of hematopoietic stem cell transplantation.

In yet another aspect, a method is provided for generating a persisting population of genetically engineered patient-specific autologous anti-tumor lymphocyte cell population(s) in a human diagnosed with cancer. In one embodiment, the method comprises administering to a human patient in need thereof one or more patient-specific autologous anti-tumor lymphocyte cell population(s) described herein, wherein the persisting population of patient-specific autologous anti-tumor lymphocyte cell population(s), or the population of progeny of the lymphocyte cells, persists in the human for at least one month, two months, three months, four months, five months, six months, seven months, eight months, nine months, ten months, eleven months, twelve months, two years, or three years after administration.

In one embodiment, the progeny lymphocyte cells in the human comprise a memory T cell. In another embodiment, the T cell is an autologous T cell.

In all of the aspects and embodiments of methods described herein, any of the aforementioned cancers, diseases, disorders or conditions associated with an elevated expression of a tumor antigen that may be treated or prevented or ameliorated using a patient-specific autologous anti-tumor lymphocyte cell population(s) comprising one or more of the Duo Car immunotherapeutic compositions as disclosed herein.

In yet another aspect, a kit is provided for making a DuoCAR immunotherapeutic composition comprising a patient-specific autologous anti-tumor lymphocyte cell population(s) as described supra or for preventing, treating, or ameliorating any of the cancers, diseases, disorders or conditions associated with an elevated expression of a tumor antigen in a subject as described supra, comprising a container comprising any one of the nucleic acid molecules, vectors, host cells, or compositions disclosed supra or any combination thereof, and instructions for using the kit.

While the compositions and methods of the present invention have been illustrated with reference to the generation and utilization of DuoCARs, it is contemplated herein that the compositions and methods are specifically intended to include the generation and utilization of TrioCARs and QuatroCARs.

In yet another aspect, an immunotherapy composition comprising one or more isolated nucleic acids encoding at least one vector, wherein said vector contains a nucleic acid sequence that results in at least one messenger RNA (i.e., a multi-cistronic nucleic acid or a nucleic acid resulting in more than one transcript) encoding a DuoCAR, resulting in the ability to bind two or more non-identical antigen targets, thereby generating multiple antigen specificities residing in a single cell expressing said vector.

In yet another aspect, an immunotherapy composition comprising one or more isolated nucleic acids encoding at least two vectors, as described supra, wherein each vector further encodes a functional tag or anti-tag binding moiety (AT-CAR) that reconstitutes a functional chimeric antigen receptor upon co-incubation or co-administration of a soluble binder (such as a tagged scFv, or a scFv linked to an anti-tag binder), whereby the combination of the two vectors results in the ability to bind two or more non-identical antigen binding domains, resulting in multiple antigen specificities residing in a cell expressing these two vectors.

In yet another aspect, an immunotherapy composition comprising one or more isolated nucleic acids encoding at least two vectors, as described supra, wherein each vector encoding a functional tag or anti-tag binding moiety (AT-CAR) that reconstitutes a functional chimeric antigen receptor upon co-incubation or co-administration of a soluble binder (such as a tagged scFv, or a scFv linked to an anti-tag binder), wherein each vector expresses a unique tag (or anti-tag) that can bind soluble protein or protein modified structures resulting in multiple antigen specificities, or wherein each vector expresses a unique tag (or anti-tag) that binds only one of the soluble binding domains resulting in a specific linkage of the AT-CAR encoded intracellular signaling motifs to the antigen-binding domains of the tagged (or anti-tagged) binder.

In a non-limiting embodiment for the manufacture of DuoCAR vectors, the each of the compositions and methods disclosed in the embodiments and aspects referred to supra, the two vectors can be made separately and then added to the T cells sequentially or at the same time. In another non limiting embodiment, the plasmid DNA of the two or more vectors can be combined before or during transfection of production cells, or integrated in the production cells genome, to produce a mixture of viral vectors that contain the multiple DuoCAR vector particles, subsequently used for the transduction and genetic modification of patient T Cells.

For each of the various aspects and embodiments of the DuoCARs, TrioCARs and QuatroCARs specifically contemplated herein, the nucleotide sequences encoding the functional CAR comprise the nucleotide sequence of SEQ ID NO: 3, 9, 21, 25, 29, 31, 35, 39, 43, 47, 49, 51, 53, 55, 59, 61, 109, 111, 113, or 115 or any combination thereof.

For each of the various aspects and embodiments of the DuoCARs, TrioCARs and QuatroCARs specifically contemplated herein, each vector encodes a functional CAR comprising the amino acid sequence of SEQ ID NO: 4, 10, 22, 26, 30, 32, 36, 40, 44, 48, 50, 52, 54, 56, 60, 62, 110, 112, 114, or 116 or any combination thereof.

It will be understood that the patient-specific autologous anti-tumor lymphocyte cell population(s), the two or more lentiviral vectors expressing chimeric antigen receptors (DuoCARs), host cells, and methods as described supra are useful beyond the specific aspects and embodiments that are described in detail herein. The foregoing features and advantages of the disclosure will become more apparent from the following detailed description, which proceeds with reference to the accompanying figures.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 21A: The triple targeting anti-CD20 and anti-CD19 anti-CD22 DuoCAR D93 is comprised of 20-19 tandem ScFv, hinge and transmembrane domain, ICOS co-stimulatory domain and the CD3z activation domain, followed by the 2A sequence, and then the single targeting CD22 CAR comprised from CD22 scFv, hinge and transmembrane domain, and CD3z activation domain. DuoCAR D94 is constructed as D93, except for the substitution of the ICOS co-stimulatory domain for OX40 domain. DuoCAR construct D95 is constructed as D94, except for the addition of the ICOS co-stimulatory domain to the CD22 CAR chain. DuoCAR construct D96 is comprised as construct D95, except for the substitution of OX40 costimulatory domain in the D95 construct for the CD27 costimulatory domain. All constructs contain CD8-derived hinge and transmembrane domains. Tandem Construct 1497, and single CAR constructs D89, D92, 1538, 1497 represent functional controls. FIG. 21B schematically depicts DuoCAR T cell, in which one tandem CAR chain and one single CAR chain are co-expressed in the same T cell, a tandem CAR, a Single CAR of the second generation (with co-stimulatory domain), and a single CAR of the first generation (without costimulatory domain).

DETAILED DESCRIPTION

Definitions

Figure 1:
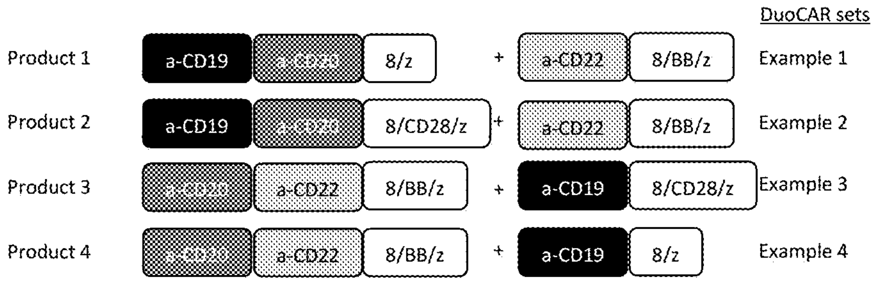
FIG. 1 depicts four (4) Products (Examples 1 through 4) that can be produced as discrete commercial entities. These DuoCARs sets can be created to target human B cell malignancies expressing three leukemia-associated antigens, CD19, CD20, and CD22. In Product 1, two gene vectors are used to co-transduce an activated T cell population. The first vector encodes two antigen binding domains (CD19, CD20) linked to a single intracellular domain (z, CD3 zeta chain) connected by virtue of a CD8 transmembrane region (8). The second vector encodes a CD22 binding domain and two signaling domains (BB, derived from CD137/4-1BB; and z). The second Product, Example 2, feature the first vector with CD19- and CD20-binding domains linked to CD28 and z signaling domains. The second vector encodes a CD22 binding domain and the BB and z signaling domains and essentially recapitulated the signaling package of a third generation CAR vector (three different signaling domains) In the third Product, Example 3, the first vector encodes CD20- and CD22-binding domain linked to BB and z signaling domains and the second vector encodes a CD19-binding domain linked to CD28 and z signaling domains. In the fourth Product, Example 4, the first vector encodes CD20- and CD22-binding domains and BB and z signaling domains. The second vector encodes a CD19 binding domains and a z signaling domain.
Figure 2:
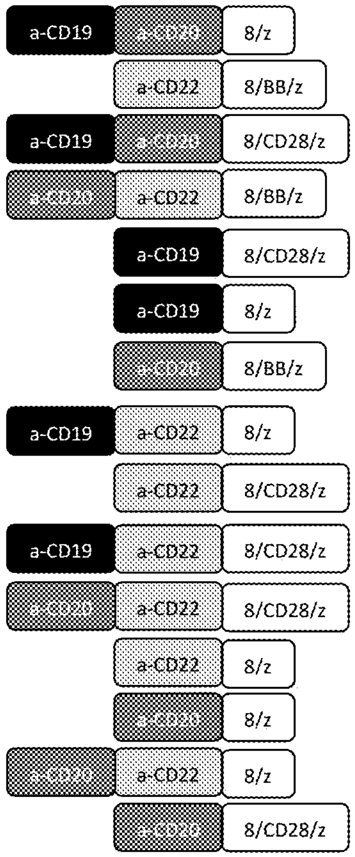
FIG. 2 depicts all potential single component that can be combined into DuoCARs for a therapeutic product targeting B cell malignancies. Nomenclature is identical to that in FIG. 1.
Figure 3:
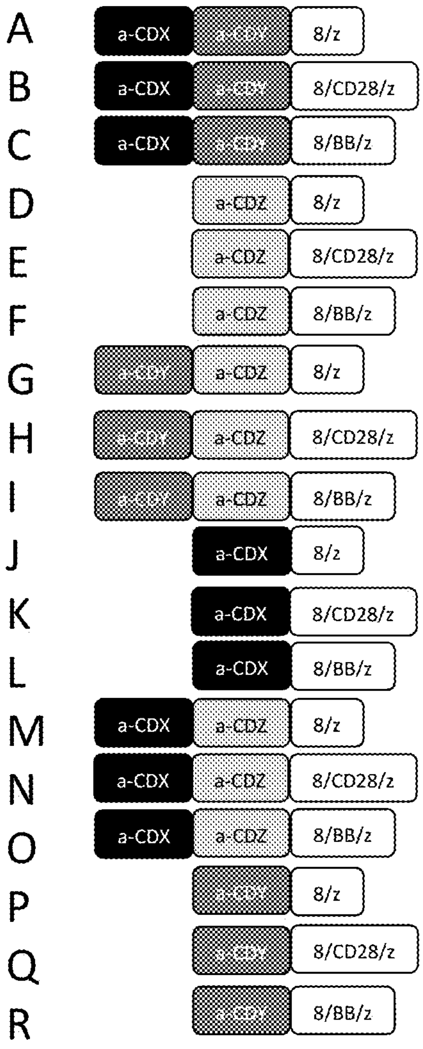
FIG. 3 depicts a generalized schema for DuoCARs that can be applied to multiple therapeutic needs, including inflammatory or autoimmune diseases and infectious diseases. In the Figure a-CDX, a-CDY, a-CDZ refer to antigen binding domains specific for three different target antigens, CDX, CDY, and CDZ, respectively. The intracellular aspect of the CARs all include the CD8 linker and transmembrane domain linked to either CD3-zeta, CD28, or 4-1BB signaling domains (as in FIG. 1). The specific combination of any of these two vectors (for example A plus F, wherein antigen X, Y, and Z would be targeted while providing intracellular signaling through CD3-zeta and 4-1BB) into a single vector will be defined according to the specific therapeutic need.
Figure 4:
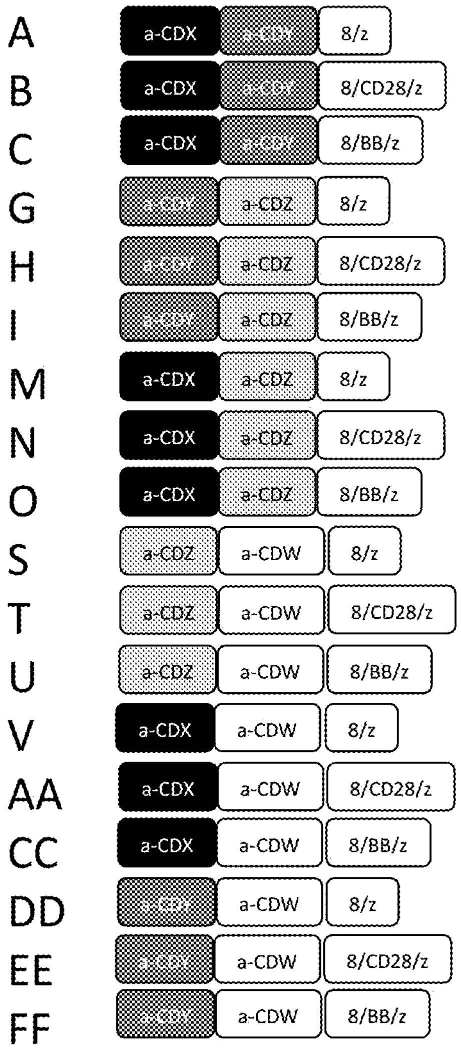
FIG. 4 depicts a generalized schema for DuoCAR sets in which two antigens are targeted by each vector. Vectors that are identical to those in FIG. 3 retain their specific letter designation (A in FIG. 3 and FIG. 4 are the same). The new, fourth, antigen binding domain is indicated by a-CDW. One product that would target 4 antigens be an A+T Duo CAR set. In this instance the extracellular antigens CDX, CDY, CDZ, and CDW would be targeted while providing both CD3-zeta and CD28 intracellular signals.

As used herein, the singular forms “a,” “an,” and “the,” refer to both the singular as well as plural, unless the context clearly indicates otherwise. For example, the term “an antigen” includes single or plural antigens and can be considered equivalent to the phrase “at least one antigen.” As used herein, the term “comprises” means “includes.” Thus, “comprising an antigen” means “including an antigen” without excluding other elements. The phrase “and/or” means “and” or “or.” It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. To facilitate review of the various embodiments, the following explanations of terms are provided:

The term “about” when referring to a measurable value such as an amount, a temporal duration, and the like, is meant to encompass variations of +/−20%, +/−10%, or more preferably +/−5%, or +/−1%, or still more preferably +/−0.1% from the specified value, as such variations are appropriate to perform the disclosed methods.

Unless otherwise noted, the technical terms herein are used according to conventional usage. Definitions of common terms in molecular biology can be found in Benjamin Lewin, Genes VII, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: A Comprehensive Desk Reference*, published by VCH Publishers, Inc., 1995; and other similar references.

The present invention relates to compositions and methods for treating diseases and/or conditions, as well as cancers including, but not limited to, hematologic malignancies and solid tumors. The present invention relates to a patient-specific, tumor-specific strategy of adoptive cell transfer of T cells transduced with two or more vectors to express one or more DuoCARs.

The present invention relates more particularly to lentiviral vectors expressing chimeric antigen receptors (DuoCARs), as well as host cells (e.g., lymphocytes, T cells) transduced with the lentiviral vectors expressing the CARs, nucleic acid molecules encoding the lentiviral vectors and chimeric antigen receptors, and methods of using same are also provided, for example, to treat a cancer in a subject.

Surprisingly and unexpectedly, it has now been discovered by the inventors that an immunotherapy composition comprising a patient-specific autologous anti-tumor lymphocyte cell population is much more effective as an anti-tumor immunotherapeutic if the autologous lymphocyte cell population is transduced with two or more lentiviral vectors encoding single or multiple chimeric antigen receptors (DuoCARs). The use of at least two or more lentiviral vectors expressing single or multiple CARS appears to promote in vivo expansion, persistence of patient-specific anti-tumor T-cells resulting in tumor stabilization, reduction, elimination, or remission of cancer, or prevention or amelioration of relapse of cancer, or any combination thereof, in a patient-specific manner.

Such active patient-specific anti-tumor T-cell populations as described herein can be infused directly back into the patient to promote in vivo expansion, persistence of patient-specific anti-tumor T-cells resulting in tumor stabilization, reduction, elimination, remission of cancer, or prevention or amelioration of relapse of cancer, or a combination thereof, in a patient-specific manner. This also includes effective expansion and rapid contraction of the therapeutic cell population.

Thus, in its broadest aspect, the novelty of this adoptive immunotherapy lies in the use of a combination of CAR-expression vectors. The differentiating feature is that contrary to the conventional use of a single vector expressing one or more chimeric antigen receptors, the Duo CAR approach confers both multiple antigen specificity and optimal signaling for anti-tumor T cell activity in vivo. Creating a system whereby three or more antigens are efficiently targeted is far superior to single or tandem approaches which allow for the tumor cancer cells to generate escape variants resulting in tumor metastasis and/or tumor relapse. The use of two or more vectors encoding single or multiple chimeric antigen receptors (DuoCARs) wherein the specific combination of least one binding domain(s) in each vector are non-identical coupled with the requirement that at least one signaling motif combination(s) are non-identical between each of the vectors, serves to ensure that genetically modified one or more lymphocyte populations transduced with such duo lentiviral vector-derived CARs generate a patient-specific autologous anti-tumor lymphocyte cell population capable of promoting in vivo expansion, persistence of patient-specific anti-tumor lymphocyte cells resulting in the stabilization, reduction, elimination, or remission of the tumor or cancer, and/or the prevention or amelioration of relapse of the tumor or cancer, or any combination thereof, in a patient-specific manner.

In one aspect, an immunotherapy composition is provided comprising one or more isolated nucleic acid molecules encoding at least two vectors (DuoCARs), each vector encoding a functional CAR, wherein at least one binding domain(s) in one of the vectors are non-identical, and whereby the combination of vectors results in the expression of two or more non-identical binding domains, wherein each vector encoded binding domain(s) are covalently linked to a transmembrane domain and one or more non-identical intracellular signaling motifs.

Figure 5:
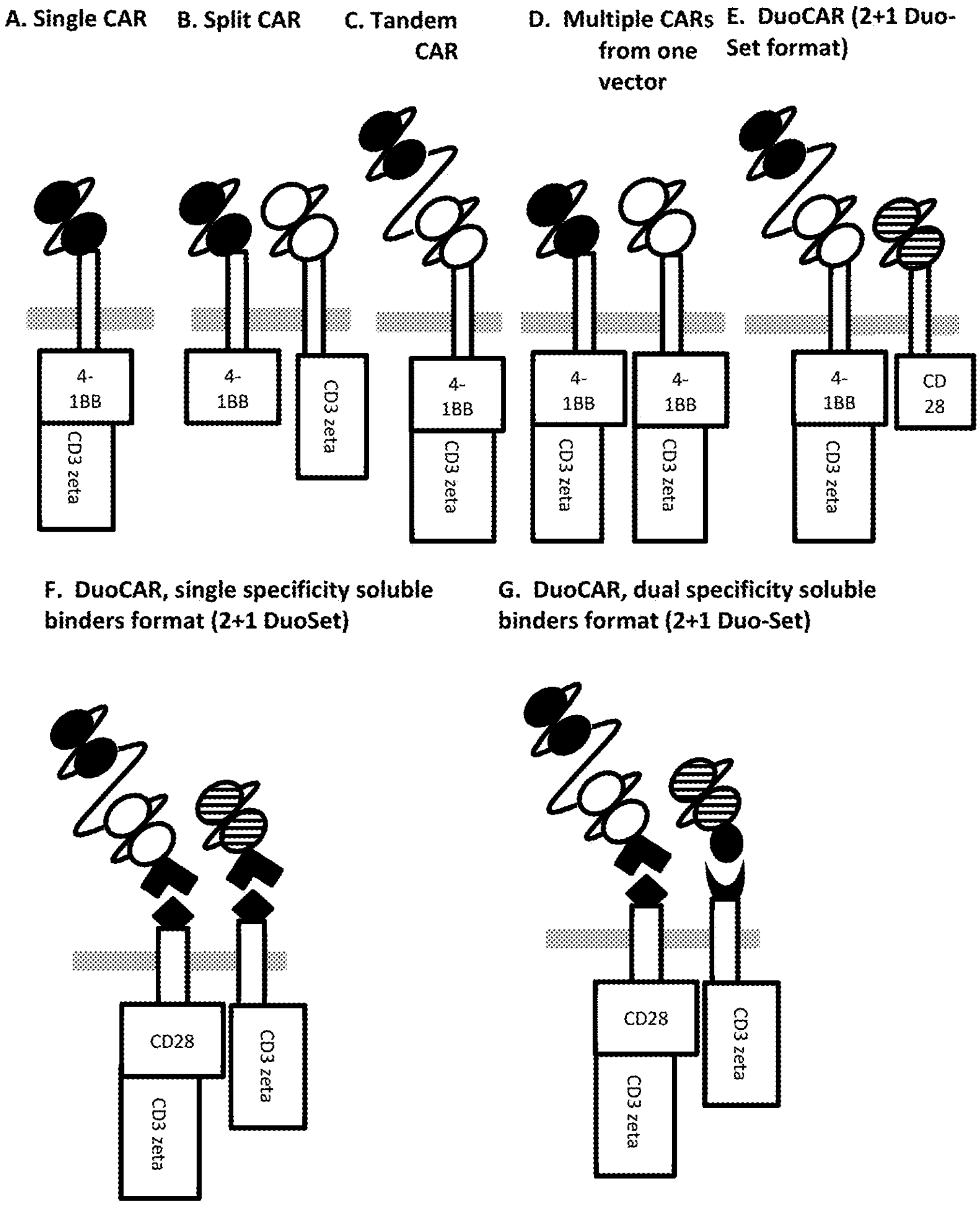
FIG. 5 depicts current CARs in the literature (A, B, C, D) in comparison to the DuoCARs of the present invention (E, F, G). CAR expression vectors can be created that induce expression of a single binding domain (paired black, open or striped spheres, each with separate specificities) connected to a linker and transmembrane domain (single open box). In the figure a thick gray line represents the plasma cell membrane. In this figure, the paired black spheres could represent anti-CD19 scFv, the paired open spheres represent anti-CD20 scFv and the paired striped spheres represent anti-CD22 scFv, all linked by joining amino acid sequences, for examples, multimers (1, 2, 3, 4, 5, or 6 repeats) of GGGGS. Intracellularly the lymphocyte signaling domains derived from 4-1BB (CD137), CD28, and the CD3-zeta chain can be combined as shown. (A) In Single CARs, a single binding domain is combined with a transmembrane and 2 signaling domains, created a second-generation CAR. (B) In Split CARs, two different binders are expressed with single signaling domains that must be combined to render effective T cell signaling upon recognition of two distinct antigens. (C) In Tandem CARs, two binding domains are linked to a single signaling domain. In this case binding of either domain induces full T cell activation. (D) In Multiple CARs from one vector, two fully functional CARs are expressed from a single vector, each able to bind only one antigen. (E) In contrast, DuoCARs are comprised of two vectors and express at least three binding domains, with multiple combinations of signaling domains possible. Essential features that differentiate the DuoCAR is the expression of two or more transcripts, the multiplicity of binding domains (at least one being multi-targeting), and the fully functional signaling characteristics of at least one of the two expressed cell surface proteins. (F) In a DuoCAR single-specificity soluble binder format, the CAR portion encoded by the vectors express a tag or an anti-tag motif that also encodes transmembrane and intracellular signaling motifs (CAR base vectors, non-identical with respect to intracellular motifs). The base vectors bind soluble proteins containing both the scFv domains that interact with antigen and a tag or anti-tag motif to mediate binding to the CAR base protein itself. Once the soluble proteins bind to the CAR base proteins, the same structural characteristics that mediate anti-tumor activity mediated by the DuoCAR [as in (E)] are reconstituted. (G) In a DuoCAR, dual-specificity soluble binder format, the dual specificity "tag"-"anti-tag" interactions are unique such that only one of the soluble binders can bind to only one of the base vectors. In this instance, the black diamond on the base vector and the angle-shaped binder on the soluble dual scFv protein may represent a "biotin"-"anti-biotin" interaction and the black crescent shape on the second CAR base vector interacts with the black oval on the single specificity scFv structure and may represent a "FITC"-"anti-FITC" interaction.

In another aspect, an immunotherapy composition is provided comprising one or more isolated nucleic acid molecules encoding at least two vectors (DuoCARs), each vector encoding a functional CAR, whereby the combination of vectors results in the expression of two or more non-identical binding domains, wherein each vector encoded binding domain(s) are covalently linked to a transmembrane domain and one or more non-identical intracellular signaling motifs, with the proviso that said immunotherapy composition specifically excludes the single CARs, the Split CARs, the Tandem CARs, or the Multiple CARs depicted in FIG. 5 (A), (B), (C), or (D), respectively.

The immunotherapeutic efficacy and prevention or amelioration of relapse of the tumor or cancer achieved with the DuoCAR Lentiviral vector-modified T cells of the present invention is significantly greater and synergistically more than that achieved with the singular conventional CAR design. It is this unique combination of biological therapeutic benefits that correlates with the increased in vivo expansion, persistence of patient-specific anti-tumor lymphocyte cells resulting in the stabilization, reduction, elimination, or remission of the tumor or cancer compared to conventional CAR-based T-cell immunotherapy.

CAR expression vectors can be created that induce expression of a single binding domain (black, open or striped spheres, each with separate specificities, FIG. 5) connected to a linker and transmembrane domain (single open box). FIG. 5, infra, depicts a comparison of the conventional CARs versus the DuoCARs of the present invention. In FIG. 5, a thick gray line represents the plasma cell membrane. Intracellularly the lymphocyte signaling domains derived from 4-1BB (CD137), CD28, and the CD3-zeta chain can be combined as shown. In all examples and uses of the CD3 signaling domain in this document, included are modifications of the CD3 zeta chain by the alteration of either one, two, or three of the immunoreceptor tyrosine-based activation motifs (ITAM) by selective mutagenesis of the tyrosine residue therein, or other such mutations that render that ITAM motif to no longer be a target for phosphorylation. In Single CARs (FIG. 5A), a single binding domain is combined with a transmembrane and 2 signaling domains. In Split CARs (FIG. 5B), two different binders are expressed with single signaling domains that must be combined to render effective signaling. In Tandem CARs (FIG. 5C), two binding domains are linked to a single signaling domain. In Multiple CARs from one vector (FIG. 5D), two fully functional CARs are expressed from a single vector. The Duo-CARs of the present invention (e.g., FIG. 5E) encode at least two vectors, each vector encoding a functional CAR, whereby the combination of vectors results in the expression of two or more non-identical binding domains, wherein each vector encoded binding domain(s) are covalently linked to a transmembrane domain and one or more non-identical intracellular signaling motifs. Essential features that differentiate the DuoCARs of the present invention is the use of two or more vectors, the multiplicity of binding domains, and the fully functional signaling characteristics (with regard to T cell expansion in vivo) of at least one of the two expressed cell surface proteins.

In another aspect, the DuoCARs are used to enhance the immune response to tumor mediated by the therapeutic T cell population. The immune response is enhanced in at least three ways.

Figure 6:
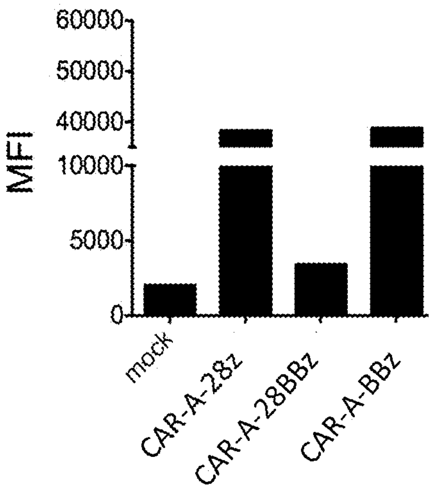
FIG. 6 depicts cell-surface expression levels of CAR constructs on primary human T cells transduced with CAR expression vectors that differ between second generation (two costimulatory domains) and third generation (three costimulatory domains) formats. T cells were transduced to express the following CARs: no CAR (mock), a second generation CAR (CAR-A-28z), a third generation CAR (CAR-A-28BBz), and an alternate second generation CAR (CAR-A-BBz). The level of surface expression of the CAR was detected by flow cytometry and is reported as mean fluorescence intensity (MF), y-axis. The MFI of both second generation CARs was much brighter, even though all construct expressed the very same CAR binding domain.

First, by providing the T cells an additional signal to expand and survive in the body, the DuoCARs of the present invention allow for the persistence of the therapeutic T cell population by virtue of stimulating the T cell population upon encountering self-antigen (for example CD19), whose loss can be tolerated by the patient, and yet which serves to provide a stimulatory signal for the therapeutic cellular population that does not reside in the tumor tissue itself. It is well known/established that third generation DuoCARs (expressing three co-stimulatory domains intracellularly, linked to a single extracellular Ig-like binder) are not expressed as well on therapeutic T cells compared to those DuoCARs expressing two intracellular co-stimulatory domains. For example, in FIG. 6 infra, the expression level of CAR constructs on primary human T cells differs between second generation (two costimulatory domains) and third generation (three costimulatory domains) constructs. T cells were transduced to express the following CARs: no CAR (mock), a second generation CAR (CAR-A-28z), a third generation CAR (CAR-A-28BBz), and an alternate second generation CAR (CAR-A-BBz). The level of surface expression of the CAR was detected by flow cytometry and is reported as mean fluorescence intensity (MF), y-axis. The MFI of both second-generation CARs was much brighter, even though all construct expressed the very same CAR binding domain.

By providing a third T cell activating sequence on a separate vector CAR construct, the inventors are able to regain the advantage of expressing three co-stimulatory domains, without incurring the disadvantage of the decreased expression of the CAR at the T cell surface.

In a second aspect, the DuoCARs of the present invention may target cell-types other than the tumor that mediate immunosuppressive effects. For example, if CD19-expressing B cells are present in the tumor lesion and also inhibit an anti-tumor immunity, as by the production of IL-4 or other mediators, the second benefit to the use of the DuoCAR-expressing tumor-specific T cell population is that the immunosuppressive cell population is also removed.

For example, if immunosuppressive B cells are present within a solid tumor lesion, these could be eliminated by the use of a B cell-specific DuoCAR (such as CD19-specific DuoCARs). If immunosuppressive fibroblast-like cells are present, these could be removed by stromal-specific DuoCARs (for example by targeting fibroblast activating protein-alpha (FAP)). If malformed vasculature is responsible for the lack of an efficacious immune response a DuoCAR specific for these types of vascular or lymph vessel specific targets (such as anti-VEGFR) may also improve therapeutic outcome.

In a third aspect, the DuoCARs of the present invention target an immunosuppressive population that is distal to the tumor, i.e. present in another compartment in the body. For example, using a DuoCAR to target myeloid derived suppressor cells (MDSCs), that may be present either in the tumor lesion itself or in the regional lymph nodes or bone marrow. It is well established that tumor-draining lymph nodes can either be loci of immune activation or immune suppression. This depends upon the overall inflammatory tone of the lymph node as well as distal dendritic cell differentiation prior to migration to the lymph node. If a tumor-draining lymph node is populated with myeloid-derived suppressor cells (MDSC) or miss-differentiated antigen presenting cells such as dendritic cells, a DuoCAR that targets these cell types, although distal to the tumor itself, may also improve therapeutic outcome. Beyond the cancer-specific DuoCAR immunotherapeutic applications, a second application of DuoCARs would be the prevention or treatment of autoimmune and/or inflammatory diseases. The difference from oncologic-based applications is that T-regulatory cells (Treg), or induced T-regulatory cells (iTreg), or other cells cultured in conditions that promote Th-2-like immune responses, would be the cellular substrate. For oncologic application Th-1 like cells are the cellular substrate. In therapeutic applications as diverse as graft-versus-host disease (GvHD) following hematopoietic stem cell transplantation (HSCT), allergic airway, gut, or other mucosal inflammation, or skin allergies, the presence of CAR-modified lymphocytes that produce immune-inhibitory cytokines, such as transforming growth factor-beta (TFG-beta), would serve to exert a broad tolerogenic signal that ameliorates the autoimmune- or inflammation-driven disease. This approach includes neurological inflammatory conditions of the periphery or central nervous system (CNS) such as Alzheimer's disease, multiple sclerosis, traumatic brain injury, Parkinson's disease, and CTE (chronic traumatic encephalopathy due to repeated concussions or micro-concussions). This approach also includes progressive scarring diseases such as COPD (chronic obstructive pulmonary disease).

In the treatment of inflammatory diseases, lymphocytes specific for tissue antigens, distress markers on the surface of inflamed cells, or misfolded proteins (such as tau protein or beta-amyloid) would be created by generating DuoCAR expression vectors that are specific for these targets. Single antibody-based therapy for Alzheimer's is already in clinical development (i.e., Solanezumab by Eli Lilly and Company and Aducanumab by Biogen, Inc.). In Alzheimer's disease, antibody to monomeric or aggregated beta-amyloid could be used in a CAR format in lieu of binders to cell surface proteins. Binders to tau protein or tau-peptides bound by MHC molecules could also be used as binding motifs for CARS. Receptors that mediate the homing of lymphocytes to specific peripheral tissues can also be included in a CAR format, in order to render regional specificity to the CAR-expressing Treg population. Adhesion receptor domains known to drive lymphocyte infiltration into specific tissues and cytokine sequences or cytokine or chemokine receptors or binders could be used as part of the CAR domain. Adhesion molecules such as CD44 and integrin alpha-4 are known to target lymphocytes to the CNS, thus including domains from adhesion molecules know to mediate CNS migratory behavior of lymphocyte populations could also be used to target CAR-expressing lymphocytes to regions of disease. The same would hold true for the gut (i.e. binders to MAdCAm-1, expression of a CCR9, or anti-CCL25, etc.), lung (i.e. P-selectin or mesothelin), skin (i.e. binders to E-selectin), or other mucosal surfaces.

To use this approach, a patient with an inflammatory condition or whose disease could be treated by mitigation of inflammatory pathology, such as Alzheimer's disease, would be admitted to the clinic and peripheral blood harvested. Treg could be selected directly by immunomagnetic beads (Regulatory T cell isolation kit, Miltenyi Biotec), or induced by culture in the appropriate cytokine milieu. These Treg or iTreg would then be transduced with a DuoCAR vector and if required expanded in vitro (Treg expansion kit, Miltenyi Biotec). The DuoCAR binding domains would be derived from antibodies or receptors that mediate tissue specific homing and disease-associated binders, such as anti-beta amyloid. The engineered immune effector cells thus generated would be targeted to the appropriate site, and produce cytokines consistent with their Th2 or Treg differentiation pattern. It is also known that CAR-T cells can be engineered to secrete specific genetic payloads upon activation of the CAR receptor. In addition to the DuoCAR payload expressed from the vector, additional therapeutic proteins or peptides could be expressed or secreted by the engineered T cell populations such as: a) A-beta DPs (amyloid beta degrading proteases), b) matrix proteases (such as MMP-9 and MMP9 inhibitors in COPD), c) peptides or soluble antibody-like binders that interfere with plaque formation, and d) cytokines (such as TGF-beta, IL-4, IL-10).

MiRNAs could also be expressed within cells to modulate T cell function. Examples of miRNAs are miR-92a, miR-21, miR-155, miR-146a, miR-3162, miR-1202, miR-1246 and miR-4281, miR-142, miR-17-92. Also shRNAs to miRNAs could be developed. Examples are shRNAs targeted to miR-28, miR-150 and miR-107, which normally bind to PD1 and increase its expression.

Beyond oncology-based and inflammatory and autoimmune disease-based applications, a third application of the Duo CAR technology is the generation of therapeutic lymphocyte populations specific for viral, bacterial, or fungal antigens. Thus, as for oncology applications described for B cell malignancies, the targeting of infectious disease would allow the DuoCAR products to mediate immunoprotective or immunotherapeutic activity against the infective agents or the diseased tissues where they reside based upon recognition of microbial antigens. Unlike T cell receptor (TCR)-based approaches, where the T cell receptor itself mediates the recognition of pathogen encoded peptides, the Duo CAR approach would utilize binding proteins expressed in a CAR vector format that would give antibody-like recognition (that is, not requiring antigen processing) to the transduced T cell population. The activation of the therapeutic T cell population would result in an immune activating locus able to eliminate the infected cells, and if the microbial antigen is not cell associated, to release soluble mediators like interferon-gamma that would enable an effective immune response to be mounted against the infectious agent.

For example, HIV is known to be highly variable, and yet specific clades or families can be categorized and antibody to clade-specific viral envelope protein (env, gp120) created. Using the DuoCAR approach, three or more clade-specific antibody-like binders are included in the CAR constructs resulting in broad anti-HIV immune activity. In addition to viral proteins, bacterial protein can be targeted. A current medical challenge is the treatment of antibiotic resistant bacterial strains that often arise in healthcare settings. These include VRE (vancomycin resistant enterococci), MRSA (methicillin-resistant *Staphylococcus aureus*), KPC (*Klebsiella pneumoniae* carbapenemase producing gram-negative bacteria, also CRKP), and others. *Klebsiella* cell surface antigens include the O antigen (9 variants) and the K antigen (appx. 80 variants). The O antigen spectrum could readily be covered with a small DuoCAR library, as could a number of the K antigens. For use, CAR constructs would be created that feature antibodies that bind to different K or O serotypes, and these CAR vectors used to transduce a Th1-like effector cell population, isolated and activated as for oncology applications. In fungal diseases, the work of L. Cooper et al. (Kumasesan, P. R., 2014, PNAS USA, 111:10660) demonstrated that a fungal binding protein normally expressed on human cells, dectin-1, can be reconfigured as a CAR, and used to control fungal growth in vitro. The human disease aspergillosis occurs in severely immunosuppressed individuals and is caused by the fungus *A. fumigatus*. Multiple groups have produced monoclonal antibodies specific for the antigenic components of the *aspergillus* cell surface, thus opening the door to adoptive immunotherapy with DuoCARs that target three or more *aspergillus* antigens on the fungal surface. Thus, in all of these infectious disease applications, the ability to create immunoglobulin-like binders to microbial antigens allows a plurality of antigens to be targeted by CAR-expressing effector lymphocyte populations.

What follows is a detailed description of the DuoCARs that may be used in the patient-specific autologous anti-tumor lymphocyte cell population(s) disclosed herein, including a description of their extracellular domain, the transmembrane domain and the intracellular domain, along with additional description of the DuoCARs, antibodies and antigen binding fragments thereof, conjugates, nucleotides, expression, vectors, and host cells, methods of treatment, compositions, and kits employing the disclosed DuoCARs. While the compositions and methods of the present invention have been illustrated with reference to the generation and utilization of DuoCARs, it is contemplated herein that the compositions and methods are specifically intended to include the generation and utilization of TrioCARs and QuatroCARs.

A. Chimeric Antigen Receptors (as Present in DuoCARs)

The DuoCARs disclosed herein comprise at least two vectors, each vector encoding a functional CAR, whereby the combination of vectors results in the expression of two or more non-identical binding domains, wherein each vector encoded binding domain(s) are covalently linked to a transmembrane domain and one or more non-identical intracellular signaling motifs, at least one extracellular domain capable of binding to an antigen, at least one transmembrane domain, and at least one intracellular domain.

A CAR is an artificially constructed hybrid protein or polypeptide containing the antigen binding domains of an antibody (e.g., single chain variable fragment (scFv)) linked to T-cell signaling domains via a transmembrane domain. Characteristics of DuoCARs include their ability to redirect T-cell specificity and reactivity toward a selected target in a non-MHC-restricted manner, and exploiting the antigen-binding properties of monoclonal antibodies. The non-MHC-restricted antigen recognition gives T cells expressing DuoCARs the ability to recognize antigen independent of antigen processing, thus bypassing a major mechanism of tumor escape. Moreover, when expressed in T-cells, DuoCARs advantageously do not dimerize with endogenous T cell receptor (TCR) alpha and beta chains.

As disclosed herein, the intracellular T cell signaling domains of the DuoCARs can include, for example, a T cell receptor signaling domain, a T cell costimulatory signaling domain, or both. The T cell receptor signaling domain refers to a portion of the CAR comprising the intracellular domain of a T cell receptor, such as, for example, and not by way of limitation, the intracellular portion of the CD3 zeta protein. The costimulatory signaling domain refers to a portion of the CAR comprising the intracellular domain of a costimulatory molecule, which is a cell surface molecule other than an antigen receptor or their ligands that are required for an efficient response of lymphocytes to antigen. In some instances the activation domains can be attenuated by the mutation of specific sites of phosphorylation, i.e. the ITAM motifs in the CD3 zeta chain, thus carefully modulating the degree of signal transduction mediated by that domain.

1. Extracellular Domain

In one embodiment, the CAR used in the patient-specific autologous anti-tumor lymphocyte cell population(s) as disclosed herein, comprises a target-specific binding element otherwise referred to as an antigen binding domain or moiety. The choice of domain depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen binding domain in the CAR include those associated with viral, bacterial and parasitic infections, autoimmune disease and cancer cells.

In one embodiment, the CAR can be engineered to target a tumor antigen of interest by way of engineering a desired antigen binding domain that specifically binds to an antigen on a tumor cell. Tumor antigens are proteins that are produced by tumor cells that elicit an immune response, particularly T-cell mediated immune responses. The selection of the antigen binding domain will depend on the particular type of cancer to be treated. Tumor antigens are well known in the art and include, for example, a glioma-associated antigen, carcinoembryonic antigen (CEA), beta-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I receptor, IGF-II receptor, IGF-I receptor and mesothelin. The tumor antigens disclosed herein are merely included by way of example. The list is not intended to be exclusive and further examples will be readily apparent to those of skill in the art.

In one embodiment, the tumor antigen comprises one or more antigenic cancer epitopes associated with a malignant tumor. Malignant tumors express a number of proteins that can serve as target antigens for an immune attack. These molecules include, but are not limited to, tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20, CD22, and CD37 are other candidates for target antigens in B-cell lymphoma. Some of these antigens (CEA, HER-2, CD19, CD20, CD22, idiotype) have been used as targets for passive immunotherapy with monoclonal antibodies with limited success.

The type of tumor antigen may also be a tumor-specific antigen (TSA) or a tumor-associated antigen (TAA). A TSA is unique to tumor cells and does not occur on other cells in the body. A TAA is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSAs or TAAs include the following: Differentiation antigens such as MART-1/MelanA (MART-I), gp100 (Pmel 17), tyrosinase, TRP-1, TRP-2 and tumor-specific multi-lineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

In a preferred embodiment, the antigen binding domain portion of the CAR targets an antigen that includes but is not limited to CD19, CD20, CD22, ROR1, Mesothelin, CD33, c-Met, PSMA, Glycolipid F77, EGFRVIII, GD-2, MY-ESO-1 TCR, MAGE A3 TCR, and the like. In yet another embodiment, a DuoCAR is provided herein comprising a Tag or anti-Tag binding domain.

Depending on the desired antigen to be targeted, the CAR can be engineered to include the appropriate antigen binding domain that is specific to the desired antigen target. For example, if CD19 is the desired antigen that is to be targeted, an antibody or the scFv subfragment thereof specific for CD19 can be used as the antigen bind domain incorporated into the CAR.

In one exemplary embodiment, the antigen binding domain portion of the CAR targets CD19. Preferably, the antigen binding domain in the CAR is anti-CD19 scFV, wherein the nucleic acid sequence of the anti-CD19 scFV comprises the sequence set forth in SEQ ID NO: 27. In one embodiment, the anti-CD19 scFV comprises the nucleic acid sequence that encodes the amino acid sequence of SEQ ID NO: 28. In another embodiment, the anti-CD19 scFV portion of the CAR comprises the amino acid sequence set forth in SEQ ID NO: 28. In a second exemplary embodiment, the antigen binding domain of the CAR targets CD20. Preferably, the antigen binding domains in the CAR is anti-CD20 scFv, wherein the nucleic acid sequence of the anti-CD20 scFv comprises the sequence set forth in SEQ ID NO: 1. In another embodiment, the anti-CD20 scFV portion of the CAR comprises the amino acid sequence set forth in SEQ ID NO: 2. In a third exemplary embodiment, the antigen binding domain of the CAR targets CD22. Preferably, the antigen binding domains in the CAR is anti-CD22 scFv, wherein the nucleic acid sequence of the anti-CD22 scFv comprises the sequence set forth in SEQ ID NO: 7. In another embodiment, the anti-CD22 scFV portion of the CAR comprises the amino acid sequcne set forth in SEQ ID NO: 8.

In one aspect of the present invention, there is provided a CAR capable of binding to a non-TSA or non-TAA including, for example and not by way of limitation, an antigen derived from Retroviridae (e.g. human immunodeficiency viruses such as HIV-1 and HIV-LP), Picornaviridae (e.g. poliovirus, hepatitis A virus, enterovirus, human coxsackievirus, rhinovirus, and echovirus), rubella virus, coronavirus, vesicular stomatitis virus, rabies virus, ebola virus, parainfluenza virus, mumps virus, measles virus, respiratory syncytial virus, influenza virus, hepatitis B virus, parvovirus, Adenoviridae, Herpesviridae [e.g. type 1 and type 2 herpes simplex virus (HSV), varicella-zoster virus, cytomegalovirus (CMV), and herpes virus], Poxviridae (e.g. smallpox virus, vaccinia virus, and pox virus), or hepatitis C virus, or any combination thereof.

In another aspect of the present invention, there is provided a CAR capable of binding to an antigen derived from a bacterial strain of Staphylococci, *Streptococcus, Escherichia coli, Pseudomonas*, or *Salmonella*. Particularly, there is provided a CAR capable of binding to an antigen derived from an infectious bacterium, for example, *Helicobacter* pyloris, *Legionella* pneumophilia, a bacterial strain of Mycobacteria sps. (e.g. *M. tuberculosis, M. avium, M. intracellulare, M. kansaii*, or *M. gordonea*), *Staphylococcus aureus, Neisseria gonorrhoeae, Neisseria meningitides, Listeria monocytogenes, Streptococcus pyogenes*, Group A *Streptococcus*, Group B *Streptococcus* (*Streptococcus agalactiae*), *Streptococcus pneumoniae*, or *Clostridium tetani*, or a combination thereof.

2. Transmembrane Domain

In the DuoCARs used in the patient-specific autologous anti-tumor lymphocyte cell population(s) as disclosed herein, the CAR comprises one or more transmembrane domains fused to the extracellular domain of the CAR.

In one embodiment, an isolated nucleic acid molecule is provided wherein the encoded linker domain is derived from the extracellular domain of CD8, and is linked to the transmembrane domain.

In one embodiment, an isolated nucleic acid molecule is provided wherein the encoded linker domain is derived from the extracellular domain of the transmembrane domain and is linked to the transmembrane domain.

In some instances, the transmembrane domain can be selected or by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, CD271, TNFRSF19, Fc epsilon R, or any combination thereof. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet or a triple alanine motif provides a particularly suitable linker.

In one embodiment, the transmembrane domain in the CAR of the invention is the CD8 transmembrane domain. In one embodiment, the CD8 transmembrane domain comprises the nucleic acid sequence of SEQ ID NO: 11. In one embodiment, the CD8 transmembrane domain comprises the nucleic acid sequence that encodes the amino acid sequence of SEQ ID NO: 12. In another embodiment, the CD8 transmembrane domain comprises the amino acid sequence of SEQ ID NO: 12.

In some instances, the transmembrane domain of the CAR comprises the CD8.alpha.hinge domain. In one embodiment, the CD8 hinge domain comprises the nucleic acid sequence of SEQ ID NO: 13. In one embodiment, the CD8 hinge domain comprises the nucleic acid sequence that encodes the amino acid sequence of SEQ ID NO: 14. In another embodiment, the CD8 hinge domain comprises the amino acid sequence of SEQ ID NO: 14.

Without being intended to limit to any particular mechanism of action, it is believed that possible reasons for the enhanced therapeutic function associated with the exemplary DuoCARs used in the patient-specific autologous anti-tumor lymphocyte cell population(s) as disclosed herein of the invention include, for example, and not by way of limitation, a) improved lateral movement within the plasma membrane allowing for more efficient signal transduction, b) superior location within plasma membrane microdomains, such as lipid rafts, and greater ability to interact with transmembrane signaling cascades associated with T cell activation, c) superior location within the plasma membrane by preferential movement away from dampening or down-modulatory interactions, such as less proximity to or interaction with phosphatases such as CD45, and d) superior assembly into T cell receptor signaling complexes (i.e. the immune synapse), or any combination thereof.

In one embodiment of the patient-specific autologous anti-tumor lymphocyte cell population(s) as disclosed herein, non-limiting exemplary transmembrane domains for use in the DuoCARs disclosed herein include the TNFRSF16 and TNFRSF19 transmembrane domains may be used to derive the TNFRSF transmembrane domains and/or linker or spacer domains as disclosed in Applicant's Provisional Patent Application No. 62/239,509, entitled CHIMERIC ANTIGEN RECEPTORS AND METHODS OF USE, as filed on Oct. 9, 2015, and assigned Lentigen Technology, Inc. matter number LEN_015PRO, including, in particular, those other TNFRSF members listed within the tumor necrosis factor receptor superfamily as listed in Table I therein.

3. Spacer Domain

In the DuoCARs used in the patient-specific autologous anti-tumor lymphocyte cell population(s) as disclosed herein, a spacer domain can be arranged between the extracellular domain and the TNFRSF transmembrane domain, or between the intracellular domain and the TNFRSF transmembrane domain. The spacer domain means any oligopeptide or polypeptide that serves to link the TNFRSF transmembrane domain with the extracellular domain and/or the TNFRSF transmembrane domain with the intracellular domain. The spacer domain comprises up to 300 amino acids, preferably 10 to 100 amino acids, and most preferably 25 to 50 amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 79,645,667, 498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

The spacer domain preferably has a sequence that promotes binding of a CAR with an antigen and enhances signaling into a cell. Examples of an amino acid that is expected to promote the binding include cysteine, a charged amino acid, and serine and threonine in a potential glycosylation site, and these amino acids can be used as an amino acid constituting the spacer domain.

As the spacer domain, the entire or a part of amino acid numbers 137 to 206 (SEQ ID NO: 15) which includes the hinge region of CD8.alpha. (NCBI RefSeq: NP.sub.-001759.3), amino acid numbers 135 to 195 of CD8.beta. (GenBank: AAA35664.1), amino acid numbers 315 to 396 of CD4 (NCBI RefSeq: NP.sub.-000607.1), or amino acid numbers 137 to 152 of CD28 (NCBI RefSeq: NP.sub.-006130.1) can be used. Also, as the spacer domain, a part of a constant region of an antibody H chain or L chain (CHI region or CL region, for example, a peptide having an amino acid sequence shown in SEQ ID NO: 16) can be used. Further, the spacer domain may be an artificially synthesized sequence.

Further, in the CAR, a signal peptide sequence can be linked to the N-terminus. The signal peptide sequence exists at the N-terminus of many secretory proteins and membrane proteins, and has a length of 15 to 30 amino acids. Since many of the protein molecules mentioned above as the intracellular domain have signal peptide sequences, the signal peptides can be used as a signal peptide for the CAR. In one embodiment, the signal peptide comprises the nucleotide sequence of the leader (signal peptide) sequence shown in SEQ ID NO: 5. In one embodiment, the signal peptide comprises the amino acid sequence shown in SEQ ID NO: 6.

4. Intracellular Domain

The cytoplasmic domain or otherwise the intracellular signaling domain of the CAR is responsible for activation of at least one of the normal effector functions of the immune cell in which the CAR has been placed in. The term “effector function” refers to a specialized function of a cell. Effector function of a T cell, for example, may be cytolytic activity or helper activity including the secretion of cytokines. Thus the term “intracellular signaling domain” refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the CARS disclosed herein include those derived from TCR zeta (CD3 Zeta), FcR gamma, FcR beta, CD3 gamma, CD3 delta, CD3 epsilon, CD5, CD22, CD79a, CD79b, and CD66d. Specific, non-limiting examples, of the ITAM include peptides having sequences of amino acid numbers 51 to 164 of CD3.zeta. (NCBI RefSeq: NP.sub.-932170.1), amino acid numbers 45 to 86 of Fc.epsilon.RI.gamma. (NCBI RefSeq: NP.sub.-004097.1), amino acid numbers 201 to 244 of Fc.epsilon-.RI.beta. (NCBI RefSeq: NP.sub.-000130.1), amino acid numbers 139 to 182 of CD3.gamma. (NCBI RefSeq: NP.sub.-000064.1), amino acid numbers 128 to 171 of CD3.delta. (NCBI RefSeq: NP.sub.-000723.1), amino acid numbers 153 to 207 of CD3.epsilon. (NCBI RefSeq: NP.sub.-000724.1), amino acid numbers 402 to 495 of CD5 (NCBI RefSeq: NP.sub.-055022.2), amino acid numbers 707 to 847 of 0022 (NCBI RefSeq: NP.sub.-001762.2), amino acid numbers 166 to 226 of CD79a (NCBI RefSeq: NP.sub.-001774.1), amino acid numbers 182 to 229 of CD79b (NCBI RefSeq: NP.sub.-000617.1), and amino acid numbers 177 to 252 of CD66d (NCBI RefSeq: NP.sub.-001806.2), and their variants having the same function as these peptides have. The amino acid number based on amino acid sequence information of NCBI RefSeq ID or GenBank described herein is numbered based on the full length of the precursor (comprising a signal peptide sequence etc.) of each protein. In one embodiment, the cytoplasmic signaling molecule in the CAR comprises a cytoplasmic signaling sequence derived from CD3 zeta. In another embodiment one, two, or three of the ITAM motifs in CD3 zeta are attenuated by mutation or substitution of the tyrosine residue by another amino acid.

In a preferred embodiment, the intracellular domain of the CAR can be designed to comprise the CD3-zeta signaling domain by itself or combined with any other desired cytoplasmic domain(s) useful in the context of the CAR. For example, the intracellular domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such costimulatory molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Specific, non-limiting examples, of such costimulatory molecules include peptides having sequences of amino acid numbers 236 to 351 of CD2 (NCBI RefSeq: NP.sub.-001758.2), amino acid numbers 421 to 458 of CD4 (NCBI RefSeq: NP.sub.-000607.1), amino acid numbers 402 to 495 of CD5 (NCBI RefSeq: NP.sub.-055022.2), amino acid numbers 207 to 235 of CD8.alpha. (NCBI RefSeq: NP.sub.-001759.3), amino acid numbers 196 to 210 of CD83 (GenBank: AAA35664.1), amino acid numbers 181 to 220 of CD28 (NCBI RefSeq: NP.sub.-006130.1), amino acid numbers 214 to 255 of CD137 (4-1BB, NCBI RefSeq: NP.sub.-001552.2), amino acid numbers 241 to 277 of CD134 (OX40, NCBI RefSeq: NP.sub.-003318.1), and amino acid numbers 166 to 199 of ICOS (NCBI RefSeq: NP.sub.-036224.1), and their variants having the same function as these peptides have. Thus, while the disclosure herein is exemplified primarily with 4-1BB as the co-stimulatory signaling element, other costimulatory elements are within the scope of the disclosure.

The cytoplasmic signaling sequences within the cytoplasmic signaling portion of the CAR may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the intracellular domain is designed to comprise the signaling domain of CD3-zeta and the signaling domain of CD28. In another embodiment, the intracellular domain is designed to comprise the signaling domain of CD3-zeta and the signaling domain of 4-1BB. In yet another embodiment, the intracellular domain is designed to comprise the signaling domain of CD3-zeta and the signaling domain of CD28 and 4-1BB.

In one embodiment, the intracellular domain in the CAR is designed to comprise the signaling domain of 4-1BB and the signaling domain of CD3-zeta, wherein the signaling domain of 4-1BB comprises the nucleic acid sequence set forth in SEQ ID NO: 17 and the signaling domain of CD3-zeta comprises the nucleic acid sequence set forth in SEQ ID NO: 19.

In one embodiment, the intracellular domain in the CAR is designed to comprise the signaling domain of 4-1BB and the signaling domain of CD3-zeta, wherein the signaling domain of 4-1BB comprises the nucleic acid sequence that encodes the amino acid sequence of SEQ ID NO: 18 and the signaling domain of CD3-zeta comprises the nucleic acid sequence that encodes the amino acid sequence of SEQ ID NO: 20.

In one embodiment, the intracellular domain in the CAR is designed to comprise the signaling domain of 4-1BB and the signaling domain of CD3-zeta, wherein the signaling domain of 4-1BB comprises the amino acid sequence set forth in SEQ ID NO: 18 and the signaling domain of CD3-zeta comprises the amino acid sequence set forth in SEQ ID NO: 20.

5. Additional Description of DuoCARs

Also expressly included within the scope of the invention are functional portions of the DuoCARs used in the patient-specific autologous anti-tumor lymphocyte cell population(s) as disclosed herein. The term "functional portion" when used in reference to a CAR refers to any part or fragment of one or more of the DuoCARs disclosed herein, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 10%, 25%, 30%, 50%, 68%, 80%, 90%, 95%, or more, of the parent CAR.

The functional portion can comprise additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent CAR.

Included in the scope of the disclosure are functional variants of the DuoCARs disclosed herein. The term "functional variant" as used herein refers to a CAR, polypeptide, or protein having substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, 50%, 75%, 80%, 90%, 98% or more identical in amino acid sequence to the parent CAR.

A functional variant can, for example, comprise the amino acid sequence of the parent CAR with at least one conservative amino acid substitution. Alternatively, or additionally, the functional variants can comprise the amino acid sequence of the parent CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR.

Amino acid substitutions of the DuoCARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, He, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gin, Ser, Thr, Tyr, etc.), an amino acid with a beta-branched side-chain substituted for another amino acid with a beta-branched side-chain (e.g., He, Thr, and Val), an amino acid with an aromatic side-chain substituted for another amino acid with an aromatic side chain (e.g., His, Phe, Trp, and Tyr), etc.

The CAR can consist essentially of the specified amino acid sequence or sequences described herein, such that other components, e.g., other amino acids, do not materially change the biological activity of the functional variant.

The DuoCARs (including functional portions and functional variants) can be of any length, i.e., can comprise any number of amino acids, provided that the DuoCARs (or functional portions or functional variants thereof) retain their biological activity, e.g., the ability to specifically bind to antigen, detect diseased cells in a mammal, or treat or prevent disease in a mammal, etc. For example, the CAR can be about 50 to about 5000 amino acids long, such as 50, 70, 75, 100, 125, 150, 175, 200, 300, 400, 500, 600, 700, 800, 900, 1000 or more amino acids in length.

The DuoCARs (including functional portions and functional variants of the invention) can comprise synthetic amino acids in place of one or more naturally-occurring amino acids. Such synthetic amino acids are known in the art, and include, for example, aminocyclohexane carboxylic acid, norleucine, -amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, a-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, -aminocyclopentane carboxylic acid, α-aminocyclohexane carboxylic acid, α-aminocycloheptane carboxylic acid, a-(2-amino-2-norbornane)-carboxylic acid, γ-diaminobutyric acid, β-diaminopropionic acid, homophenylalanine, and a-tert-butylglycine.

The DuoCARs (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The DuoCARs (including functional portions and functional variants thereof) can be obtained by methods known in the art. The DuoCARs may be made by any suitable method of making polypeptides or proteins. Suitable methods of de novo synthesizing polypeptides and proteins are described in references, such as Chan et al., Fmoc Solid Phase Peptide Synthesis, Oxford University Press, Oxford, United Kingdom, 2000; Peptide and Protein Drug Analysis, ed. Reid, R., Marcel Dekker, Inc., 2000; Epitope Mapping, ed. Westwood et al., Oxford University Press, Oxford, United Kingdom, 2001; and U.S. Pat. No. 5,449,752. Methods of generating chimeric antigen receptors, T cells including such receptors, and their use (e.g., for treatment of cancer) are known in the art and further described herein (see, e.g., Brentjens et al., 2010, Molecular Therapy, 18:4, 666-668; Morgan et al., 2010, Molecular Therapy, published online Feb. 23, 2010, pages 1-9; Till et al., 2008, Blood, 1 12:2261-2271; Park et al., Trends Biotechnol., 29:550-557, 2011; Grupp et al., N Engl J Med., 368:1509-1518, 2013; Han et al., J. Hematol Oncol., 6:47, 2013; Tumaini et al., Cytotherapy, 15, 1406-1417, 2013; Haso et al., (2013) Blood, 121, 1165-1174; PCT Pubs. WO2012/079000, WO2013/126726; and U.S. Pub. 2012/0213783, each of which is incorporated by reference herein in its entirety). For example, a nucleic acid molecule encoding a disclosed chimeric antigen binding receptor can be included in an expression vector (such as a lentiviral vector) used to transduce a host cell, such as a T cell, to make the disclosed CAR. In some embodiments, methods of using the chimeric antigen receptor include isolating T cells from a subject, transducing the T cells with an expression vector (such as a lentiviral vector) encoding the chimeric antigen receptor, and administering the CAR-expressing T cells to the subject for treatment, for example for treatment of a tumor in the subject.

B. Antibodies and Antigen Binding Fragments

One embodiment further provides a CAR used in the patient-specific autologous anti-tumor lymphocyte cell population(s) disclosed herein, a T cell expressing a CAR, an antibody, or antigen binding domain or portion thereof, which specifically binds to one or more of the antigens disclosed herein. As used herein, a "T cell expressing a CAR," or a "CAR T cell" means a T cell expressing a CAR, and has antigen specificity determined by, for example, the antibody-derived targeting domain of the CAR.

As used herein, and "antigen binding domain" can include an antibody and antigen binding fragments thereof. The term "antibody" is used herein in the broadest sense and encompasses various antibody structures, including but not limited to monoclonal antibodies, polyclonal antibodies, multi-specific antibodies (e.g., bispecific antibodies), and antigen binding fragments thereof, so long as they exhibit the desired antigen-binding activity. Non-limiting examples of antibodies include, for example, intact immunoglobulins and variants and fragments thereof known in the art that retain binding affinity for the antigen.

A "monoclonal antibody" is an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. The modifier "monoclonal" indicates the character of the antibody as being obtained from a substantially homogeneous population of antibodies, and is not to be construed as requiring production of the antibody by any particular method. In some examples, a monoclonal antibody is an antibody produced by a single clone of B lymphocytes or by a cell into which nucleic acid encoding the light and heavy variable regions of the antibody of a single antibody (or an antigen binding fragment thereof) have been transfected, or a progeny thereof. In some examples monoclonal antibodies are isolated from a subject. Monoclonal antibodies can have conservative amino acid substitutions which have substantially no effect on antigen binding or other immunoglobulin functions. Exemplary methods of production of monoclonal antibodies are known, for example, see Harlow & Lane, Antibodies, A Laboratory Manual, 2nd ed. Cold Spring Harbor Publications, New York (2013).

Typically, an immunoglobulin has heavy (H) chains and light (L) chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda (2) and kappa (κ). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain; see, e.g., Kindt et al. Kuby Immunology, 6.sup.th ed., W.H. Freeman and Co., page 91 (2007).) In several embodiments, the heavy and the light chain variable regions combine to specifically bind the antigen. In additional embodiments, only the heavy chain variable region is required. For example, naturally occurring camelid antibodies consisting of a heavy chain only are functional and stable in the absence of light chain (see, e.g., Hamers-Casterman et al., Nature, 363:446-448, 1993; Sheriff et al., Nat. Struct. Biol., 3:733-736, 1996). References to "VH" or "VH" refer to the variable region of an antibody heavy chain, including that of an antigen binding fragment, such as Fv, scFv, dsFv or Fab. References to "VL" or "VL" refer to the variable domain of an antibody light chain, including that of an Fv, scFv, dsFv or Fab.

Light and heavy chain variable regions contain a "framework" region interrupted by three hypervariable regions, also called "complementarity-determining regions" or "CDRs" (see, e.g., Kabat et al., Sequences of Proteins of Immunological Interest, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," 5th Ed. Public Health Service, National Institutes of Health, Bethesda, MD, 1991; "Kabat" numbering scheme), Al-Lazikani et al., (JMB 273,927-948, 1997; "Chothia" numbering scheme), and Lefranc et al. ("IMGT unique numbering for immunoglobulin and T cell receptor variable domains and Ig superfamily V-like domains," Dev. Comp. Immunol., 27:55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a VH CDR3 is the CDR3 from the variable domain of the heavy chain of the antibody in which it is found, whereas a VL CDR1 is the CDR1 from the variable domain of the light chain of the antibody in which it is found. Light chain CDRs are sometimes referred to as LCDR1, LCDR2, and LCDR3. Heavy chain CDRs are sometimes referred to as LCDR1, LCDR2, and LCDR3.

An "antigen binding fragment" is a portion of a full length antibody that retains the ability to specifically recognize the cognate antigen, as well as various combinations of such portions. Non-limiting examples of antigen binding fragments include Fv, Fab, Fab', Fab'-SH, F(ab') 2; diabodies; linear antibodies; single-chain antibody molecules (e.g. scFv); and multi-specific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, 2nd Ed., Springer Press, 2010).

A single-chain antibody (scFv) is a genetically engineered molecule containing the VH and VL domains of one or more antibody (ies) linked by a suitable polypeptide linker as a genetically fused single chain molecule (see, for example, Bird et al., Science, 242:423 426, 1988; Huston et al., Proc. Natl. Acad. Sci., 85:5879 5883, 1988; Ahmad et al., Clin. Dev. Immunol., 2012, doi: 10.1155/2012/980250; Marbry, IDrugs, 13:543-549, 2010). The intramolecular orientation of the VH-domain and the VL-domain in a scFv, is typically not decisive for scFvs. Thus, scFvs with both possible arrangements (VH-domain-linker domain-VL-domain; VL-domain-linker domain-VH-domain) may be used.

In a dsFv the heavy and light chain variable chains have been mutated to introduce a disulfide bond to stabilize the association of the chains. Diabodies also are included, which are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., Proc. Natl. Acad. Sci., 90:6444 6448, 1993; Poljak et al., Structure, 2:1121 1123, 1994).

Antibodies also include genetically engineered forms such as chimeric antibodies (such as humanized murine antibodies) and heteroconjugate antibodies (such as bispecific antibodies). See also, Pierce Catalog and Handbook, 1994-1995 (Pierce Chemical Co., Rockford, IL); Kuby, J., Immunology, 3rd Ed., W. H. Freeman & Co., New York, 1997.

Non-naturally occurring antibodies can be constructed using solid phase peptide synthesis, can be produced recombinantly, or can be obtained, for example, by screening combinatorial libraries consisting of variable heavy chains and variable light chains as described by Huse et al., Science 246:1275-1281 (1989), which is incorporated herein by reference. These and other methods of making, for example, chimeric, humanized, CDR-grafted, single chain, and bifunctional antibodies, are well known to those skilled in the art (Winter and Harris, Immunol. Today 14:243-246 (1993); Ward et al., Nature 341:544-546 (1989); Harlow and Lane, supra, 1988; Hilyard et al., Protein Engineering: A practical approach (IRL Press 1992); Borrabeck, Antibody Engineering, 2d ed. (Oxford University Press 1995); each of which is incorporated herein by reference).

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Antibody competition assays are known, and an exemplary competition assay is provided herein.

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, which typically are of different species. In some examples, a chimeric antibody includes one or more CDRs and/or framework regions from one human antibody and CDRs and/or framework regions from another human antibody.

A "fully human antibody" or "human antibody" is an antibody which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. Phage display: A Laboratory Manuel. 1st Ed. New York: Cold Spring Harbor Laboratory Press, 2004. Print.; Lonberg, Nat. Biotech., 23:1117-1125, 2005; Lonenberg, Curr. Opin. Immunol., 20:450-459, 2008).

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

Methods of testing antibodies for the ability to bind to any functional portion of the CAR are known in the art and include any antibody-antigen binding assay, such as, for example, radioimmunoassay (RIA), ELISA, Western blot, immunoprecipitation, and competitive inhibition assays (see, e.g., Janeway et al., infra, U.S. Patent Application Publication No. 2002/0197266 A1, and U.S. Pat. No. 7,338, 929).

Also, a CAR, a T cell expressing a CAR, an antibody, or antigen binding portion thereof, can be to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

C. Conjugates

The DuoCARs used in the patient-specific autologous anti-tumor lymphocyte cell population(s) disclosed herein, a T cell expressing a CAR, or monoclonal antibodies, or antigen binding fragments thereof, specific for one or more of the antigens disclosed herein, can be conjugated to an agent, such as an effector molecule or detectable marker, using any number of means known to those of skill in the art. Both covalent and noncovalent attachment means may be used. Conjugates include, but are not limited to, molecules in which there is a covalent linkage of an effector molecule or a detectable marker to an antibody or antigen binding fragment that specifically binds one or more of the antigens disclosed herein. One of skill in the art will appreciate that various effector molecules and detectable markers can be used, including (but not limited to) chemotherapeutic agents, anti-angiogenic agents, toxins, radioactive agents such as $^{125}I$, $^{32}p$, $^{14}C$, $^{3}H$ and $^{35}S$ and other labels, target moieties and ligands, etc.

The choice of a particular effector molecule or detectable marker depends on the particular target molecule or cell, and the desired biological effect. Thus, for example, the effector molecule can be a cytotoxin that is used to bring about the death of a particular target cell (such as a tumor cell).

The procedure for attaching an effector molecule or detectable marker to an antibody or antigen binding fragment varies according to the chemical structure of the effector. Polypeptides typically contain a variety of functional groups; such as carboxylic acid (COOH), free amine ($—NH_2$) or sulfhydryl (—SH) groups, which are available for reaction with a suitable functional group on an antibody to result in the binding of the effector molecule or detectable marker. Alternatively, the antibody or antigen binding fragment is derivatized to expose or attach additional reactive functional groups. The derivatization may involve attachment of any of a number of known linker molecules such as those available from Pierce Chemical Company, Rockford, IL. The linker can be any molecule used to join the antibody or antigen binding fragment to the effector molecule or detectable marker. The linker is capable of forming covalent bonds to both the antibody or antigen binding fragment and to the effector molecule or detectable marker. Suitable linkers are well known to those of skill in the art and include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side groups (such as through a disulfide linkage to cysteine) or to the alpha carbon amino and carboxyl groups of the terminal amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 79,645,667, 498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

In some embodiments, the linker is cleavable under intracellular conditions, such that cleavage of the linker releases the effector molecule or detectable marker from the antibody or antigen binding fragment in the intracellular environment. In yet other embodiments, the linker is not cleavable and the effector molecule or detectable marker is released, for example, by antibody degradation. In some embodiments, the linker is cleavable by a cleaving agent that is present in the intracellular environment (for example, within a lysosome or endosome or caveolea). The linker can be, for example, a peptide linker that is cleaved by an intracellular peptidase or protease enzyme, including, but not limited to, a lysosomal or endosomal protease. In some embodiments, the peptide linker is at least two amino acids long or at least three amino acids long. However, the linker can be 4, 5, 6, 7, 8, 9, 10, 11, 12, 13, 14 or 15 amino acids long, such as 1-2, 1-3, 2-5, 3-10, 3-15, 1-5, 1-10, 1-15 amino acids long. Proteases can include cathepsins B and D and plasmin, all of which are known to hydrolyze dipeptide drug derivatives resulting in the release of active drug inside target cells (see, for example, Dubowchik and Walker, 1999, Pharm. Therapeutics 83:67-123). For example, a peptide linker that is cleavable by the thiol-dependent protease cathepsin-B, can be used (for example, a Phenylalanine-Leucine or a Glycine-Phenylalanine-Leucine-Glycine linker). Other examples of such linkers are described, for example, in U.S. Pat. No. 6,214,345, incorporated herein by reference. In a specific embodiment, the peptide linker cleavable by an intracellular protease is a Valine-Citruline linker or a Phenylalanine-Lysine linker (see, for example, U.S. Pat. No. 6,214,345, which describes the synthesis of doxorubicin with the Valine-Citruline linker).

In other embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (for example, a hydrazone, semicarbazone, thiosemicarbazone, cis-aconitic amide, orthoester, acetal, ketal, or the like) can be used. (See, for example, U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, for example, a thioether attached to the therapeutic agent via an acylhydrazone bond (see, for example, U.S. Pat. No. 5,622,929).

In other embodiments, the linker is cleavable under reducing conditions (for example, a disulfide linker). A variety of disulfide linkers are known in the art, including, for example, those that can be formed using SATA (N-succinimidyl-S-acetylthioacetate), SPDP (N-succinimidyl-3-(2-pyridyldithio) propionate), SPDB (N-succinimidyl-3-(2-pyridyldithio) butyrate) and SMPT (N-succinimidyl-oxycarbonyl-alpha-methyl-alpha-(2-pyridyl-dithio) toluene)-, SPDB and SMPT. (See, for example, Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987); Phillips et al., Cancer Res. 68:92809290, 2008). See also U.S. Pat. No. 4,880,935.)

In yet other specific embodiments, the linker is a malonate linker (Johnson et al., 1995, Anticancer Res. 15:1387-93), a maleimidobenzoyl linker (Lau et al., 1995, Bioorg-Med-Chem. 3 (10): 1299-1304), or a 3'-N-amide analog (Lau et al., 1995, Bioorg-Med-Chem. 3 (10): 1305-12).

In yet other embodiments, the linker is not cleavable and the effector molecule or detectable marker is released by antibody degradation. (See U.S. Publication No. 2005/0238649 incorporated by reference herein in its entirety).

In several embodiments, the linker is resistant to cleavage in an extracellular environment. For example, no more than about 20%, no more than about 15%, no more than about 10%, no more than about 5%, no more than about 3%, or no more than about 1% of the linkers, in a sample of conjugate, are cleaved when the conjugate is present in an extracellular environment (for example, in plasma). Whether or not a linker is resistant to cleavage in an extracellular environment can be determined, for example, by incubating the conjugate containing the linker of interest with plasma for a predetermined time period (for example, 2, 4, 8, 16, or 24 hours) and then quantitating the amount of free effector molecule or detectable marker present in the plasma. A variety of exemplary linkers that can be used in conjugates are described in WO 2004-010957, U.S. Publication No. 2006/0074008, U.S. Publication No. 20050238649, and U.S. Publication No. 2006/0024317, each of which is incorporated by reference herein in its entirety.

In several embodiments, conjugates of a CAR, a T cell expressing a CAR, an antibody, or antigen binding portion thereof, and one or more small molecule toxins, such as a calicheamicin, maytansinoids, dolastatins, auristatins, a trichothecene, and CC1065, and the derivatives of these toxins that have toxin activity, are provided.

Maytansine compounds suitable for use as maytansinoid toxin moieties are well known in the art, and can be isolated from natural sources according to known methods, produced using genetic engineering techniques (see Yu et al (2002) PNAS 99:7968-7973), or maytansinol and maytansinol analogues prepared synthetically according to known methods. Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, each of which is incorporated herein by reference. Conjugates containing maytansinoids, methods of making same, and their therapeutic use are disclosed, for example, in U.S. Pat. Nos. 5,208,020; 5,416,064; 6,441, 163 and European Patent EP 0 425 235 B1, the disclosures of which are hereby expressly incorporated by reference.

Additional toxins can be employed with a CAR, a T cell expressing a CAR, an antibody, or antigen binding portion thereof. Exemplary toxins include *Pseudomonas* exotoxin (PE), ricin, abrin, diphtheria toxin and subunits thereof, ribotoxin, ribonuclease, saporin, and calicheamicin, as well as botulinum toxins A through F. These toxins are well known in the art and many are readily available from commercial sources (for example, Sigma Chemical Company, St. Louis, MO). Contemplated toxins also include variants of the toxins (see, for example, see, U.S. Pat. Nos. 5,079,163 and 4,689,401).

Saporin is a toxin derived from *Saponaria officinalis* that disrupts protein synthesis by inactivating the 60S portion of the ribosomal complex (Stirpe et al., Bio/Technology, 10:405-412, 1992). However, the toxin has no mechanism for specific entry into cells, and therefore requires conjugation to an antibody or antigen binding fragment that recognizes a cell-surface protein that is internalized in order to be efficiently taken up by cells.

Diphtheria toxin is isolated from *Corynebacterium diphtheriae*. Typically, diphtheria toxin for use in immunotoxins is mutated to reduce or to eliminate non-specific toxicity. A mutant known as CRM107, which has full enzymatic activity but markedly reduced non-specific toxicity, has been known since the 1970's (Laird and Groman, J. Virol. 19:220, 1976), and has been used in human clinical trials. See, U.S. Pat. Nos. 5,792,458 and 5,208,021.

Ricin is the lectin RCA60 from *Ricinus communis* (Castor bean). For examples of ricin, see, U.S. Pat. Nos. 5,079,163 and 4,689,401. *Ricinus communis* agglutinin (RCA) occurs in two forms designated RCA60 and RCA120 according to their molecular weights of approximately 65 and 120 kD, respectively (Nicholson & Blaustein, J. Biochim. Biophys. Acta 266:543, 1972). The A chain is responsible for inactivating protein synthesis and killing cells. The B chain binds ricin to cell-surface galactose residues and facilitates transport of the A chain into the cytosol (Olsnes et al., Nature 249:627-631, 1974 and U.S. Pat. No. 3,060,165).

Ribonucleases have also been conjugated to targeting molecules for use as immunotoxins (see Suzuki et al., Nat. Biotech. 17:265-70, 1999). Exemplary ribotoxins such as α-sarcin and restrictocin are discussed in, for example Rathore et al., Gene 190:31-5, 1997; and Goyal and Batra, Biochem. 345 Pt 2:247-54, 2000. Calicheamicins were first isolated from *Micromonospora echinospora* and are members of the enediyne antitumor antibiotic family that cause double strand breaks in DNA that lead to apoptosis (see, for example Lee et al., J. Antibiot. 42:1070-87,1989). The drug is the toxic moiety of an immunotoxin in clinical trials (see, for example, Gillespie et al., Ann. Oncol. 11:735-41, 2000).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B chain (abrin-b) binds to D-galactose residues (see, Funatsu et al., Agr. Biol. Chem. 52:1095, 1988; and Olsnes, Methods Enzymol. 50:330-335, 1978).

The CAR used in the patient-specific autologous anti-tumor lymphocyte cell population(s), a T cell expressing a CAR, monoclonal antibodies, antigen binding fragments thereof, specific for one or more of the antigens disclosed herein, can also be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). A CAR, a T cell expressing a CAR, an antibody, or antigen binding portion thereof, can also be conjugated with enzymes that are useful for detection, such as horseradish peroxidase, β-galactosidase, luciferase, alkaline phosphatase, glucose oxidase and the like. When a CAR, a T cell expressing a CAR, an antibody, or antigen binding portion thereof, is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. A CAR, a T cell expressing a CAR, an antibody, or antigen binding portion thereof, may also be conjugated with biotin, and detected through indirect measurement of avidin or streptavidin binding. It should be noted that the avidin itself can be conjugated with an enzyme or a fluorescent label.

A CAR, a T cell expressing a CAR, an antibody, or antigen binding portion thereof, may be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitopes recognized by a secondary reporter (such as leucine zipper pair sequences, binding sites for secondary antibodies, metal binding domains, epitope tags).

A CAR, a T cell expressing a CAR, an antibody, or antigen binding portion thereof, can also be conjugated with a radiolabeled amino acid. The radiolabel may be used for both diagnostic and therapeutic purposes. For instance, the radiolabel may be used to detect one or more of the antigens disclosed herein and antigen expressing cells by x-ray, emission spectra, or other diagnostic techniques. Further, the radiolabel may be used therapeutically as a toxin for treatment of tumors in a subject, for example for treatment of a neuroblastoma. Examples of labels for polypeptides include, but are not limited to, the following radioisotopes or radionucleotides: $^{3}H$, $^{14}C$, $^{15}N$, $^{35}S$, $^{90}Y$, $^{99}Tc$, $^{111}In$, $^{125}I$, $^{131}I$.

Means of detecting such detectable markers are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

D. Nucleotides, Expression, Vectors, and Host Cells

Further provided by an embodiment of the invention is a nucleic acid comprising a nucleotide sequence encoding any of the DuoCARs, an antibody, or antigen binding portion thereof, described herein (including functional portions and functional variants thereof). The nucleic acids of the invention may comprise a nucleotide sequence encoding any of the leader sequences, antigen binding domains, transmembrane domains, and/or intracellular T cell signaling domains described herein.

In one embodiment, an isolated nucleic acid molecule encoding a chimeric antigen receptor (DuoCARs) is provided comprising, from N-terminus to C-terminus, at least one extracellular antigen binding domain, at least one transmembrane domain, and at least one intracellular signaling domain.

In one embodiment of the CAR used in the patient-specific autologous anti-tumor lymphocyte cell population(s), an isolated nucleic acid molecule encoding the CAR is provided wherein the encoded extracellular antigen binding domain comprises at least one single chain variable fragment of an antibody that binds to the antigen.

In another embodiment of the CAR used in the patient-specific autologous anti-tumor lymphocyte cell population(s), an isolated nucleic acid molecule encoding the CAR is provided wherein the encoded extracellular antigen binding domain comprises at least one heavy chain variable region of an antibody that binds to the antigen.

In yet another embodiment of the CAR used in the patient-specific autologous anti-tumor lymphocyte cell population(s), an isolated nucleic acid molecule encoding the CAR is provided wherein the encoded CAR extracellular antigen binding domain comprises at least one lipocalin-based antigen binding antigen (anticalins) that binds to the antigen.

In one embodiment of the CAR used in the patient-specific autologous anti-tumor lymphocyte cell population(s), an isolated nucleic acid molecule is provided wherein the encoded extracellular antigen binding domain is connected to the transmembrane domain by a linker domain.

In another embodiment of the DuoCARs used in the patient-specific autologous anti-tumor lymphocyte cell population(s), an isolated nucleic acid molecule encoding the CAR is provided wherein the encoded extracellular antigen binding domain is preceded by a sequence encoding a leader or signal peptide.

In yet another embodiment of the DuoCARs used in the patient-specific autologous anti-tumor lymphocyte cell population(s), an isolated nucleic acid molecule encoding the CAR is provided wherein the encoded extracellular antigen binding domain targets an antigen that includes, but is not limited to, CD19, CD20, CD22, ROR1, mesothelin, CD33/IL3Ra, CD38, CD123 (IL3RA), CD138, BCMA (CD269), GPC2, GPC3, FGFR4, c-Met, PSMA, Glycolipid F77, EGFRVIII, GD-2, NY-ESO-1 TCR, MAGE A3 TCR, or any combination thereof.

In certain embodiments of the DuoCARs used in the patient-specific autologous anti-tumor lymphocyte cell population(s), an isolated nucleic acid molecule encoding the CAR is provided wherein the encoded extracellular antigen binding domain comprises an anti-CD19 scFV antigen binding domain, an anti-CD20 scFV antigen binding domain, an anti-CD22 scFV antigen binding domain, an anti-ROR1 scFV antigen binding domain, an anti-TSLPR scFV antigen binding domain, an anti-mesothelin scFV antigen binding domain, an anti-CD33/IL3Ra scFV antigen binding domain, an anti-CD38 scFV antigen binding domain, an anti-CD123 (IL3RA) scFV antigen binding domain, an anti-CD138 scFV antigen binding domain, an anti-BCMA (CD269) scFV antigen binding domain, an anti-GPC2 scFV antigen binding domain, an anti-GPC3 scFV antigen binding domain, an anti-FGFR4 scFV antigen binding domain, an anti-c-Met scFV antigen binding domain, an anti-PMSA scFV antigen binding domain, an anti-glycolipid F77 scFV antigen binding domain, an anti-EGFRvIII scFV antigen binding domain, an anti-GD-2 scFV antigen binding domain, an anti-NY-ESo-1 TCR scFV antigen binding domain, an anti-MAGE A3 TCR scFV antigen binding domain, or an amino acid sequence with 85%, 90%, 95%, 96%, 97%, 98% or 99% identity thereof, or any combination thereof.

In one aspect of the DuoCARs used in the patient-specific autologous anti-tumor lymphocyte cell population(s), the DuoCARs provided herein further comprise a linker domain.

In one embodiment of the DuoCARs used in the patient-specific autologous anti-tumor lymphocyte cell population(s), an isolated nucleic acid molecule encoding the CAR is provided wherein the extracellular antigen binding domain, the intracellular signaling domain, or both are connected to the transmembrane domain by a linker domain.

In one embodiment of the DuoCARs used in the patient-specific autologous anti-tumor lymphocyte cell population(s), an isolated nucleic acid molecule encoding the CAR is provided wherein the encoded linker domain is derived from the extracellular domain of CD8, and is linked to the transmembrane domain.

In yet another embodiment of the DuoCARs used in the patient-specific autologous anti-tumor lymphocyte cell population(s), an isolated nucleic acid molecule encoding the CAR is provided wherein the nucleic acid sequence encoding the transmembrane domain comprises a nucleotide sequence with 85%, 90%, 95%, 96%, 97%, 98% or 99% identity thereof.

In one embodiment of the DuoCARs used in the patient-specific autologous anti-tumor lymphocyte cell population(s), an isolated nucleic acid molecule encoding the CAR is provided wherein the encoded transmembrane domain comprises an amino acid sequence comprising at least one but not more than 10 modifications, or a sequence with 85%, 90%, 95%, 96%, 97%, 98% or 99% identity thereof.

In another embodiment of the DuoCARs used in the patient-specific autologous anti-tumor lymphocyte cell population(s), an isolated nucleic acid molecule encoding the CAR is provided wherein the encoded CAR further comprises a transmembrane domain that comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154, or a combination thereof.

In yet another embodiment of the DuoCARs used in the patient-specific autologous anti-tumor lymphocyte cell population(s), an isolated nucleic acid molecule encoding the CAR is provided wherein the encoded intracellular signaling domain further comprises a CD3 zeta intracellular domain.

In one embodiment of the CAR disclosed herein, an isolated nucleic acid molecule encoding the CAR is provided wherein the encoded intracellular signaling domain is arranged on a C-terminal side relative to the CD3 zeta intracellular domain.

In another embodiment of the DuoCARs used in the patient-specific autologous anti-tumor lymphocyte cell population(s), an isolated nucleic acid molecule encoding the CAR is provided wherein the encoded at least one intracellular signaling domain comprises a costimulatory domain, a primary signaling domain, or a combination thereof.

In further embodiments of the DuoCARs used in the patient-specific autologous anti-tumor lymphocyte cell population(s), an isolated nucleic acid molecule encoding the CAR is provided wherein the encoded at least one costimulatory domain comprises a functional signaling domain of OX40, CD70, CD27, CD28, CD5, ICAM-1, LFA-1 (CD11a/CD18), ICOS (CD278), DAP10, DAP12, and 4-1BB (CD137), or a combination thereof.

In one embodiment of the DuoCARs used in the patient-specific autologous anti-tumor lymphocyte cell population(s), an isolated nucleic acid molecule encoding the CAR is provided that further contains a leader sequence or signal peptide sequence.

In some embodiments, the nucleotide sequence may be codon-modified. Without being bound to a particular theory, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency.

In an embodiment of the invention, the nucleic acid may comprise a codon-modified nucleotide sequence that encodes the antigen binding domain of the inventive CAR. In another embodiment of the invention, the nucleic acid may comprise a codon-modified nucleotide sequence that encodes any of the DuoCARs described herein (including functional portions and functional variants thereof).

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Sambrook et al., supra. The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Integrated DNA Technologies (Coralville, IA, USA).

The nucleic acid can comprise any isolated or purified nucleotide sequence which encodes any of the DuoCARs or functional portions or functional variants thereof. Alternatively, the nucleotide sequence can comprise a nucleotide sequence which is degenerate to any of the sequences or a combination of degenerate sequences.

An embodiment also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive DuoCARs. It is generally appreciated that conditions can be rendered more stringent by the addition of increasing amounts of formamide.

Also provided is a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

In an embodiment, the nucleic acids can be incorporated into a recombinant expression vector. In this regard, an embodiment provides recombinant expression vectors comprising any of the nucleic acids. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors are not naturally-occurring as a whole.

However, parts of the vectors can be naturally-occurring. The recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences, Glen Burnie, MD), the pBluescript series (Stratagene, LaJolla, CA), the pET series (Novagen, Madison, WI), the pGEX series (Pharmacia Biotech, Uppsala, Sweden), and the pEX series (Clontech, Palo Alto, CA).

Bacteriophage vectors, such as λῦTIO, λϋTI 1, λZapII (Stratagene), EMBL4, and ANMI 149, also can be used. Examples of plant expression vectors include pBIO1, pBI101.2, pBHO1. 3, pBI121 and pBIN19 (Clontech). Examples of animal expression vectors include pEUK-C1, pMAM, and pMAMneo (Clontech). The recombinant expression vector may be a viral vector, e.g., a retroviral vector or a lentiviral vector. A lentiviral vector is a vector derived from at least a portion of a lentivirus genome, including especially a self-inactivating lentiviral vector as provided in Milone et al., Mol. Ther. 17 (8): 1453-1464 (2009). Other examples of lentivirus vectors that may be used in the clinic, include, for example, and not by way of limitation, the LENTIVECTOR.RTM. gene delivery technology from Oxford BioMedica plc, the LENTIMAX.TM. vector system from Lentigen and the like. Nonclinical types of lentiviral vectors are also available and would be known to one skilled in the art.

A number of transfection techniques are generally known in the art (see, e.g., Graham et al., Virology, 52:456-467 (1973); Sambrook et al., supra; Davis et al., Basic Methods in Molecular Biology, Elsevier (1986); and Chu et al., Gene, 13:97 (1981).

Transfection methods include calcium phosphate co-precipitation (see, e.g., Graham et al., supra), direct micro injection into cultured cells (see, e.g., Capecchi, Cell, 22:479-488 (1980)), electroporation (see, e.g., Shigekawa et al., BioTechniques, 6:742-751 (1988)), liposome mediated gene transfer (see, e.g., Mannino et al., BioTechniques, 6:682-690 (1988)), lipid mediated transduction (see, e.g., Feigner et al., Proc. Natl. Acad. Sci. USA, 84:7413-7417 (1987)), and nucleic acid delivery using high velocity microprojectiles (see, e.g., Klein et al., Nature, 327:70-73 (1987)).

In an embodiment, the recombinant expression vectors can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papilloma virus, and the like.

The recombinant expression vector may comprise regulatory sequences, such as transcription and translation initiation and termination codons, which are specific to the type of host cell (e.g., bacterium, fungus, plant, or animal) into which the vector is to be introduced, as appropriate, and taking into consideration whether the vector is DNA- or RNA-based. The recombinant expression vector may comprise restriction sites to facilitate cloning.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the CAR (including functional portions and functional variants thereof), or to the nucleotide sequence which is complementary to or which hybridizes to the nucleotide sequence encoding the CAR. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, Suicide Gene Therapy: Methods and Reviews, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

An embodiment further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5a *E. coli* cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5a cell. For purposes of producing a recombinant CAR, the host cell may be a mammalian cell. The host cell may be a human cell. While the host cell can be of any cell type, can originate from any type of tissue, and can be of any developmental stage, the host cell may be a peripheral blood lymphocyte (PBL) or a peripheral blood mononuclear cell (PBMC). The host cell may be a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, CD4+/CD8+ double positive T cells, CD4+ helper T cells, e.g., Thi and Th2 cells, CD8+ T cells (e.g., cytotoxic T cells), tumor infiltrating cells, memory T cells, naive T cells, and the like. The T cell may be a CD8+ T cell or a CD4+ T cell.

In an embodiment, the DuoCARs as described herein can be used in suitable non-T cells. Such cells are those with an immune-effector function, such as, for example, NK cells, and T-like cells generated from pluripotent stem cells.

Also provided by an embodiment is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

DuoCARs (including functional portions and variants thereof), nucleic acids, recombinant expression vectors, host cells (including populations thereof), and antibodies (including antigen binding portions thereof), can be isolated and/or purified. For example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example at least about 70%, of the total cell content of the preparation. For example, the purity can be at least about 50%, can be greater than about 60%, about 70% or about 80%, or can be about 100%.

E. Methods of Treatment

It is contemplated that the DuoCARs used in the patient-specific autologous anti-tumor lymphocyte cell population(s) can be used in methods of treating or preventing a disease in a mammal. In this regard, an embodiment provides a method of treating or preventing cancer in a mammal, comprising administering to the mammal the DuoCARs, the nucleic acids, the recombinant expression vectors, the host cells, the population of cells, the antibodies and/or the antigen binding portions thereof, and/or the pharmaceutical compositions in an amount effective to treat or prevent cancer in the mammal. Additional methods of use of the aforementioned DuoCARs have been disclosed supra.

An embodiment further comprises lymphodepleting the mammal prior to administering the DuoCARs disclosed herein. Examples of lymphodepletion include, but may not be limited to, nonmyeloablative lymphodepleting chemotherapy, myeloablative lymphodepleting chemotherapy, total body irradiation, etc.

For purposes of the methods, wherein host cells or populations of cells are administered, the cells can be cells that are allogeneic or autologous to the mammal. Preferably, the cells are autologous to the mammal. As used herein, allogeneic means any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically. As used herein, "autologous" means any material derived from the same individual to whom it is later to be re-introduced into the individual.

The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

With respect to the methods, the cancer can be any cancer, including any of acute lymphocytic cancer, acute myeloid leukemia, alveolar rhabdomyosarcoma, bladder cancer (e.g., bladder carcinoma), bone cancer, brain cancer (e.g., medulloblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer, larynx cancer, leukemia, liquid tumors, liver cancer, lung cancer (e.g., non-small cell lung carcinoma and lung adenocarcinoma), lymphoma, mesothelioma, mastocytoma, melanoma, multiple myeloma, nasopharynx cancer, non-Hodgkin lymphoma, B-chronic lymphocytic leukemia (CLL), hairy cell leukemia, acute lymphocytic leukemia (ALL), acute myeloid leukemia (AML), and Burkitt's lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, synovial sarcoma, gastric cancer, testicular cancer, thyroid cancer, and ureter cancer.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the methods can provide any amount or any level of treatment or prevention of cancer in a mammal.

Furthermore, the treatment or prevention provided by the method can include treatment or prevention of one or more conditions or symptoms of the disease, e.g., cancer, being treated or prevented. Also, for purposes herein, "prevention" can encompass delaying the onset of the disease, or a symptom or condition thereof.

Another embodiment provides a method of detecting the presence of cancer in a mammal, comprising: (a) contacting a sample comprising one or more cells from the mammal with the DuoCARs, the nucleic acids, the recombinant expression vectors, the host cells, the population of cells, the antibodies, and/or the antigen binding portions thereof, or the pharmaceutical compositions, thereby forming a complex, (b) and detecting the complex, wherein detection of the complex is indicative of the presence of cancer in the mammal.

The sample may be obtained by any suitable method, e.g., biopsy or necropsy. A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., cancer.

With respect to an embodiment of the method of detecting the presence of a proliferative disorder, e.g., cancer, in a mammal, the sample comprising cells of the mammal can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the mammal, e.g., the cells of any organ or tissue, including blood cells or endothelial cells.

The contacting can take place in vitro or in vivo with respect to the mammal. Preferably, the contacting is in vitro.

Also, detection of the complex can occur through any number of ways known in the art. For instance, the DuoCARs disclosed herein, polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles) as disclosed supra.

Methods of testing a CAR for the ability to recognize target cells and for antigen specificity are known in the art. For instance, Clay et al., J. Immunol, 163:507-513 (1999), teaches methods of measuring the release of cytokines (e.g., interferon-γ, granulocyte/monocyte colony stimulating factor (GM-CSF), tumor necrosis factor a (TNF-a) or interleukin 2 (IL-2)). In addition, CAR function can be evaluated by measurement of cellular cytotoxicity, as described in Zhao et al., J. Immunol. 174:4415-4423 (2005).

Another embodiment provides for the use of the DuoCARs, nucleic acids, recombinant expression vectors, host cells, populations of cells, antibodies, or antigen binding portions thereof, and/or pharmaceutical compositions of the invention, for the treatment or prevention of a proliferative disorder, e.g., cancer, in a mammal. The cancer may be any of the cancers described herein.

Any method of administration can be used for the disclosed therapeutic agents, including local and systemic administration. For example, topical, oral, intravascular such as intravenous, intramuscular, intraperitoneal, intranasal, intradermal, intrathecal and subcutaneous administration can be used. The particular mode of administration and the dosage regimen will be selected by the attending clinician, taking into account the particulars of the case (for example the subject, the disease, the disease state involved, and whether the treatment is prophylactic). In cases in which more than one agent or composition is being administered, one or more routes of administration may be used; for example, a chemotherapeutic agent may be administered orally and an antibody or antigen binding fragment or conjugate or composition may be administered intravenously. Methods of administration include injection for which the CAR, CAR T Cell, conjugates, antibodies, antigen binding fragments, or compositions are provided in a nontoxic pharmaceutically acceptable carrier such as water, saline, Ringer's solution, dextrose solution, 5% human serum albumin, fixed oils, ethyl oleate, or liposomes. In some embodiments, local administration of the disclosed compounds can be used, for instance by applying the antibody or antigen binding fragment to a region of tissue from which a tumor has been removed, or a region suspected of being prone to tumor development. In some embodiments, sustained intra-tumoral (or near-tumoral) release of the pharmaceutical preparation that includes a therapeutically effective amount of the antibody or antigen binding fragment may be beneficial. In other examples, the conjugate is applied as an eye drop topically to the cornea, or intravitreally into the eye.

The disclosed therapeutic agents can be formulated in unit dosage form suitable for individual administration of precise dosages. In addition, the disclosed therapeutic agents may be administered in a single dose or in a multiple dose schedule. A multiple dose schedule is one in which a primary course of treatment may be with more than one separate dose, for instance 1-10 doses, followed by other doses given at subsequent time intervals as needed to maintain or reinforce the action of the compositions. Treatment can involve daily or multi-daily doses of compound(s) over a period of a few days to months, or even years. Thus, the dosage regime will also, at least in part, be determined based on the particular needs of the subject to be treated and will be dependent upon the judgment of the administering practitioner.

Typical dosages of the antibodies or conjugates can range from about 0.01 to about 30 mg/kg, such as from about 0.1 to about 10 mg/kg.

In particular examples, the subject is administered a therapeutic composition that includes one or more of the conjugates, antibodies, compositions, DuoCARs, CAR T cells or additional agents, on a multiple daily dosing schedule, such as at least two consecutive days, 10 consecutive days, and so forth, for example for a period of weeks, months, or years. In one example, the subject is administered the conjugates, antibodies, compositions or additional agents for a period of at least 30 days, such as at least 2 months, at least 4 months, at least 6 months, at least 12 months, at least 24 months, or at least 36 months.

In some embodiments, the disclosed methods include providing surgery, radiation therapy, and/or chemotherapeutics to the subject in combination with a disclosed antibody, antigen binding fragment, conjugate, CAR or T cell expressing a CAR (for example, sequentially, substantially simultaneously, or simultaneously). Methods and therapeutic dosages of such agents and treatments are known to those skilled in the art, and can be determined by a skilled clinician. Preparation and dosing schedules for the additional agent may be used according to manufacturer's instructions or as determined empirically by the skilled practitioner. Preparation and dosing schedules for such chemotherapy are also described in Chemotherapy Service, (1992) Ed., M. C. Perry, Williams & Wilkins, Baltimore, Md.

In some embodiments, the combination therapy can include administration of a therapeutically effective amount of an additional cancer inhibitor to a subject. Non-limiting examples of additional therapeutic agents that can be used with the combination therapy include microtubule binding agents, DNA intercalators or cross-linkers, DNA synthesis inhibitors, DNA and RNA transcription inhibitors, antibodies, enzymes, enzyme inhibitors, gene regulators, and angiogenesis inhibitors. These agents (which are administered at a therapeutically effective amount) and treatments can be used alone or in combination. For example, any suitable anti-cancer or anti-angiogenic agent can be administered in combination with the CARS, CAR-T cells, antibodies, antigen binding fragment, or conjugates disclosed herein. Methods and therapeutic dosages of such agents are known to those skilled in the art, and can be determined by a skilled clinician.

Additional chemotherapeutic agents for combination immunotherapy include, but are not limited to alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; antimetabolites, such as folic acid (for example, methotrexate, pemetrexed, and raltitrexed), purine (for example, cladribine, clofarabine, fludarabine, mercaptopurine, and tioguanine), pyrimidine (for example, capecitabine), cytarabine, fluorouracil, and gemcitabine; plant alkaloids, such as *podophyllum* (for example, etoposide, and teniposide), taxane (for example, docetaxel and paclitaxel), *vinca* (for example, vinblastine, vincristine, vindesine, and vinorelbine); cytotoxic/antitumor antibiotics, such as anthracycline family members (for example, daunorubicin, doxorubicin, epirubicin, idarubicin, mitoxantrone, and valrubicin), bleomycin, rifampicin, hydroxyurea, and mitomycin; topoisomerase inhibitors, such as topotecan and irinotecan; monoclonal antibodies, such as alemtuzumab, bevacizumab, cetuximab, gemtuzumab, rituximab, panitumumab, pertuzumab, and trastuzumab; photosensitizers, such as aminolevulinic acid, methyl aminolevulinate, porfimer sodium, and verteporfin; and other agents, such as alitretinoin, altretamine, amsacrine, anagrelide, arsenic trioxide, asparaginase, axitinib, bexarotene, bevacizumab, bortezomib, celecoxib, denileukin diftitox, erlotinib, estramustine, gefitinib, hydroxycarbamide, imatinib, lapatinib, pazopanib, pentostatin, masoprocol, mitotane, pegaspargase, tamoxifen, sorafenib, sunitinib, vemurafinib, vandetanib, and tretinoin. Selection and therapeutic dosages of such agents are known to those skilled in the art, and can be determined by a skilled clinician.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun 73:316-321, 1991; Bierer et al., Curr. Opin. Immun 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used.

The combination therapy may provide synergy and prove synergistic, that is, the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation, a synergistic effect may be attained when the compounds are administered or delivered sequentially, for example by different injections in separate syringes. In general, during alternation, an effective dosage of each active ingredient is administered sequentially, i.e. serially, whereas in combination therapy, effective dosages of two or more active ingredients are administered together.

In one embodiment, an effective amount of an antibody or antigen binding fragment that specifically binds to one or more of the antigens disclosed herein or a conjugate thereof is administered to a subject having a tumor following anti-cancer treatment. After a sufficient amount of time has elapsed to allow for the administered antibody or antigen binding fragment or conjugate to form an immune complex with the antigen expressed on the respective cancer cell, the immune complex is detected. The presence (or absence) of the immune complex indicates the effectiveness of the treatment. For example, an increase in the immune complex compared to a control taken prior to the treatment indicates that the treatment is not effective, whereas a decrease in the immune complex compared to a control taken prior to the treatment indicates that the treatment is effective.

F Biopharmaceutical Compositions

Biopharmaceutical or biologics compositions (hereinafter, "compositions") are provided herein for use in gene therapy, immunotherapy, adoptive immunotherapy, and/or cell therapy that include one or more of the disclosed DuoCARs, or T cells expressing a CAR, antibodies, antigen binding fragments, conjugates, DuoCARs, or T cells expressing a CAR that specifically bind to one or more antigens disclosed herein, in a carrier (such as a pharmaceutically acceptable carrier). The compositions can be prepared in unit dosage forms for administration to a subject. The amount and timing of administration are at the discretion of the treating clinician to achieve the desired outcome. The compositions can be formulated for systemic (such as intravenous) or local (such as intra-tumor) administration. In one example, a disclosed DuoCARs, or T cells expressing a CAR, antibody, antigen binding fragment, conjugate, is formulated for parenteral administration, such as intravenous administration. Compositions including a CAR, or T cell expressing a CAR, a conjugate, antibody or antigen binding fragment as disclosed herein are of use, for example, for the treatment and detection of a tumor, for example, and not by way of limitation, a neuroblastoma. In some examples, the compositions are useful for the treatment or detection of a carcinoma. The compositions including a CAR, or T cell expressing a CAR, a conjugate, antibody or antigen binding fragment as disclosed herein are also of use, for example, for the detection of pathological angiogenesis.

The compositions for administration can include a solution of the CAR, or T cell expressing a CAR, conjugate, antibody or antigen binding fragment dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents, adjuvant agents, and the like, for example, sodium acetate, sodium chloride, potassium chloride, calcium chloride, sodium lactate and the like. The concentration of a CAR, or T cell expressing a CAR, antibody or antigen binding fragment or conjugate in these formulations can vary widely, and will be selected primarily based on fluid volumes, viscosities, body weight and the like in accordance with the particular mode of administration selected and the subject's needs. Actual methods of preparing such dosage forms for use in in gene therapy, immunotherapy and/or cell therapy are known, or will be apparent, to those skilled in the art.

A typical composition for intravenous administration includes about 0.01 to about 30 mg/kg of antibody or antigen binding fragment or conjugate per subject per day (or the corresponding dose of a CAR, or T cell expressing a CAR, conjugate including the antibody or antigen binding fragment). Actual methods for preparing administrable compositions will be known or apparent to those skilled in the art and are described in more detail in such publications as *Remington's Pharmaceutical Science,* 19th ed., Mack Publishing Company, Easton, PA (1995).

A CAR, or T cell expressing a CAR, antibodies, antigen binding fragments, or conjugates may be provided in lyophilized form and rehydrated with sterile water before administration, although they are also provided in sterile solutions of known concentration. The DuoCARs, or T cells expressing a CAR, antibody or antigen binding fragment or conjugate solution is then added to an infusion bag containing 0.9% sodium chloride, USP, and in some cases administered at a dosage of from 0.5 to 15 mg/kg of body weight. Considerable experience is available in the art in the administration of antibody or antigen binding fragment and conjugate drugs; for example, antibody drugs have been marketed in the U.S. since the approval of RITUXAN® in 1997. A CAR, or T cell expressing a CAR, antibodies, antigen binding fragments and conjugates thereof can be administered by slow infusion, rather than in an intravenous push or bolus. In one example, a higher loading dose is administered, with subsequent, maintenance doses being administered at a lower level. For example, an initial loading dose of 4 mg/kg antibody or antigen binding fragment (or the corresponding dose of a conjugate including the antibody or antigen binding fragment) may be infused over a period of some 90 minutes, followed by weekly maintenance doses for 4-8 weeks of 2 mg/kg infused over a 30 minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, PA, (1995). Particulate systems include microspheres, microparticles, microcapsules, nanocapsules, nanospheres, and nanoparticles. Microcapsules contain the therapeutic protein, such as a cytotoxin or a drug, as a central core. In microspheres, the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, for example, Kreuter, J., *Colloidal Drug Delivery Systems*, J. Kreuter, ed., Marcel Dekker, Inc., New York, NY, pp. 219-342 (1994); and Tice & Tabibi, Treatise on Controlled Drug Delivery, A. Kydonieus, ed., Marcel Dekker, Inc. New York, NY, pp. 315-339, (1992).

Polymers can be used for ion-controlled release of the DuoCARs, or T cells expressing a CAR, antibody or antigen binding fragment or conjugate compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44 (2): 58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, PA (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

G. Kits

In one aspect, Kits employing the DuoCARs disclosed herein are also provided. For example, kits for treating a tumor in a subject, or making a CAR T cell that expresses one or more of the DuoCARs disclosed herein. The kits will typically include a disclosed antibody, antigen binding fragment, conjugate, nucleic acid molecule, CAR or T cell expressing a CAR as disclosed herein. More than one of the disclosed antibodies, antigen binding fragments, conjugates, nucleic acid molecules, DuoCARs or T cells expressing a CAR can be included in the kit.

The kit can include a container and a label or package insert on or associated with the container. Suitable containers include, for example, bottles, vials, syringes, etc. The containers may be formed from a variety of materials such as glass or plastic. The container typically holds a composition including one or more of the disclosed antibodies, antigen binding fragments, conjugates, nucleic acid molecules, DuoCARs or T cells expressing a CAR. In several embodiments the container may have a sterile access port (for example the container may be an intravenous solution bag or a vial having a stopper pierceable by a hypodermic injection needle). A label or package insert indicates that the composition is used for treating the particular condition.

The label or package insert typically will further include instructions for use of a disclosed antibodies, antigen binding fragments, conjugates, nucleic acid molecules, DuoCARs or T cells expressing a CAR, for example, in a method of treating or preventing a tumor or of making a CAR T cell. The package insert typically includes instructions customarily included in commercial packages of therapeutic products that contain information about the indications, usage, dosage, administration, contraindications and/or warnings concerning the use of such therapeutic products. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

Examples

This invention is further illustrated by the examples of the DuoCARs depicted within the accompanying Figures infra and the disclosure at pages 17-27, inclusive supra, which examples are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference, and may be employed in the practice of the invention. More generally, documents or references are cited in this text, either in a Reference List before the claims, or in the text itself, and, each of these documents or references ("herein cited references"), as well as each document or reference cited in each of the herein cited references (including any manufacturer's specifications, instructions, etc.), is hereby expressly incorporated herein by reference.

The foregoing description of some specific embodiments provides sufficient information that others can, by applying current knowledge, readily modify or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. In the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein. Those skilled in the art will recognize, or be able to ascertain using no more than routine experimentation, many equivalents to the embodiments of the invention described herein. Such equivalents are encompassed by the following claims.

Description of Examples

Five examples are provided whereby the expression of three functional binding domains on the surface of a LV-transduced human T cell population, and combination of different co-stimulatory intracellular domains proves the feasibility of the DuoSet technology (Example 1), and the functional activity of this population against three different leukemia antigens proves its effectiveness (Example 2). Comparison of expression and function of DuoCARs generated co-transfection, aka transduction with single LV product encoding both DuoCAR chains (generated by co-transfection of the packaging line with two CAR encoding plasmids) are described in Example 3. In Example 4, DuoCARs transduced with LV generated by co-transfection method, and bicistronic DuoCARs encoded by a single construct, in which two DuoCAR chains are separated by a ribosomal skip site are compared for transduction efficiency and function.

Examples of the single specificity CARs on which this technology is based and which may be included as a DuoSet component in a DuoCAR include the single CD20 targeting vector LTG1495, nucleotide sequence SEQ ID NO: 3 and amino acid sequence SEQ ID NO: 4. A second example is the single specificity CAR LTG2200, specific for CD22, nucleotide sequence SEQ ID NO: 9 and amino acid sequence SEQ ID NO: 10. An important molecular aspect in creating DuoCARs is the inclusion of non-redundant compatible sequences, and the evaluation of those sequence in transduced T cells such that no untoward recombination or intracellular association occurs. This can occur both in the producer cell line of the vector, or in the target cell population. For this reason, variant CAR structures that are known to be compatible in the DuoCAR setting were included. These include the CD19-specific CAR LTG1494 described in nucleotide sequence SEQ ID: 29 and amino acid sequence SEQ ID: 30, respectively. This sequence includes the well-described linker that joins the heavy and light chains of the scFv referred to as the Whitlow linker (amino acid sequence GSTSGSGKPGSGEGSTKG (SEQ ID NO: 107), see Whitlow M., et al., 1993, Protein Eng. 6:989-995). In some cases the Whitlow linker was substituted for a $(GGGGS)_n$ linker, for example in a CD19 CAR format, as in LTG1538, nucleotide sequence SEQ ID NO: 31 and amino acid sequence SEQ ID NO: 32, respectively. In another example CARs were created that have alternate transmembrane domains. The anti-CD19 CAR LTG1562, nucleotide sequence SEQ ID NO: 21 and amino acid sequence SEQ ID NO: 22, respectively, utilizes the CD4 (as opposed to CD8) transmembrane domain. Similarly the anti-CD19 CAR LTG1563 has an alternate transmembrane derived from TNFRSF19, nucleotide sequence SEQ ID NO: 49 and amino acid sequence SEQ ID NO:50, respectively. DuoCARs can also be targeted to solid tumors, for example those expressing the mesothelin tumor antigen. For example, scFV binders have been created for mesothelin, as disclosed in Applicant's Provisional Patent Application No. 62/444,201, entitled Compositions and Methods for Treating Cancer with Anti-Mesothelin Immunotherapy, as filed on Jan. 9, 2017, and assigned Lentigen Technology, Inc. matter number LEN_017, nucleotide sequence SEQ ID NO: 37 and amino acid sequence SEQ ID NO: 38, respectively, that can be incorporated into functional CARs, nucleotide sequence SEQ ID NO: 39 and amino acid sequence SEQ ID NO: 40, respectively, and that can thereby be incorporated into a DuoCAR therapy. In addition to scFv sequences, single chain antigen binders (as opposed to scFv) can be incorporated into a DuoCAR application. For example, the CD33-specific heavy chain only binder, as disclosed in Applicant's Provisional Patent Application No. 62/476,438, entitled Compositions and Methods For Treating Cancer With Anti-CD33 Immunotherapy, as filed on Mar. 24, 2017, and assigned Lentigen Technology, Inc. matter number LEN_018, nucleotide sequence SEQ ID NO: 41 and amino acid sequence SEQ ID NO: 42, respectively, can be incorporated into a functional CAR, LTG1906, nucleotide sequence SEQ ID NO: 43 and amino acid sequence SEQ ID NO: 44, respectively, that targets CD33-expressing malignancies. One example of a DuoCAR therapeutic application would be the treatment of leukemia that expresses the CD19, CD20, and TSLPR antigens. In this case, LTG1496 or LTG1497 (SEQ ID NOs: 35, 26, respectively) could be combined with a TSLPR-specific CAR (LTG1789), SEQ ID NO: 47 and amino acid sequence SEQ ID NO: 48, respectively, that had been created from TSLPR-specific scFV domains, nucleotide sequence SEQ ID NO: 45 and amino acid sequence SEQ ID NO: 46.

Another example of a DuoCAR therapeutic application would be the treatment of cancer that expresses the CD38 antigen. For instance, the CD38-specific binders, as disclosed in Applicant's Provisional Patent Application No. 62/773,940; entitled Compositions and Methods For Treating Cancer With Anti-CD38 Immunotherapy; as filed on Nov. 30, 2018; and assigned Lentigen Technology, Inc. matter number LEN_026; can be incorporated into one or more functional CARs that target CD38-expressing malignancies, as disclosed in Applicant's Provisional Patent Application No. 62/773,940, the entirety of which is incorporated by reference herein.

Another example of a DuoCAR therapeutic application would be the treatment of cancer that expresses the CD123 antigen. For instance, the CD123-specific binders, as disclosed in Applicant's co-pending U.S. patent application Ser. No. 16/578,063; entitled Compositions and Methods For Treating Cancer With Anti-CD123 Immunotherapy; as filed on Sep. 20, 2019; and assigned Lentigen Technology, Inc. matter number LEN_024; and claiming priority to Provisional Patent Application No. 62/734,106; as filed on Sep. 20, 2018; can be incorporated into one or more functional CARs that target CD123-expressing malignancies, as disclosed in Applicant's co-pending U.S. patent application Ser. No. 16/578,063, the entirety of which is incorporated by reference herein.

Another example of a DuoCAR therapeutic application would be the treatment of cancer that expresses the BCMA antigen. For instance, the BCMA-specific binders, as disclosed in Applicant's Provisional Patent Application No. 62/854,574; entitled Fully Human BCMA CAR T Cells for the Treatment of Multiple Myeloma and Other BCMA-Positive Malignancies; as filed on May 30, 2019; and assigned Lentigen Technology, Inc. matter number MBG_13; can be incorporated into one or more functional CARs that target BCMA-expressing malignancies, as disclosed in Applicant's Provisional Patent Application No. 62/854,574, the entirety of which is incorporated by reference herein.

Examples of tandem-CARs (containing 2 scFv domains, as described in nucleotide sequence SEQ ID: 23 and amino acid sequence SEQ ID: 24) on which this technology is based include the CD20_CD19 CAR LTG1497, nucleotide sequence SEQ ID NO: 25 and amino acid sequence SEQ ID NO: 26. In some cases reversing the order of the two binders may provide a better DuoCAR expression in target cells. Thus, LTG1497, where the CD19 scFv is more proximal, as shown in nucleotide sequence SEQ ID NO: 25 and amino acid sequence SEQ ID NO: 26; and LTG1496 where the CD19 scFV is more distal to the membrane, as shown in nucleotide sequence SEQ ID NO: 33 and amino acid sequence SEQ ID NO: 34, can both be used as one of the members of a DuoSet comprising a DuoCAR.

Methods Utilized in Examples 1 and 2

Cell Lines (PBMC and Targets)

All cell lines and reagents were purchased from American Tissue Culture Collection (ATCC, Manassas, VA), unless otherwise noted. The Burkitt lymphoma cell line Raji, the acute lymphocytic leukemia cell lines REH, as well as the chronic myelogenous leukemia cell line K562, were cultured in RPMI-1640 medium supplemented with 10% heat-inactivated fetal bovine serum (FBS, Hyclone, Logan, UT) and 2 mM L-Glutamax (Thermo Fisher Scientific, Grand Island, NY). The human embryonic kidney cell line 293T was propagated in Dulbecco's modified Eagle medium supplemented with 10% heat-inactivated FBS.

Single-cell clones of luciferase-expressing cell lines were generated by stably transducing wild-type tumor lines with lentiviral vector encoding firefly luciferase (Lentigen Technology, Inc., Gaithersburg, MD), followed by cloning and selection of luciferase-positive clones. The mouse-adapted Raji-luc line was generated by engrafting a Raji clone stably expressing firefly luciferase into NSG mice (NOD.Cg-Prkd$^{scid}$ I2rg$^{tm1Wjl}$/SzJ), The Jackson Laboratory Sacramento, CA), isolating the engrafted Raji-luc tumor cells from mouse spleens by either positive (CD19 microBeads, human, Miltenyi Biotec, Bergisch Gladbach, Germany) or negative selection (mouse cell depletion kit, Miltenyi Biotec), expanding in culture, and re-cloning to facilitate the selection of clones with high expression of firefly luciferase. Whole blood was collected from healthy volunteers at Oklahoma Blood Institute (OBI, Oklahoma City, OK) with donors' written consent. Processed buffy coats were purchased from OBI. The CD4-positive and CD8-positive human T cells were purified from buffy coats via positive selection using a 1:1 mixture of CD4- and CD8-MicroBeads (Miltenyi Biotec) according to manufacturer's protocol.

Creation of Chimeric Antigen Receptor (CAR)-Expressing Vectors Comprising DuoCARs CAR antigen-binding domains, scFv, sequences were derived from the mouse hybridoma FMC-63 for CD19 (FMC-63: AA 1-267, GenBank ID: HM852952.1) and Leu-16 for CD20 [1], entire sequence of VL and VH. The CD22 scFv binding was created from publicly available sequences. Tandem CAR19_20 or CAR20_19 were generated by linking scFv of each antibody in frame to CD8 hinge and transmembrane domains (AA 123-191, Ref sequence ID NP_001759.3), 4-1BB (CD137, AA 214-255, UniProt sequence ID Q07011) transactivation domain and CD3 zeta signaling domain (CD247, AA 52-163, Ref sequence ID: NP_000725.1). The scFv regions of 19A and 20A were linked in sequence by a flexible interchain linker $(GGGGS)_5$ (SEQ ID NO: 108), followed by CD8, 4-1BB and CD3 zeta domains. Leader sequence from human granulocyte macrophage colony stimulating factor receptor alpha subunit was included in all constructs, as described in [2]. CAR constructs sequences were codon optimized (DNA2.0, Newark, CA) and cloned into a third generation lentiviral plasmid backbone (Lentigen Technology Inc., Gaithersburg, MD)

under the regulation of a human EF-1α promoter. Lentiviral vector (LV) containing supernatants were generated by transient transfection of HEK 293T cells, as previously described [3]. Harvested pelleted lentiviral supernatants were stored at −80° C.

Primary T Cell Transduction:

Selected CD4+ and CD8+ human primary T cells from normal donors were cultivated in TexMACS medium (serum-free) supplemented with 40 IU/ml IL-2 at a density of 0.3 to $2\times10^6$ cells/ml, activated with CD3/CD28 MACS® GMP TransAct reagent (Miltenyi Biotec) and transduced on day 3 with lentiviral vectors encoding CAR constructs in the presence of 10 μg/ml protamine sulfate (Sigma-Aldrich, St. Louis, MO) overnight, and media exchanged on day 4. On day 5, cultures were transferred to TexMACS medium supplemented with 200 IU/ml IL-2, and propagated until harvest on day 10-13.

Immune effector assays: To determine cell-mediated cytotoxicity (CTL assay), 5,000 target cells stably transduced with firefly luciferase were combined with CAR T cells at various effector to target ratios and incubated overnight. SteadyGlo reagent (Promega, Madison WI) was added to each well and the resulting luminescence was analyzed on an EnSpire plate reader (Perkin Elmer, Shelton, Connecticut) and recorded as counts per second (sample CPS). Target only wells (max CPS) and target only wells plus 1% Tween-20 (min CPS) were used to determine assay range. Percent specific lysis was calculated as: (1-(sample CPS-min CPS)/(max CPS-min CPS)).

Flow Cytometric analysis: All cell staining reagents for flow cytometry were from Miltenyi Biotec, unless otherwise noted. One million CAR T transduced cells were harvested from culture, washed two times in cold staining buffer (AutoMACS solution with 0.5% bovine serum albumin) and pelleted at 350×g for 5 minutes at 4° C. CAR surface expression on transduced T cells was initially detected by staining with protein L-biotin conjugate (stock 1 mg/ml, 1:1000 dilution, GenScript, Piscataway, NJ) for 30 minutes at 4° C., followed by two washes and staining with streptavidin-PE conjugate for 30 minutes at 4° C. (stock: 1.0 ml, 1:200 dilution, Jackson ImmunoResearch Laboratories, West Grove, PA). Non-transduced cells and transduced cells stained with streptavidin-PE only, were used as negative controls. Anti-CD4 antibody was employed to determine CD4 to CD8 ratio of CAR T positive population, and was added during the second incubation step. Dead cells were excluded by 7AAD staining (BD Biosciences, San Jose, CA). Cells were washed twice and resuspended in 200 ul Staining Buffer before quantitative analysis by flow cytometry. Specific DuoSet CAR T staining was carried out on Human T cells activated with CD3-CD28 nanomatrix (TransAct, Miltenyi Biotec) transduced with DuoSet vectors in the presence of IL-2, and analyzed for expression of CD19-, CD20-, or CD22-scFv domains by flow cytometry using recombinant CD19, CD20, or CD22 for staining, as for antibodies.

Anti-CD19 scFv activity was detected with CD19-Fc (R&D Biosystems), used at 1 ug/sample, and stained with goat anti-human Fc-gamma-R-PE (Jackson ImmuoResearch Laboratories, Inc.) at 0.75 ug/smaple. Anti-CD20 scFv activity was detected with CD20-biotin (Miltenyi Biotech), 0.1 ug/sample, detected with streptavidinpAPC (Miltenyi Biotec) at 0.2 ug/sample. Anti-CD22 scFc activity was detected with CD22-His (Thermo Fisher) at 0.1 ug/sample, and detected with anti-His FITC (Miltenyi Biotec). Flow cytometric analysis was performed on a MACSQuantR 10 Analyzer (Miltenyi Biotec). Characterization of target tumor lines and luciferase-positive sub clones was performed using CD19-FITC, CD20 VioBlue, and CD22-APC antibodies. Dead cells were excluded from analysis by 7AAD staining (BD Biosciences, San Jose, CA).

Example 1

Expression of a DuoCAR (2+1 DuoSet) on Primary Human T cells

Figure 7:
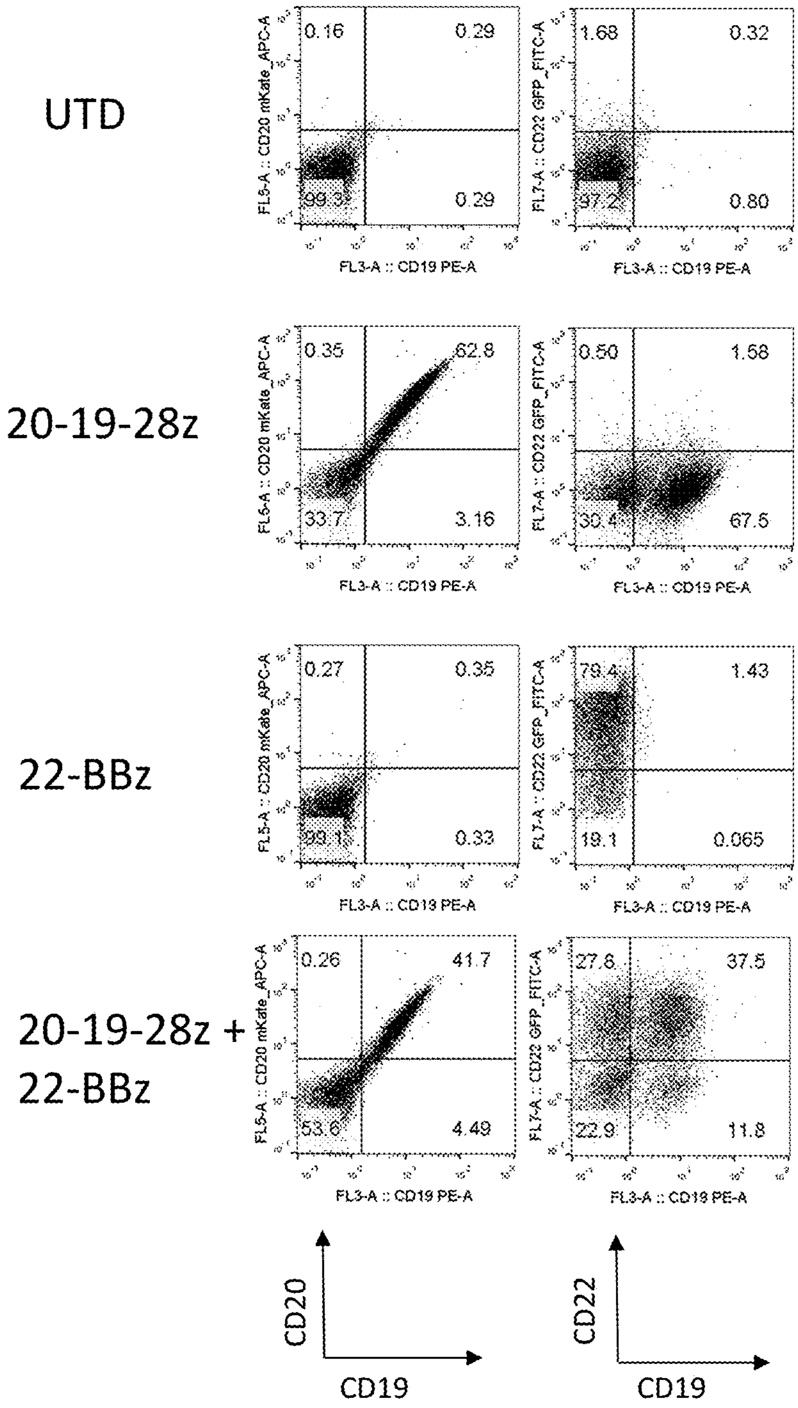
FIG. 7 depicts DuoCAR cell surface expression in human T cells. Human T cells were activated with CD3-CD28 nanomatrix (TransAct, Miltenyi Biotec) in the presence of IL-2, transduced with two vectors (one encoding a tandem CD20-CD19 CAR and one encoding a single CD22 CAR, thus a 2+1 Duo-Set format), and then analyzed for expression of CD19-, CD20-, or CD22-scFv domains by flow cytometry using recombinant CD19, CD20, or CD22 for staining. The paired columns show dual staining for CD20 and CD19 scFvs, left column, and CD22 and CD19 scFvs, right column. Row 1 shows T cells that were not transduced (UTD) and thus show no binding. Row 2 shows T cells transduced with LV encoding a CD20_CD19 CAR vector with a CD8 transmembrane and intracellular CD28 and CD3-zeta signaling domains (20-19-28z). While dual staining is seen for CD20 and CD19 binding (left panel), only CD19 binding is seen in the right panel. Row 3 shows T cells transduced with a CD22 CAR vector with a CD8 transmembrane and intracellular 4-1BB and CD3-zeta signaling domains (22-BBz). No dual staining is seen with CD19 or CD20 (left panel) and only a single population of cells able to bind CD22 is seen (right panel). In Row 4 T cells are transduced with a DuoSet comprised of both vectors in Row 2 and Row 3. Only the DuoSet express all three CAR-encoded binding domains (42% of the cells express CD20_19 (left panel), and 38% expresses CD22 and CD19 binding domains (right panel). As CD22 and CD19 scFv are on each of the two separate transmembrane proteins comprising the DuoSet, 38% represents the true DuoSet expressing population in this example.

As a proof of principle, a DuoSet comprised of two CAR-T vectors was created. One member of the set expressed a tandem CD20_CD19 binding domain linked to CD8 transmembrane and CD28 and CD3-zeta signaling domains (LTG2228), SEQ ID NO: 51 and SEQ ID NO: 52. The second member of the DuoSet was a CAR construct with a single CD22 binder linked to CD8 transmembrane and 4-1BB and CD3-zeta signaling domains (LTG2200), SEQ ID NO: 9 and SED ID NO: 10. In FIG. 7, the paired columns show dual staining for CD20 and CD19 scFvs, left column, and CD22 and CD19 scFvs, right column. Row 1 shows T cells that were not transduced (UTD) and thus show no binding. Row 2 shows T cells transduced with LV encoding a CD20_CD19 CAR vector with a CD8 transmembrane and intracellular CD28 and CD3-zeta signaling domains (20-19-28z). While dual staining is seen for CD20 and CD19 binding (left panel), only CD19 binding is seen in the right panel. Row 3 shows T cells transduced with a CD22 CAR vector with a CD8 transmembrane and intracellular 4-1BB and CD3-zeta signaling domains (22-BBz). No dual staining is seen with CD19 or CD20 (left panel) and only a single population of cells able to bind CD22 is seen (right panel). In Row 4 T cells are transduced with a DuoSet comprised of both vectors in Row 2 and Row 3. Only the DuoSet express all three CAR-encoded binding domains (42% of the cells express CD20_19 (left panel), and 38% expresses CD22 and CD19 bonding domains (right panel). As CD22 and CD19 scFv are on each of the two separate transmembrane proteins comprising the DuoSet, 38% represents the true DuoSet expressing population in this example.

Example 2

Figure 8:
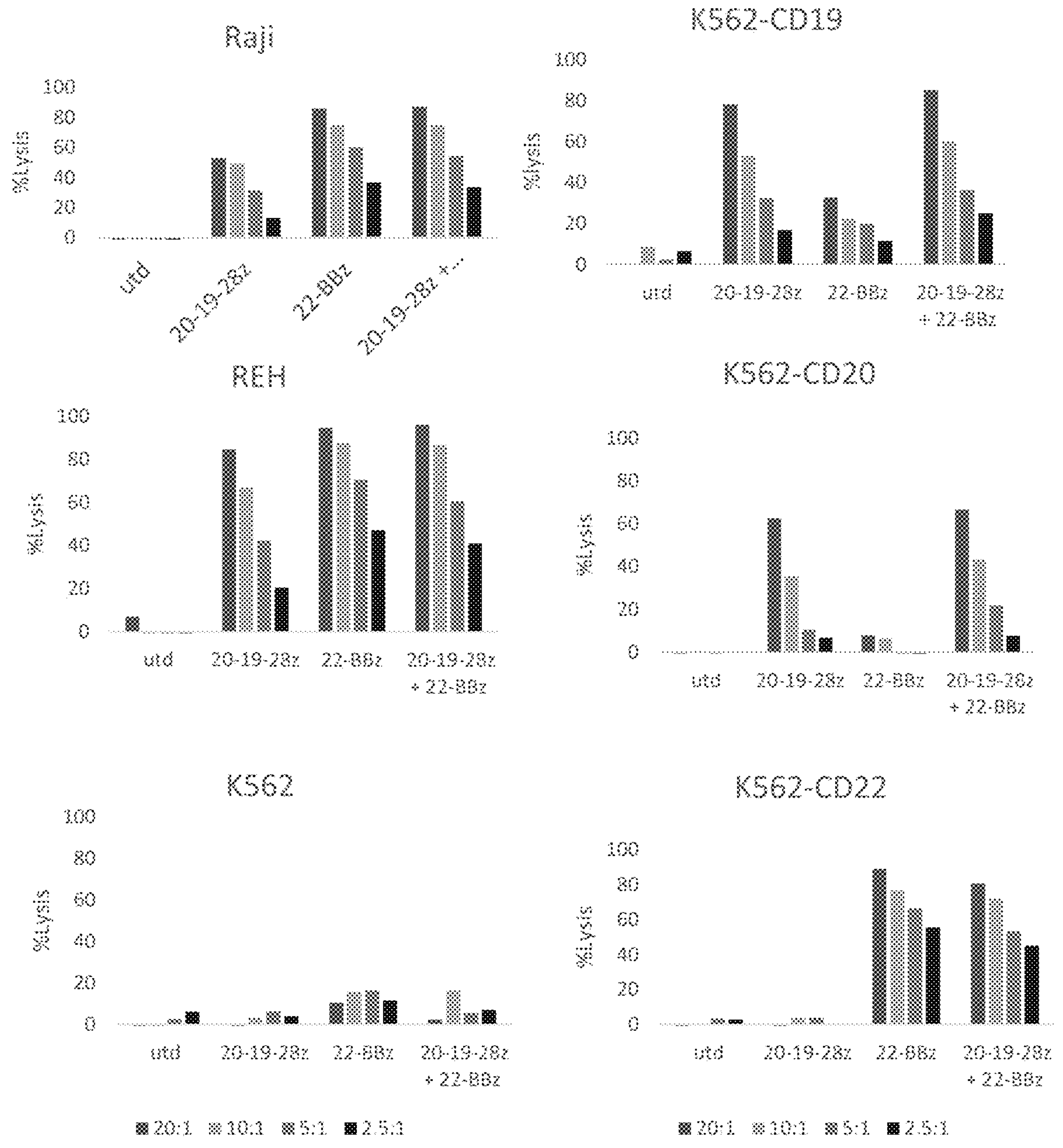
FIG. 8 depicts the anti-tumor cytolytic activity of DuoCAR expressing T cells. Human T cells transduced with single CAR components (20_19-28z or 22-BBz) or DuoCARs (20_19-28z+22-BBz), as described in FIG. 7, were used in cytotoxic T cells assay at four different effector to target ratios (20:1, 10:1, 5:1, 2.5:1, as indicated). The leukemia cell lines used as CAR-T targets were: Raji (expresses all three target antigens), REH (expresses all three target antigens), K562 (control, no targets expressed), K562-CD19 (expresses CD19), K562-CD20 (expresses CD20), and K562-CD22 (expresses CD22). Only the DuoCAR-transduced cells (20-19-28z+22-BBz, 2+1 DuoSet) exhibited high cytolytic activity against both leukemia cell lines (Raji and REH), and all three single-expressing K562 target cells lines (K562-CD19, K562-CD20, K562-CD22).

Anti-Leukemia Activity of a Human T cell Preparation Expressing DuoCARs Generated by Co-Transduction Method Anti-leukemia activity of a human T cell preparation expressing a DuoCAR that targets three leukemia antigens simultaneously (c.f., see FIG. 7 for DuoCAR expression characteristics). A DuoSet comprised of a CD20_19 tandem CAR and a CD22-specific single CAR (prepared as in Example 1) was used an effector T cell population in a cytotoxic T cell assay using leukemia cell line and model cell lines as targets. Human T cells transduced with single CAR components (20_19-28z or 22-BBz) or DuoCARs (20_19-28z+22-BBz), were used in cytotoxic T cells assay at four different effector to target ratios (20:1, 10:1, 5:1, 2.5:1, as indicated) (c.f., see FIG. 8). The leukemia cell lines used as CAR-T targets were: Raji (expresses all three target antigens), REH (expresses all three target antigens), K562 (control, no targets expressed), K562-CD19 (expresses CD19), K562-CD20 (expresses CD20), and K562-CD22 (expresses CD22). Only the DuoCAR-transduced cells (20-19-28z+22-BBz) exhibited high cytolytic activity against both leukemia cell lines (Raji and REH), and all three single-expressing K562 target cells lines (K562-CD19, K562-CD20, K562-CD22). This demonstrates that the Duo- CAR technology can uniquely target three leukemia antigens simultaneously, in the same effector T cell population, and thus demonstrates superior anti-neoplastic activity by being able to target more than one or two target antigens at a time, thus decreasing the possibility of the malignancy generating escape mutants (cells clones that have lost or down-modulate one or two antigens and this escaped immune-ablation. The end result will be higher cure rates for patients, due to escape and outgrowth of antigen-loss variants, which in the end is a relapse.

Example 3

Figure 9:
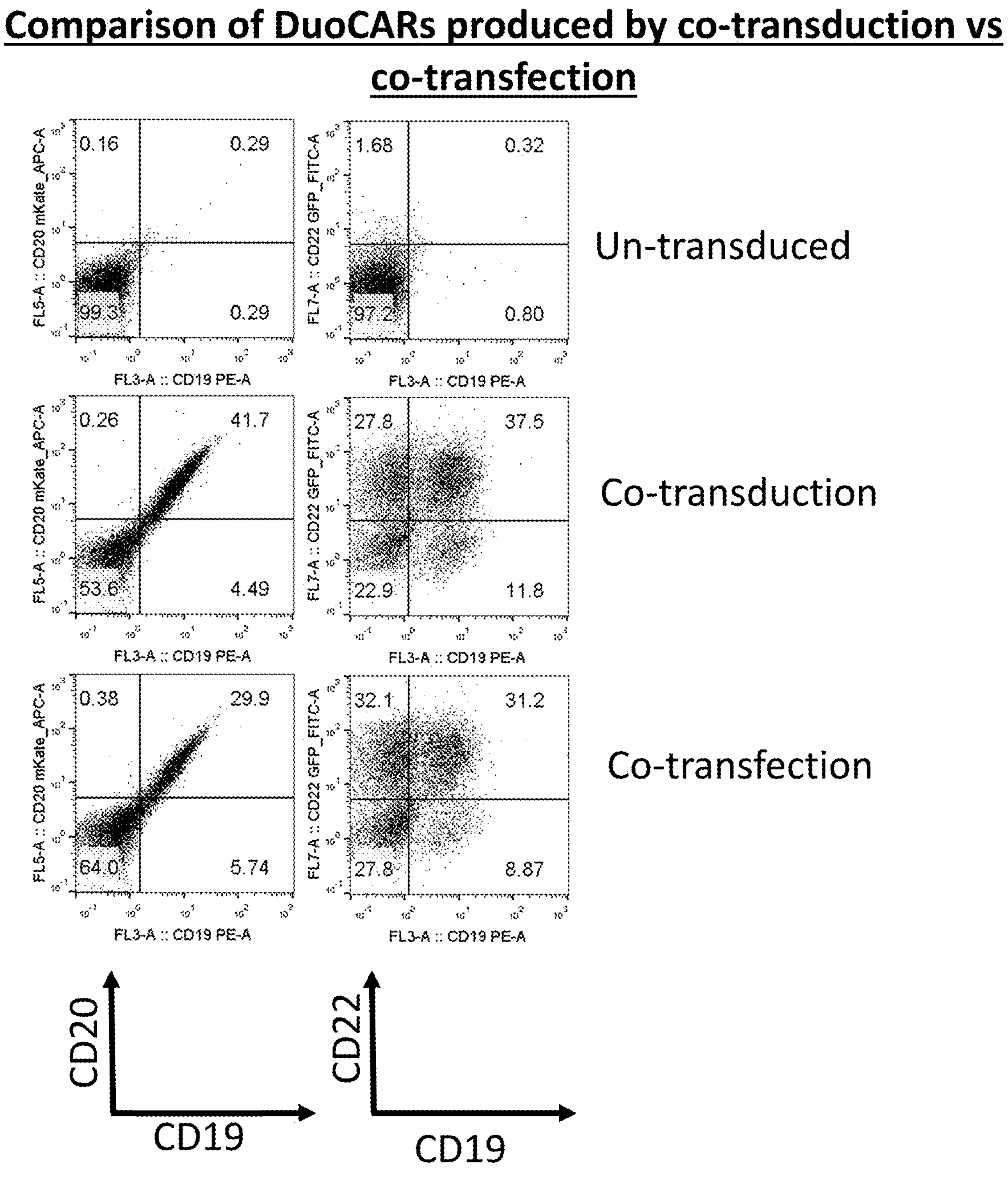
FIG. 9 depicts DuoCAR cell surface expression in primary human T cells, as achieved by two different methods of LV preparation. The same methods and data analyses were used as in FIG. 7, thus cells transduced with a DuoCAR specific for CD19, CD20, and CD22 (a 2+1 DuoSet where one CAR is a tandem CD20 and CD19 binder and the second CAR is comprised of a CD22 binder) were created. The first column of data shows flow cytometric analysis for the expression of CD19 and CD20 binders, whereas the second column shows flow cytometric analysis for CD22 and CD19 binders present as CARs in DuoCAR expressing cells for four distinct populations corresponding to the non-transduced, the singly CD22-CAR transduced, the dually transduced with CD22 and CD20_19 CARs, and singly transduced with the tandem CD20_CD19 CAR in the lower left, upper left, upper right, and lower right quadrants, respectively. Both the two LV transduction method (co-transduction) and the single LV transduction method (co-transfection) gave a similar DuoCAR staining pattern, where more than 30% of the T cell population was specific for CD19, CD20, and CD22, by virtue of expressing both CAR cell surface proteins.

Anti-Leukemia Activity of a Human T cell Preparation Expressing DuoCARs Generated by Co-Transfection Methods The DuoCAR technology described in this application generates a population of therapeutic lymphocytes, in this example human T cells, that express more than two antigen specificities from more than one transmembrane protein encoded by a gene vector. In this example, this is achieved by two different means. FIG. 9 contains three rows of data, labeled "un-transduced," "co-transduction," and "co-transfection". FIG. 9 contains two columns of data, generated as in FIG. 7, wherein the first column is analyzed by flow cytometry for the expression of CD20- and CD19-specific specific binding, and the second column is analyzed by flow cytometry for the expression of CD22- and CD19-binding activity. In the first row of data, un-transduced human T cells are shown. No binding activity is seen for the CD19, CD20, or CD22 recombinant protein indicators of CAR-derived binding activity, demonstrating no DuoCAR expression. In the second row, "co-transduction" was used to generate DuoCARs. In this data set, two LV were used to simultaneously transduce activated T cells. As in FIG. 7, one CAR in the DuoSet comprising the DuoCAR was a tandem CD20 and CD19 binder linked to CD28 signaling and CD3-zeta signaling motifs; and the other CAR was a CD22 binder, linked to 4-1BB and CD3-zeta signaling motifs. The upper right quadrant in column one shows a very specific pattern of unitary staining for CD20 and CD19-scFv activity. This is due to both binders being on the same surface glycoprotein, and thus they are co-expressed with equal intensity, generating the very specific linear pattern seen. In the second column of the co-transduction data, a more traditional pattern is seen when the two glycoproteins are not expressed in a uniform pattern on each cell. Thus a pattern of 4 distinct populations is seen. In the lower left quadrant, cells expressing neither binder are seen. In the upper left, cells expressing only the CD22 CAR are seen. In the lower right quadrant cells expressing only the CD20 CD19 tandem CAR are seen. Finally, in the upper right quadrant cells expressing both members of the CAR DuoSet, comprising the DuoCAR, are seen.

In the bottom row, cell populations expressing the DuoCAR are generated in a different manner. Unlike the co-transduction method, where 2 LV preparations created independently are used at the time of the T cell transduction, "co-transfection" refers to a method wherein two backbone plasmids (encoding the two CARs comprising the DuoCAR) are simultaneously transfected into the 293T packaging cell line for LV production. The helper plasmids comprising this third generation LV system are identical in both methods. The advantage of the co-transfection method is that a single preparation of LV, containing vectors encoding both CARs is created. As can be seen from the data, using the co-transfection method nearly identical patterns of CD20-CD19 CAR and CD22 CAR expression are seen, as compared to the co-transduction method in the second row. The staining pattern for both glycoproteins induced by LV generated by co-transfection (CD22 for the CD22-CAR and CD19 co-staining for the CD20_19 CAR) in the upper right quadrant of the data in the second column, demonstrates that both methods efficiently generate DuoCARs.

REFERENCED LITERATURE

1) Wu, A. M., et al., Multimerization of a chimeric anti-CD20 single-chain Fv-Fc fusion protein is mediated through variable domain exchange. Protein engineering, 2001. 14 (12): p. 1025-1033.
2) Haso, W., et al., Anti-CD22-chimeric antigen receptors targeting B-cell precursor acute lymphoblastic leukemia. Blood, 2013. 121 (7): p. 1165-1174.
3) Kuroda, H., et al., Simplified lentivirus vector production in protein-free media using polyethylenimine-mediated transfection. Journal of virological methods, 2009. 157 (2): p. 113-121.

Example 4

Comparison of DuoCARs Generated by Co-Transfection Method and Bicistronic DuoCAR Constructs Methods Utilized in Example 4

Cell lines (PBMC and targets): All cell lines and reagents were purchased from American Tissue Culture Collection (ATCC, Manassas, VA), unless otherwise noted. The Burkitt's lymphoma cell line Raji, the acute lymphocytic leukemia cell lines REH, as well as the chronic myelogenous leukemia cell line K562, were cultured in RPMI-1640 medium supplemented with 10% heat-inactivated fetal bovine serum (FBS, Hyclone, Logan, UT) and 2 mM L-Glutamax (Thermo Fisher Scientific, Grand Island, NY). The human embryonic kidney cell line 293T was propagated in Dulbecco's modified Eagle medium supplemented with 10% heat-inactivated FBS.

Single-cell clones of luciferase-expressing cell lines were generated by stably transducing wild-type tumor lines with lentiviral vector encoding firefly luciferase (Lentigen Technology, Inc., Gaithersburg, MD), followed by cloning and selection of luciferase-positive clones. The mouse-adapted Raji-luc line was generated by engrafting a Raji clone stably expressing firefly luciferase into NSG mice (NOD.Cg-Prkd$^{cscid}$ I12rg$^{tm1\,Wjl}$/SzJ), The Jackson Laboratory Sacramento, CA), isolating the engrafted Raji-luc tumor cells from mouse spleens by either positive (CD19 microBeads, human, Miltenyi Biotec, Bergisch Gladbach, Germany) or negative selection (mouse cell depletion kit, Miltenyi Biotec), expanding in culture, and re-cloning to facilitate the selection of clones with high expression of firefly luciferase. Whole blood was collected from healthy volunteers at Oklahoma Blood Institute (OBI, Oklahoma City, OK) with donors' written consent. Processed buffy coats were purchased from OBI. The CD4-positive and CD8-positive human T cells were purified from buffy coats via positive selection using a 1:1 mixture of CD4- and CD8-MicroBeads (Miltenyi Biotec) according to manufacturer's protocol.

Creation of Chimeric Antigen Receptor (CAR)—Expressing Vectors Comprising DuoCARs:

CAR antigen-binding domains, scFv, sequences were derived from the mouse hybridoma FMC-63 for CD19 (FMC-63: AA 1-267, GenBank ID: HM852952.1) and Leu- 16 for CD20 [1], entire sequence of VL and VH. Several anti CD22 scFv binding sequences were used. Tandem CAR19_20 or CAR20_19 were generated by linking scFv of each antibody in frame to CD8 hinge and transmembrane domains (AA 123-191, Ref sequence ID NP_001759.3), 4-1BB (CD137, AA 214-255, UniProt sequence ID Q07011) transactivation domain and CD3 zeta signaling domain (CD247, AA 52-163, Ref sequence ID: NP_000725.1). The scFv regions of 19A and 20A were linked in sequence by a flexible interchain linker $(GGGGS)_5$ (SEQ ID NO: 108), followed by CD8, 4-1BB and CD3 zeta domains. Leader sequence from human granulocyte macrophage colony stimulating factor receptor alpha subunit was included in all constructs, as described in [2]. In bicistronic CAR designs, two CAR chains were encoded within the same expression cassette, separated by ribosomal skip element 2A. CAR constructs sequences were codon optimized (DNA2.0, Newark, CA) and cloned into a third generation lentiviral plasmid backbone (Lentigen Technology Inc., Gaithersburg, MD) under the regulation of a human EF-1a of MSCV promoter. Lentiviral vector (LV) containing supernatants were generated by transient transfection of HEK 293T cells, as previously described [3]. For co-transfection experiments, equal amounts of two transfer plasmids encoding each of the DuoCAR chains were combined and applied, together with helper plasmids to the HEK 293T packaging cell line during transfection step, and resulting viral vector preparations were used for transduction of primary human T cells. Harvested pelleted lentiviral supernatants were stored at −80° C.

Primary T cell transduction: Selected CD4+ and CD8+ human primary T cells from normal donors were cultivated in TexMACS medium (serum-free) supplemented with 40 IU/ml IL-2 at a density of 0.3 to $2\times10^6$ cells/ml, activated with CD3/CD28 MACS® GMP TransAct reagent (Miltenyi Biotec) and transduced on day 3 with lentiviral vectors encoding CAR constructs in the presence of 10 μg/ml protamine sulfate (Sigma-Aldrich, St. Louis, MO) overnight, and media exchanged on day 4. On day 5, cultures were transferred to TexMACS medium supplemented with 200 IU/ml IL-2, and propagated until harvest on day 10-13.

Immune effector assays: To determine cell-mediated cytotoxicity (CTL assay), 5,000 target cells stably transduced with firefly luciferase were combined with CAR T cells at various effector to target ratios and incubated overnight. SteadyGlo reagent (Promega, Madison WI) was added to each well and the resulting luminescence was analyzed on an EnSpire plate reader (Perkin Elmer, Shelton, Connecticut) and recorded as counts per second (sample CPS). Target only wells (max CPS) and target only wells plus 1% Tween-20 (min CPS) were used to determine assay range. Percent specific lysis was calculated as: (1-(sample CPS-min CPS)/(max CPS-min CPS)).

Flow Cytometric analysis: All cell staining reagents for flow cytometry were from Miltenyi Biotec, unless otherwise noted. One million CAR T transduced cells were harvested from culture, washed two times in cold staining buffer (AutoMACS solution with 0.5% bovine serum albumin) and pelleted at 350×g for 5 minutes at 4° C. CAR surface expression on transduced T cells was initially detected by staining with protein L-biotin conjugate (stock 1 mg/ml, 1:1000 dilution, GenScript, Piscataway, NJ) for 30 minutes at 4° C., followed by two washes and staining with streptavidin-PE conjugate for 30 minutes at 4° C. (stock: 1.0 ml, 1:200 dilution, Jackson ImmunoResearch Laboratories, West Grove, PA). Non-transduced cells and transduced cells stained with streptavidin-PE only, were used as negative controls. Anti-CD4 antibody was employed to determine CD4 to CD8 ratio of CAR T positive population, and was added during the second incubation step. Dead cells were excluded by 7AAD staining (BD Biosciences, San Jose, CA). Cells were washed twice and resuspended in 200 ul Staining Buffer before quantitative analysis by flow cytometry. Specific DuoSet CAR T staining was carried out on Human T cells activated with CD3-CD28 nanomatrix (TransAct, Miltenyi Biotec) transduced with DuoSet vectors in the presence of IL-2, and analyzed for expression of CD19-, CD20-, or CD22-scFv domains by flow cytometry using recombinant CD19, CD20, or CD22 for staining, as for antibodies.

Anti-CD19 scFv activity was detected with CD19-Fc (R&D Biosystems), used at 1 ug/sample, and stained with goat anti-human Fc-gamma-R-PE (Jackson ImmuoResearch Laboratories, Inc.) at 0.75 ug/sample. Anti-CD20 scFv activity was detected with CD20-biotin (Miltenyi Biotech), 0.1 ug/sample, detected with streptavidin APC (Miltenyi Biotec) at 0.2 ug/sample. Anti-CD22 scFv activity was detected with CD22-His (Thermo Fisher) at 0.1 ug/sample, and detected with anti-His FITC (Miltenyi Biotec). Flow cytometric analysis was performed on a MACSQuantR 10 Analyzer (Miltenyi Biotec). Characterization of target tumor lines and luciferase-positive sub clones was performed using CD19-FITC, CD20 VioBlue, and CD22-APC antibodies. Dead cells were excluded from analysis by 7AAD staining (BD Biosciences, San Jose, CA).

Generating Bicistronic DuoCARs Using 2A Ribosomal Skip Sequence

Figure 10:
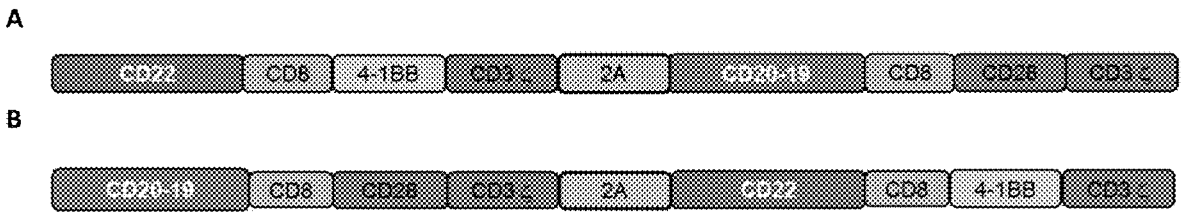
FIG. 10 depicts a schematic representation of DuoCAR bicistronic constructs. DuoCAR constructs are expressed from a single bicistronic open reading frame, containing sequences of two CAR chains separated by 2A peptide. One CAR is comprised of CD22 scFv, linked in frame to CD8 hinge and transmembrane domain, 4-1BB costimulatory domain and CD3 zeta activation domain. Another CAR is comprised of a tandem CD20 CD19 scFv-based targeting domain, followed by CD8 hinge and transmembrane domain, CD28 costimulatory domain and CD3 zeta activation domain.

In addition to co-transduction and co-transfection approaches described in EXAMPLE 2 and EXAMPLE 3 supra, DuoCARs simultaneously targeting the three hematologic tumor antigens, CD19, CD20, CD22 and featuring different costimulatory domains, simultaneous expression of two CAR chains from a single mRNA transcript can be facilitated by use of self-cleavage element 2A. The 2A element mediates ribosomal skip during translation of the mRNA transcript to protein, thus enabling production of two discreet CAR protein chains at equimolar ratio. In this example, one CAR chain is comprised of CD22 scFv, linked in frame to CD8 hinge and transmembrane domain, 4-1BB costimulatory domain and CD3 zeta activation domain. The second CAR chain is comprised of a tandem CD20 CD19 scFv-based targeting domain, followed by CD8 hinge and transmembrane domain, CD28 costimulatory domain and CD3 zeta activation domain. The two designs differ in the order of CAR chains, such as in one design the CD22 CAR is first, followed by 2A element and the tandem 2019 CAR, and vice versa (FIG. 10).

First, a set of four bicistronic DuoCAR designs targeting CD19, CD20 and CD22 antigens simultaneously, under the control of EF1a promoter were constructed as described above (Set 1, Table 1 infra).

TABLE 1 list of Bicistronic DuoCAR Constructs and Single CAR Controls

| Bicistronic DuoCAR Construct Number | Description | Set # |
|---|---|---|
| LTG2515 | EF1A-2019-28z-2A-m971-BBz | Set 1 |
| LTG2228 | EF1A-20-19-28z | Set 1 |
| LTG2520 | EF1A-2019-28z-2A-16P17-BBz | Set 1 |

TABLE 1-continued list of Bicistronic DuoCAR Constructs and Single CAR Controls

| Bicistronic DuoCAR Construct Number | Description | Set # |
|---|---|---|
| LTG2521 | EF1A-2019-28z-2A-16P8-BBz | Set 1 |
| LTG2200 | EF1A-m971 CD22 CAR control | Set 1 |
| LTG2209 | EF1A-16p17-BBz | Set 1 |
| LTG2218 | EF1A-16p8-BBz | Set 1 |
| D0043 | MSCV_20-19-28z-2A-m971-BBz | Set 2 |
| D0044 | MSCV_20-19-28z-2A-16p8-BBz | Set 2 |
| D0046 | MSCV_m971-BBz-2A-20-19-28z | Set 2 |
| D0047 | MSCV_16p8-BBz-2A-20-19-28z | Set 2 |

Figure 11:
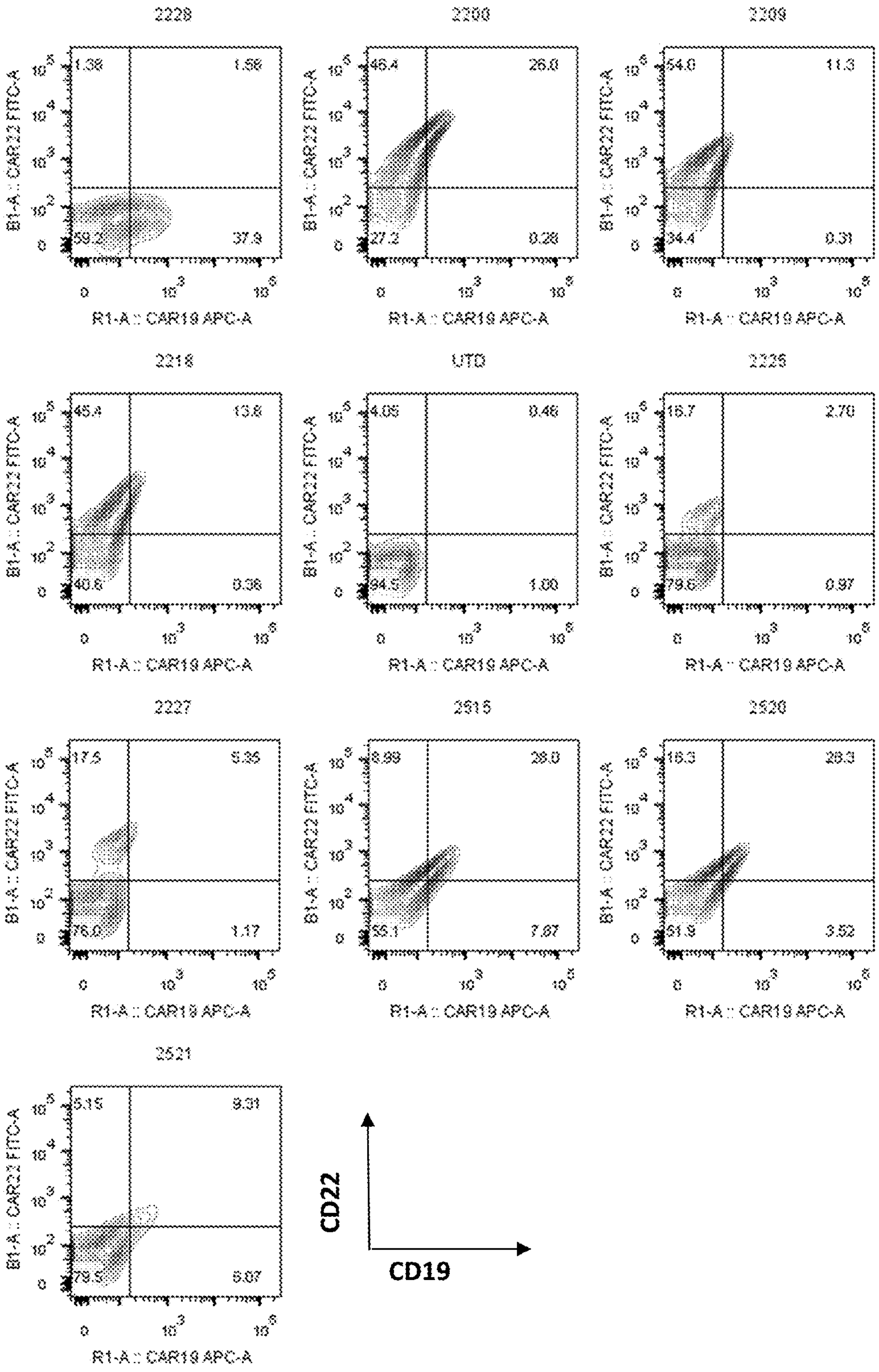
FIG. 11 depicts cell surface expression of Set 1 Bicistronic DuoCARs on primary human T cells transduced with DuoCAR expression vectors and controls as measured by flow cytometry. T cells were transduced to express the following CARs: no CAR (UTD), construct number 2228 (2019 tandem CAR), construct numbers 2200, 2209, 2218, 2225, 2227 (CD22 CAR variants), construct numbers (2515, 2520, 2521 Bicistronic CARs containing one CAR chain targeted to CD22, and another tandem CAR chain targeted to CD20 and CD19 tumor antigens). In bipartite plots shown, the CAR 22 expression is shown on the Y axis, and CAR 19 expression, representing the tandem 2019 CAR chain, is shown on the X axis. Percentage positive cells is denoted in each quadrant. Data are representative of three transduction experiments in T cells from separate healthy donors.
Figure 12:
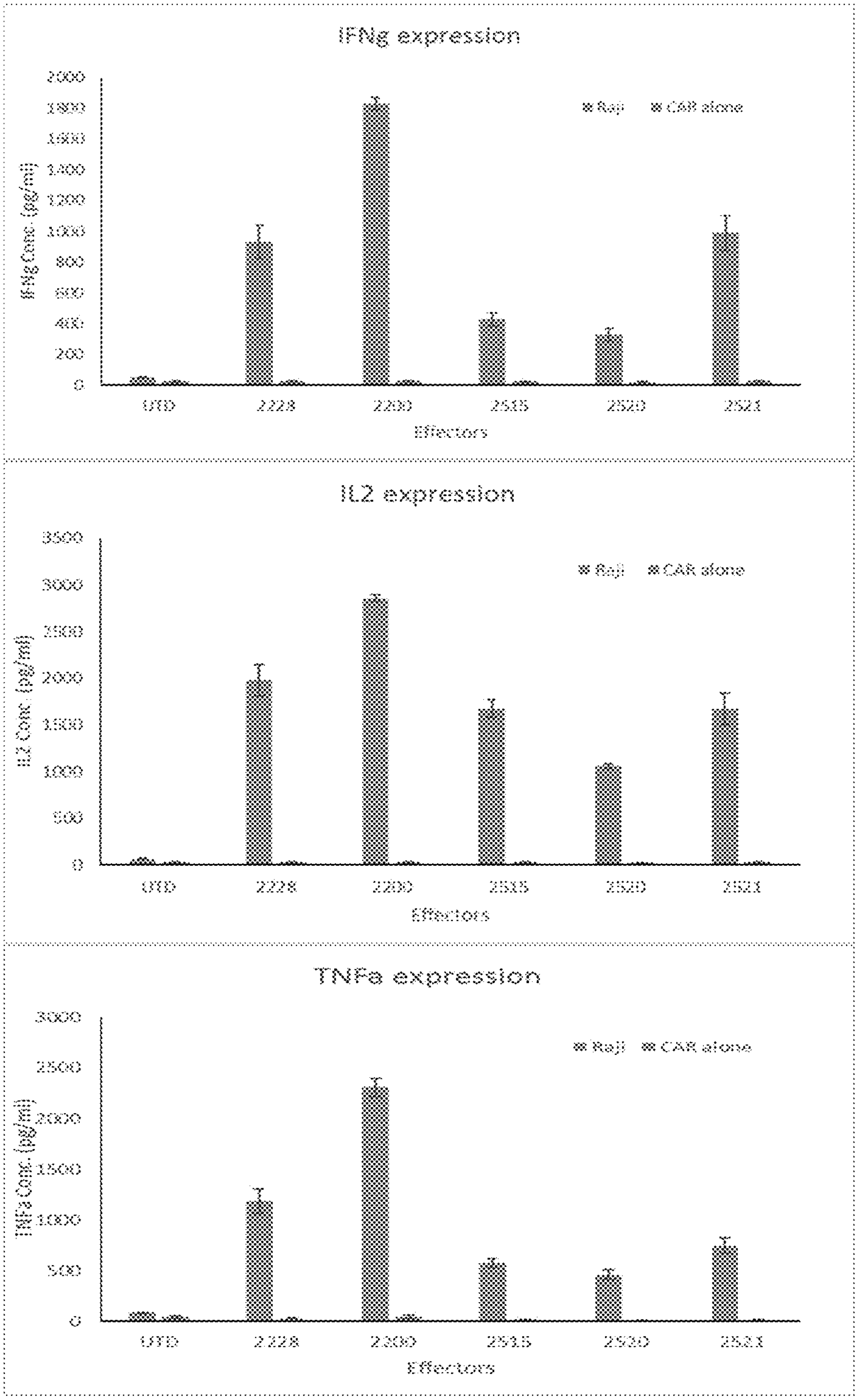
FIG. 12 depicts cytokine response of Bicistronic DuoCARs set 1 co-incubated with Raji tumor cells. T cells were transduced to express the following CARs: no CAR (UTD), construct number 2228 (-2019 tandem CAR), construct number 2200 (-CD22 CAR), construct numbers 2515, 2520, 2521 DuoCAR T cells and controls were incubated with triple positive Raji cells overnight, then supernatants were harvested and analyzed by ELISA for IFNg, TNFa and IL-2. N=3, +/−SD. One experiment representing three separate experiments in T cells from separate donors is shown.

To facilitate optimal expression of CD22-targeting CAR moiety in DuoCAR format, the CD22-targeting CAR chain incorporated one of CD22-reactive scFv sequences 16P8, or 16P17. The CD22 scFv m971 was used as a comparator, and untransduced cells (UTD) served as a CAR-negative control). Co-expression of the CD20-CD19 targeting CAR chain and the CD22-targeting CAR chain was facilitated by 2A ribosomal skip sequence as described above. Individually encoded CAR chains were included as expression controls. Human primary T cells from a healthy donor were transduced with lentiviral vectors encoding each DuoCAR or single CAR control. Upon completion of T cell culture expansion, CAR expression was assessed by flow cytometry. The percentage of $CAR20^{+}CAR22^{+}$ double-positive cells in DuoCAR groups, representing co-expression of the tandem CD20-CD19 CAR chain and the CD22-CAR chain in the same cell, (LTG2515, LTG2520, LTG2521) was relatively low, and ranged from 28% (LTG2515, LTG2520) to 9% (LTG2521) (FIG. 11). By contrast, the expression of individual CAR controls was considerably greater, at ~72% for CD22-targeting construct (LTG2200), and at ~38% for the tandem CD20-CD19 targeting CAR (LTG 2228, FIG. 11). The functionality of DuoCARs was then tested in cytokine release assay. DuoCAR effector cells of controls were combined with Raji target cells at effector to target ratio (E:T) of 10 overnight. At the end of incubation period, cell culture supernatants were harvested and assayed for secreted T cell cytokines IFN gamma, TNF alpha and IL-2 (FIG. 12). Effectors incubated under similar conditions in the absence of tumor target cells were used as an additional control for spontaneous cytokine release. Co-incubation of Raji tumor cells with CAR effectors yielded strong upregulation of IFN gamma, IL-2 and TNFa for all constructs. Notably, none of the CARs produced cytokines spontaneously. However, the magnitude of cytokine secretion tended to be lower for all DuoCAR constructs as compared to positive controls CAR22 LTG2200, and tandem 2019 CAR LTG2228, likely due to relatively modest expression of the DuoCARs, as seen in FIG. 11.

Modest DuoCAR expression and cytokine response as compared to single CAR controls (FIG. 11, FIG. 12) suggested that the large payload size may be detrimentally impacting DuoCAR expression efficiency in the present configuration. In order to improve DuoCAR transduction efficiency, select DuoCAR sequences were codon re-optimized as needed, and expression cassettes were re-cloned into a new expression backbone, under the control of MSCV internal promoter for improved bicistronic expression (Set 2, Table 1).

Figure 13:
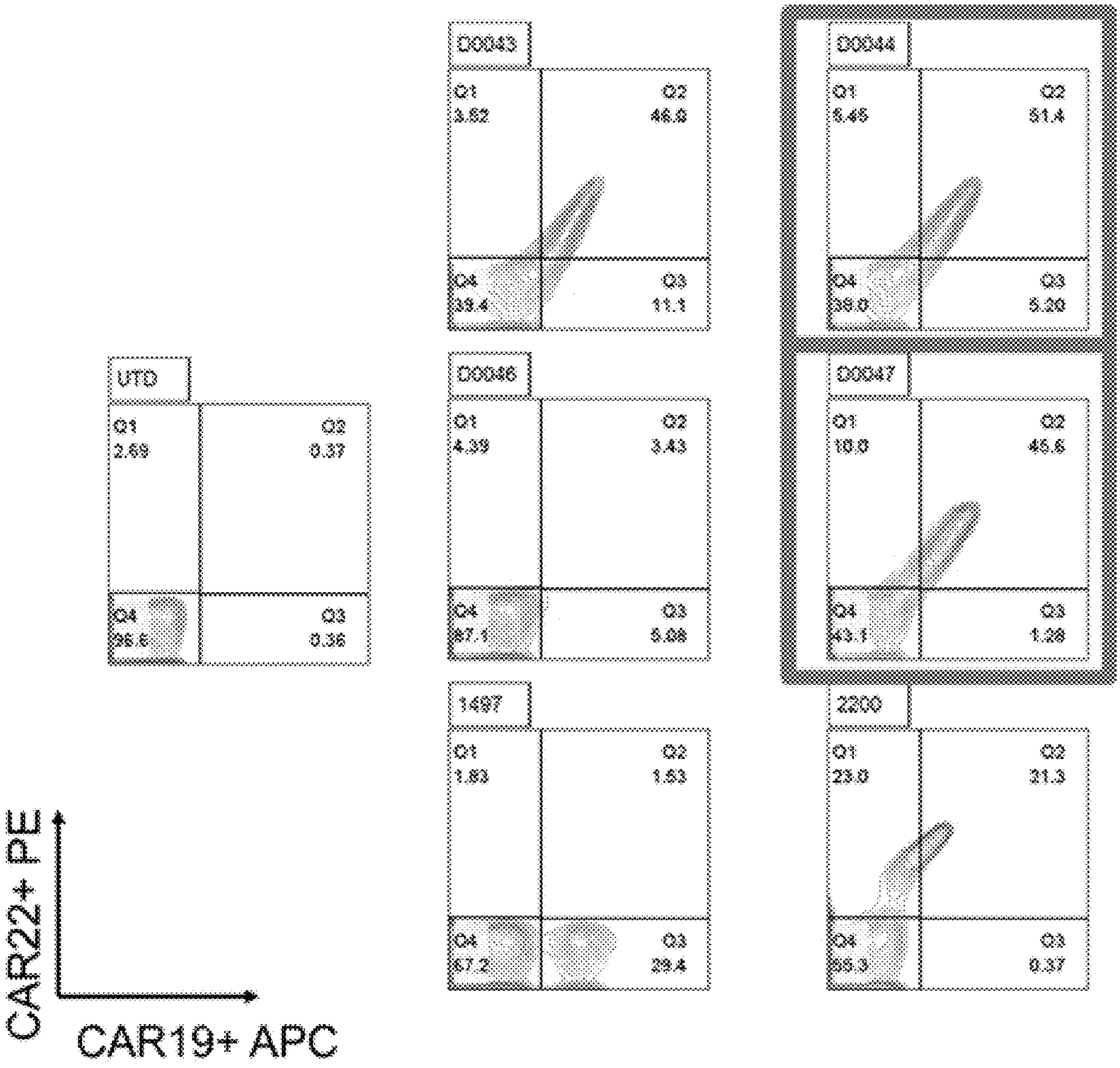
FIG. 13 depicts cell surface expression of Set 2 Bicistronic DuoCARs on primary human T cells transduced with DuoCAR expression vectors and controls as measured by flow cytometry. T cells were transduced to express the following CARs: no CAR (UTD), construct number 1497 (-2019 tandem CAR), construct number 2200 (-CD22 CAR), construct numbers D0043, D0044, D0046, D0047-Bicistronic CARs containing one CAR chain targeted to CD22, and another tandem CAR chain targeted to CD20 and CD19 tumor antigens. In bipartite plots shown, the CAR 22 expression is shown on the Y axis, and CAR 19 expression, representing the tandem 2019 CAR chain, is shown on the X axis. Percentages of positive cells are denoted in each quadrant. Data are representative of three transduction experiments in T cells from three separate healthy donors.

Lentiviral vectors were generated for each new DuoCAR construct, and CAR T cells were transduced and expanded as described in materials and methods. DuoCAR expression was determined by flow cytometry. The percentage of CD19+CD22+ T cells represents cells co-expressing the two chains of the DuoCAR (FIG. 13). Here, high transduction efficiency was achieved for DuoCAR Constructs D0044 (MSCV_20-19-28z-2A-16p8-BBz) and D0047 (MSCV_16p8-BBz-2A-20-19-28z), both containing the anti CD22 scFv 16P8 (FIG. 13, 51% and 45%, respectively). Unexpectedly, DuoCAR D0043, containing the comparator m971 CD22 scFv was expressed well in the distal orientation (MSCV_20-19-28z-2A-m971-BBz, 46% positive), but showed no expression in the reverse orientation (D0046, MSCV_m971-BBz-2A-20-19-28z). Therefore the choice of scFv sequences included in DuoCAR design as well as sequence codon optimization and choice of expression backbone all are critical for optimal DuoCAR expression.

Figure 14:
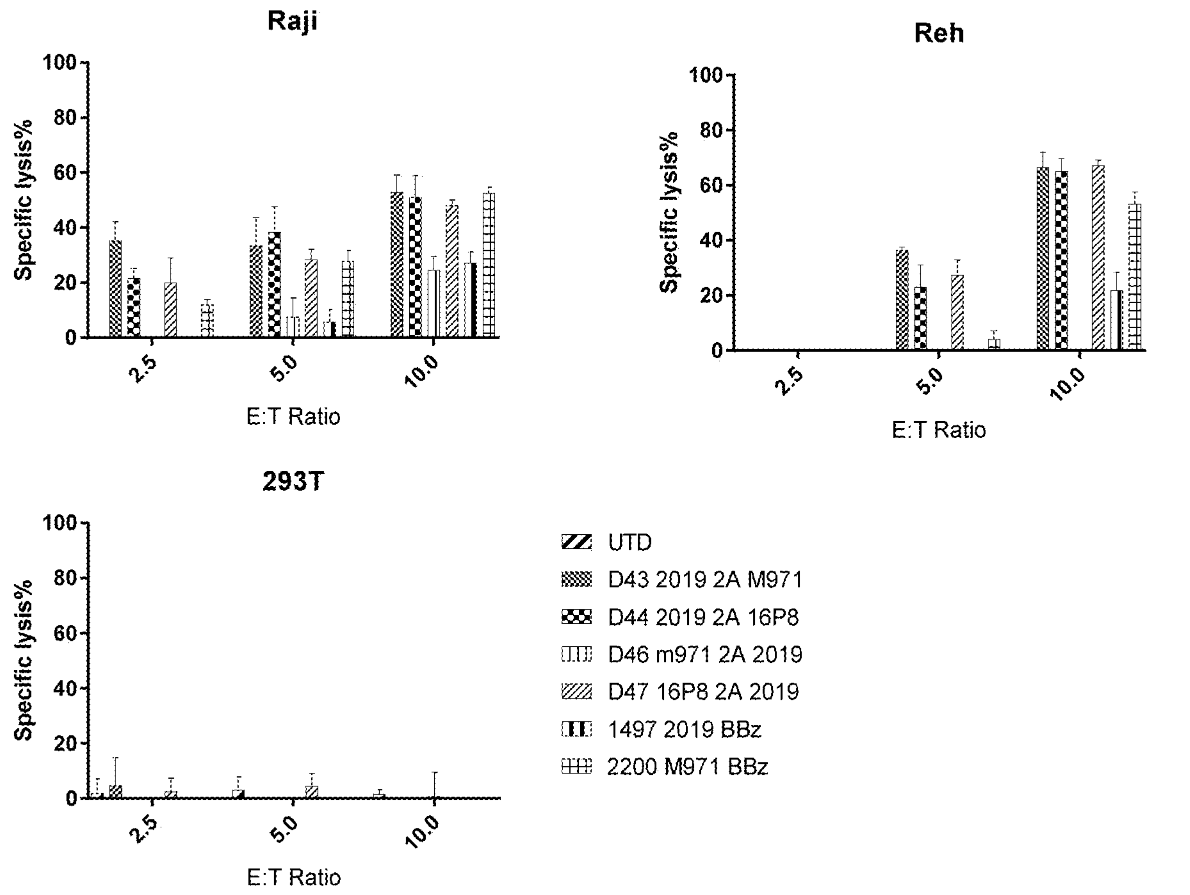
FIG. 14 depicts the anti-tumor cytolytic activity of Set 2 Bicistronic DuoCARs-expressing T cells. Human T cells transduced with single CAR components (LTG1497, 20_19-28z or LTG2200, 22-BBz) or DuoCARs (construct numbers D0043, D0044, D0046, D0047, encoding 20_19-28z+22-BBz), were used in cytotoxic T cells assay at four different effector to target ratios (10:1, 5:1, 2.5:1, as indicated, zeroes between "D" and the numerical designation in the construct name were omitted for simplicity). The leukemia cell lines used as CAR-T targets were: Raji (expresses all three target antigens), Reh (expresses all three target antigens), 392T (devoid of all three target antigens). DuoCARs lysed triple-positive cell lines in E:T dependent manner, and no lysis occurred in target negative 293T cell line.
Figure 15:
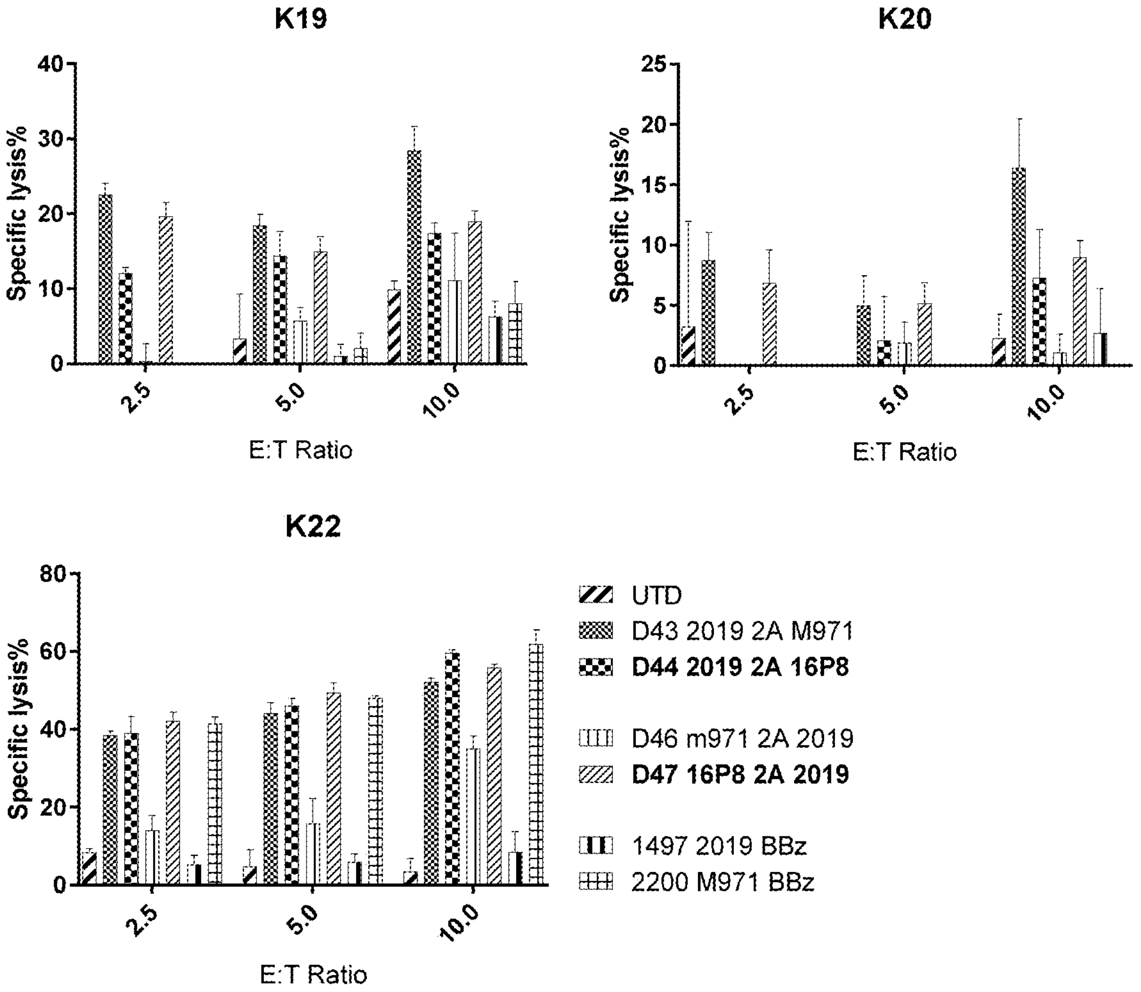
FIG. 15 depicts the anti-tumor cytolytic activity of Bicistronic DuoCAR Set 2 expressing T cells. Human T cells transduced with single CAR components (LTG1497, 20_19-28z or LTG 2200, 22-BBz) or DuoCARs (construct numbers D0043, D0044, D0046, D0047, encoding 20_19-28z+22-BBz), were used in cytotoxic T cells assay at four different effector to target ratios (10:1, 5:1, 2.5:1. As indicated, zeroes between "D" and the numerical designation in the construct name were omitted for simplicity). The single-positive tumor cell lines used as CAR-T targets were: K19 (expresses CD19), K20 (expresses CD20), and K22 (expresses CD22). The three single-positive tumor cell lines were developed on the background of the parent K562 erythroleukemia line, which is naturally devoid of CD19, CD20 or CD22 expression, by stable transduction of the desired single antigen (CD19, CD20, or CD22) and the firefly luciferase gene. DuoCARs lysed single-positive cell lines in E:T dependent manner, and no lysis above background level was mediated by CAR controls with mismatched antigen targeting domains (CAR 22, LTG 2200 vs K19 and K20, tandem CAR 2019, LTG 1479 vs K22).

The cytotoxic function of DuoCAR set 2-transduced T cells was assayed in overnight killing assay vs a panel tumor lines with varying expression of tumor antigens CD19, CD20 and CD22. All lines were stably transduced to express firefly luciferase, and killing assays were performed as described in materials and methods. First, DuoCARs were combined with CD19+CD20+CD22+ with Non-Hodgkin's lymphoma Raji, or acute lymphoblastic leukemia Reh cells, or CD19-CD20-CD22-human embryonic kidney 293T cell line (FIG. 15). DuoCAR D0044 and D0047 bicistronically encoding CAR 20-19-28z and CD22 CAR 16p8-BBz CAR, and single CAR 22 control LTG2200, and tandem CAR control 20-19 LTG1497, as well as untransduced T cell control (UTD) were included (FIG. 14) Constructs D0043, D0044, D0046 and D0047 are noted in figure legend as D43, D44, D46 and D47, respectively, for brevity (FIG. 14). Effector and target cells were incubated at ratios of 2.5, 5 or 10 overnight in triplicate, then plates were harvested and developed with SteadyGlo reagent, and luciferase activity of the surviving tumor cells was determined by luminometry. Overall, CAR cytolytic function correlated with DuoCAR expression (FIG. 13). DuoCARs D0047 and D0044 potently lysed CD19, CD20 and CD22 triple-positive tumor lines Raji and Reh, as did the positive control DuoCAR D0043, whereas the sub-optimally expressed construct D0046 had relatively low lytic function (FIG. 14). No lysis of the CD19-CD20-CD22-triple negative line was caused by either CAR construct, underscoring the specificity of CAR-mediated lysis to cognate antigens.

To further delineate the specificity of DuoCAR constructs, transgenic K562 lines expressing either CD19, CD20 or CD22 antigens, termed K19, K20, K22, respectively were generated (FIG. 15). In co-incubation assays with single-positive tumor lines, DuoCARs D44 and D47, featuring CAR chains targeting CD19, CD20 and CD22, potently lysed each target line in effector to target ratio dependent manner, and were similar in their function to the comparator DuoCAR D0043 (construct designations in figure legends were shortened from D0043, D0044, D0046, D0047 to D43, D44, D46 and D47, respectively-FIG. 15). Control T cells expressing a tandem 2019 CAR (1497), lysed tumor lines K19 and K20, but had only negligible background lytic effect in K22 (less than 10% lysis at the highest E:T ratio of 10). The single CD22 control CAR potently lysed K22 tumor cells, but had no function in K20 cells, and only showed background lysis in K19 cells (10% lysis at the highest E:T of 10:1). Therefore, this experimental system enables testing of CAR reactivity to each tumor antigen with high accuracy. In summary, both DuoCARs D0044 and D0047 demonstrated that each of their tumor targeting domains is functional in this single antigen expressing test system (FIG. 15).

Figure 16:
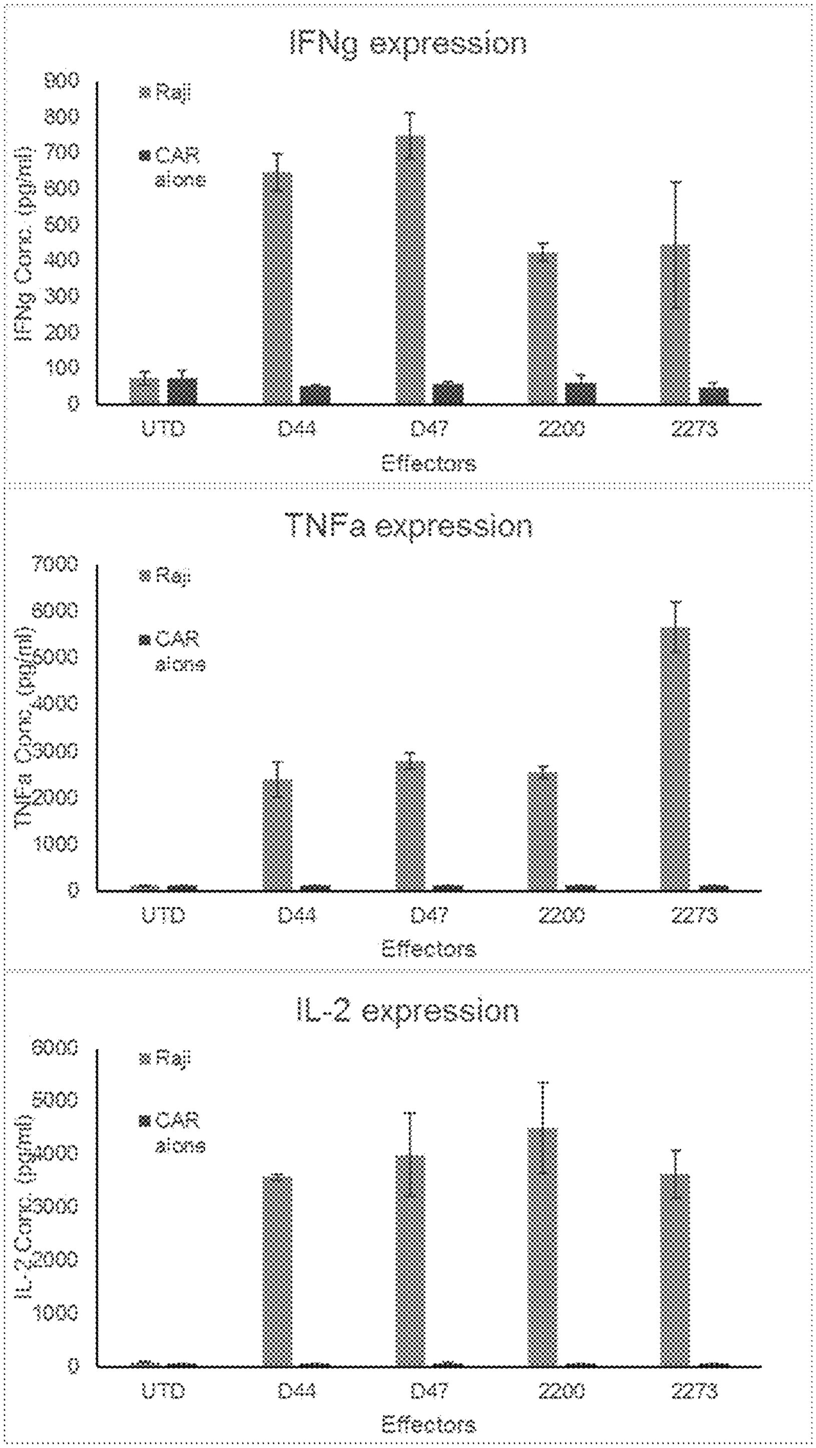
FIG. 16 depicts cytokine response of Bicistronic DuoCARs version 2 co-incubated with Raji tumor cells or incubated in the absence of tumors (CAR alone). T cells were transduced to express the following CARs: no CAR (UTD), construct number 2273 (—2019 tandem single chain CAR), construct number 2200 (CD22 single chain CAR), construct numbers D44, D47 (reference to D0044 and D0047 CAR constructs, respectively, zeroes between "D" and the numerical designation in the construct name were omitted for simplicity). DuoCARs and T cells and controls were incubated with triple positive Raji cells overnight, then supernatants were harvested and analyzed by ELISA for IFNg, TNFa and IL-2. N=3, +/−SD. One experiment representing three separate experiments in T cells from separate donors is shown.

To characterize the cytokine release response of DuoCAR constructs, each of the DuoCAR T cell preparations D0044, D0047 (Figure legend: D44, D47, respectively) with the CD19+CD20+CD22+ were combined with Raji tumor cells at E:T ratio of 10 overnight, and analyzed culture supernatants by ELISA for T cell cytokines IFNg, TNFa and IL-2 (FIG. 16). Single CAR22 construct LTG2200 and Tandem 2019 CAR construct LTG2273 were included for comparison, and untransduced T cells (UTD) were used a s a negative control. In parallel, CAR T cells from each group were incubated under similar conditions but in the absence of tumor cells, to test for spontaneous cytokine release (FIG. 16). It was found that whereas none of the constructs yielded spontaneous release of cytokines, both DuoCARs D44 and D47 manifested strong induction of IL-2, IFNg and TNFa after co-incubation with Raji targets, underscoring the potency of these DuoCAR constructs. Notably, despite co-expressing two chains simultaneously in the same cell, no evidence of tonic signaling was detected, as attested by complete absence of spontaneous cytokine release (FIG. 16).

Figure 17:
FIG. 17 depicts a schematic representation of two CAR chains that can be combined for co-expression in the same cell or population of cells to generate DuoCARs by way of co-transfection or co-transduction. One CAR chain is comprised of CD22 scFv, linked in frame to CD8 hinge and transmembrane domain, 4-1BB costimulatory domain and CD3 zeta activation domain. Another CAR chain is comprised of a tandem CD20 CD19 scFv-based targeting domain, followed by CD8 hinge and transmembrane domain, CD28 costimulatory domain and CD3 zeta activation domain.

Having achieved the successful development of bicistronic DuoCARs targeting three distinct tumor antigens CD19, CD20, CD22 and comprised of two CAR chains possessing costimulatory domains with distinct and complimentary functions, the question was asked whether similar construct can be generated by other approaches. Successful bicistronic expression of separate CAR chains within the same ORF requires multiple optimization and refinement steps, and will be unique for each new set of sequences. By contrast, combining two CAR sequences during lentiviral vector manufacturing or during CAR T transduction, may offer a more universal approach and a fast method for creating CAR combinations to be expressed in the same cell, or same T cell population, while using a single lentiviral preparation for T cell transduction. In this example, as in the DuoCAR approach, one CAR chain is comprised of CD22 scFv, linked in frame to CD8 hinge and transmembrane domain, 4-1BB costimulatory domain and CD3 zeta activation domain. The second CAR chain is comprised of a tandem CD20 CD19 scFv-based targeting domain, followed by CD8 hinge and transmembrane domain, CD28 costimulatory domain and CD3 zeta activation domain (FIG. 17). In co-transfection approach, two transfer plasmids, each encoding one CAR chain, are mixed together and combined with the helper plasmids during vector production step, as per standard protocol (see materials and methods). The resulting lentiviral preparation will thus encode the mixture of the two CAR chains. Using this approach, a set of lentiviral preparations encoding two CAR chains simultaneously were generated (Table 2 infra).

TABLE 2

Constructs used in Co-Transfection co-transduction experiments

| CAR construct number | Description |
|---|---|
| D1 | MSCV-AscI-16P17- CD8 4-1BBz |
| D2 | MSCV-AscI-16P8- CD8 4-1BBz |
| D3 | MSCV-AscI-16P13- CD8 4-1BBz |
| 2273 | MSCV-20-19-28z |

TABLE 2-continued

Constructs used in Co-Transfection co-transduction experiments

| CAR construct number | Description |
|---|---|
| D1 + 2273 | combination |
| D2 + 2273 | combination |
| D3 + 2273 | combination |

Transfer plasmids for CAR 22 utilizing scFv 16P17, 16P8, 16P13 CAR22-4-1BB-CD3zeta, under the control of MSCV promoter (D1, D2, D3 respectively) and tandem CAR 2019-28-CD3zeta under the control of MSCV (LTG 2273) were constructed. Lentiviral vectors encoding each CAR chain alone were produced in parallel. High titers for all DuoCAR co-transfection preparations ($10^{10}$ TU/ml, not shown) were routinely achieved, underscoring the efficiency of this approach.

Figure 18:
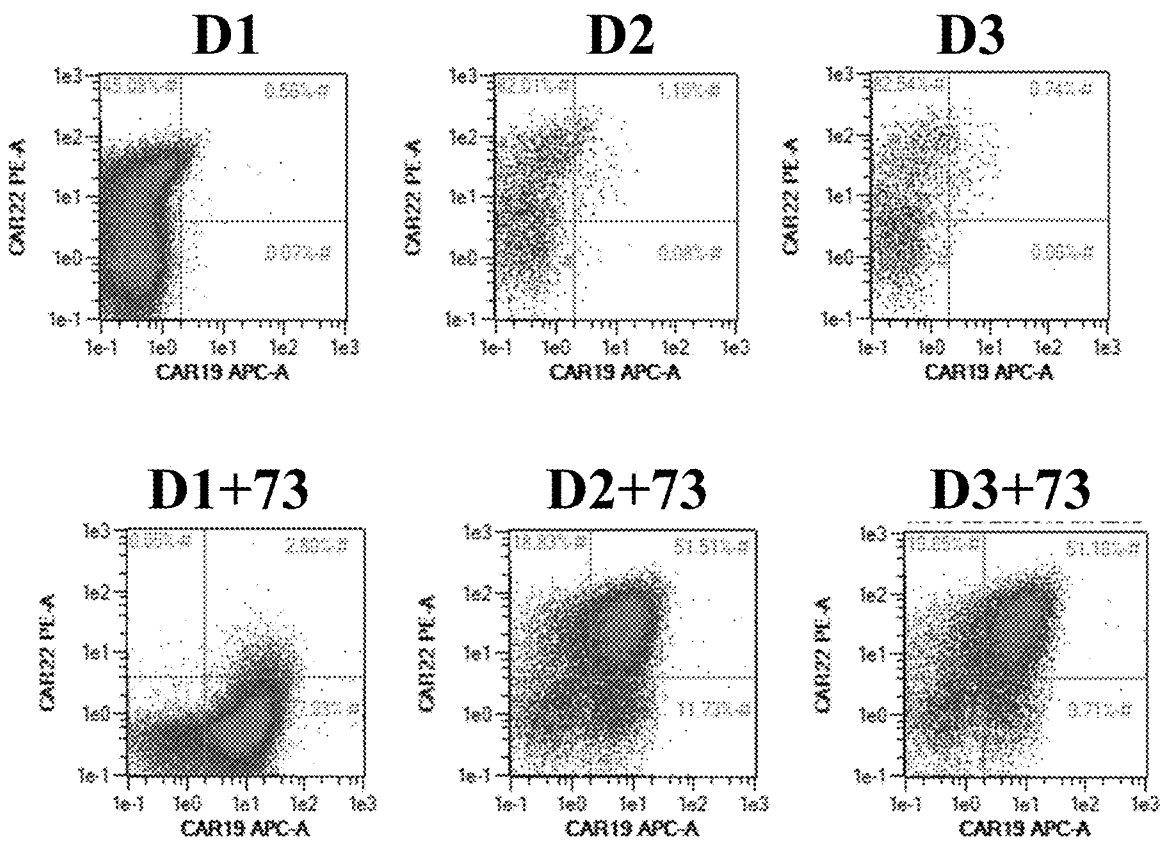
FIG. 18 depicts cell surface expression of DuoCARs and controls on primary human T cells transduced with DuoCAR expression vector preps generated by co-transfection of two transfer plasmids to produce LV or individually transduced single vector controls (top panel) as measured by flow cytometry. T cells were transduced to express the following CARs: construct numbers 2273, 2228 (—2019 tandem CAR), D1, D2, D3, CD22 CAR, and DuoCARs (construct numbers D1+2273, D2+2273, D3+2273). In scatter plots shown, the CAR 22 expression is shown on the Y axis, and CAR 19 expression, representing the tandem 2019 CAR chain, is shown on the X axis. Percentages of positive cells are denoted in each quadrant. Representative data for three experiments using T cells from three donors.
Figure 19A:
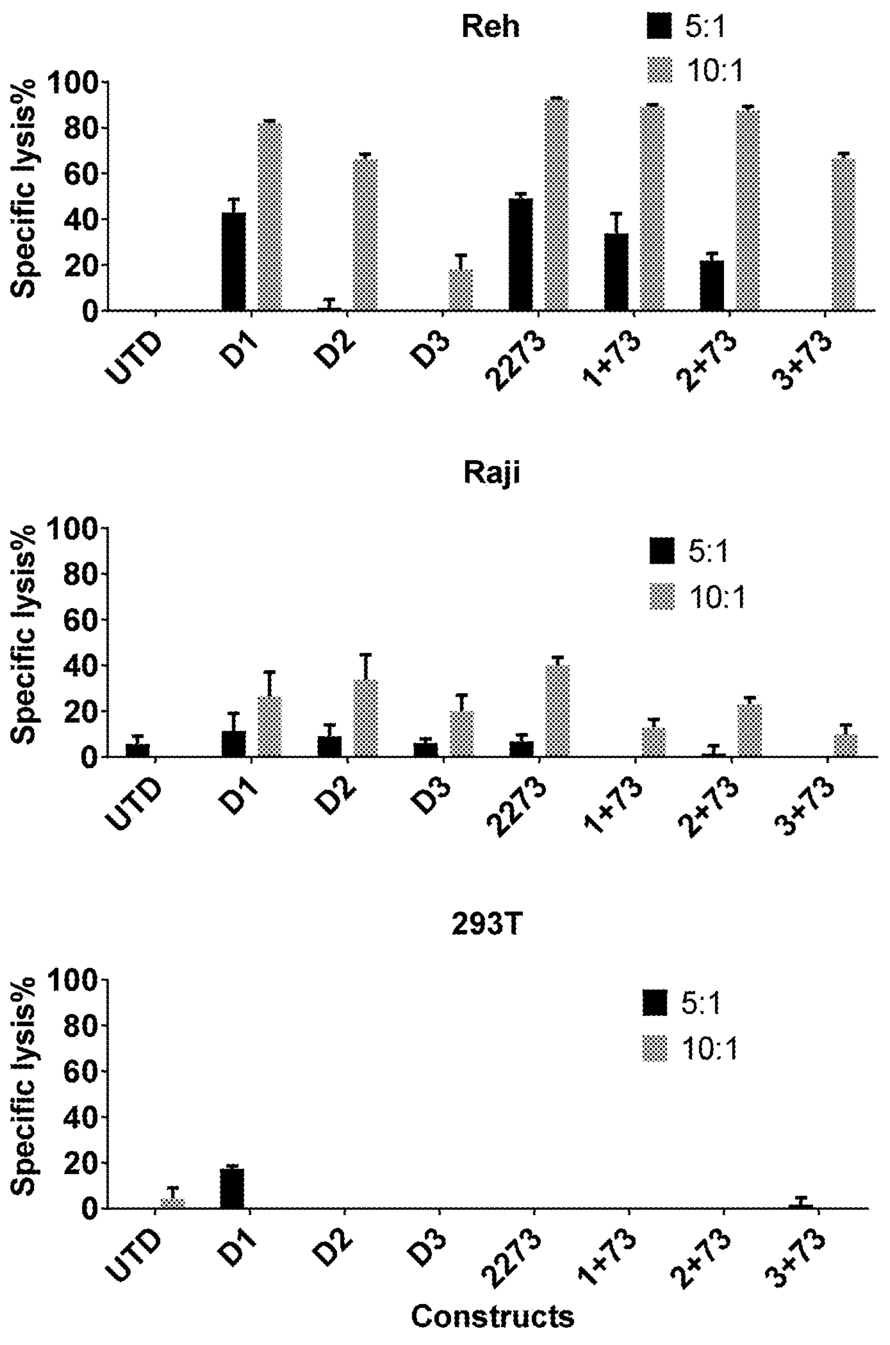
FIGS. 19A and 19B depict the anti-tumor cytolytic activity of DuoCAR cells or single chain CAR controls. The DuoCAR T cells were generated by co-transfection of two transfer plasmids to produce lentiviral vectors. T cells were transduced with the resulting DuoCAR vectors or with single chain CAR controls to express the following CARs: construct number 2273 (—the 2019 single chain tandem CAR); construct numbers D1, D2, D3 (—CD22 single chain CARs); and DuoCARs (construct numbers D1+2273, D2+2273, D3+2273, "D" in the designation omitted for brevity) generated by combination of two single CAR chains in the same CAR T product. The resulting CAR T cells were analyzed in a cytotoxic T cells assay at two different effector to target ratios (10:1, 5:1, as indicated) against native leukemia lines that are CD19+CD20+CD22+ (Raji, Reh) or CD19, CD20, CD22 triple-negative control line 293T (FIG. 19A). The native target lines Raji and Reh were lysed by single-chain CAR constructs by all DuoCAR groups construct numbers D1+2273, D2+2273, D3+2273, ("D" in the designation omitted for brevity), as well as by single chain CAR controls. By contract, DuoCARs and single CAR controls were not cytolytic vs the CD19, CD20, CD22-triple negative line 293T, demonstration target specificity of CAR constructs. Since DuoCARs target three target antigens simultaneously, and to further address the question of target-specificity, DuoCARs were tested against transgenic single-positive tumor lines generated on the background of K562 erythroleukemia cells, which are naturally devoid of CD19, CD20 or CD22 expression. The single-positive tumor cell lines used as CAR-T targets were: K19 (expresses CD19), K20 (expresses CD20), and K22 (expresses CD22), FIG. 19B. DuoCARs lysed single-positive cell lines in E:T dependent manner, indicating that all targeting domains of DuoCARs are functional, and specific to their cognate target molecules (FIG. 19B). Moreover, CAR single chain controls with mismatched antigen targeting domains (CAR 22, LTG 2200 vs K19 and K20, tandem CAR 2019, LTG 1479 vs K22) had no specific lytic activity (FIG. 19B).
Figure 19B:
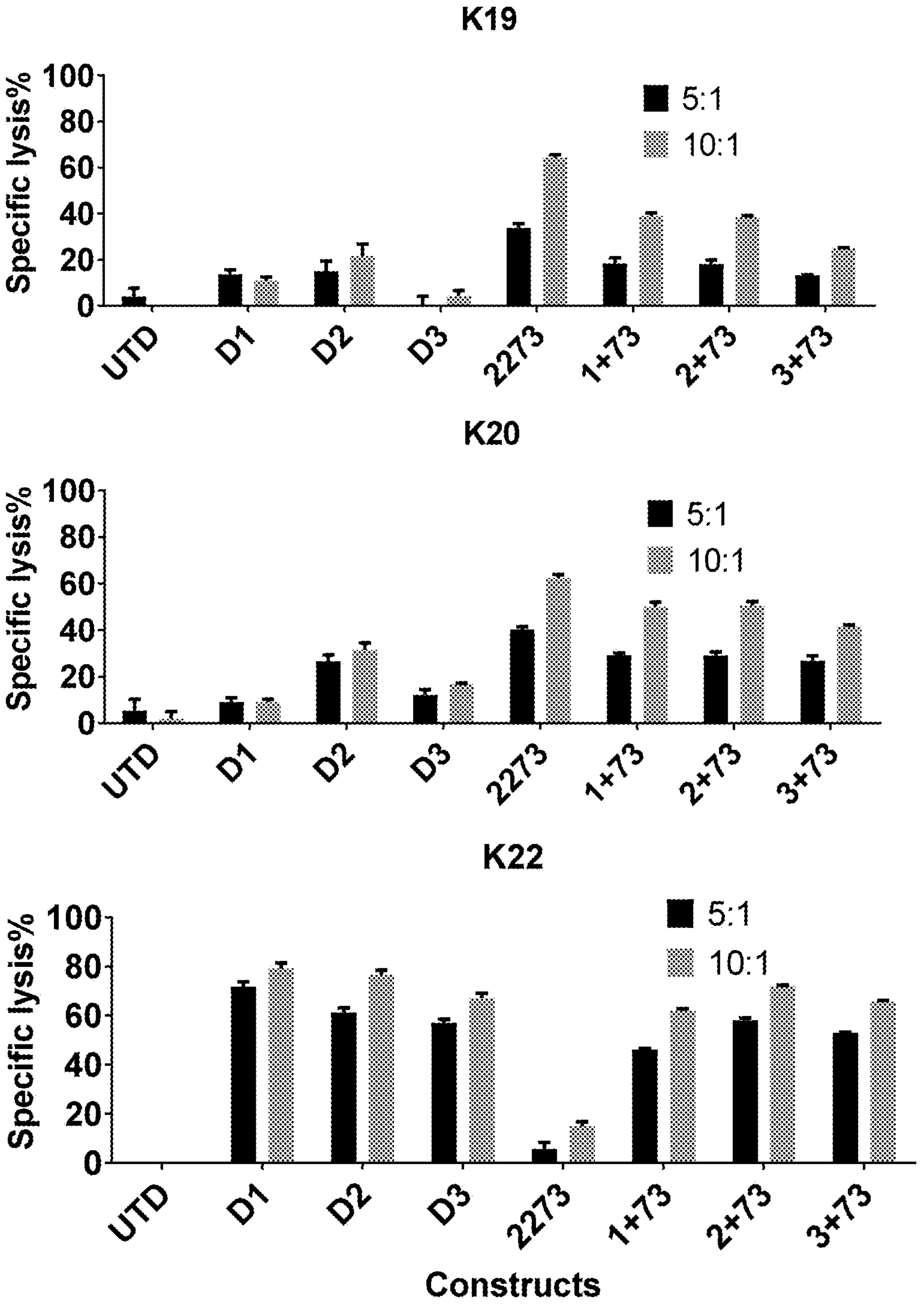
Figure 20:
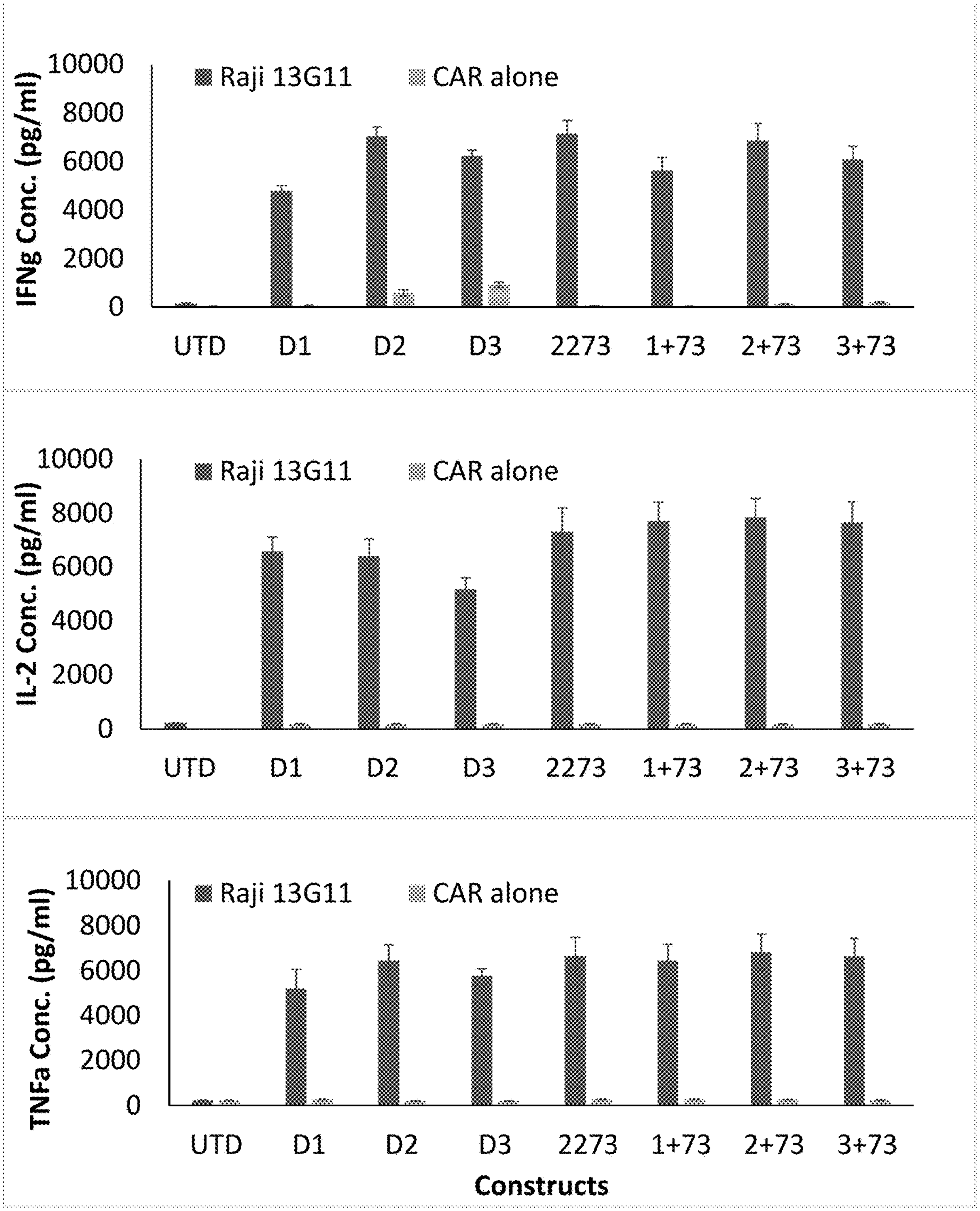
FIG. 20 depicts the cytokine release activity of DuoCAR cells or single chain CAR controls in response to Raji13G11, a CD19+CD20+CD22+ clone. The DuoCAR T cells were generated by co-transfection of two transfer plasmids to produce lentiviral vectors. T cells were transduced with the resulting DuoCAR vectors of single chain CAR control vectors to express the following CARs: construct number 2273 (—2019 tandem CAR); construct numbers D1, D2, D3 (—CD22 CAR); and three DuoCARs (D1+2273, D2+2273, D3+2273, FIG. 20, "D" in the group labels omitted for brevity). The resulting CAR T cells were combined with the triple positive Raji tumor line at E:T ratio of 10 overnight and culture supernatants were analyzed for IFNg, TNFa and IL-2. All DuoCAR constructs elaborated high levels of the three cytokines in response to Raji cells. DuoCARs alone controls, comprised of CAR T cells incubated in the absence of Raji targets, produced no appreciable cytokines in response to Raji 13G11 cells, demonstrating that the cytokine response is target-specific (FIG. 20).

To optimize DuoCAR function, a series of CAR22 constructs comprised of scFvs 16P17, 16P8, and 16P13, were designed (constructs D1, D2, D3, respectively) under the control of MSCV promoter and used a tandem CAR 2019 (LTG2273), also driven by MSCV promoter for DuoCAR co-transfection combinations (Table 2 and FIG. 18). Lentiviral vectors were prepared by co-transfection of LTG2273 with one of the CD22 CAR plasmids, and yielded high infective titers (not shown). Each LV was used at multiplicity of infection (MOI) 20 for transduction of health donor T cells and CAR expression was determined by flow cytometry (FIG. 18). All control groups transduced with LV encoding a single CAR control yielded high CAR expression (45% for D1, 82% for D2, 82% for D3, 87% for 2273 (not shown). Surprisingly and unexpectedly, in combination co-transfection, groups D2+73 and D3+73 yielded efficient and nearly identical co-expression of the two CAR chains (51%), whereas combinations D1+73 failed to co-express (2.8% CAR+), FIG. 18. To determine whether these DuoCARs possess lytic function, CAR T cells from each group on a panel of tumor lines were tested (FIG. 19, in the labels of groups D1+2273, D2+2273, D3+2273, “D” was omitted for brevity). All DuoCAR preparations efficiently lysed triple-positive tumor lines Raji and Reh, but not triple negative line 293T, attesting to DuoCAR specificity (FIG. 19A). In addition, all DuoCARs showed above-background lytic function against single-antigen tumor lines K19, K20 and K22, whereas single control CARs with mismatched targeting domains showed no specific lysis: see D1 through D3 in K19; D1 through D3 in K20, 2273 in K22, (FIG. 19B). The capability of DuoCARs to induce cytokines upon co-incubation with specific tumor targets was then assayed (FIG. 20; in the labels of groups D1+2273, D2+2273, D3+2273, “D” was omitted for brevity). DuoCAR T cell, single CAR controls and untransduced T cells (UTD) were combined with triple CD19+CD20+CD22+ Raji tumor cells and incubated overnight. In parallel, CAR T cells in the absence of tumor were incubated under similar conditions to rule out spontaneous cytokine release. At the end of incubation period, culture supernatants were assayed for cytokines IFNg, TNFa and IL-2 by ELISA (FIG. 20). All CAR groups produced high IFNg levels upon co-incubation with Raji. Whereas some single CD22 CAR controls had moderate spontaneous IFNg release (D2, D3), none of the DuoCARs produced IFNg spontaneously, suggesting a potential greater margin of safety for DuoCARs. IL-2 and TNFa expression were also highly induced by Raji co-incubation in all CAR groups with the exception of CAR 2272 (FIG. 20).

In summary, described here are the generation of functional and highly specific DuoCARs by co-transfection of individual CAR chains during LV preparation and applying the resulting LV preparation in T cell transduction. Moreover, using transgenic cell lines expressing only a single target antigen (K19, K20, K22) it was demonstrated that each of the CAR targeting domains is functional and can elicit DuoCAR function against target-expressing tumor cells. Surprisingly and unexpectedly, only a few combinations were able to demonstrate both robust CAR expression and potent cytotoxic function, therefore DuoCAR design is not trivial.

Example 5

Bicistronic DuoCARs Potently Eradicate Lymphoma Tumors.

Materials and Methods Used in Example 5

(a) Cell Lines

The Burkitt lymphoma cell line Raji, and the chronic myelogenous leukemia line K562 were purchased from American Tissue Culture Collection (ATCC, Manassas, VA). The REH leukemia line was purchased from DSMZ (Leibniz Institute DSMZ, Braunschweig, Germany). Cells were cultured in RPMI-1640 medium supplemented with 10% heat-inactivated fetal bovine serum (FBS, Hyclone, Logan, UT) and 2 mM L-Glutamax (Thermo Fisher Scientific, Grand Island, NY). Human Embryonic kidney line 293T was purchased from ATCC (Gibco/Thermo Fisher Scientific, Grand Island, NY). Single-cell clones of luciferase-expressing cell lines were generated by stably transducing wild-type tumor lines with lentiviral vector encoding firefly luciferase (Lentigen Technology, Inc., Gaithersburg, MD), followed by cloning and selection of luciferase-positive clones. The Raji 13G11 clone was generated by passaging luciferase-transduced Raji cells in the mice and was selected for its proliferative capacity. Whole blood was collected from healthy volunteers at Oklahoma Blood Institute (OBI) with donors' written consent. Processed buffy coats were purchased from OBI (Oklahoma City, OK). The CD4-positive and CD8-positive human T cells were purified from buffy coats via positive selection using a 1:1 mixture of CD4- and CD8-MicroBeads (Miltenyi Biotec, Bergisch Gladbach, Germany) according to manufacturer's protocol.

(b) Creation of Chimeric Antigen Receptor (CAR)—Expression Vectors

The DuoCAR constructs were designed as bicistronic sequences incorporation one tandem CD19- and CD20-targeting CAR, and one single CD22-targeting CAR. The bicistronic expression of the two CAR constructs from same mRNA template was facilitated by ribosomal skip element 2A. CAR antigen-binding single and tandem domains were derived from human anti-CD22 single chain variable fragments (ScFv), or the tandem 20-19 targeting scFv described previously (Schneider, D. et al., (2017). Journal for immunotherapy of cancer, 5 (1), 42). The CAR T-encoding sequences were generated by linking the binder sequence in frame to CD8a linking and transmembrane domains (aa 123-191, Ref sequence ID NP_001759.3). The C-terminal segment of the CAR constructs contained a CD3 zeta signaling domain (CD247, aa 52-163, Ref sequence ID: NP_000725.1). Some designs also included a co-stimulatory domain, derived from human 4-1BB, ICOS, OX40 or CD27 proteins. CAR constructs sequences were cloned into a third generation lentiviral plasmid backbone (Lentigen Technology Inc., Gaithersburg, MD). Lentiviral vector (LV) containing supernatants were generated by transient transfection of HEK 293T cells and vector pelleted by centrifugation of lentiviral vector-containing supernatants, and stored at −80° C.

(c) Primary T Cell Purification and Transduction

Human primary T cells from healthy volunteers were purified from whole blood or buffy coats (purchased from commercial provider with donor's written consent) using immunomagnetic bead selection of CD4+ and CD8+ cells according to manufacturer's protocol (Miltenyi Biotec, Bergisch Gladbach, Germany). T cells were cultivated in TexMACS medium supplemented with 200 IU/ml IL-2 at a density of 0.3 to $2\times10^6$ cells/ml, activated with CD3/CD28 MACS® GMP T Cell TransAct reagent (Miltenyi Biotec) and transduced on day 2 with lentiviral vectors encoding CAR constructs in the presence of 10 μg/ml protamine sulfate (Sigma-Aldrich, St. Louis, MO) overnight, and media exchanged on day 3. Cultures were propagated in TexMACS medium supplemented with 200 IU/ml IL-2 until harvest on day 8-10.

(d) Immune Effector Assays (CTL and Cytokine)

To determine cell-mediated cytotoxicity (CTL assay), 5,000 target cells stably transduced with firefly luciferase were combined with CAR T cells at various effector to target ratios and incubated overnight. SteadyGlo reagent (Promega, Madison WI) was added to each well and the resulting luminescence quantified as counts per second (sample CPS). Target only wells (max CPS) and target only wells plus 1% Tween-20 (min CPS) were used to determine assay range. Percent specific lysis was calculated as: (1-(sample CPS-min CPS)/(max CPS-min CPS)). Supernatants from co-cultures at E:T ratio of 10:1 were removed and analyzed by ELISA (eBioscience, San Diego, CA) for IFNγ, TNFα and IL-2 concentration.

(e) Flow Cytometric Analysis

For cell staining, half a million CAR T transduced cells were harvested from culture, washed two times in cold AutoMACS buffer supplemented with 0.5% bovine serum albumin (Miltenyi Biotec), and CAR surface expression detected by staining with CD19-Fc and CD20-Biotin or CD19-Fc and CD22-His peptide followed by secondary peptide-specific fluorescent conjugates (Jackson ImmunoResearch, West Grove, PA). Anti-CD4 antibody conjugated to VioBlue fluorophore (Miltenyi Biotec) was used where indicated, as per vendors' protocol. Non-transduced cells were used as negative controls. Dead cells in all studies were excluded by 7AAD staining (BD Biosciences, San Jose, CA). Cells were washed twice and resuspended in 200 ul Staining Buffer before quantitative analysis by flow cytometry. Flow cytometric analysis was performed on a MACSQuant®10 Analyzer (Miltenyi Biotec), and data plots were generated using FlowJo software (Ashland, OR).

Generation of trivalent DuoCARs targeting CD19, CD20, CD22

Figure 21:
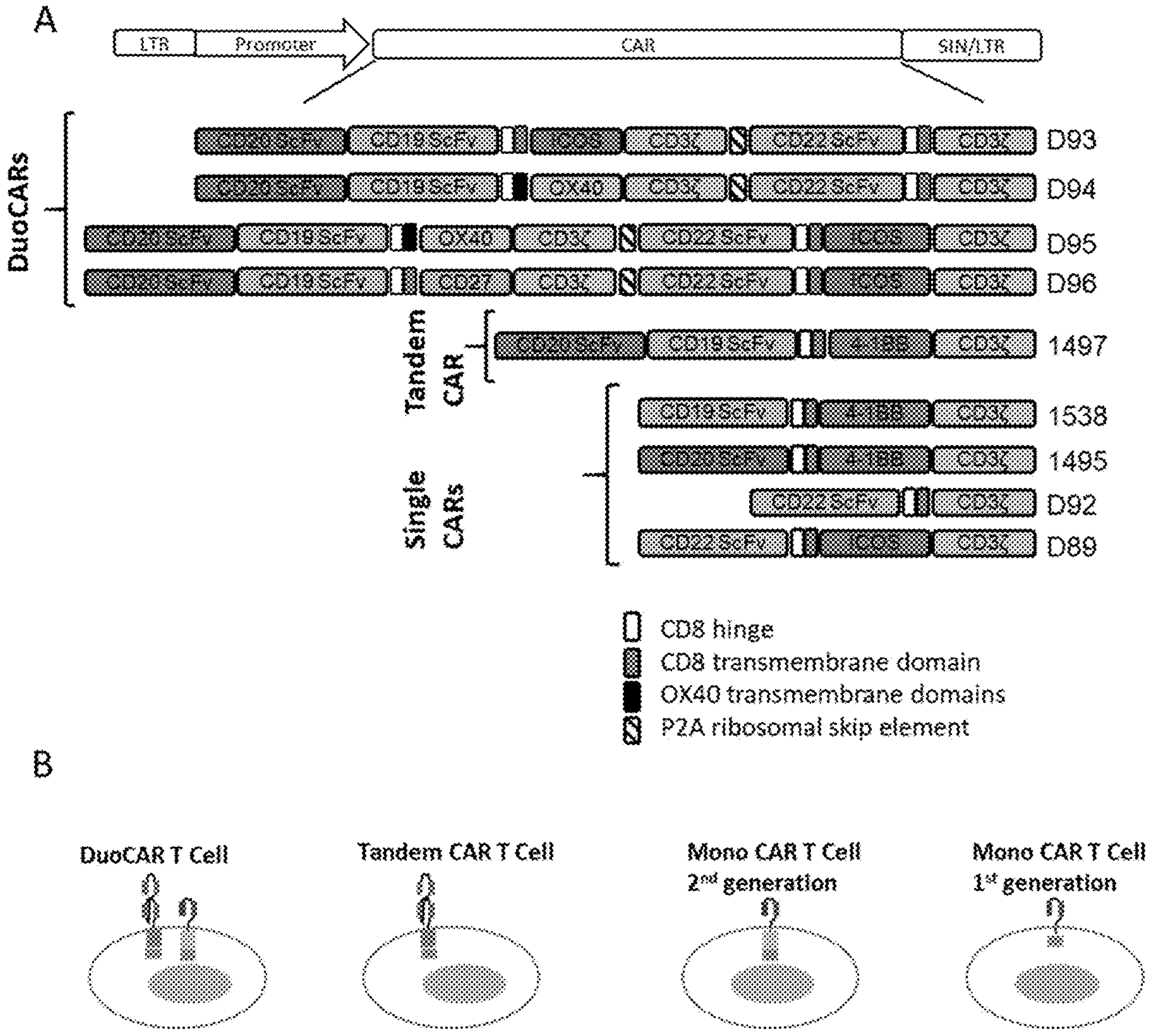
FIGS. 21A and 21B depict the construction of a DuoCARs targeting CD19, CD20 and CD22 simultaneously, as well as tandem and single CAR controls. Each DuoCAR is comprised of a tandem CD20 and CD19 dual targeting CAR, co-expressed with a first generation, or a second generation, single-targeting CD22 CAR. The two CAR constructs are co-expressed in a bicistronic format and are linked by ribosomal skip site 2A sequence, to assure stoichiometrically equal expression of the two CAR chains. Due to the nature of this bicistronic expression cassette, both CAR chains are co-expressed in each transduced T cell.
Figure 22:
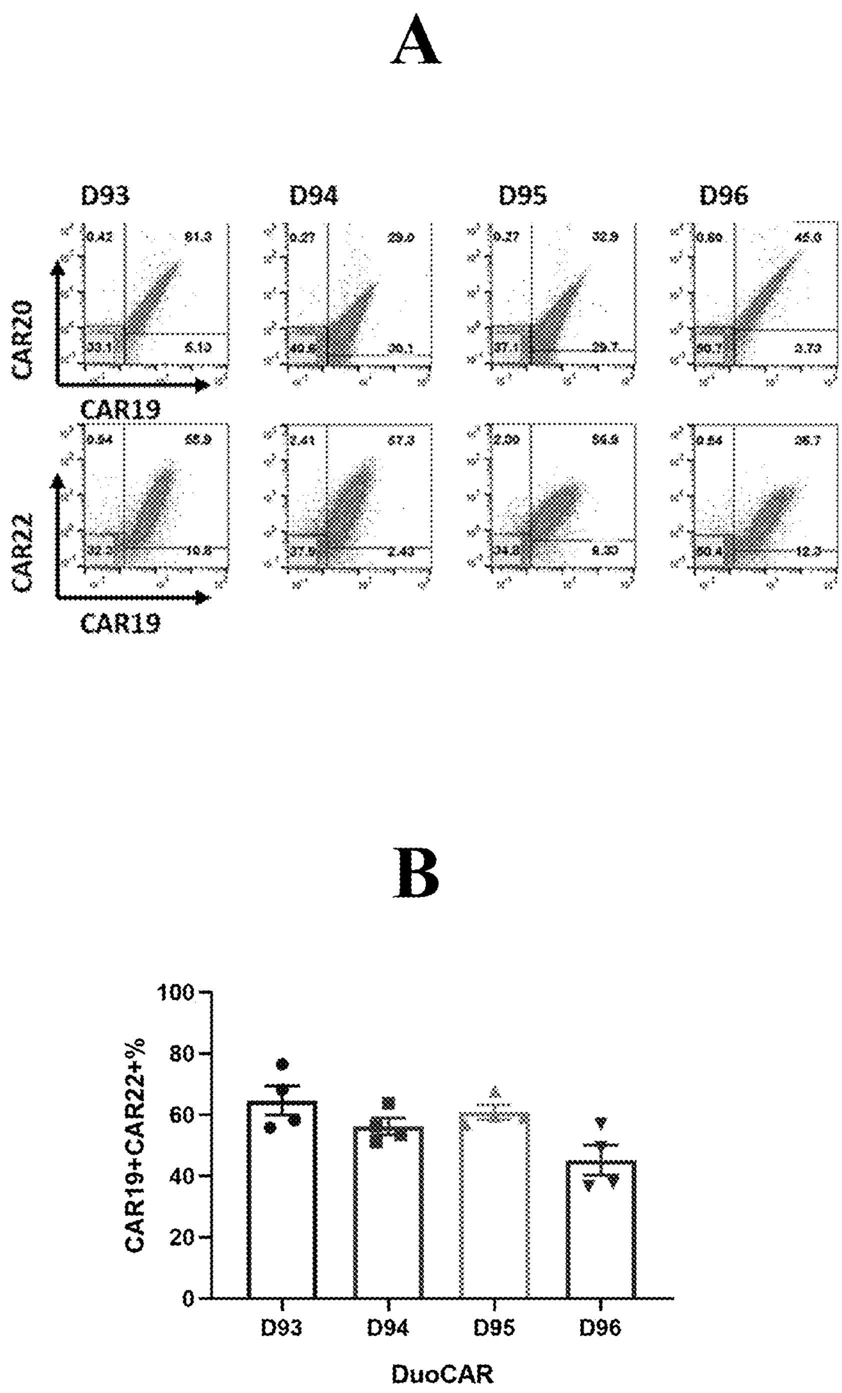
FIG. 22: Surface expression of Duo-CAR T constructs D93, D94, D95, D96 and a tandem CAR 1497 (comparison) on human primary T cells. CAR T expression was determined by flow cytometry. T cells were activated with Miltenyi Biotec TransAct™ CD3 CD28 reagent in the presence of IL-2, and transduced with LV at MOI 80, as described in Materials and Methods. On culture day 8, viable transduced T cells (7-AAD negative) were assayed for CAR surface expression using one of three staining methods: CD19 Fc followed by anti-Fc-AF647, CD20 biotin reagent followed by streptavidin PE, or CD22-his reagent followed by anti-his-PE staining. (A) One representative transduction experiment, out of four experiments, is shown. Expression of CD20-targeting scFv in relation to CD19 targeting scFv is shown in the top panel, and the expression of CD22 targeting scFv in relation to the expression of the CD19-targeting scFv is shown in the bottom panel. The LV used in transduction is listed on the top of each column. Percentage of CAR T-positive populations is noted in each quadrant of the histogram. (B) Mean percentage DuoCAR expression±SEM for four transduction experiments performed in T cells from different donors is shown. CAR-transduced T cells were defined as CAR19+CAR22+ cells, representing simultaneous detection of the two DuoCAR chains co-expressed in each cell.

Trivalent DuoCARs were constructed by linking a tandem 2019-targeting CAR chain to a 22-targeting CAR chain via P2A ribosomal skip element. Four distinct DuoCAR constructs were designed based on best combinations previously identified in optimization co-transduction experiments. The optimization studies involved testing each CAR moiety (i.e. a CD20/19 tandem CAR and a CD22 single CAR) containing a 41BB, CD28, OX40, ICOS, or CD27 costimulatory domain, or no costimulatory domain, either alone or in combination. Specific parameters tested were CAR expression levels and in vitro anti-tumor activity. DuoCAR construct structures are shown in FIG. 21A, termed D93, D94, D95 and D96. DuoCAR Construct D93 was comprised of tandem scFv binder domain targeting B cell antigens CD19 and CD20, hinge and transmembrane domain derived from CD8, followed by ICOS co-stimulatory domain, and CD33 activation domains. This CAR construct sequence was linked via P2A ribosomal skip element to CD22-targeting first generation CAR, thus creating a bicistronic, triple-targeting DuoCAR (FIG. 21). Use of the 2A ribosomal skip element assures the following CAR attributes: (i) the production of one uniform cellular product, and (ii) stoichiometrically equal expression of the two CAR moieties within the individual cell; the combination of which achieves optimal anti-tumor function. DuoCAR construct D94 was identical to D93, except that the ICOS co-stimulatory domain was substituted for OX40 domain. Construct D95 was comprised of CD20- and CD19-tandem targeting OX40z CAR chain, identical to that of D94, followed by a second generation CD22 CAR chain with ICOS co-stimulatory domain and CD33 activation domain. Finally, DuoCAR construct D96 contained the CD20 and CD19 tandem targeting CAR chain with CD27 co-stimulatory domain, followed by CD22 targeting single CAR chain with ICOS co-stimulatory domain, each with CD35 activation domain (FIG. 21A). DuoCAR constructs were encoded into lentiviral vectors and transduced into human primary T cells. The DuoCARs were robustly expressed in T cells, ranging 30%-70% CAR T+ cells between three different constructs and donors (FIG. 22A, 22B).

In addition, several control CAR constructs, including single-targeting CARs and a tandem targeting CAR were constructed (FIG. 21A). The single-targeting CARs comprised either anti-CD22 scFv, anti-CD19 scFv, or anti-CD20 scFv, followed by CD8 hinge and transmembrane domain, either linked directly to the CD3z activation domain (D92, CAR22, first generation) or also incorporating a co-stimulatory domain (D89, 1538, 1495, second generation), FIG. 21A. The tandem control CAR targeting CD20 and CD19, termed 1497 CAR was comprised of the tandem CD20-CD19 scFv linked in frame to CD8 hinge and transmembrane domain, 4-1BB co stimulatory and CD3z activation domain. Tandem control constructs D88, D90, D91 were designed as tandem CAR 1497, except for the substitution of the 4-1BB co-stimulatory domain with ICOS, OX40 or CD27 domains, respectively (not shown). These constructs exhibit anti-tumor activity against unmodified tumors expressing all three target antigens, CD19, CD20 and CD22, but in contrast to the DuoCARs D93, D94, D95 and D96, the tandem constructs are not able to prevent antigen escape of tumor cells that are double-negative for CD19 and CD20. The positioning and composition of CAR chains within T cell is schematically shown for DuoCAR, tandem CAR, and single CAR T cell of the first or the second generation in FIG. 21B. All single and tandem CAR constructs achieved robust expression in human primary T cells by lentiviral transduction.

DuoCARs potently and specifically lyse tumor targets in vitro

Figure 23:
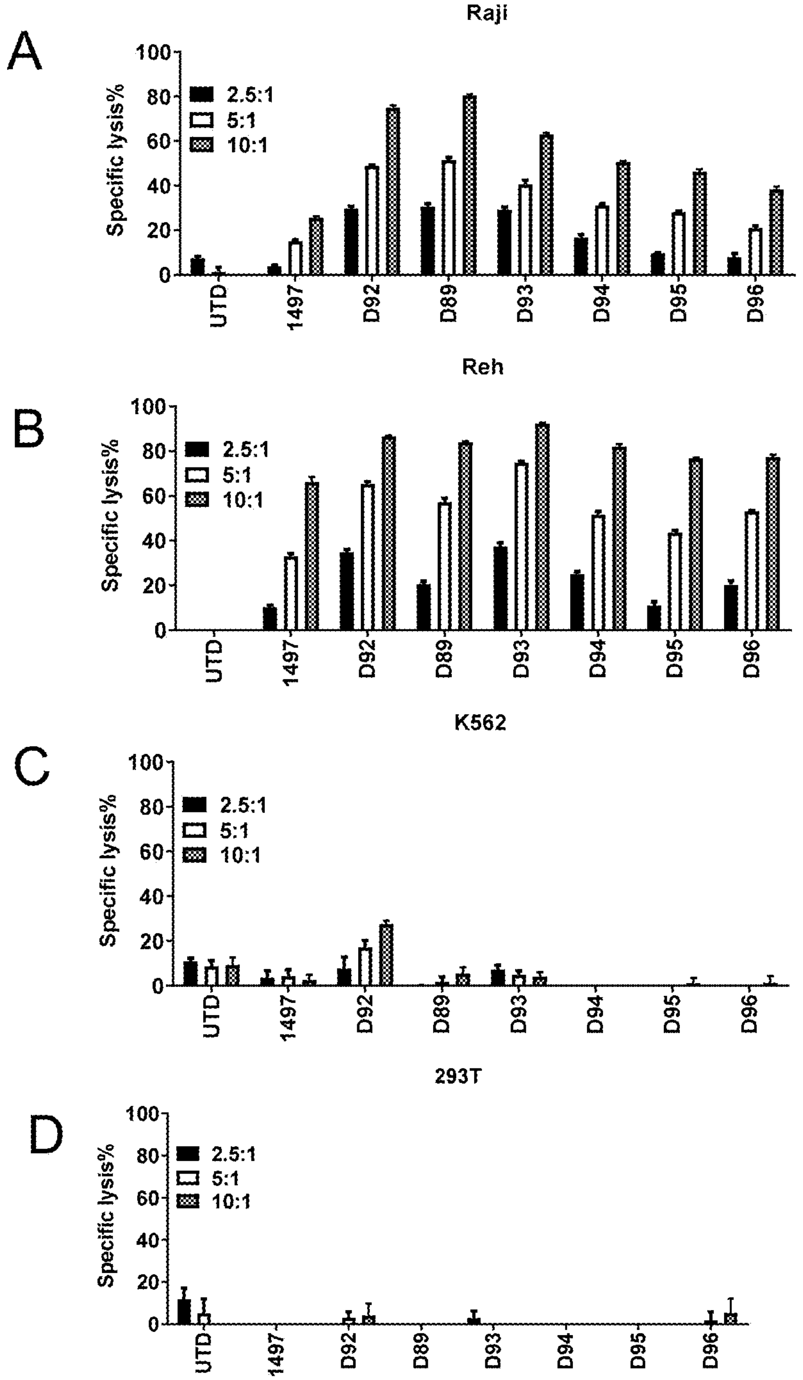
FIGS. 23A, 23B, 23C, and 23D depict CAR T cytotoxicity in vitro. Luciferase-based cytotoxicity assays were performed using, Raji 13G11 CD19+CD20+CD22+, REH CD19+CD20lowCD22+, or CD19− CD22− cell lines (293T or K562), stably transduced with luciferase. Specific lysis of target cells by DuoCARs D1-D4, tandem CAR 1497, or single CARs D89 and D92 is shown for (FIG. 23A) Raji cells, (FIG. 23B) Reh cells, (FIG. 23C) K562 cells or (FIG. 23D) 293T cells. Negative control UTD-untransduced T cells was included. CAR T cells and target tumor cells were co-incubated overnight at the listed effector to target (E:T) ratios, x-axis. Error bars represent mean values from three technical replicates. One experiment representing three separate experiments in T cells from three donors, is shown. Bars represent mean+/−SD values from three independent experiments performed with CAR T cells from three separate donors.

In order to evaluate the functionality of the constructed DuoCARs, the constructed DuoCARs were combined with luciferase-expressing target tumor lines for an overnight killing assay. Antigen-positive lines, the NHL line Raji (CD19+CD20+CD22+), and the B-ALL line Reh (CD19+ CD20lowCD22+) were used to test the capability of DuoCARs to lyse tumor cells in antigen-specific manner. Negative control lines, myelogenous leukemia K562, and human embryonic kidney line 293T, which are both CD19−CD20−CD22−, were also included (FIG. 23).

Tandem CAR 1497, and single CAR controls D89 and D92, the CD22 targeting CARs of the second and the first generation, respectively, were included for comparison.

CAR T cells and target cells were combined at effector to target (E:T) ratios of 10:1, 5:1 or 2.5:1, and at the completion of incubation period specific lysis was calculated for each condition as described in Materials and methods.

All single and tandem CARs lysed target-positive tumor lines, Raji and Reh, in E:T-dependent manner (FIG. 23A, 23B). The DuoCARs constructs potently lysed target cell lines which express the targeted antigens CD19, CD20 and CD22 at all E:T ratios (FIG. 23A, 23B). The tandem control CAR 1497, targeting the CD19 and CD20 antigens, resulted in a relatively modest tumor lysis at the E:T ratio tested, as compared to the DuoCARs D93, D94, D95 and D96 in Raji cells (FIG. 23A). By comparison, in Reh cells, the lytic potency of 1497 was similar to the lytic potency of DuoCARs D93, D94, D95 and D96 (FIG. 23B). The single-targeting CAR22 constructs D89 and D92 tended to be the most potent tumor cell killers for the CD22 antigen-positive target lines Raji and Reh. By contrast, none of the DuoCAR constructs or controls lysed target-negative tumor lines K562 and 293T (FIG. 23C, 23D), with the exception of single targeting CAR22 construct D92 in K562 cells, which produced 27% non-specific lysis at the highest E:T ratio of 10 (FIG. 23C). Therefore, the DuoCARs performed equally well, or were superior to 1497 tandem construct in the lysis of antigen-positive target lines, and produced no background lysis in antigen negative lines, demonstrating antigen-dependence. Notably, despite non-specific lytic activity of the single CAR 22, D92, in K562 cells, the incorporation D92 sequence into DuoCAR constructs D1 and D2 did not result in non-specific target lysis by DuoCARs. Therefore, the DuoCAR design appears to tamper down the undesired spontaneous lytic activity seen in the first generation CAR D92 (FIG. 23C).

Cytokine response of DuoCARs

Figure 24:
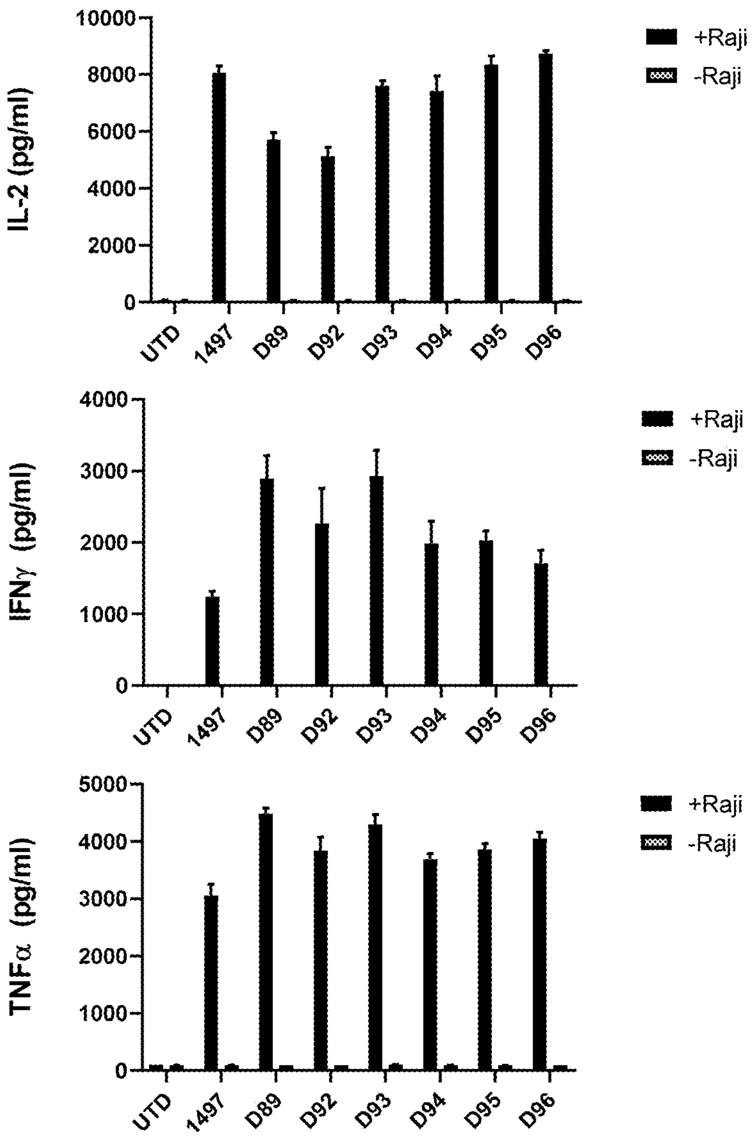
FIG. 24 depicts CAR T cytokine release in response to leukemia cell lines. Cytokine IL-2, IFNγ and TNFα production by CAR-T, listed on the x-axis, upon overnight co-culture with the Raji leukemia line at an E:T ratio of 10:1, was measured using ELISA. Bars represent mean +SD of three replicate samples. Data are representative of three independent experiments performed with CAR T cells from three separate donors.
Figure 25:
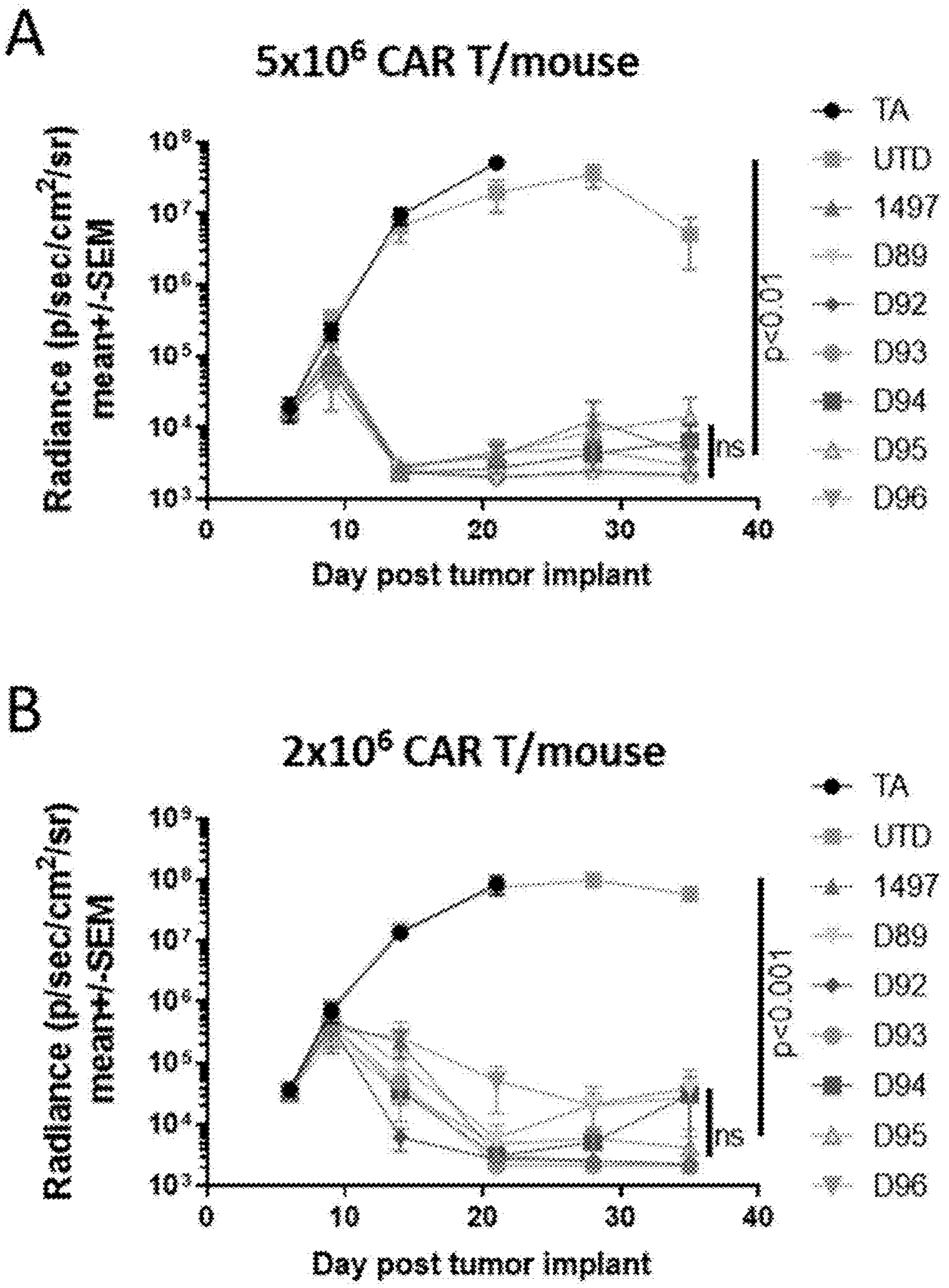
FIGS. 25A and 25B depict in vivo anti-tumor activity of DuoCARs. NSG mice bearing Raji tumors were treated with DuoCAR T cells D93, D94, D95 and D96, or tandem CAR 1497, or single CARs D89 or D92. CAR T cells were injected i.v. seven days after tumor inoculation, either at dose of 5 million CAR T cells per mouse (FIG. 25A) or at two million CAR T cells per mouse (FIG. 25B). Tumor burden was evaluated by bioluminescence on days indicated. N=6 mice per group, mean Radiance±SEM is shown.

To characterize the cytokine production of DuoCARs in response to target cells, supernatants were collected form co-cultures of DuoCARs with CD19+CD20+CD22+ Raji target cells following overnight incubation. The concentration of T cell pro-inflammatory and homeostatic cytokines IL-2, IFNγ and TNFα in culture supernatants were determined by ELISA (FIG. 24, blue bars). Non-transduced T cells from same donor and batch (UTD) were included as a CAR-negative control. Further, to control for possible spontaneous cytokine release by CAR T cells in the absence of triggering target cell, each CAR T cell group was also incubated without Raji targets (FIG. 24, light grey bars). DuoCARs, as well as single and tandem control CARs strongly induced the production of IL-2, IFNγ and TNFα in response to target Raji cells as compared to UTD, however none of the DuoCAR lines or CAR controls were prone to spontaneous release of these soluble factors in the absence of target cells (FIG. 24).

DuoCAR efficiently lyse CD19+CD20+CD22+ Raji tumors in vivo

Having established the cytotoxic and cytokine release functionality of DuoCARs against antigen-positive target cells in vitro, DuoCAR function was then demonstrated in vivo. NSG (NOD.Cg-Prkdc$^{scid}$Il2rg$^{tm1Wjl}$/SzJ) mouse xenograft of Raji cells stably transduced with firefly luciferase was utilized. DuoCARs D93, D94. D95 and D96, as well as tandem control CAR 1497, and single controls D89 and D92 were included (FIG. 26A). Tumor bearing mice were administered either five million CAR T cells, or two million CAR T cells each, or dose-matched UTD controls, on study day 7, and tumor rejection was measured by bioluminescent imaging periodically up to study day 28 (FIGS. 26B-26E). In the high CAR T dose regiment of five million cells per mouse, DuoCARs potently suppressed Raji tumor progression from day 14 and onward, whereas tumors in tumor alone group (TA), and the non-transduced T cell group (UTD) progressed unabated. The tumor repression mediated by DuoCARs and single and tandem CAR controls, as compared to the TA and UTD negative controls, was statistically significant. The DuoCAR D93, and the single CARs D89 and D92 tended to generate the greatest tumor regression over the study period, whereas the DuoCAR D95 and the tandem CAR 1497 tended to be the least potent among the CAR constructs. However, the differences between the individual CAR constructs at this dosage level were not statistically significant (FIG. 26B). To better pinpoint the minor differences between DuoCAR constructs and to test whether they remain functional at low dose regiments, Raji-bearing mice were dosed with two million CAR T cells each (FIG. 26C, 26E). Despite the low CAR T dose, all CAR constructs significantly controlled Raji tumor burden as compared to TA and UTD controls at this level. Whereas none of the DuoCAR constructs or control CARs were significantly better than other CARs, DuoCAR D93 and D94 tended to maintain best tumor control, whereas DuoCAR D96 tended to be less potent than other CARs (FIG. 26C). Of note, tumor regression in 1497, the tandem CAR group, appeared delayed as compared to DuoCARs D93-D96, suggesting a possible superiority of the DuoCAR constructs in this setting (FIG. 26C). In addition, The single CAR D92 tended to reduce tumor burden faster than the other CAR constructs, in concordance with high potency, but also lower specificity observed for this construct in the in the in vitro cytotoxicity experiment against antigen-positive and antigen-negative target lines (FIG. 23).

Trispecific DuoCARs require only a single antigen for anti-tumor function, and are potently killing antigen-erased target cells in a model of tumor antigen loss of either CD19, CD20, or CD22.

Figure 26:
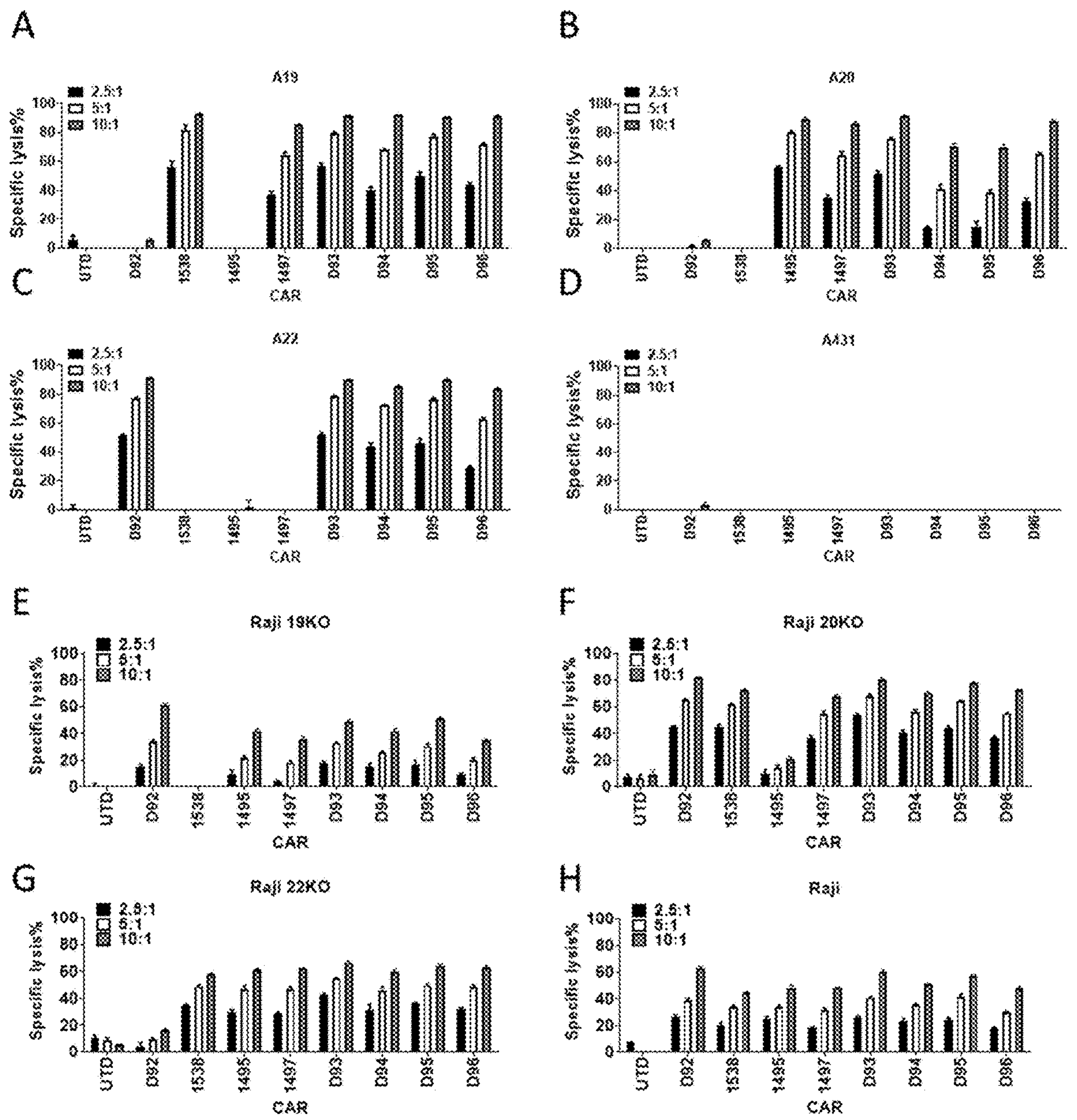
FIGS. 26A-26H depict CAR T cytotoxicity in vitro against A431 tumor line clones transduced to over express one target antigen only, in order to confirm the specificity of the CD22 CD19-targeting CAR T cells (FIGS. 26A-D), and the parental A431 negative control line, or Raji leukemia line clones engineered to lack expression of either CD19, CD20, or CD22, representing antigen-escaped clones, and the parental Raji line for comparison (FIGS. 26E-H). All target lines stably expressed firefly luciferase. Bars indicate mean±SEM values from triplicate determination from one experiment, representing three independent experiments performed with CAR T cells from three separate donors.

Having demonstrated that the DuoCARs mediated a potent rejection of CD19+CD20+CD22+, wild-type Raji xenograft in vivo, even at the low dose regiment of two million CAR T+ cells/mouse, the sufficiency of each single antigen to trigger DuoCAR activation was verified in vitro. CAR constructs included in this experiment are schematically shown in FIG. 26A. Experimental groups included the DuoCARs D93, D94, D95 and D96, the tandem CAR control 1497, and single CAR controls D92, 1538 and 1495, targeting the CD22, CD19 and the CD20 antigens, respectively (FIG. 26).

The DuoCARs are postulated to function as a logical [OR] gate constructs, such as the presence of either one or more of the three targeted antigens is sufficient for triggering CAR activation and anti-tumor function. It was then confirmed that each of the three reactivities is intact in DuoCARs D93, D93, D95, and D96. To this end, the A431 squamous cell carcinoma line was engineered, which is naturally devoid of B cell surface molecules, to stably express either CD19, or CD20, or CD22. To facilitate quantitation of tumor lysis, each target A431 line also stably expressed firefly luciferase. DuoCAR T cells and control CARs were tested in in vitro cytotoxicity assay against each of the A431 clones expression one antigen only, and the parental A431 parental line was included as a control target-negative (FIG. 26A-26D).

DuoCARs D93, D93, D95, and D96 effectively lysed tumors expressing a single antigen each only: CD19 (FIG. 26A), CD20 (FIG. 26B) or CD22 (FIG. 26C), but not the parental line A431 lacking the expression of these target molecules (FIG. 26D). Tumor lysis by DuoCARs of target cells with cognate antigen expression was dependent on effector to target ratio, demonstrating precise specificity of the DuoCAR constructs. As expected, single CARs could not lyse target clones if those clones lacked the expression of the targeted antigens. Line A19 was lysed by single CAR19, 1538, but not by single CAR targeting CD22-D92, or targeting CD20-1495 (FIG. 26A). Similarly, target line A20 was lysed by CAR20 1495, but not by single CARs CD22-D92, or CD19 CAR-1538 (FIG. 26B). Moreover only the CD22-targeted single CARs D92 and D89, but not the CD19 and CD20 targeted CARs 1538 and 1495, respectively, lysed the A22 target line (FIG. 26C). None of the constructs lysed the parental line A431, in concordance with lack of expression of CD19, CD20 or CD22 on this tumor line (FIG. 26D). Therefore, DuoCARs were reactive with each one of the target antigens CD19, CD20, CD22, in an isolated fashion, independently of other two antigens. Further, the presence of each single antigen CD19, CD20 or CD22 in isolation was sufficient to trigger DuoCAR function.

It was then shown that in a model of tumor antigen escape, Raji clones with erased expression of either CD19, CD20 or CD22, DuoCARs were able to lyse target cells despite the lack of either one of the three targeted molecules (FIG. 26E-26G), and the magnitude of lysis was comparable to the DuoCAR lysis of the parental Raji line, in which the expression of all three antigens was intact (FIG. 26H). By contrast, the single-targeting CARs were lytic only against clones in which their cognate targets were present. Specifically, single CARs 20 and 22, D92 and 1495, but not single CAR 19, 1538, lysed Raji 19KO (FIG. 26E), Single CARs 19 and CAR22, but not CAR 20 lysed the Raji 20KO (FIG. 26F), and single CAR 19 and 20, but not CAR22 lysed the Raji 22 KO line (FIG. 26G). By comparison, none of the single CAR controls D92, 1538 or 1495 showed any impairment in the lysis of the parental Raji clone, expressing all three target antigens (FIG. 26H). These results demonstrate the superiority of DuoCARs in targeting tumor cells which lack the expression of one of the targeted antigens.

Figure 27:
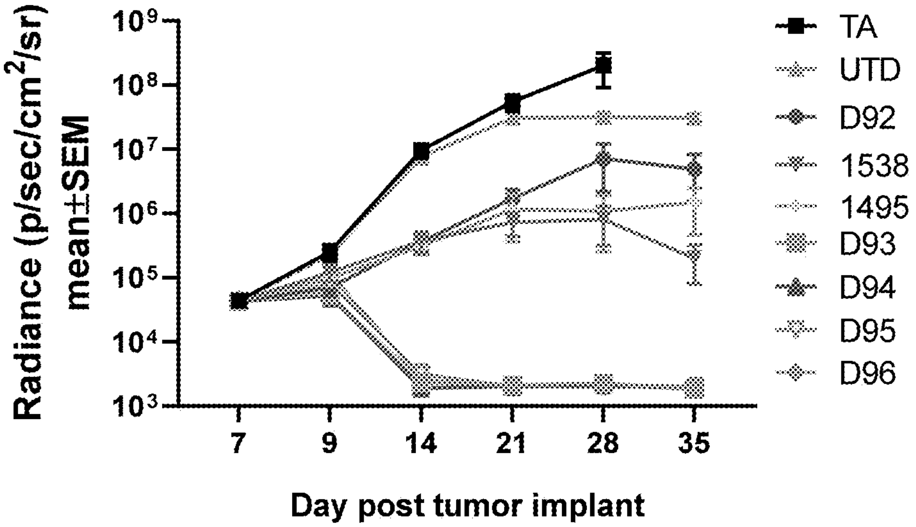
FIG. 27 depicts in vivo anti-tumor activity of DuoCARs in a model of tumor antigen escape. NSG mice were inoculated with a mixture of Raji CD19neg, Raji CD20neg, Raji CD22neg, and the parental Raji clone in equal proportions. Raji tumors were treated with DuoCAR T cells D93, D94, D95 or D96, which are capable of targeting CD19, CD20, or CD22 antigens, or single CAR controls: CAR22 D92, CAR19 1538, or CAR20 1495. T cells were injected i.v. seven days after tumor inoculation, at dose of 5 million CAR T cells per mouse or Tumor burden was evaluated by bioluminescence on days indicated. N=6 mice per group, mean Radiance±SEM is shown.

Tumor antigen escape, when expression of one or more of the targeted antigens diminishes or disappears completely, and tumor heterogeneity, whereas a single agent/CAR is incapable to target tumor cell population in its entirety, due to heterogeneous expression of the targeted antigen, remain a major obstacle to CAR T immunotherapy. To demonstrate the ability of DuoCARs to combat tumors which have lost expression of some of their target antigens, a heterogeneous xenograft tumor model was generated (FIG. 27). NSG mice were implanted with a mixture of luciferase-positive, antigen-deleted Raji clones: Raji 19KO, Raji 20KO, Raji 22KO, and the parental Raji clone, at equal proportions. Seven days after tumor implant, mice were treated with five million CAR T+ DuoCAR cells, or single CAR controls targeting CD19, CD20 or CD22. Tumor burden was measured by bioluminescence. Strikingly, starting on study day 14 an downwards, DuoCARs D93, D94, D95 or D96 have completely rejected the heterogeneous Raji tumors. By contrast, tumors continued to grow in mice receiving single targeting CARs CAR19-1538, CAR20-1495 or CAR22-D92 (FIG. 27).

In summary, described here are four novel DuoCAR designs, D93. D94, D95 and D96, which enable production of highly-functional, triple-targeting CAR T cells. DuoCAR T cells were reactive to CD19, CD20 and CD22 antigens in vitro and in vivo with high specificity, and demonstrated an extremely potent function and complete tumor rejection in a disseminated in vivo xenograft Raji tumor model with varied expression of CD19, CD20 and CD22, whereas single-targeting CARs could not prevent tumor progression in this model of tumor antigen escape. Therefore, DuoCAR T cells represent a novel solution to tackling antigen-heterogeneous tumor population and mitigating tumor antigen escape, and thus provide an opportunity for improving clinical outcomes in CAR T-treated patient population.

What is claimed is:

1. An immunotherapy composition comprising: at least one multicistronic vector comprising a promoter operably linked to a multi-cistronic nucleic acid sequence encoding two or more functional CARs comprising an extracellular antigen binding domain, a transmembrane domain, one or more non-identical intracellular signaling motifs, wherein each of the encoded two or more functional CARs comprises a non-identical amino acid sequence that is independently selected from the group consisting of the amino acid sequence of SEQ ID NO:110, 112, 114, and 116;

and wherein the at least one multi-cistronic vector is used to genetically modify one or more lymphocyte populations.

2. The immunotherapy composition of claim 1, wherein the extracellular antigen binding domain of each of the two or more functional CARs targets an antigen comprising CD19, CD20, CD22, ROR1, TSLPR, mesothelin, CD33, CD38, CD123 (IL3RA), CD138, BCMA (CD269), GPC2, GPC3, FGFR4, c-Met, PSMA, Glycolipid F77, EGFRVIII, GD-2, NY-ESO-1 TCR, MAGE A3 TCR, or any combination thereof.

3. A pharmaceutical composition comprising an antitumor effective amount of a population of isolated human lymphocyte cells, wherein the cells of the population include cells comprising (a) nucleic acid molecules encoding at least one multicistronic vector; (b) wherein the at least one multicistronic vector comprises a promoter operably linked to a multicistronic nucleic acid sequence encoding two or more functional CARs comprising an extracellular antigen binding domain, a transmembrane domain, one or more non-identical intracellular signaling motifs, wherein each of the encoded two or more functional CARs comprises a non-identical amino acid sequence that is independently selected from the group consisting of the amino acid sequence of SEQ ID NO: 110, 112, 114, and 116, wherein the at least one multicistronic vector is used to genetically modify the population of human lymphocyte cells.

4. The pharmaceutical composition of claim 3, wherein the population of isolated human lymphocytes are isolated T cells of a human having leukemia or lymphoma.

5. The pharmaceutical composition of claim 4, wherein the leukemia is chronic lymphocytic leukemia (CLL), acute lymphocytic leukemia (ALL), acute myeloid leukemia (AML), or chronic myelogenous leukemia (CML).

6. The pharmaceutical composition of claim 4, wherein the lymphoma is mantle cell lymphoma, non-Hodgkin's lymphoma or Hodgkin's lymphoma.

7. The pharmaceutical composition of claim 3, wherein the population of isolated human lymphocytes are isolated T cells of a human having multiple myeloma.

8. The pharmaceutical composition of claim 3, wherein the population of human lymphocytes are T cells of a human having an adult carcinoma selected from the group consisting of: an oral and pharynx cancer, a digestive system cancer, a respiratory system cancer, bones and joint cancers, a soft tissue cancer, a skin cancer, a cancer of the central nervous system, a breast cancer, a genital cancer, an urinary cancer, a cancer of the eye and orbit, and endocrine cancer, and a brain cancer.

* * * * *

UNITED STATES PATENT AND TRADEMARK OFFICE

CERTIFICATE OF CORRECTION

PATENT NO. : 12,365,718 B2
APPLICATION NO. : 17/540377
DATED : July 22, 2025
INVENTOR(S) : Rimas J. Orentas et al.

It is certified that error appears in the above-identified patent and that said Letters Patent is hereby corrected as shown below:

In the Claims

<u>Column 323</u>
Line 29, in Claim 2, delete “EGFRVIII,” and insert -- “EGFRvIII, --

Signed and Sealed this
Second Day of September, 2025

Coke Morgan Stewart
*Acting Director of the United States Patent and Trademark Office*